US009078867B2

(12) United States Patent
Thirion et al.

(10) Patent No.: US 9,078,867 B2
(45) Date of Patent: Jul. 14, 2015

(54) VACCINE AGAINST BETA-HERPESVIRUS INFECTION AND USE THEREOF

(76) Inventors: Christian Thirion, Munich (DE); Ulrich Koszinowski, Feldafing (DE); Christian A. Mohr, Munich (DE); Zsolt Ruzsics, Diessen am Ammersee (DE)

( * ) Notice: Subject to any disclaimer, the term of this patent is extended or adjusted under 35 U.S.C. 154(b) by 0 days.

(21) Appl. No.: 13/695,668

(22) PCT Filed: May 5, 2011

(86) PCT No.: PCT/EP2011/002252
§ 371 (c)(1),
(2), (4) Date: Dec. 14, 2012

(87) PCT Pub. No.: WO2011/138040
PCT Pub. Date: Nov. 10, 2011

(65) Prior Publication Data
US 2013/0202638 A1      Aug. 8, 2013

(30) Foreign Application Priority Data

May 5, 2010   (EP) ..................... 10004751
May 12, 2010   (EP) ..................... 10005045

(51) Int. Cl.
| A61K 39/245 | (2006.01) |
| C12N 7/00 | (2006.01) |
| C12N 15/38 | (2006.01) |
| A61K 39/00 | (2006.01) |

(52) U.S. Cl.
CPC .............. *A61K 39/245* (2013.01); *C12N 7/00* (2013.01); *A61K 2039/5254* (2013.01); *C12N 2710/16111* (2013.01); *C12N 2710/16121* (2013.01); *C12N 2710/16134* (2013.01); *C12N 2710/16152* (2013.01); *C12N 2710/16162* (2013.01); *C12N 2710/16511* (2013.01); *C12N 2830/003* (2013.01)

(58) Field of Classification Search
CPC .............. A61K 35/763; A61K 39/245; A61K 2039/5254; A61K 2039/525; A61K 39/12; A61K 39/25; C12N 15/86; C12N 15/8258; C12N 2710/16062; C12N 2710/16032; C12N 15/869; C12N 2710/16121; C12N 2710/16152
See application file for complete search history.

(56) References Cited

U.S. PATENT DOCUMENTS

| 7,892,822 B1 * | 2/2011 | Koszinowski et al. ...... 435/320.1 |
| 2005/0064394 A1 * | 3/2005 | Liu et al. .................... 435/5 |
| 2008/0199493 A1 * | 8/2008 | Picker et al. ............... 424/208.1 |

FOREIGN PATENT DOCUMENTS

| WO | WO2005/012545 | 2/2005 |

OTHER PUBLICATIONS

Isaacson MK, Compton T. Human cytomegalovirus glycoprotein B is required for virus entry and cell-to-cell spread but not for virion attachment, assembly, or egress. J Virol. Apr. 2009;83(8):3891-903. Epub Feb. 4, 2009.*
Dudek T, Knipe DM. Replication-defective viruses as vaccines and vaccine vectors. Virology. Jan. 5, 2006;344(1):230-9.*
Rawlinson WD, Farrell HE, Barrell BG. Analysis of the complete DNA sequence of murine cytomegalovirus. J Virol. Dec. 1996;70(12):8833-49.*
Heineman TC. Human cytomegalovirus vaccines. In: Arvin A, Campadelli-Fiume G, Mocarski E, et al., editors. Human Herpesviruses: Biology, Therapy, and Immunoprophylaxis. Cambridge: Cambridge University Press; 2007. Chapter 71. Available from: http://www.ncbi.nlm.nih.gov/books/NBK47380/.*
Mohr CA, Cicin-Sain L, Wagner M, Sacher T, Schnee M, Ruzsics Z, Koszinowski UH. Engineering of cytomegalovirus genomes for recombinant live herpesvirus vaccines. Int J Med Microbiol. Jan. 2008;298(1-2):115-25. Epub Aug. 16, 2007.*
Liu Y, Cui Z, Zhang Z, Wei H, Zhou Y, Wang M, Zhang XE. The tegument protein UL94 of human cytomegalovirus as a binding partner for tegument protein pp28 identified by intracellular imaging. Virology. May 25, 2009;388(1):68-77.*
Pass RF. Development and evidence for efficacy of CMV glycoprotein B vaccine with MF59 adjuvant. J Clin Virol. Dec. 2009;46 Suppl 4:S73-6. Epub Jul. 31, 2009.*
Mohr et al: "A Cytomegalovirus deficient in viral spread has full immunogenic competence", poster presented at 12th International CMV/BetaHerpesvirus Workshop, Boston, Massachusettes, May 10-14, 2009.
Mohr et al: "A Cytomegalovirus deficient in viral spread has full immunogenic competence", abstract of the poster contained in the abstract book presented at 12th International CMV/BetaHerpesvirus Workshop, Boston, Massachusettes, May 10-14, 2009.
A. Bubeck et al: "Comprehensive Mutational Analysis of a Herpesvirus Gene in the Viral Genome Context Reveals a Region Essential for Virus Replication", Journal of Virology, vol. 78, No. 15, Aug. 1, 2004, pp. 8026-8035, XP55004753, ISSN: 0022-538X, DOI: 10.1128/JVI.78.15.8026-8035.2004 *concerns Invention 1*; p. 8028, paragraph 2—p. 8029, right-hand column, paragraph 1; table 2.
B. Rupp et al: "Conditional Cytomegalovirus Replication in Vitro and in Vivo", Journal of Virology, vol. 79, No. 1, Jan. 1, 2005, pp. 486-494, XP55004778, ISSN: 0022-538X, DOI: 10.1128/JVI.79.1. 486-494.2005 *concerns Invention 1*; p. 488, right-hand column, paragraph 2; figures 1C, 3.
Christopher M. Snyder et al: "Cross-Presentation of a Spread-Defective MCMV Is Sufficient to Prime the Majority of Virus-Specific CD8+ T Cells", Plos one, vol. 5, No. 3, Jan. 1, 2010, pp. E9681-E9681, XP55004357, ISSN: 1932-6203, DOI: 10.1371/journal. pone.0009681 p. 2, left-hand column, paragraph 2—p. 3, right-hand column, paragraph 1; figures 1, 2, p. 6, left-hand column, paragraph 2.
W. Dunn: "Functional profiling of a human cytomegalovirus genome", Proceedings of the National Academy of Sciences, vol. 100, No. 24, Jan. 1, 2003, pp. 14223-14228, XP55004412, ISSN: 0027-8424, DOI; 10.1073/pnas.2334032100 *concerns Invention 3*; figure 1; table 1.

(Continued)

*Primary Examiner* — Benjamin P Blumel
*Assistant Examiner* — Rachel Gill
(74) *Attorney, Agent, or Firm* — Winthrop & Weinstine, P.A.

(57) ABSTRACT

The present invention is related to a beta-herpesvirus, wherein the beta-herpesvirus is spread-deficient.

9 Claims, 9 Drawing Sheets

(56) References Cited

OTHER PUBLICATIONS

D. Yu et al: "Functional map of human cytomegalovirus AD169 defined by global mutational analysis", Proceedings of the National Academy of Sciences, vol. 100, No. 21, Oct. 1, 2003, pp. 12396-12401, XP55037376, ISSN: 0027-8424, DOI: 10.1073/pnas. 1635160100 *concerns Invention 3*, p. 12400, right-hand column, lines 13-15, figure 2; table 1 E.

C.A. Mohr et al: "A Spread-Deficient Cytomegalovirus for Assessment of First-Target Cells in Vaccination", Journal of Virology, vol. 84, No. 15, Aug. 1, 2010, pp. 7730-7742, XP55000990, ISSN: 0022-538X, DOI: 10.1128/JVI.02696-09; the whole document.

C. Sinzger et al: "Cloning and sequencing of a highly productive, endotheliotropic virus strain derived from human cytomegalovirus TB40/E", Journal of General Virology, vol. 89, No. 2, Feb. 1, 2008, pp. 359-368, XP55001586, ISSN: 0022-1317, DOI: 10.1099/vir.0. 83286-0 the whole document.

Cui X et al: "Cytomegalovirus vaccines fail to induce epithelial entry neutralizing antibodies comparable to natural infection", Vaccine Elsevier Ltd, GB, vol. 26 No. 45, Oct. 23, 2008, pp. 5760-5766, XP026046073, ISSN: 0264-410X, DOI: 10.1016/J. Vaccine.2008. 07.092 [retrieved on Aug. 19, 2008] the whole document.

Dudek T et al: "Replication-defective viruses as vaccines and vaccine vectors", Virology, Academic Press, Orlando, US, vol. 344, No. 1, Jan. 5, 2006, pp. 230-239, XP024896310, ISSN: 0042-6822, DOI: 10.1016/J. virol.2005.09.020 [retrieved on Jan. 5, 2006], right-hand column, line 3—p. 233, left-hand column, line 5; figure 1.

\* cited by examiner

VACCINE AGAINST BETA-HERPESVIRUS INFECTION AND USE THEREOF

The present invention is related to a beta-herpesvirus, preferably a recombinant beta-herpesvirus, the use of the beta-herpesvirus for the manufacture of a medicament, the use of the beta-herpesvirus for the manufacture of a vaccine, a nucleic acid coding for the beta-herpesvirus, a vector comprising the nucleic acid coding for the beta-herpesvirus, and a host cell comprising the nucleic acid coding for the beta-herpesvirus or the vector. In a preferred embodiment, the beta-herpesvirus is a human cytomegalovirus.

Human cytomegalovirus (CMV), a member of the beta-herpesvirus subfamily is the medically most significant herpesvirus infecting humans (Arvin et al. 2004 Clin. Infect. Dis. 39:233-239.; Stratton et al. 1999 Vaccines for the 21st Century: A Tool for Decisionmaking National Academy Press). Most of the human CMV infection is acquired without symptomatic disease via breast feeding or saliva/urine contact in early childhood. This results in nearly 100% prevalence of HCMV in developing countries. In industrialized countries about 30% of the population gets infected in the childhood and the prevalence of human CMV infection increases up to ~50% by early adulthood.

Human CMV can also be transmitted from the mother to the fetus during pregnancy leading to mental retardation and developmental disabilities in the infected child. Human CMV is the most important causative agent of congenital infections in industrialized countries with one out of 1000 newborn affected. To date 30,000-40,000 infants are annually born with congenital cytomegalovirus infection in the United States, making cytomegalovirus by far the most common and important of all congenital infections. The likelihood of congenital infection and the extent of disease in the newborn depend on the maternal immune status. If primary maternal infection occurs during pregnancy, the average rate of transmission to the fetus is 40%; about 65% of these newborns will have congenital inclusion disease (CID). With recurrent maternal infection going along with reactivation from latency, the risk of transmission to the fetus becomes lower ranging only from 0.5 to 1.5% and the majority of these infants will also be symptomless. Although natural infections before pregnancy cause a risk of reactivation associated feto-maternal transmission the induced immunity is a major protective factor against CID.

The infection at birth bears the risk of serious complications; the primary infection with HCMV is generally symptomless in immunologically competent individuals. The major risk groups comprise organ transplant recipients and acquired immunodeficiency syndrome (AIDS) patients in which human CMV induces life-threatening inflammatory diseases with high probability. Moreover, after primary infection at any age, CMV establishes lifelong latency, leaving the infected individuals at danger of later reactivation upon immune suppression.

Although enormous progress has recently been made in molecular biology and immunology of cytomegaloviruses (Murphy et al. 2008 Curr. Top. Microbiol. Immunol. 325:1-19), to date there is no commercially available vaccine and the single hit chemotherapy is the only way of controlling acute HCMV infection (Mocarski et al. 2007, p. 2701-2772 in D. M. Knipe and P. M. Howley (eds.), Fields Virology, Lippincott Williams and Wilkins, a Wolters Kluwer Business, Philadelphia, Pa.). This chemotherapy causes severe side effects and application is often restricted to the most severe cases.

The development of vaccines against CMV infection is reviewed in Schleiss et al. (Schleiss et al. 2005 Herpes. 12:66-75; Schleiss et al. 2008 Curr. Top. Microbiol. Immunol. 325: 361-382.).

One strategy for the development of a human CMV vaccine is the use of live attenuated HCMV. Live attenuated CMV are generated by multiple cell culture passages. In accordance therewith, in live attenuated vaccines the administered viruses are infectious. However due to the adaptation to the cell culture a loss of functional genes occurs whereby the lost genes are not required for virus propagation in vitro, but are important for virus infection in vivo. Such live attenuated CMV are therefore less pathogenic to the host.

The first human CMV vaccine candidate which was tested in clinical trials was a live attenuated vaccine. This was the AD169 strain of HCMV which was attenuated by extensive tissue culture passages in human primary fibroblasts. This attenuation is a result of a selective adaptation of the virus to the conditions of the cell and cell culture. It is likely that the loss of virulence is the result of affecting genes not relevant for the in vitro situation but important for the virus in its natural host. Therefore, it is not surprising that AD169, extensively passaged on fibroblasts, lost its ability to infect endothelial cells and monocytes. The majority of seronegative adults inoculated with AD169 vaccine developed HCMV specific immune response. This vaccine was found to be safe and generally well tolerated. However, injection site reactions were common, and several patients developed mild systemic symptoms consisting of fever, headache, fatigue and myalgia.

Since the AD169 strain was too aggressive, a more attenuated preparation of laboratory adapted HCMV, the Towne strain, was developed in a manner similar to AD169 as a potential live attenuated vaccine. This strain was more extensively passaged in cell culture and in vitro appeared to be also phenotypically similar to AD169.

The initial human trial showed that, as expected, the Towne strain was much better tolerated than the AD169. After this positive initial test the efficacy of the Towne vaccine was extensively studied. These studies showed that the Towne vaccine is safe and well tolerated in humans and induces both humoral and cellular immunity specific to human CMV. Although the Towne vaccine appears to provide some protection against human CMV disease in certain settings, unfortunately, vaccination is less protective than natural immunity. Therefore, the Towne strain is most likely over-attenuated rendering it of suboptimal efficacy as a vaccine.

Consequently, new human CMV strains with intermediate attenuation have been produced. Chimeric viruses have been constructed by genetic recombination between Towne strain and Toledo strain, which is a wild type like clinical isolate of human CMV not attenuated by tissue culture passages.

Interestingly, an essential feature of the Towne strain and the vaccine based thereon is its incapability of efficiently infecting endothelial cells. Furthermore, vaccination with the Towne strain does not induce antibodies that are capable of neutralizing endotheliotropic CMV infection, more specifically Towne does not induce antibodies against endotheliotropic human CMV strains (Cui et al. 2008 Vaccine 26:5760-5766.).

To differentiate between neutralization of endotheliotropic and non-endotheliotropic viruses, Gerna et al. (Gerna et al. 2008 J Gen Virol 89:853-865.) proposed the testing of human sera and quantification of the neutralizing potency against human CMV clinical isolates via propagation and testing in endothelial (or epithelial) cells and against the same virus infecting human fibroblasts (Gerna et al. supra).

It is important to note that in addition to the inability of the Towne strain to infect endothelial cells and the inability of the Towne strain to induce antibodies that are capable of neutralizing endotheliotropic human CMV infection, the Towne strain is lacking genes compared with clinical wild type human CMV isolates. More specifically, the Towne strain is lacking the genes UL133, UL134, UL135, UL136, UL137, UL138, UL139, UL140, UL141, UL142, UL143, UL144, and UL145 as also described by Cha et al. (Cha et al. 1996 J. Virol Vol. 70, No. 1 p. 78-83).

A further strategy for developing a HCMV vaccine is based on the deletion of an essential gene from a viral genome and was described for many viruses such as adenoviruses, alpha-herpesviruses, and retroviruses. Immunization trials using replication defective or single-cycle viruses as vaccines against herpesviruses were, to date, only described for alpha-herpesviruses (Dudek et al. 2006 Virology 344:230-239). The propagation of these viruses is facilitated by complementing cells that express the lacking genomes and support the growth of the defective viruses. Propagation of such viruses with the deletion of a gene on complementing cells results in vaccine-virus particles that possess a wild type virion surface and a tropism like wild type virus for the first target cells. These viruses are infectious upon vaccination for the first line target cells. In said first line target cells, the deleted or inactivated gene leads to either the abrogation of virus replication or the formation of virus particles with diminished infectivity or tropism.

The design of an alpha-herpesvirus vaccine by deletion of one gene essential for DNA replication or the abrogation of production of infectious particles by deletion of the targeting complex, namely glycoprotein gB is reviewed in Dudek et al. (Dudek et al. supra). Two types of these viruses were described: the so called "replication-defective" and the so called "single-cycle" viruses.

Replication-defective alpha-herpesviruses were generated by the deletion of genes essential for the DNA replication cycle. The deletion of genes essential for the viral DNA replication e.g. the major DNA binding protein ICP8, was used to generate respective deletion viruses. Said viruses can be propagated in vitro by using stably transformed cells that complement the product of the lacking gene (Forrester et al. 1992 J Virol 66:341-348.). Several publications from Knipe and colleagues prove that such viruses can induce protective immune responses (see Morrison et al. 1998 Virology 243: 178-187; Morrison et al. 1994 J Virol 68:689-696.; Morrison et al. 1996 Virology 220:402-413; Morrison et al. 1997 Virology 239:315-326.).

Single-cycle viruses lack glycoproteins of targeting complexes e.g. glycoprotein gB or fusion complexes e.g. gH/gL (Dudek et al. supra). Such virus mutants are described in U.S. Pat. No. 7,374,768 by Inglis et al. Said complexes are described to be important for the attachment to the cell and/or fusion of virus and cell, as initiation steps for infection of this cell. The deletion of said glycoproteins will generate single-cycle vaccine virus particles that infect first line target cells. It is important to note that said cells in the host form virus particles which do not possess a wild type-like virion surface since they lack the glycoprotein mentioned above. These particles lacking the glycoprotein, are not infectious or at least possess limited tropism or infectivity for the next cells to be infected. Further, the deletion of said glycoprotein leads to a lacking expression of said glycoprotein preferably being effective as an antigen in the infected cell.

Due to society costs caused by human CMV infection in both morbidity groups and the emerging epidemiological situation the development of an effective HCMV vaccine has been emphasize as a highest level priority by the National Vaccine Committee of the Institute of Medicine (US) (Stratton et al. supra).

Thus the problem underlying the present invention was to provide an effective HCMV vaccine and a beta-herpesvirus contained in such vaccine, respectively.

This problem is solved by the attached independent claims. Preferred embodiments may be taken from the attached dependent claims.

The claims are recited in the following as embodiments. It will be acknowledged that further embodiments may result from the disclosure of the instant specification which is insofar not limited to the embodiments being a recitation of the claims.

Embodiment 1 A beta-herpesvirus, preferably a recombinant beta-herpesvirus, wherein the beta-herpesvirus is spread-deficient.

Embodiment 2 The beta-herpesvirus according to embodiment 1, wherein the beta-herpesvirus is endotheliotropic and/or has a wild type-like virion surface.

Embodiment 3 The beta-herpesvirus according to any one of embodiments 1 to 2, wherein the beta-herpesvirus is endotheliotropic and has a wild type-like virion surface.

Embodiment 4 The beta-herpesvirus according to any one of embodiments 1 to 3, wherein the beta-herpesvirus is suitable to or capable of inducing an immune response, wherein preferably the immune response comprises neutralizing antibodies against beta-herpesvirus and $CD4^+$ and $CD8^+$ T-cells directed against epitopes of beta-herpesvirus.

Embodiment 5 The beta-herpesvirus according to embodiment 4, wherein the immune response comprises neutralizing antibodies, wherein beta-herpesvirus is prevented from infecting endothelial cells and/or epithelial cells by the neutralizing antibodies.

Embodiment 6 The beta-herpesvirus according to embodiment 5, wherein beta-herpesvirus which is prevented from infecting endothelial cells and/or epithelial cells by the neutralizing antibodies, is a pathogen, preferably a human pathogen.

Embodiment 7 The beta-herpesvirus according to any one of embodiments 1 to 6, wherein the beta-herpesvirus is a human beta-herpesvirus.

Embodiment 8 The beta-herpesvirus according to any one of embodiments 1 to 7, wherein the beta-herpesvirus is a cytomegalovirus.

Embodiment 9 The beta-herpesvirus according to any one of embodiments 7 and 8, wherein the beta-herpesvirus is a human cytomegalovirus.

Embodiment 10 The beta-herpesvirus according to any one of embodiment 1 to 9, preferable embodiment 9, wherein the beta-herpesvirus is deficient in at least one gene product involved in primary and/or secondary envelopment.

Embodiment 11 The beta-herpesvirus according to embodiment 10, wherein the at least one gene product is involved in primary envelopment Embodiment 12 The beta-herpesvirus according to embodiment 11, wherein the at least one gene product is encoded by a gene selected from the group comprising UL50 and UL 53 and homologs of each thereof.

Embodiment 13 The beta-herpesvirus according to embodiment 10, wherein the at least one gene product is involved in secondary envelopment.

Embodiment 14 The beta-herpesvirus according to embodiment 13, wherein the at least one gene product is encoded by a gene selected from the group comprising UL94 and UL99 and homologs each thereof.

Embodiment 15 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 181652 of the nucleotide sequence according to SEQ.ID.NO:20 and a third nucleotide sequence represented by nucleotides 189192 to 233681 of the nucleotide sequence according to SEQ.ID.NO:20 and wherein nucleotide 122630 of the nucleotide sequence according to SEQ.ID.NO:20 is covalently linked to nucleotide 123668 of the nucleotide sequence according to SEQ.ID.NO:20 and wherein nucleotide 181652 of the nucleotide sequence according to SEQ.ID.NO:20 is covalently linked to nucleotide 189192 of the nucleotide sequence according to SEQ.ID.NO:20.

Embodiment 16 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 181652 of the nucleotide sequence according to SEQ.ID.NO:20, a third nucleotide sequence represented by nucleotides 189192 to 233681 of the nucleotide sequence according to SEQ.ID.NO:20 and a fourth nucleotide sequence comprising a nucleotide sequence according to SEQ.ID.NO:34.

Embodiment 17 The beta-herpesvirus according to embodiment 16, wherein nucleotide 122630 of the nucleotide sequence according to SEQ.ID.NO:20 is covalently linked to nucleotide 1 of the nucleotide sequence according to SEQ.ID.No: 34, wherein nucleotide 252 of the nucleotide sequence according to SEQ.ID.No: 34 is covalently linked to nucleotide 123668 of the nucleotide sequence according to SEQ.ID.NO:20 and wherein nucleotide 181652 of the nucleotide sequence according to SEQ.ID.NO:20 is covalently linked to nucleotide 189192 of the nucleotide sequence according to SEQ.ID.NO:20.

Embodiment 18 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 130670 of the nucleotide sequence according to SEQ.ID.NO:20, a third nucleotide sequence represented by nucleotides 131243 to 181652 of the nucleotide sequence according to SEQ.ID.NO:20 and a fourth nucleotide sequence represented by nucleotides 189192 to 233681 of the nucleotide sequence according to SEQ.ID.NO:20 and wherein nucleotide 122630 of the nucleotide sequence according to SEQ.ID.NO:20 is covalently linked to nucleotide 123668 of the nucleotide sequence according to SEQ.ID.NO:20, wherein the nucleotide 130670 of the nucleotide sequence according to SEQ.ID.NO:20 is covalently linked to the nucleotide 131243 of the nucleotide sequence according to SEQ.ID.NO:20 and wherein the nucleotide 181652 of the nucleotide sequence according to SEQ.ID.NO:20 is covalently linked to the nucleotide 189192 of the nucleotide sequence according to SEQ.ID.NO:20.

Embodiment 19 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 130670 of the nucleotide sequence according to SEQ.ID.NO:20, a third nucleotide sequence represented by nucleotides 131243 to 181652 of the nucleotide sequence according to SEQ.ID.NO:20, a fourth nucleotide sequence represented by nucleotides 189192 to 233681 of the nucleotide sequence according to SEQ.ID.NO:20, a fifth nucleotide sequence comprising a nucleotide sequence according to SEQ.ID.No: 34 and a sixth nucleotide sequence comprising a nucleotide sequence according to SEQ.ID.No: 35.

Embodiment 20 The beta-herpesvirus according to embodiment 19, wherein nucleotide 122630 of the nucleotide sequence according to SEQ.ID.NO:20 is covalently linked to nucleotide 1 of the nucleotide sequence according to SEQ.ID.No: 34, wherein nucleotide 252 of the nucleotide sequence according to SEQ.ID.No: 34 is covalently linked to nucleotide 123668 of the nucleotide sequence according to SEQ.ID.NO:20, wherein nucleotide 130670 of the nucleotide sequence according to SEQ.ID.NO:20 is covalently linked to nucleotide 1 of the nucleotide sequence according to SEQ.ID.No: 35, wherein nucleotide 67 of the nucleotide sequence according to SEQ.ID.NO:35 is covalently linked to nucleotide 131243 of the nucleotide sequence according to SEQ.ID.No: 20, and wherein nucleotide 181652 of the nucleotide sequence according to SEQ.ID.NO:20 is covalently linked to nucleotide 189192 of the nucleotide sequence according to SEQ.ID.NO:20.

Embodiment 21 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 181652 of the nucleotide sequence according to SEQ.ID.NO:20 and a third nucleotide sequence represented by nucleotides 189192 to 233681 of the nucleotide sequence according to SEQ.ID.NO:20 and wherein nucleotide 58442 of the nucleotide sequence according to SEQ.ID.NO:20 is covalently linked to nucleotide 59623 of the nucleotide sequence according to SEQ.ID.NO:20 and wherein nucleotide 181652 of the nucleotide sequence according to SEQ.ID.NO:20 is covalently linked to the nucleotide 189192 of the nucleotide sequence according to SEQ.ID.NO:20.

Embodiment 22 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 181652 of the nucleotide sequence according to SEQ.ID.NO:20, a third nucleotide sequence represented by nucleotides 189192 to 233681 of the nucleotide sequence according to SEQ.ID.NO:20 and a fourth nucleotide sequence comprising a nucleotide sequence according to SEQ.ID.No: 32.

Embodiment 23 The beta-herpesvirus according to embodiment 22, wherein nucleotide 58442 of the nucleotide sequence according to SEQ.ID.NO:20 is covalently linked to nucleotide 1 of the nucleotide sequence according to SEQ.ID.No: 32, wherein nucleotide 179 of the nucleotide sequence according to SEQ.ID.No: 32 is covalently linked to nucleotide 59623 of the nucleotide sequence according to SEQ.ID.NO:20 and wherein nucleotide 181652 of the nucleotide sequence according to SEQ.ID.NO:20 is covalently linked to nucleotide 189192 of the nucleotide sequence according to SEQ.ID.NO:20.

Embodiment 24 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 62129 of the nucleotide sequence according to SEQ.ID.NO:20, a second nucleotide sequence represented by nucleotides 63261 to 181652 of the nucleotide sequence according to SEQ.ID.NO:20 and a third nucleotide sequence represented by nucleotides 189192 to 233681 of the nucleotide sequence according to SEQ.ID.NO:20 and wherein nucleotide 62129 of the nucleotide sequence according to SEQ.ID.NO:20 is covalently linked to nucleotide 63261 of the nucleotide sequence according to SEQ.ID.NO: 20 and wherein the nucleotide 181652 of the nucleotide sequence according to SEQ.ID.NO:20 is covalently linked to the nucleotide 189192 of the nucleotide sequence according to SEQ.ID.NO:20.

Embodiment 25 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 62129 of the nucleotide sequence according to SEQ.ID.NO:20, a second nucleotide sequence represented by nucleotides 63261 to 181652 of the nucleotide sequence according to SEQ.ID.NO:20, a third nucleotide sequence represented by nucleotides 189192 to 233681 of the nucleotide sequence according to SEQ.ID.NO:20 and a fourth nucleotide sequence comprising a nucleotide sequence according to SEQ.ID.No: 33.

Embodiment 26 The beta-herpesvirus according to embodiment 25, wherein nucleotide 62129 of the nucleotide sequence according to SEQ.ID.NO:20 is covalently linked to nucleotide 1 of the nucleotide sequence according to SEQ.ID.No: 33, wherein nucleotide 38 of the nucleotide sequence according to SEQ.ID.No: 33 is covalently linked to nucleotide 63261 of the nucleotide sequence according to SEQ.ID.NO:20 and wherein nucleotide 181652 of the nucleotide sequence according to SEQ.ID.NO:20 is covalently linked to nucleotide 189192 of the nucleotide sequence according to SEQ.ID.NO:20.

Embodiment 27 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 62129 of the nucleotide sequence according to SEQ.ID.NO:20, a third nucleotide sequence represented by nucleotides 632161 to 181652 of the nucleotide sequence according to SEQ.ID.NO:20 and a fourth nucleotide sequence represented by nucleotides 189192 to 233681 of the nucleotide sequence according to SEQ.ID.NO:20 and wherein nucleotide 58442 of the nucleotide sequence according to SEQ.ID.NO:20 is covalently linked to nucleotide 59623 of the nucleotide sequence according to SEQ.ID.NO:20, wherein the nucleotide 62129 of the nucleotide sequence according to SEQ.ID.NO:20 is covalently linked to the nucleotide 63261 of the nucleotide sequence according to SEQ.ID.NO:20 and wherein the nucleotide 181652 of the nucleotide sequence according to SEQ.ID.NO:20 is covalently linked to the nucleotide 189192 of the nucleotide sequence according to SEQ.ID.NO:20.

Embodiment 28 The beta-herpesvirus according to any one of embodiments 1 to 14, wherein the beta-herpesvirus comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 62129 of the nucleotide sequence according to SEQ.ID.NO:20, a third nucleotide sequence represented by nucleotides 63261 to 181652 of the nucleotide sequence according to SEQ.ID.NO:20, a fourth nucleotide sequence represented by nucleotides 189192 to 233681 of the nucleotide sequence according to SEQ.ID.NO: 20, a fifth nucleotide sequence comprising a nucleotide sequence according to SEQ.ID.No: 32 and a sixth nucleotide sequence comprising a nucleotide sequence according to SEQ.ID.No: 33.

Embodiment 29 The beta-herpesvirus according to embodiment 28, wherein nucleotide 58442 of the nucleotide sequence according to SEQ.ID.NO:20 is covalently linked to nucleotide 1 of the nucleotide sequence according to SEQ.ID.No: 32, wherein nucleotide 179 of the nucleotide sequence according to SEQ.ID.No: 32 is covalently linked to nucleotide 59623 of the nucleotide sequence according to SEQ.ID.NO:20, wherein nucleotide 62129 of the nucleotide sequence according to SEQ.ID.NO:20 is covalently linked to nucleotide 1 of the nucleotide sequence according to SEQ.ID.No: 33, wherein nucleotide 38 of the nucleotide sequence according to SEQ.ID.NO:33 is covalently linked to nucleotide 63261 of the nucleotide sequence according to SEQ.ID.No: 20, and wherein nucleotide 181652 of the nucleotide sequence according to SEQ.ID.NO:20 is covalently linked to nucleotide 189192 of the nucleotide sequence according to SEQ.ID.NO:20.

Embodiment 30 The beta-herpesvirus according to any one of embodiment 1 to 29, wherein the beta-herpesvirus comprises one or more genes selected from the group comprising UL133, UL134, UL135, UL136, UL137, UL138, UL139, UL140, UL141, UL142, UL143, UL144 and UL145

Embodiment 31 The beta-herpesvirus according to any one of embodiment 1 to 30, wherein the beta herpesvirus comprises the nucleotide sequence according to SEQ.ID.NO:23.

Embodiment 32 The beta-herpesvirus according to any one of embodiments 1 to 31, wherein the beta-herpesvirus is deficient in at least one gene product encoded by an immune evasive gene.

Embodiment 33 The beta-herpesvirus according to embodiment 32, wherein the at least one gene product encoded by an immune evasive gene is selected from the group comprising gene products regulating MHC class I presentation and gene products regulating NK cell response.

Embodiment 34 The beta-herpesvirus according to embodiment 33, wherein the at least one gene product encoded by an immune evasive gene is a gene product regulating MHC class I presentation.

Emodiment 35 The beta-herpesvirus according to embodiment 34, wherein the gene product regulating MHC class I presentation is selected from the group comprising US6, US3, US2, UL18, US11, UL83 and UL40.

Embodiment 36 The beta-herpesvirus according to embodiment 33, wherein the at least one gene product encoded by an immune evasive gene is a gene product regulating NK cell response.

Embodiment 37 The beta-herpesvirus according to embodiment 36, wherein the gene product regulating NK cell response is selected from the group comprising gene products encoded by the genes UL40, UL16 and UL18.

Embodiment 38 The beta-herpesvirus according to any one of embodiments 1 to 37, wherein the beta-herpesvirus encodes a heterologous nucleic acid.

Embodiment 39 The beta-herpesvirus according to embodiment 41, wherein the heterologous nucleic acid is a functional nucleic acid, preferably selected from the group comprising antisense molecules, ribozymes and RNA interference mediating nucleic acids.

Embodiment 40 The beta-herpesvirus according to embodiment 38, wherein the nucleic acid is a nucleic acid coding for a peptide, oligopeptide, polypeptide or protein.

Embodiment 41 The beta-herpesvirus according to embodiment 40, wherein the peptide, oligopeptide, polypeptide or protein comprises at least one antigen.

Embodmient 42 The beta-herpesvirus according to embodiment 41, wherein the antigen is an antigen selected from the group comprising viral antigens, bacterial antigens and parasite antigens.

Embodiment 43 The beta-herpesvirus according to any one of embodiments 1 to 42 for or suitable for use in a method for the treatment of a subject and/or for use in a method for the vaccination of a subject.

Embodiment 44 The beta-herpesvirus according to embodiment 43, wherein the subject is a mammal, preferably a human.

Embodiment 45 The beta-herpesvirus according to embodiment 43 or 44, wherein the beta-herpesvirus is human cytomegalovirus.

Embodiment 46 The beta-herpesvirus according to any one of embodiments 43 to 45, wherein the subject is suffering from a disease or is at risk of suffering from a disease.

Embodiment 47 The beta-herpesvirus according to any one of embodiments 43 to 46, wherein the vaccination is a vaccination against a disease.

Embodiment 48 The beta-herpesvirus according to any one of embodiments 46 and 47, wherein the disease is a disease or condition which is associated with beta-herpesvirus infection, preferably human cytomegalovirus infection.

Embodiment 49 The beta-herpesvirus according to embodiment 48, wherein the disease or condition is selected from the group comprising congenital inclusion disease.

Embodiment 50 The beta-herpesvirus according to any one of embodiment embodiments 43 to 49, wherein the subject is a pregnant female or female of reproductive age, preferably a pregnant woman or a woman of reproductive age.

Embodiment 51 The beta-herpesvirus according to embodiment 50, wherein the treatment is or is suitable for or capable of preventing the transfer of a beta-herpesvirus, preferably human cytomegalovirus, from the female to a fetus and/or to an embryo carried or to be carried in the future by the female.

Embodiment 52 The beta-herpesvirus according to embodiment 50, wherein the treatment is for or is suitable for the generation of or capable of generating an immune response in the female body or the immune response in the female body, whereby preferably such immune response confers protection to a fetus and/or to an embryo carried or to be carried in the future by the female against beta-herpesvirus, preferably human cytomegalovirus, and/or a disease or condition associated with beta-herpesvirus infection, preferably human cytomegalovirus infection.

Embodiment 53 Use of a beta-herpesvirus according to any of embodiments 1 to 47 for the manufacture of a medicament.

Embodiment 54 Use according to embodiment 53, wherein the medicament is for the treatment and/or prevention of beta-herpesvirus infection.

Embodiment 55 Use according to embodiment 53, wherein the medicament is for the treatment and/or prevention of a disease or condition associated with beta-herpesvirus infection, preferably human cytomegalovirus infection.

Embodiment 56 Use of a beta-herpesvirus according to any of embodiments 1 to 47 for the manufacture of a vaccine.

Embodiment 57 Use according to embodiment 56, wherein the vaccine is for the treatment and/or prevention of beta-herpesvirus infection.

Embodiment 58 Use according to embodiment 57, wherein the vaccine is for the treatment and/or prevention of a disease or condition associated with beta-herpesvirus infection, preferably human cytomegalovirus infection.

Embodiment 59 Use according to any one of embodiments 56 to 58, wherein the vaccine is or is suitable for the administration to a subject, whereby the subject is selected form the group comprising a pregnant female, a female of reproductive age, a donor of a transplant, a recipient of a transplant and a subject being infected with HIV or being at risk of being infected with HIV.

Embodiment 60 Use according to embodiment 59, wherein the donor is a potential donor and/or the recipient is a potential recipient.

Embodiment 61 A nucleic acid coding for a beta-herpesvirus according to any of the preceding embodiments.

Embodiment 62 A vector comprising the nucleic acid according to embodiment 61.

Embodiment 63 A vector comprising the nucleic acid according to embodiment 62, wherein the vector comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 233681 of the nucleotide sequence according to SEQ.ID.NO:20 and wherein nucleotide 122630 of the nucleotide sequence according to SEQ.ID.NO:20 is covalently linked to nucleotide 123688 of the nucleotide sequence according to SEQ.ID.NO:20.

Embodiment 64 A vector comprising the nucleic acid according to embodiment 62, wherein the vector comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 233681 of the nucleotide sequence according to SEQ.ID.NO: 20 and a third nucleotide sequence comprising a nucleotide sequence according to SEQ.ID.No: 34.

Embodiment 65 The vector according to embodiment 64, wherein nucleotide 122630 of the nucleotide sequence according to SEQ.ID.NO:20 is covalently linked to nucleotide 1 of the nucleotide sequence according to SEQ.ID.No: 34 and wherein nucleotide 252 of the nucleotide sequence according to SEQ.ID.No: 34 is covalently linked to nucleotide 123668 of the nucleotide sequence according to SEQ.ID.NO: 20.

Embodiment 66 A vector comprising the nucleic acid according to embodiment 62, wherein the vector comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 130670 of the nucleotide sequence according to SEQ.ID.NO:20, a third nucleotide sequence represented by nucleotides 131243 to 233681 of the nucleotide sequence according to SEQ.ID.NO: 20 and wherein nucleotide 122630 of the nucleotide sequence according to SEQ.ID.NO:20 is covalently linked to nucleotide 123668 of the nucleotide sequence according to SEQ.ID.NO:20 and wherein the nucleotide 130670 of the nucleotide sequence according to SEQ.ID.NO:20 is covalently linked to the nucleotide 131243 of the nucleotide sequence according to SEQ.ID.NO:20.

Embodiment 67 A vector comprising the nucleic acid according to embodiment 62, wherein the vector comprises a nucleotide sequence, wherein the nucleotide sequence comprises a first nucleic acid sequence represented by nucleotides 1 to 122630 of the nucleotide sequence according to SEQ.ID.NO:20, a second nucleotide sequence represented by nucleotides 123668 to 130670 of the nucleotide sequence according to SEQ.ID.NO:20, a third nucleotide sequence represented by nucleotides 131243 to 233681 of the nucleotide sequence according to SEQ.ID.NO:20, a third nucleotide sequence comprising a nucleotide sequence according to SEQ.ID.No: 34 and a fourth nucleotide sequence comprising a nucleotide sequence according to SEQ.ID.No: 35

Embodiment 68 The vector according to embodiment 67, wherein nucleotide 122630 of the nucleotide sequence according to SEQ.ID.NO:20 is covalently linked to nucleotide 1 of the nucleotide sequence according to SEQ.ID.No: 34, wherein nucleotide 252 of the nucleotide sequence according to SEQ.ID.No: 34 is covalently linked to nucleotide 123668 of the nucleotide sequence according to SEQ.ID.NO:20, wherein nucleotide 130670 of the nucleotide sequence according to SEQ.ID.NO:20 is covalently linked to nucleotide 1 of the nucleotide sequence according to SEQ.ID.No: 35 and wherein nucleotide 67 of the nucleotide sequence according to SEQ.ID.NO:35 is covalently linked to nucleotide 131243 of the nucleotide sequence according to SEQ.ID.No:20

Embodiment 69 A vector comprising the nucleic acid according to embodiment 62, wherein the vector comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 233681 of the nucleotide sequence according to SEQ.ID.NO:20 and wherein nucleotide 58442 of the nucleotide sequence according to SEQ.ID.NO:20 is covalently linked to nucleotide 59623 of the nucleotide sequence according to SEQ.ID.NO:20.

Embodiment 70 A vector comprising the nucleic acid according to embodiment 62, wherein the vector comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 233681 of the nucleotide sequence according to SEQ.ID.NO: 20 and a third nucleotide sequence comprising a nucleotide sequence according to SEQ.ID.No: 32.

Embodiment 71 The vector according to embodiment 70, wherein nucleotide 58442 of the nucleotide sequence according to SEQ.ID.NO:20 is covalently linked to nucleotide 1 of the nucleotide sequence according to SEQ.ID.No: 32 and wherein nucleotide 179 of the nucleotide sequence according to SEQ.ID.No: 32 is covalently linked to nucleotide 59623 of the nucleotide sequence according to SEQ.ID.NO: 20.

Embodiment 72 A vector comprising the nucleic acid according to embodiment 62, wherein the vector comprises a nucleotide sequence, wherein the nucleotide sequence comprises a first nucleic acid sequence represented by nucleotides 1 to 62129 of the nucleotide sequence according to SEQ.ID.NO:20, a second nucleotide sequence represented by nucleotides 63261 to 233681 of the nucleotide sequence according to SEQ.ID.NO:20 and wherein nucleotide 62129 of the nucleotide sequence according to SEQ.ID.NO:20 is covalently linked to nucleotide 63261 of the nucleotide sequence according to SEQ.ID.NO:20.

Embodiment 73 A vector comprising the nucleic acid according to embodiment 62, wherein the vector comprises a nucleotide sequence, wherein the nucleotide sequence comprises a first nucleic acid sequence represented by nucleotides 1 to 62129 of the nucleotide sequence according to SEQ.ID.NO:20, a second nucleotide sequence represented by nucleotides 63261 to 233681 of the nucleotide sequence according to SEQ.ID.NO: 20 and a third nucleotide sequence comprising a nucleotide sequence according to SEQ.ID.No: 33

Embodiment 74 The vector according to embodiment 73, wherein nucleotide 62129 of the nucleotide sequence according to SEQ.ID.NO:20 is covalently linked to nucleotide 1 of the nucleotide sequence according to SEQ.ID.No: 33 and wherein nucleotide 38 of the nucleotide sequence according to SEQ.ID.No: 33 is covalently linked to nucleotide 63261 of the nucleotide sequence according to SEQ.ID.NO: 20.

Embodiment 75 A vector comprising the nucleic acid according to embodiment 62, wherein the vector comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 62129 of the nucleotide sequence according to SEQ.ID.NO:20, a third nucleotide sequence represented by nucleotides 63261 to 233681 of the nucleotide sequence according to SEQ.ID.NO: 20 and wherein nucleotide 58442 of the nucleotide sequence according to SEQ.ID.NO:20 is covalently linked to nucleotide 59623 of the nucleotide sequence according to SEQ.ID.NO:20 and wherein the nucleotide 62129 of the nucleotide sequence according to SEQ.ID.NO:20 is covalently linked to the nucleotide 63261 of the nucleotide sequence according to SEQ.ID.NO:20.

Embodiment 76 A vector comprising the nucleic acid according to embodiment 62, wherein the vector comprises a nucleotide sequence, wherein the nucleotide sequence comprises a first nucleic acid sequence represented by nucleotides 1 to 58442 of the nucleotide sequence according to SEQ.ID.NO:20, a second nucleotide sequence represented by nucleotides 59623 to 62129 of the nucleotide sequence according to SEQ.ID.NO:20, a third nucleotide sequence represented by nucleotides 63261 to 233681 of the nucleotide sequence according to SEQ.ID.NO:20, a fourth nucleotide sequence comprising a nucleotide sequence according to SEQ.ID.No: 32 and a fifth nucleotide sequence comprising a nucleotide sequence according to SEQ.ID.No: 33.

Embodiment 77 The vector according to embodiment 76, wherein nucleotide 58442 of the nucleotide sequence according to SEQ.ID.NO:20 is covalently linked to nucleotide 1 of the nucleotide sequence according to SEQ.ID.No: 32, wherein nucleotide 179 of the nucleotide sequence according to SEQ.ID.No: 32 is covalently linked to nucleotide 59623 of the nucleotide sequence according to SEQ.ID.NO:20, wherein nucleotide 62129 of the nucleotide sequence according to SEQ.ID.NO:20 is covalently linked to nucleotide 1 of the nucleotide sequence according to SEQ.ID.No: 33 and wherein nucleotide 38 of the nucleotide sequence according to SEQ.ID.NO:33 is covalently linked to nucleotide 632161 of the nucleotide sequence according to SEQ.ID.No: 20.

Embodiment 78 A host cell comprising a nucleic acid according to embodiment 61 or a vector according to any one of embodiments 62 to 77.

Embodiment 79 A pharmaceutical composition comprising a beta-herpesvirus according to any one of the preceding embodiments, a nucleic acid according to embodiment 61 and/or a vector according to any one of the preceding embodiments, and a pharmaceutically acceptable carrier.

The present inventors have surprisingly found that the infection of endothelial cells of a host organism such as man by beta-herpesvirus and more specifically CMV of the invention will result in eliciting an immune response against CMV. More specifically, the immune response is an anti-CMV response which comprises neutralizing antibodies against beta-herpesvirus and $CD4^+$ and $CD8^+$ T-cells directed against epitopes of beta-herpesvirus. Furthermore, the present inventors have surprisingly found that such immune response can be elicited by the beta-herpesvirus and more specifically the human cytomegalovirus of the invention being spread-deficient. It has to be acknowledged that any characteristic feature, embodiment of and any statement made in relation to beta-herpesviruses such as murine CMV equally applies to human CMV. Furthermore, it will be acknowledged that the beta-herpesvirus according to the present invention will, in a preferred embodiment, exhibit the following characteristics as observed for human and murine, respectively, CMV: multiple infections occur with mouse and human CMV, in mouse and human, respectively, (Boppana, S. B. et al., 2001. Intrauterine transmission of cytomegalovirus to infants of women with preconceptional immunity. N. Engl. J. Med 344:1366-1371; Cicin-Sain, L. et al., 2005. Frequent coinfection of cells explains functional in vivo complementation between cytomegalovirus variants in the multiply infected host. J Virol 79:9492-9502.); an unusually high response of neutralizing antibodies against CMV is caused by infection with mouse and human CMV, in mouse and human, respectively (Farrell, H. E. and G. R. Shellam, 1990. Characterization of neutralizing monoclonal antibodies to murine cytomegalovirus. J. Gen. Virol. 71 (Pt 3):655-664; Farrell, H. E. and G. R. Shellam, 1991. Protection against murine cytomegalovirus infection by passive transfer of neutralizing and non-neutralizing monoclonal antibodies. J. Gen. Virol. 72 (Pt 1):149-156; Gerna, G., A. et al., 2008. Human cytomegalovirus serum neutralizing antibodies block virus infection of endothelial/epithelial cells, but not fibroblasts, early during primary infection. J. Gen. Virol. 89:853-865); memory inflation, which represents a very characteristic CD8+ T cell response, is caused by infection with mouse and human CMV, in mouse and human, respectively, and has almost identical kinetics (Karrer, U. et al., 2003. Memory inflation: continuous accumulation of antiviral CD8+ T cells over time. J. Immunol. 170:2022-2029; Karrer, U. et al. 2004. Expansion of protective CD8+ T-cell responses driven by recombinant cytomegaloviruses. J. Virol. 78:2255-2264; Klenerman, P. and P. R. Dunbar, 2008. CMV and the art of memory maintenance. Immunity. 29:520-522; Komatsu, H. et al., 2003. Population analysis of antiviral T cell responses using MHC class I-peptide tetramers. Clin. Exp. Immunol. 134:9-12;). In connection with the present invention a person skilled in the art will also acknowledge that a murine CMV gene can replace a homolog of said murine CMV gene in a human CMV. (Schnee, M. et al., 2006. Common and specific properties of herpesvirus UL34/UL31 protein family members revealed by protein complementation assay. J Virol 80:11658-11666)

In a preferred embodiment the beta-herpesvirus according to the present invention is different from the Towne strain as described by Liu et al. in U.S. Pat. No. 7,407,744, i.e. a Towne strain where the genes UL133, UL134, UL135, UL136, UL137, UL138, UL139, UL140, UL141, UL142, UL143, UL144, and UL145 are deleted, preferably compared to wild type. A person skilled in the art will further acknowledge that the Towne strain is not endotheliotropic and has also a defective gH/gL complex.

In a further preferred embodiment the beta-herpesvirus according to the present invention comprises a nucleotide sequence according to SEQ.ID.No:23.

In still further preferred embodiment the beta-herpesvirus according to the present invention is different form the Toledo strain.

Spread-deficient as used herein, preferably means that the virus which is spread-deficient infects a cell and no viral particle is released from the infected cell, whereby the viral DNA is replicated, the viral proteins except those which are deleted in accordance with the present invention are expressed in the infected cell, preferably all viral glycoproteins are expressed, more preferably all viral glycoproteins are expressed, that mediate entry of the virus into a cell, whereby, preferably, the cell is an endothelial and/or an epithelial cell. The assay which is preferably used in accordance with the present invention so as to determine whether or not a virus is spread-deficient, is described herein as Example 1.

A wild type CMV strain as preferably used herein means that the virus is a beta-herpesvirus strain which has been isolated from its native host and which has maintained its ability to infect endothelial cells in tissue culture. More specifically the wild type human CMV strain as preferably used herein contains, among others, the genes UL133, UL134, UL135, UL136, UL137, UL138, UL139, UL140, UL141, UL142, UL143, UL144, and UL145 (Cha et al. supra) and more specifically the wild type CMV strain as preferably used herein is TB40/E and FIX-BAC (Sinzger et al. 1999 Journal of General Virology, 80, 2867-2877; Hahn et al. 2002 J. Virol. 76(18): 9551-9555) and/or TB40E-BAC4-FRT (SEQ.ID.NO:20) (Scrivano, L. et al., 2011. HCMV spread and cell tropism are determined by distinct virus populations. PLoS. Pathog. 7:e1001256) for human CMV or Smith strain for MCMV (Rawlinson et al. 1996 J Virol 70:8833-8849). In a preferred embodiment of the present invention the wild type CMV strain as preferably used herein comprises a nucleotide sequence according to SEQ.ID.No:23. The sequence of the pTB40E-BAC4-FRT, which is the molecular infectious BAC plasmid according to TB40E-BAC4-FRT has the nucleotide sequence according to SEQ.ID.NO:20.

Said pTB40E-BAC4-FRT is consisting of viral sequences encoded by nt 1-181652 and by nt 189192-233681, as well as BAC sequences represented by nt 181653-189191. A person skilled in the art will acknowledge that a BAC plasmid such as pTB40E-BAC4-FRT comprising a virus genome such as the virus genome of TB40E-BAC4-FRT is circular in *E. coli* therefore the nucleotide 233681 of the nucleotide sequence according to SEQ.ID.NO:20 is covalently linked to nucleotide 1 of the nucleotide sequence according to SEQ.ID.NO: 20. A person skilled in the art will know methods for reconstitute a virus from a BAC plasmid comprising the viral genome of said virus, for example for reconstitute TB40E-BAC4-FRT from pTB40E-BAC4-FRT comprising the viral genome of TB40E-BAC4-FRT. Such methods comprise among others transfection of cells, comprising complementing cells.

As used herein, the term "deficient in at least one gene product" preferably means that the at least one gene product which is a biochemical material such as a nucleic acid, DNA, RNA or a peptide, polypeptide or protein, resulting from expression of the gene does not show at least one of the functions displayed by said gene product in the wild type strain. Preferably, said at least one of the functions not shown is the function which is responsible for spread of the betaherpesvirus. Also preferably, all of the functions of said gene product in the wild type strain are not shown. This may be the result of a complete or partial deletion or mutation of the gene coding for said gene product, of a complete or partial deletion of a mutation, of the nucleic acid controlling the expression of the gene coding of said gene product, of a truncation of said gene product, or of the inhibition of the otherwise compete gene product.

As used herein, the term "DNA is replicated" preferably means that the replication occurs like replication of a wild type virus.

As used herein, a wild type-like virion surface is preferably a surface displayed by a beta-herpesvirus of the wild type as defined herein, more specifically by a cytomegalovirus wild type strain as defined herein. The molecules which are used to define the surface displayed by a beta-herpesvirus of the wild type are glycoproteins expressed by said wild type virus mediating the entry of said wild type virus into a cell, preferably an endothelial cell. In other words, a virus according to the present invention having a wild type-like virion surface has a virion surface which, after infection of primary fibroblasts, displays or expresses the same glycoproteins identical to, essentially identical to or at least not significantly different from the wild type virus based on which the deletions were or may be made to generate the virus of the present invention. The determination of the expression of glycoproteins is known to the ones skilled in the art and may be performed by a quantitative RT-PCR or mass spectrometry (Britt et al. 1990. J Virol 64:1079-1085) although other methods suitable for such purpose are knoen to the person skilled in the art.

So as to determine whether the beta-herpesvirus of the invention and particularly the human cytomegalovirus of the invention is endotheliotropic, preferably, the assay as described in Example 2 is used.

So as to determine whether the immune response elicited by the beta-herpesvirus of the invention and particularly the human cytomegalovirus of the invention comprises at least neutralizing antibody, and whereby the at least neutralizing antibody is preventing said viruses from infecting endothelial cells and/or epithelial cells, the assay described by Cui et al. (Cui et al. supra) may preferably be used.

It will be acknowledged that viral DNA replication is abrogated in replication-defective virus mutants and therefore gene expression does not exploit the total set of viral epitopes. Especially glycoproteins and structural virion components are not expressed.

In order to further illustrate the present invention the biology of human cytomegalovirus will be outlined in the following.

Human cytomegalovirus is one of eight human herpesviruses, which are clustered in three subfamilies (alpha (α), beta (β), gamma (γ)) based on biological properties and molecular phylogenetic relationships to other herpesviruses. Cytomegalovirus belongs to the beta-herpesvirus subfamily and possesses the largest genome in the herpesvirus families: its genome of 240 kbp is capable of encoding more than 200 potential gene products (Murphy et al. supra).

The viral particle of cytomegaloviruses consist of three major constituents, namely the internal icosahedral capsid, which packages the double stranded linear DNA genome; the tegument which is a less organized protein meshwork surrounding the capsid; and the outermost envelop which is a lipid bilayer embedded with viral glycoprotein complexes.

The infection of a host cell by the virus particles is mediated by the contact of the viral glycoproteins with the molecular structures of the host cell surface. CMVs can infect many different cell types and the mechanism of virus entry is known to be dependent on the specific cell type and can occur via two major routes: (a) the free, i.e. non-cell associated virus particles can encounter the host cell directly, or (b) the virus is transferred from the infected cell to a non-infected one by a preformed, i.e. non-virus-induced cell-cell contact, or virus induced cell-cell contact, the so called cell to cell spread.

After attachment with high affinity to a set of cellular receptors the viral glycoproteins induce fusion between the viral envelope and a host cell membrane. After entry of an CMV particle into the host cell the HCMV genome is targeted to the nucleus where it either establishes latency which is characterized by a symptomless maintenance of the more or less silent genome, or induces a lytic infection leading to propagation of new infectious CMV particles.

The lytic replication cycle of CMV is divided into three phases of regulated gene expression: immediate early, early, and late. The hallmarks of the replication stages are the specific gene clusters which are expressed with characteristic kinetics. Immediate early gene transcription occurs at first and leads to synthesis of viral master regulators that reprogram the host cell according to the needs of virus production. Following the synthesis of immediate early gene products, the early genes are transcribed. Early gene products include DNA replication proteins and regulators and enzymes which are important in nucleotide metabolism. Finally, the late genes are transcribed after the onset of DNA replication, and the gene products of said late genes are mainly structural proteins that are involved in the assembly of and egress of new infectious virus particles.

The late gene products comprise many viral antigens including the viral glycoproteins such as the gB and the gH/gL complex, which are the major targets of neutralizing antibodies against CMV (Schleiss et al. 2008 supra) and the major tegument protein the phosphoprotein 65 (pp65) and the immediate early 1 protein which are the major targets of the cellular immune response to CMV.

A further step in the lytic replication cycle of CMV is the maturation of novel infectious virus particles which comprises steps of envelopment of the pre-mature virus particle with membrane structures. The steps of envelopment comprise a primary envelopment, de-envelopment and secondary envelopment.

The primary envelopment at the membranes of the nucleus is crucial for the egress of virus capsids out of the nucleus. Proteins as part of the protein complex which is also referred to as nuclear egress complex (NEC) playing an essential role in this primary envelopment, were recently identified as M50 and M53 of mouse CMV (Lotzerich et al. 2006 J Virol 80:73-84.) or as UL50 and UL53 being their homologs in human CMV.

A homologues gene as used herein is preferably the gene of one herpesvirus referred to be a homolog of the gene of another herpesvirus according to Fossum et al. (Fossum et al. PLoS Pathog. 2009 September; 5(9): e1000570) or Davison et al. (Davison et al. (2010) Vet Microbiol. 2010 Feb. 11. Herpesvirus systematics; and Davison et al. 2004 Compendium of Human Herpesvirus gene names; Reno).

Further, homologs of UL50 are listed in Mocarski (Mocarski Jr. ES.: Comparative analysis of herpesvirus-common proteins. In Human Herpesviruses: Biology, Therapy, and Immunoprophylaxis. Cambridge: Cambridge University Press; 2007. Chapter 4 Editors: Arvin A, Campadelli-Fiume G, Mocarski E, Moore PS, Roizman B, Whitley R, Yamanushi K, editors.)

The secondary envelopment occurs at the membranes of the Golgi-apparatus and/or the endoplasmatic reticulum. In connection with said secondary envelopment a protein complex which is also referred to as secondary envelopment complex (SEC), was identified comprising at least the gene product of M94 of mouse CMV or its homolog in human CMV, i.e. UL94. The gene UL94 of HCMV is conserved in all herpesvirus sub-families (Chee et al. 1991 Transplant Proc 23:174-80; Chee et al. 1990 Curr Top Microbiol Immunol 154:125-169; Higgins et al. 1989 Comput. Appl. Biosci. 5:151-153) and was found only at a late stage of infection (Scott et al. 2002 Virus Genes 24:39-48; Wing et al. 1996 J Virol 70:3339-3345). It was recently shown that UL94 is part of the virion (Kalejta et al. 2008 Microbiol Mol Biol Rev 72:249-65; Kattenhorn et al. 2004 J Virol 78:11187-11197; Wing et al. op.cit). UL94 is essential in the infection of the Towne strain of HCMV shown by transposon-mediated mutagenesis (Dunn et al. 2003 Proc Natl Acad Sci USA 100:14223-14228. That M94 is essential in mouse CMV infection is disclosed herein in the example part.

Homologs of UL94 are listed in the Mocarski (Mocarski Jr. ES.: Comparative analysis of herpesvirus-common proteins. In Human Herpesviruses: Biology, Therapy, and Immunoprophylaxis. Cambridge: Cambridge University Press; 2007. Chapter 4 Editors: Arvin A, Campadelli-Fiume G, Mocarski E, Moore PS, Roizman B, Whitley R, Yamanishi K, editors.)

The high viral load of CMV in salivary glands indicates the transmission of CMV by direct contact via secretions. After initial replication in the first target cells at the entry site, CMV is disseminated through the body by blood and lymph. Most likely the virus is taken up by white blood cells which carry the virus from the primary infection site to almost every internal organ.

The interplay between the CMV and its host, i.e. humans or mice, is very complex. On the one hand, the immune response of the host is controlling the virus replication very efficiently. Therefore, most of the CMV infections are symptomless which means that virus replication is controlled before the tissue damage reaches an observable pathological level of local or systemic inflammation. On the other hand, the virus itself is controlling the immune response resulting in efficient clearance of the virus from the host. In almost all cases of immune competence natural CMV infection ends up with a situation where the virus is controlled by the immune system without being totally cleared from the host (Reddehase et al. 2002 J Clin Virol 25 Suppl 2:S23-S36).

In recent years an impressive body of knowledge was generated by studying the molecular mechanisms of immune suppressive functions of CMV. It is acknowledged that more than half of the CMV genes encode gene products interfering with different immune mechanisms at all stages of the immune system, the so-called immune evasive genes. There is evidence that neither the humoral nor the cellular immune response alone is sufficient to control CMV infection; a concerted action of both is needed to keep the balance with the viral immune evasion (Adler et al. 1995 J Infect Dis 171:26-32; Reddehase et al. 1987 J Virol 61:3102-3108).

Diseases and conditions of a subject which is infected by beta-herpesvirus and human CMV, respectively, are, among others, mononucleosis-like symptoms, splenomegaly, pneumonitis, blindness, hearing loss, congenital inclusion disease, and organ damage and organ failure, respectively, of the organ infected by HCMV. It is to be acknowledged that said diseases and conditions are diseases and conditions which can be treated and/or prevented by the beta-herpesvirus of the present invention.

Typically, human CMV infection becomes clinically apparent only if the host immune system is vulnerable or suppressed. There are several major risk groups of public health importance.

One situation where the host immune system is vulnerable, is where non-pregnant women of reproductive age or women being pregnant get infected by human CMV. If the human CMV infection is transmitted from the mother to the fetus and embryo, respectively, during pregnancy, due to the immature immune system of the fetus and embryo, respectively, direct cytotoxic pathology of the human CMV infection can develop which is called congenital inclusion disease (CID). The symptoms of CID are dominated by the cause that the human CMV infects the central nervous system comprising microcephaly, cerebral atrophy, chorioretinitis, and sensorineural hearing loss, which are typically combined with consequences of infection of other visceral organs including intrauterine growth retardation, hepatosplenomegaly, hematological abnormalities such as thrombocytopenia, and various cutaneous manifestations appearing as rushes, i.e. petechiae and purpura. CID is the most frequent infectious congenital disorder in developed countries. Furthermore, human CMV infection is the major cause of hearing loss acquired after viral infection.

A second scenario of clinically significant human CMV infection is formed by immunocompromised or immunosuppressed patients. This kind of patient is, e.g., a HIV-positive patient or a transplant recipient. In these patients the disease manifestations vary depending on the quality and the degree of immune dysfunction. Infection mostly occurs because of reactivation of latent viral infection, however, may be as well newly acquired via virus reactivation from organ or bone marrow transplant derived from an already infected donor in case of a transplant recipient.

In the absence of sufficient immune control CMV infection leads to inflammatory diseases of various organs. In connection therewith the most frequent clinical manifestations consist of pneumonitis, gastrointestinal diseases, hepatitis, and retinitis. In bone marrow transplant recipients HCMV pneumonitis occurs with mortality rates of 90%. It is to be acknowledged that said diseases and conditions are diseases and conditions which can be treated and/or prevented by the beta-herpesvirus of the present invention.

In AIDS patients opportunistic human CMV infection is common and occurs at a frequency of almost 100%, if anti-retroviral therapy fails or not applicable/available. This is still the case in non-industrialized countries were an effective therapy is not yet available. Before the availability of highly active anti-retroviral therapy for human immunodeficiency virus (HIV) infection, HCMV retinitis was the most common cause of blindness in adult patients with acquired immunodeficiency syndrome (AIDS), with an overall lifetime prevalence of more than 90%.

In an embodiment of the beta-herpesvirus of the invention the beta-herpesvirus is used as a vaccine and/or vector. In a further embodiment thereof such beta-herpesvirus encodes for a heterologous nucleic acid. Preferably such heterologous nucleic acid codes for an antigen, more preferably an antigen of a pathogen. Because of this such vaccine and vector, respectively, is suitable for the treatment and/or prevention of a disease caused by or associated with said pathogen. Such pathogens preferably comprise viruses and bacteria. In an embodiment the antigen is NP-NT60 of Influenza, whereby the vector then is useful in the treatment of influenza. In a further embodiment the antigen is ORF Rv3407 from *Mycobacterium tuberculosis* strain H37Rv, whereby the vector then is useful in the treatment of tuberculosis.

In an embodiment the beta-herpesvirus of the present invention is a recombinant beta-herpesvirus.

In a further embodiment the beta-herpesevirus of the present invention is a human beta-herpesvirus, preferably a recombinant human beta-herpesvirus.

In a preferred embodiment the individual nucleotides of the beta-herpesvirus of the invention are linked, preferably covalently linked, through phosphodiester bonds. Such phosphodiester bonds are those phosphodiester bonds which are contained in nucleic acid molecules contained or produced in biological material such as cells.

It will be acknowledged that the beta-herpesvirus of the present invention is part of a pharmaceutical composition. Preferably, such pharmaceutical composition contains, a part from the beta-herpesvirus of the present invention and/or a nucleic acid coding for the same, a pharmaceutically acceptable carrier. The ingredients of such pharmaceutical composition and their respective contents are known to a person skilled in the art. It will be further acknowledged that such pharmaceutical composition is for or is for use in the treatment of the diseases and conditions as disclosed herein in connection with the beta-herpesvirus of the present invention.

It will be acknowledged by a person skilled in the art that the experimental evidence provided in the example part of the instant application is based on murine CMV, but that such evidence can be directly and immediately transferred to HCMV, so that the present invention is plausible to a person skilled in the art. The reason for this being that the genomes of different herpesvirus strains including CMV are linearly correlated and the mode of action of human CMV in a human host and of mouse CMV in a murine host are essentially identical.

The various SEQ.ID. Nos., the chemical nature of the nucleic acid molecules, proteins and peptides according to the present invention, the actual sequence thereof and the internal reference number is summarized in the following table. To the extent that the particular sequences are not displayed in this table they are contained in the attached sequence listing which is part of the instant specification.

| SEQ. ID. No. | Sequence | internal reference number |
|---|---|---|
| 1 | GTGGGATCCACCATGTACCCCTACGACGT GCCCGACTACGCCACGTCCAGACTATCC | HAM94for |
| 2 | ACTCTAGAGTCGACTTCACATGTGCTCGA GAACA | M94rev |
| 3 | AATTCATGATAACTTCGTATAGCATACAT TATACGAAGTTATCCGGAGATATCCACCG GTCTGGCGGCCGC | ATGlox1 |
| 4 | TCGAGCGGCCGCCAGACCGGTGGATATCT CCGGATAACTTCGTATAATGTATGCTATA CGAAGTTATCATG | ATGlox2 |
| 5 | CGT GGT CAA GCC GGT CGT GTT GTA CCA GAA CTC GAC TTC GGT CGC GTT GCT TAC AAT TTA CGC GCG GG | 5'-Δm157-pCR3-FRT-Kan$^r$-FRT |
| 6 | CCC CGA TAT TTG AGA AAG TGT ACC CCG ATA TTC AGT ACC TCT TGA CTA AGA AGC CAT AGA GCC CAC CGC | 3'-Δm157-flox-egfp |
| 7 | TGC TTC CCG GCG GCT TCT GCG CGA CCT TCC AGC TGC AGG TAG ACC ACG GCG ACG TCC AGA CTA TCC GTG AAA AGT TTG AGA AGC ATC AGT AGC CGA TTT CGG CCT ATT GGT T | 5'ΔM94-pO6-tTA |
| 8 | CAT GGA TGG GTT GGT TGA TTT GTA TGT CTG TTG GCT ACT CAC ATG TGC TCG AGA AGC CAG TGT GAT GGA TGA TCC TC | 3'-ΔM94-pO6-tTA |
| 9 | SIINFEKL | OVA-MHC-I Peptide |
| 10 | TVYGFCLL | m139 MHC-I Peptide |
| 11 | RALEYKNL | ie3 MHC-I Peptide |
| 12 | SCLEFWQRV | M57 MHC-I Peptide |
| 13 | HGIRNASFI | M45 MHC-I Peptide |
| 14 | FAM-AACGTACATCGCTCTCTGCTGGCCG-TAMRA | Taqman-Probe M54 |
| 15 | Ttactgggtgctgccgggcggctttgccgtctcttcgcgcgtcactct tcacggcctggcccagcgagccctgcgggaccggttccaaaacttc gaggccgtgctggcccggggcatgcacgtggaggccggccggca ggagcccgagaccccccgggtgagcggccggcggctgcccttcg acgacctgtgatccggaggacgacggctcgtgtatcttgtgccaatt gctgttgctctaccgcgacggcgaatggatcctctgtctttgctgcaa cggccgttatcaaggccactatggcggggtctgacagttcacgggg agaagaaacaagaaacaacaaaaaaaaaagaggagatctgcggc cgctagggataacagggtaatcgatgttgacaattaatcatcggcata | LIFdelUL94 |

-continued

| SEQ. ID. No. | Sequence | internal reference number |
|---|---|---|
| | gtatatcggcatagtataatacgacaaggtgaggaactaaaccatgg caaaaactgaccagcgcagttccggttctgaccgcacgtgatgttgcc ggtgccgttgaattttggaccgatcgtctgggttttagccgtgattttgt ggaagatgattttgccggtgttgttcgtgatgatgttaccctgtttattag cgcagttcaggatcaggttgttccggataatacccttggcatgggtttg ggttcgtggtctggataactgtatgcagaatggtcagaagttgtgag caccaattttcgtgatgcaagcggtccggcaatgaccgaaattggtg aacagccgtggggtcgtgaatttgcactgcgtgatccggcaggtaat tgtgttcattttgttgcagaagaacaggattaacctcgattaattaattgt aacattaccctgttatccctaccggtgtcctaggcggggtctgacagt tcacggggagaagaaacaagaaacaacaaaaaaaaaagagg | |
| 16 | cgtgttagaccgttggagtcgcgacctgtcccgcaagacgaaccta ccgatctgggtcgccaacagcgccaacgagtacgtcgtcagctccg tgccccgccccgtcagtccgtagaagtaactcataaactttcaggtct cgcgtacgattcgcgagtcgggaatgtagggataacagggtaatcg atgttgacaattaatcatcggcatagtatatcggcatagtataatacga caaggtgaggaactaaaccatggcaaaactgaccagcgcagttcc ggttctgaccgcacgtgatgttgccggtgccgttgaattttggaccga tcgtctgggttttagccgtgattttgtggaagatgattttgccggtgttgt tcgtgatgatgttaccctgtttattagcgcagttcaggatcaggttgttc cggataatacccttggcatgggtttgggttcgtggtctggataactgt atgcagaatggtcagaagttgtgagcaccaattttcgtgatgcaagc ggtccggcaatgaccgaaattggtgaacagccgtggggtcgtgaat ttgcactgcgtgatccggcaggtaattgtgttcattttgttgcagaaga acaggattaacctcgattaattaattgtaacattaccctgttatccctaa agtaactcataaactttcaggtctcgcgtacgattcgcgagtcgggaa tg | LIF-delUL99 |
| 17 | as contained in the sequence listing | pCB-Ubic-UL94-IRES-mChe |
| 18 | as contained in the sequence listing | pCB-Ubic-UL99-IRES-gfp |
| 19 | as contained in the sequence listing | pLV-Ubiqc-BLAs-IRES-Puro |
| 20 | as contained in the sequence listing | pTB40E-BAC4-FRT |
| 21 | as contained in the sequence listing | pBSK-OVA |
| 22 | as contained in the sequence listing | pTRE-HAM94 |
| 23 | as contained in the sequence listing | Unique\in\TB40\(UL133-UL145) |
| 24 | MGSGIGAASMEFCFDVFKELKVHHANENIFYCPIAIMSAL AMVYLGAKDSTRTQINKVVRFDKLPGFGDSIEAQCGTSVN VHSSLRDILNQITKPNDVYSFSLASRLYAEERYPILPEYL QCVKELYRGGLEPINFQTAADQARELINSWVESQTNGIIR NVLQPSSVDSQTAMVLVNAIVFKGLWEKTFKDEDTQAMPF RVTEQESKPVQMMYQIGLFRVASMASEKMKILELPFASGT MSMLVLLPDEVSGLEQLESIINFEKLTEWTSSNVMEERKI KVYLPRMKMEEKYNLTSVLMAMGITDVFSSSANLSGISSA ESLKISQAVHAAHAEINEAGREVVGSAEAGVDAASVSEEF RADHPFLFCIKHIATNAVLFFGRCVSP | OVA |
| 25 | MSGQGTKRSYEQMETDGERQNATEIRASVGKMIGGIGRFY IQMCTELKLSDYEGRLIQNSLTIERMVLSAFDERRNKYLE EHPSAGKDPKKTGGPIYRRVNGKWMRELILYDKEEIRRIW RQTNNGDDATAGLTHMMIWHSNLNDATYQRTRALVRTGMD PRMCSLMQGSTLPRRSGAAGAAVKGVGTMVMELVRMIKRG INDRNFWRGENGRKTRIAYERMCNILKGKFQTAAQKAMMD QVRESRNPGNAEFEDLTFLARSALILRGSVAHKSCLPACV YGPAVASGYDFEREGYSLVGIDPFRLLQNSQVYSLIRPNE NPAHKSQLVWMACHSAAFEDLRVLSFIKGTKVLPRGKLST RGVQIASNENMDAMESSTLELRSRYWAIRTRSGGNTNQQR ASAGQISIQPTFSVQRNLPFDRTTIMAAFNGNTEGRTSDM RTEIIRMMESARPEDVSFQGRGVFELSDEKAASPIVPSFD MSNEGSYFFGDNAEEYDN | NP-NT60 of Influenza |
| 26 | MRATVGLVEAIGIRELRQHASRYLARVEAGEELGVTNKGR LVARLIPVQAAERSREALIESGVLIPARRPQNLLDVTAEP ARGRKRTLSDVLNEMRDEQ | ORF Rv3407 from *Mycobacterium tuberculosis* strain H37Rv |
| 27 | MAWRSGLCETDSRTLKQFLQEECMWKLVGKSRKHREYRAV ACRSTIFSPEDDGSCILCQLLLLYRDGEWILCLCCNGRYQ GHYGVGHVHRRRRRICHLPTLYQLSFGGPLGPASIDFLPS FSQVTSSMTCDGITPDVIYEVCMLVPQDEAKRILVKGHGA | UL94 |

-continued

| SEQ. ID. No. | Sequence | internal reference number |
|---|---|---|
| | MDLTCQKA<u>VTLGGAGAWLLP</u>RPEGYTLFFYILCYDLFTSC GNRCDIPSMTRLMAAATACGQAGCSFCTDHEGHVDPTGNY VGCTPDMGRCLCYVPCGPMTQSLIHNDEPATFFCESDDAK YLCAVGSKTAAQVTLGDGLDYHIGVKDSEGRWLPVKTDVW DLVKVEEPVSRMIVCSCPVLKNLVH | |
| 28 | VTLGGAGAWLLP | SSc cross-reactive UL94 peptide |
| 29 | MGGELCKRICCEFGTTSGEPLKDALGRQVSLRSYDNIPPT SSSDEGEDDDDGEDDDNEERQQKLRLCGSGCGGNDSSSGS HREATHDGPKKNAVRSTFREDKAPKPSKQSKKKKKPSKHH HHQQSSIMQETDDLDEEDTSIYLSPPPVPPVQVVAKRLPR PDTPRTPRQKKISQRPPTPGTKKPAAPLSF | UL99 |
| 30 | MATSRLSVKSLRSISRFVQWECCWMLVNKSARYREFRAVT SQSPGLGKVSSTDDGRCLAASMMLFRRDGNFVLCLVVNKE PVGQFGCSGMRREKMVIDGLQEPVYVMRLLAPLIPVKLGF SPYMLPPKSIGGSGGLDPSVIYQNASVVTPEEAATVTMQG SGIVTVGLSGVGSWVQIKDGGNMKLFVFALCFDVFTACCD RLAFPSLAKIYSETVSCEADKCGFCRDSGRHVDPTGRFVG CVPDSGVCLCYSPCRGTDAAVSVRSWLPYLELEDGANTHS LFVRRYDGRKGLPATISDYLGARNSEGDEIPLRTEPWQLL KIEPTLSAMIIMACPLLKKIVLEHM | M94 |
| 31 | MYPYDVPDYATSRLSVKSLRSISRFVQWECCWMLVNKSAR YREFRAVTSQSPGLGKVSSTDDGRCLAASMMLFRRDGNFV LCLVVNKEPVGQFGCSGMRREKMVIDGLQEPVYVMRLLAP LIPVKLGFSPYMLPPKSIGGSGGLDPSVIYQNASVVTPEE AATVTMQGSGIVTVGLSGVGSWVQIKDGGNMKLFVFALCF DVFTACCDRLAFPSLAKIYSETVSCEADKCGFCRDSGRHV DPTGRFVGCVPDSGVCLCYSPCRGTDAAVSVRSWLPYLEL EDGANTHSLFVRRYDGRKGLPATISDYLGARNSEGDEIPL RTEPWQLLKIEPTLSAMIIMACPLLKKIVLEHM | HA-M94 |
| 32 | gaccgcgccacagcagagccagcaccagcagaagagccagcac cagcgggcccagagtcgcaaagcgcgcgggcagccacggccca gactgcggtcgcgatggcccggagcgcgctcgccaccacgatgac ggtgcccaacgataaccagtccgctcccgcaccgacgccaccgcc gat | delUL50S |
| 33 | atgtctagcgttttctcaacagcattcgtgcgccttga | delUL53S |
| 34 | cacggcctggcccagcgagccctgcgggaccggttccaaaacttc gaggccgtgctggcccggggcatgcacgtggaggccggccggca ggagcccgagaccccccgggtgagcggccggcggctgcccttcg acgacctgtgatccggaggacgacggctcgtgtatcttgtgccaatt gctgttgctctaccgcgacggcgaatggatcctctgtctttgctgcaa cggccgttatcaaggccactatgg | delUL94S |
| 35 | ctgggtcgccaacagcgccaacgagtacgtcgtcagctccgtgccc cgccccgtcagtccgtagaag | delUL99S |

It will be acknowledged by a person skilled in the art and is in so far also within the scope of the present invention that each and any of the above nucleic acid sequences can be replaced by nucleic acid sequences which, due to the degeneracy of the genetic code, code for the same or functionally homolog peptides and proteins, respectively, as the above indicated nucleic acid sequences.

The present invention is now further illustrated by the following figures and examples from which further features, embodiments and advantages may be taken.

More specifically,

Figure 8:
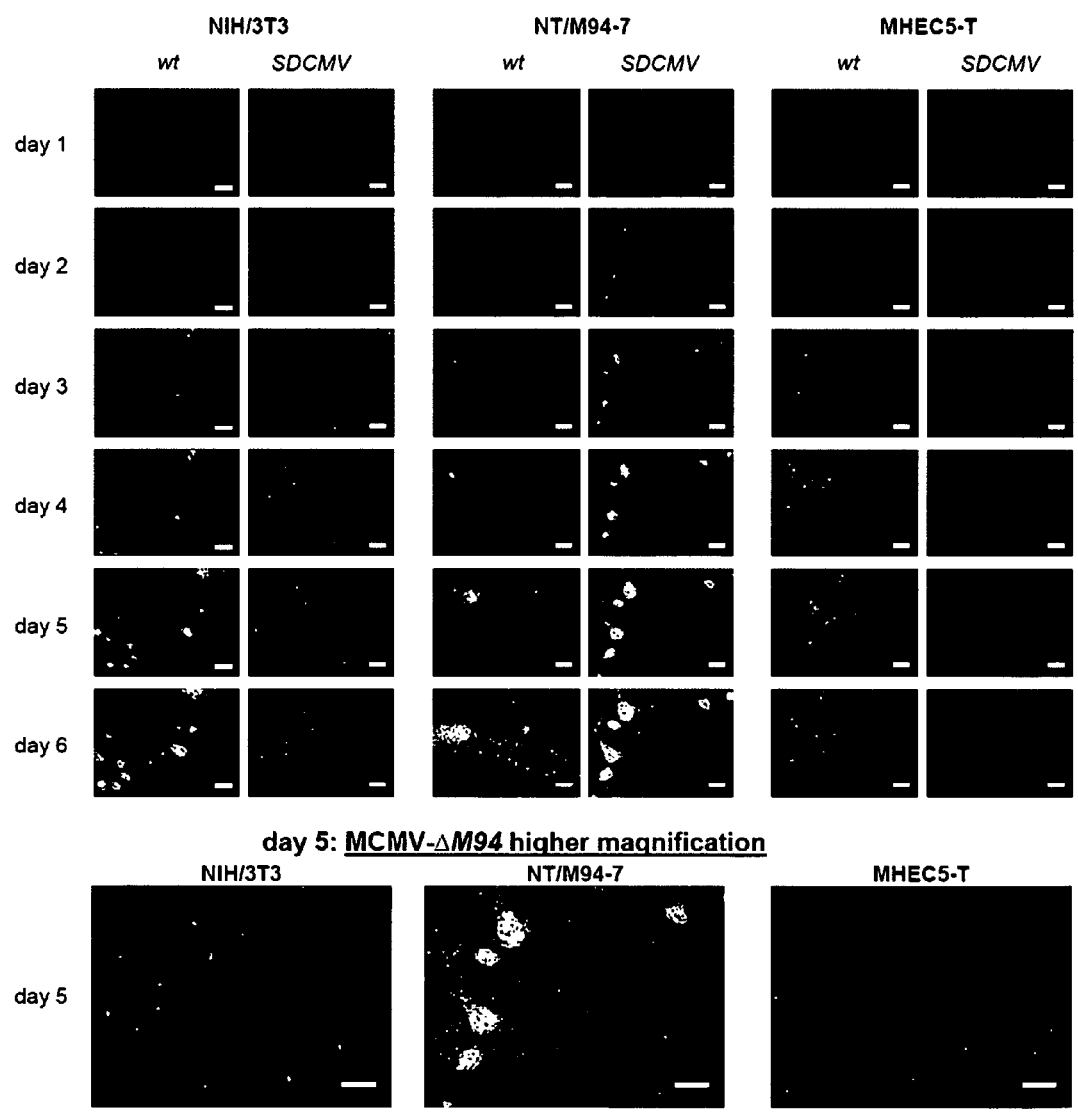

FIGS. 7C and D are diagrams indicating the challenge virus load in different organs of vaccinated mice;

FIG. 8 is a series of microphotographs of cells of different cell-lines infected with and MCMV-Δm157-rec-egfp-ΔM94.

FIG. 9A is a schematic overview of a spread-assay

FIG. 9B is a series of microphotographs

FIG. 9C is a diagram showing the results of a spread-assay

EXAMPLE 1

Spread Assay

The spread assay described herein may be used in connection with the characterization of a beta-herpesvirus and a human cytomegalovirus so as to determine whether such virus is spread-deficient.

Primary fibroblast cell lines MRCS for human CMV and NIH/3T3 for mouse CMV and complementing cell lines TCL94/99-BP and NTM94-7, respectively, are plated and infected at an MOI of about 0.25 for 1 h and then washed twice with D-PBS. Cells are incubated for 6 h and afterwards washed four times with D-PBS. Equal numbers of non-infected cells were stained with 5 µM CFSE for 8 min and blocked by 2% FCS/D-PBS, then washed twice with 2% FCS/D-PBS and subsequently seeded on top of the unstained but infected cells.

EXAMPLE 2

Assay for Determining Whether a Virus is Endotheliotropic

The assay described herein is used for determining whether a virus is endotheliotropic.

As to determine whether a human CMV is endotheliotropic a primary human fibroblast cell line, a complementing cell line which complements the product of the gene in relation to which the HCMV of the invention is deficient, and a human endothelial cell line are plated and infected at an MOI of about 0.1 with HCMV wild type or the virus of the present invention. 24 hours after infection immediate early staining is performed by incubating fixed cells with a monoclonal antibody against immediate early gene product of the beta-herpesvirus of the invention, more specifically CMV IE 1/2 monoclonal Antibody CH160 (Plachter et al. supra), commercially available from Virusys Co. in 3% BSA/D-PBS. After three D-PBS washes, cells are incubated with an Alexa Fluor 555-coupled secondary antibody directed against the monoclonal antibody against human immediate early 1 of HCMV in 3% BSA/D-PBS. Finally cells are washed three times and imaged by UV microscopy. Cells infected with wild type HCMV are used as positive control and counted immediate early 1- and CFSE-positive cells using the ImageJ Cell Counter plugin (Rasband supra).

As to determine whether a mouse CMV is endotheliotropic a primary mouse fibroblast cell line, a complementing cell line which complements the product of the gene in relation to which the MCMV of the invention is deficient, and a mouse endothelial cell line are plated and infected at an MOI of about 0.1 with MCMV wild type or the virus of the present invention. 24 hours after infection immediate early staining is performed by incubating fixed cells with a monoclonal antibody against immediate early gene product of the beta-herpesvirus of the invention, more specifically Croma 101 designated as antibody 6/20/1 in Keil et al. (Keil et al., supra) in 3% BSA/D-PBS. After three D-PBS washes, cells are incubated with an Alexa Fluor 555-coupled secondary antibody directed against the mouse monoclonal antibody against immediate early 1 of mouse CMV in 3% BSA/D-PBS. Finally cells are washed three times and imaged by UV microscopy. Cells infected with wild type mouse CMV are used as positive control and counted immediate early 1 positive cells using the ImageJ Cell Counter plugin (Rasband supra).

EXAMPLE 3

Materials and Methods

Cells and Mice

The fibroblast cell line NIH/3T3 and BALB/c derived murine embryonic fibroblasts (MEF) were cultured as described in Cicin-Sain et al., (Cicin-Sain et al. 2005 J Virol 79:9492-9502.). C57BL/6 (B6) mice, B6.SJL-Ptpr$^c$ (Ptpr$^c$) mice and 129.IFNαβR$^{-/-}$ mice were purchased from Elevage Janvier (Le Genest Saint Isle, France), Jackson Laboratories (Bar Harbor, Me., USA) and B&K Universal Limited (Grimston, England), respectively. 129.IFNαβR$^{-/-}$ mice (Muller et al. 1994 Science 264:1918-1921.) were backcrossed on the B6 background (B6.IFNαβR$^{-/-}$). T cell receptor transgenic mice OT-I (Hogquist et al. 1994 Cell 76:17-27.) and OT-II (Barnden et al. 1998 Immunol Cell Biol 76:34-40.) were backcrossed to Ptpr$^c$ (CD45.1) or Thy1.1 (CD90.1) congenic mice, respectively. Alb-cre (Postic et al. 1999 J Biol Chem 274:305-315.) and Tie2-cre (Constien et al. 2001 Genesis 30:36-44.) were maintained on the B6 background. Mice were kept under specified pathogen free conditions. Animal experiments were approved by the responsible office of the state of Bavaria (approval no. 55.2-1-54-2531-111-07) or by the Ethics Committee at the University of Rijeka.

Generation of the Trans-Complementing Cell Line NT/M94-7

The conditional trans-complementing cell line NT/M94-7 was generated according to (Lotzerich et al. supra). Briefly, the M94 ORF was amplified from pSM3fr (Sacher et al. 2008 Cell Host Microbe 3:263-272.) using primers HΔM94for (SEQ.ID.No.1) and M94rev (SEQ.ID.No.2) thereby introducing an HA tag at the N-terminus. The PCR product was digested with BamHI and XbaI and inserted into the BamHI- and NheI-cleaved pTRE2Hyg vector (BD Biosciences Clontech, Heidelberg, Germany), resulting in pTRE-HΔM94 (SEQ.ID.NO:22) putting HΔM94 expression, the HΔM94 protein is depicted in SEQ.ID.NO:31, under the control of the tetracycline (tet) inducible promoter. Stable NIH/3T3 transfectants harboring pTRE-HΔM94 were selected with 50 µg/ml Hygromycin B. The deletion virus MCMV-ΔM94 was reconstituted by transfecting different NT/M94 cell clones with the respective BAC. The most productively infected trans-complementing cell line NT/M94-7 was subcloned using limiting dilution. The trans-complementing cell line was deposited under the Budapest Treaty with the DSZM, Germany on May 5, 2010.

Generation of Recombinant Viruses

Recombinant mouse CMV (MCMV) mutants were derived from the MCMV bacterial artificial chromosome (BAC) clone pSM3fr, originated from Smith strain (Messerle et al. 1997 Proc Natl Acad Sci USA 94:14759-14763.). Nucleotide positions are given according to Rawlinson et al. (Rawlinson et al. supra). The 1.4 kilo base pair (bp) SmaI fragment of pCP15 carrying the FRT flanked kanamycin resistance gene (Kan$^r$) was introduced into the BssHII site of pCR3 (Invitrogen, Basel, Switzerland) resulting in pCR3-FRT-Kan$^r$-FRT. A fragment containing an ATG start codon and a loxP site was generated by annealing the oligonucleotides ATGlox1 (SEQ.ID.No.3) and ATGlox2 (SEQ.ID.No.4). This fragment was inserted into the EcoRI and XhoI site positioned between the major immediate early promoter of HCMV (IEP) and the polyA signal of the bovine growth hormone of pCR3-FRT-Kan$^r$-FRT to obtain pCR3-FRT-Kan$^r$-FRT-ATG-loxP. The ovalbumin gene (ova) was synthesized as contained in pBSK-OVA (SEQ.ID.NO: 21) introducing GGAA after nt position 9 resulting in a BspEI restriction site for further cloning. Ova was inserted in frame using BspEI and NotI of pCR3-FRT-Kan$^r$-FRT-ATG-loxP resulting in a full length ova with inserted loxP site after the initial ATG under control of IEP named pCR3-FRT-Kan$^r$-FRT-ATG-loxP-ova. To obtain a construct with Cre inducible ovalbumin (OVA) expression (SEQ.ID.NO: 24) a floxstop cassette (Sacher et al. supra) was inserted into the EcoRI and BspEI sites of pCR3-ATG-loxP-ova resulting in pCR3-ATG-flox-stop-ova. Using these constructs as templates and oligonucleotides 5'-Δm157-pCR3-FRT-Kan$^r$-FRT (SEQ.ID.No.5) (nt position 216243 to 216290) and 3'-Δm157-flox-egfp (SEQ.ID.No.6) (nt position 216885 to 216930) as primers a linear DNA fragment containing the IEP-ova cassette, the FRT flanked Kan$^r$, and the viral homology sequences to the MCMV genome target site m157 was generated. In a similar procedure the firefly luciferase gene (luc) was cloned under control of the IEP into pCP 15 carrying the FRT flanked Kan$^r$. These fragments were introduced into m157 of pSM3fr as described (Sacher et al. supra) resulting in pSM3fr-Δm157-ova, pSM3fr-Δm157-flox-ova and pSM3fr-Δm157-luc. For excision of the FRT flanked Kan$^r$ FLP recombinase was transiently expressed from plasmid pCP20.

Generation of Spread-Deficient Virus Mutants

Figure 1:
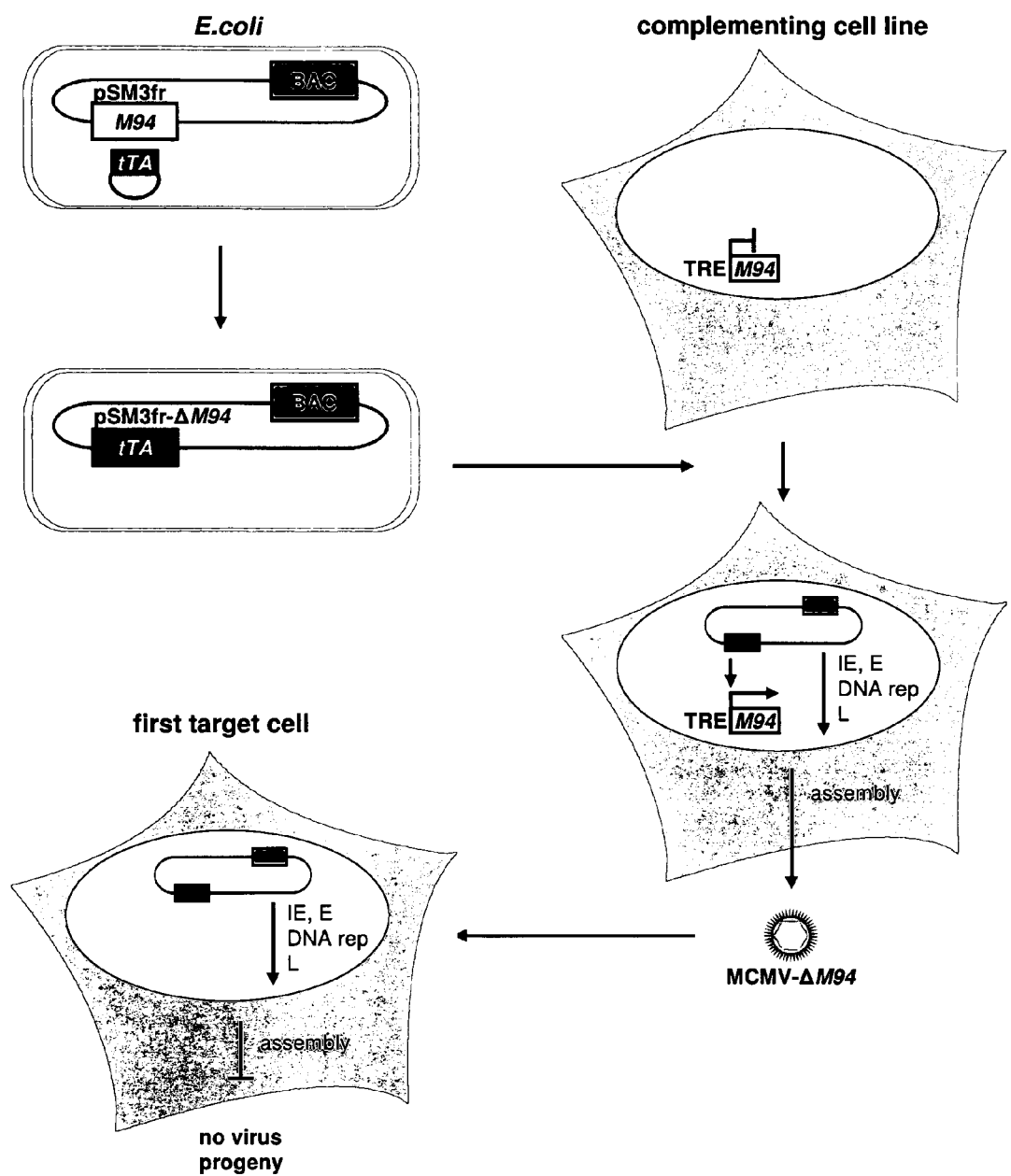
FIG. 1 is a schematic illustration of the concept of inducible trans-complementation.

As shown in FIG. 1 in *E. coli* the BAC pSM3fr-ΔM94 was generated by insertion of the tTA transactivator cassette into pSM3fr thereby deleting M94. The trans-complementing cell line NT/M94-7 expresses pM94 under control of the Tet inducible promoter. Upon transfection with pSM3fr-ΔM94 expression of tTA by the viral genome induces expression of pM94 by the cell leading to the production of trans-complemented MCMV-ΔM94. This virus is able to infect non complementing first target cells. Due to the lack of the essential gene M94 the release of infectious virus particles is impossible although immediate early (IE), early (E) and late (L) viral gene expression as well as DNA replication (DNA rep) occur.

For generation of the recombinant MCMV lacking the M94 sequence the parental MCMV BACs pSM3fr (MCMV-wt), pSM3fr-Δm157-ova (MCMV-ova) and pSM3fr-Δm157-rec-egfp (MCMV-Δm157-rec-egfp) (Sacher et al. supra) were applied to a second mutagenesis step. Therefore, the plasmid pO6-tTA-mFRT-Kan$^r$-mFRT was obtained by insertion of the Kan$^r$, on both sides flanked by mutant 34 bp FRT sites from pO6ie-F5 into pO6-tTA (Lotzerich et al. supra) to express the tTA transactivation gene under control of the IEP necessary for trans-complementation of pM94 (SEQ.ID:NO: 30). A linear DNA fragment containing the tTA cassette, the Kan$^r$ and viral homology sequences to the MCMV genome target site (MCMV upstream-homology: nt position 136189 to 136234 and MCMV downstream-homology: nt position 137256 to 137309) was generated using primer 5' ΔM94-pO6-tTA (SEQ.ID.No.7), primer 31-ΔM94-pO6-tTA (SEQ.ID.No.8) and plasmid pO6-ITA-mFRT-Kan$^r$-mFRT as template. This PCR fragment was inserted into the different parental pSM3fr clones, hereby deleting the M94 gene. Since ORFs of M94 and M93 are overlapping 47 bp of homology had to be left at the 5'-end of M94 to keep the M93 ORF intact and 17 bp homology are still present at the former 3'-end of M94. Again FLP recombinase was expressed for excision of the Kan$^r$. Construction of pSM3fr-ΔM94, pSM3fr-ova-ΔM94, pSM3fr-flox-ova-ΔM94 and pSM3fr-Δm157-rec-egfp-ΔM94 was confirmed by restriction digest analysis and sequencing.

Viruses were reconstituted from BAC DNA, propagated on NT/M94-7 complementing cells and purified on a sucrose cushion as previously described (Sacher et al. supra). For analysis of virus replication supernatants from infected cells were taken every 24 h. Quantification of infectious virus was done using TCID$_{50}$ (median tissue culture infectious dose) method on NIH/3T3 or complementing NT/M94-7 cells. For the determination of virus replication in vivo virus load was determined by standard plaque assay as plaque forming units (PFU) per gram organ as described (Sacher et al. supra). Spread-deficiency of each virus stock of M94 deficient mutants (MCMV-ΔM94, MCMV-ova-ΔM94, MCMV-flox-ova-ΔM94 and MCMV-Δm157-rec-egfp-ΔM94) was confirmed by the absence of plaque formation after infection of non-complementing MEF, although CPE of individually infected cells was detectable. The *E. coli* containing the pSM3fr-ΔM94 BAC of the spread-deficient MCMV-ΔM94 was deposited under the Budapest Treaty with the DSZM on Apr. 28, 2010 as DSM 23561.

UV Inactivation of Virus

For in vivo application, a fraction of the MCMV-wt virus preparation used for immunization was inactivated by exposure to 1.5 kJ/cm$^2$ UV light at a distance of 5 cm in a UV-crosslinker (Stratagene, Amsterdam, Netherlands) at 4° C. Viral infectivity was decreased by factor 2.4×10$^7$. The same treatment was sufficient to abolish viral gene expression when MCMV-Δm157-rec-egfp was subjected to different doses (0.5, 1.0 and 1.5 kJ/cm$^2$) of UV light and subsequently titrated on MEF. After 4 days post infection (p.i.) EGFP expression was monitored in single infected cells if virus was irradiated with low dose (0.5 kJ/cm$^2$) of UV and no EGFP expression was seen after strong irradiation (1.5 kJ/cm$^2$). Untreated MCMV-Δm157-rec-egfp formed EGFP$^+$ plaques.

Immunization and Challenge of Mice 8 to 10 weeks old female B6 mice were immunized by intraperitoneal (i.p.) or subcutaneous (s.c.) injection of either MCMV-wt or mutant MCMV. Each mouse received 100 μl of virus suspension s.c. or 300 μl i.p. C57BL/6 mice were immunized with 1×10$^5$ TCID$_{50}$ MCMV-wt or MCMV-deltaM94, 129.IFNαβR$^{-/-}$ with 2.5×10$^5$ TCID$_{50}$ of MCMV-deltaM94 or UV irradiated MCMV-wt, and B6.IFNαβR$^{-/-}$ with 3×10$^5$ TCID$_{50}$ of MCMV-ΔM94 or MCMV-wt. Mock treated mice received same volumes of PBS. To boost mice, this procedure was repeated 14 days p.i. Sera collected from mice 12 weeks p.i. were used to determine amounts of virus specific antibodies by virus neutralization assay, as described below.

28 days or 20 weeks post priming, mice were challenged by intravenous (i.v.) injection of 10$^6$ PFU of tissue culture derived MCMV-wt. Five days post challenge lungs, liver and spleen were collected under sterile conditions and stored at −80° C. Organ homogenates were analyzed for infectious virus load by standard plaque assay on MEF cells. Salivary glands derived MCMV (sgMCMV-wt) was generated as a homogenate of salivary glands from mice infected with tissue culture derived MCMV-wt as described in Trgovcich et al. (Trgovcich et al. 2000 Arch Virol 145:2601-2618). The isolated sgMCMV-wt is more virulent compared to tissue culture derived MCMV-wt (Pilgrim et al. 2007 Exp Mol. Pathol. 82:269-279). Vaccinated B6.IFNαβR$^{-/-}$ mice were challenged with 2×10⁵ PFU sgMCMV-wt and 129.IFNαβR⁻/⁻ mice were challenged with 2.5×10⁵ TCID$_{50}$ tissue culture derived MCMV-wt.

Virus Neutralization Assay

Heat inactivated serum (56° C., 30 min) from 5 immunized mice 12 weeks p.i. were pooled and serially diluted 1:2 in DMEM containing a final concentration of 10% guinea-pig complement. Each dilution was mixed with 50 PFU of MCMV-luc and incubated for 90 min at 37° C. and subsequently added to NIH/3T3 cells in a 96 well format. After 1 h at 37° C. the virus inoculum was removed and NIH/3T3 medium added. The cultures were incubated for 24 h and luciferase activity was determined in cell extracts using the luciferase assay (Promega, Mannheim, Germany) in a luminometer (Berthold, Bad Wildbad, Germany) according to the supplier's and manufacturer's instructions, respectively.

In Vivo Cytotoxicity Assay

To evaluate CD8⁺ T cell effector function in vivo, splenocytes of congenic CD45.1⁺ Ptpr$^c$ mice were incubated with 2 µM of the indicated peptide and stained with 2 µM, 0.7 µM, or 0.1 µM carboxyfluorescein succinimidyl ester (CFSE) and PKH26 Red Fluorescent Cell Linker Mini Kit according to the manufacturer's instructions (Sigma-Aldrich). At day 6 p.i., labeled CD45.1⁺ cells were transferred into B6 (CD45.2⁺) recipients. After 16 h spleens of recipient mice were removed and flow cytometrical analysis of the target cells was performed. Specific cytotoxicity of target cells was calculated using the equation: % spec lysis=(1−ratio unprimed/ratio primed)*100; ratio=(% CFSE low/% CFSE high) (Lauterbach et al. 2005 J Gen Virol 86:2401-2410.). The OVA derived class I peptide (SEQ.ID.NO.9) and MCMV specific peptides derived from m139 (SEQ.ID.No.10), ie3 (SEQ.ID.No.11), M57 (SEQ.ID.No.12) and M45 (SEQ.ID.No.13) (Snyder et al. 2008 supra) were purchased from Metabion, Germany and were dissolved and stored according to manufacturer's device.

Adoptive Transfer and Flow Cytometrical Analysis

OVA specific CD8⁺ T cells were isolated from spleen and cervical, axillary, brachial and inguinal lymph nodes of OT-I TCR transgenic mice backcrossed to congenic CD45.1⁺ mice. OT-I cells were purified by negative selection via the CD8α⁺ T Cell Isolation Kit (Miltenyi Biotec, Bergisch Gladbach, Germany). 3×10⁵ transgenic T cells were injected i.v. into recipient B6 mice one day prior to i.p. infection with 10⁵ TCID$_{50}$ MCMV. To follow expansion of the transferred OT-I T cells 100 µl blood was taken 3, 6 and 8 days p.i., erythrocytes were lysed (PharmLyse, BD Biosciences, Heidelberg, Germany) and remaining cells were incubated with PE-TexasRed coupled α-CD8α (5H10; Caltag, Sacramento, Calif., USA) and PE coupled α-CD45.1 antibodies (A20; BD Biosciences Pharmingen). Flow cytometrical acquisition was performed using an Epics XL-MCL (Beckman-Coulter) and data were analyzed using FlowJo software (Tristar, Ashland, Oreg., USA).

OVA specific CD4⁺ T cells were isolated from spleen and cervical, axillary, brachial and inguinal lymph nodes of OT-II TCR transgenic mice backcrossed to congenic CD90.1⁺ mice. After lysis of erythrocytes 3×10⁵ transgenic T cells were injected i.v. into recipient mice one day prior to infection with 10⁵ TCID$_{50}$ MCMV. Spleens were removed and splenocytes were incubated with Fc block (2.4G2; BD Biosciences) and subsequently stained with PE conjugated α-CD90.1 (HIS51; eBioscience) and PE-Cy5.5 coupled α-CD4 (RM 4-5; eBioscience). Flow cytometrical acquisition was performed using a FACS Calibur (BD Biosciences) and data were analyzed using FlowJo software.

Quantification of Viral Genomes in Organ Homogenates

Lungs were removed from mice twelve month after infection. Organs were homogenized and DNA was extracted using the DNeasy Blood & Tissue Kit from Qiagen (Hilden, Germany). Elution was done with 100 µl of the supplied elution buffer and genomic DNA concentration of each sample was quantified in duplicates using a NanoDrop ND-1000 UV-Vis Spectrophotometer. To quantify the viral DNA a quantitative realtime PCR specific for the MCMV M54 gene (Cicin-Sain et al. 2005 supra) was performed using a specific Taqman-Probe (SEQ.ID.No.14) and the Taqman 1000 RXN PCR Core Reagents kit on an ABI PRISM 7700 Sequence Detector (Applied Biosystems, Carlsbad, Calif., USA). To calculate the viral genome copy number, a standard curve of the BAC plasmid pSM3fr containing the M54 gene was included.

Statistical Analysis

EXAMPLE 4

MCMV-ΔM94 is Spread-Deficient

The HCMV virion protein pUL94 is essential for virus replication (Dunn et al. supra) and is expressed with late kinetics (Wing et al. supra). It has been found that pM94, the MCMV homolog, is also essential and plays a crucial role in a post nuclear step of virus maturation. In order to trans-complement the essential M94 gene product and reconstitute an M94 deletion mutant the NIH/3T3 derived complementing cell line NT/M94-7 harbouring the M94 gene under control of the TRE promoter was generated. The TRE promoter is only active in the presence of the Tet trans-activator (tTA). To provide the tTA for trans-complementation of pM94 the tTA expression cassette was introduced into pSM3fr (Messerle et al. supra) disrupting M94 generating pSM3fr-ΔM94. MCMV-ΔM94 virus was reconstituted by transfecting NT/M94-7 cells (FIG. 1). Next, multistep growth analysis infecting NT/M94-7 cells as well as parental NIH/3T3 fibroblasts with MCMV-ΔM94 or MCMV-wt were performed.

Figure 2:
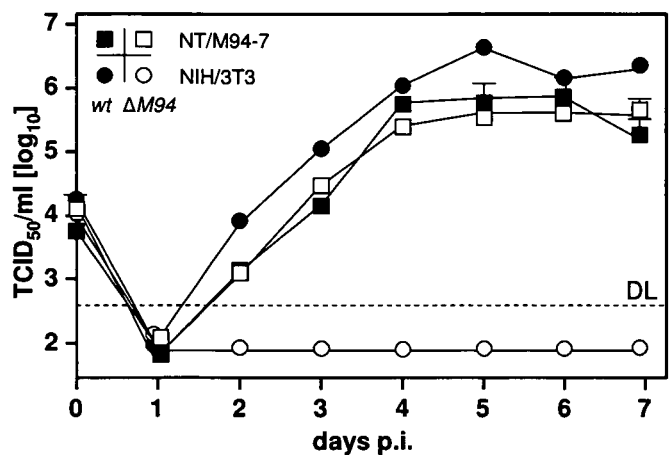
FIG. 2A is a diagram indicating $TCID_{50}$ as a function of time.
FIG. 2B is a series of microphotographs.
FIG. 2C is a survivorship curve indicating survival of mice as a function of time.
Figure 2:
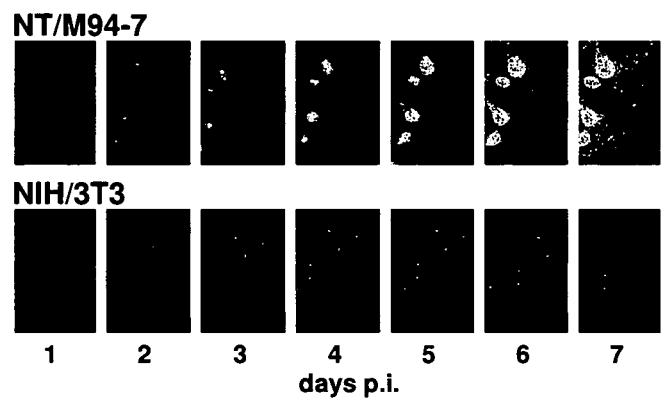
Figure 2:
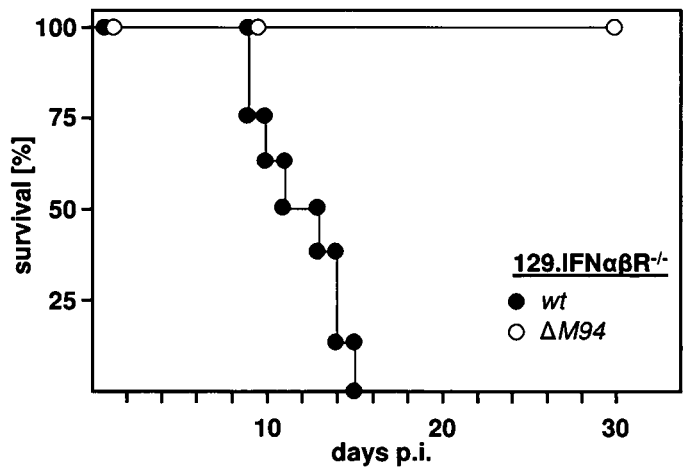

The results of this Example are shown in FIG. 2. In FIG. 2A Parental NIH/3T3 (circles) and NT/M94-7 fibroblasts (boxes) were infected at 0.1 TCID$_{50}$/cell with MCMV-wt (wt; closed symbol) or MCMV-ΔM94 (ΔM94; open symbol). At indicated days, infectious virus in the supernatant was quantified on NT/M94-7 cells by TCID$_{50}$ endpoint titration. Shown is the mean+/−SD of titrated duplicates. At day 5 p.i. supernatants were additionally titrated on MEF. No PFU was found within 1 ml supernatant of MCMV-ΔM94 infected NT/M94-7. p.i.=post infection; DL=detection limit.

As shown in FIG. 2B Parental NIH/3T3 (lower panel) and NT/M94-7 (upper panel) fibroblasts were infected with MCMV-Δm157-rec-egfp-ΔM94. At indicated time points EGFP expressing cells were monitored. hpi=hours post infection.

As shown in FIG. 2C 129.IFNαβR⁻/⁻ mice (n=15 for MCMV-ΔM94, open symbols; n=8 for MCMV-wt, closed symbols) were infected with 2.5×10⁵ TCID$_{50}$ i.p. and survival was followed for 30 days p.i.

While MCMV-ΔM94 replicated to MCMV-wt-like titers on NT/M94-7 cells, no infectious virus was detectable in the supernatant of NIH/3T3 cells (FIG. 2A). As the defect of MCMV-ΔM94 to release infectious virus particles into the supernatant does not exclude cell-associated virus spread, a ΔM94 mutant expressing the enhanced green fluorescent protein EGFP (MCMV-Δm157-rec-egfp-ΔM94) was constructed. While MCMV-Δm157-rec-egfp-ΔM94 spread with kinetics comparable to MCMV-wt on NT/M94-7 cells, MCMV-Δm157-rec-egfp-ΔM94 remained strictly confined to the first infected NIH/3T3 cells (FIG. 2B). This result was confirmed also in endothelial cells (FIG. 8). In summary, M94 is essential and deletion abrogates virus release and cell-to-cell spread. In addition, MCMV-ΔM94 can be efficiently produced by trans-complementation.

Complementing NT/M94-7, parental NIH/3T3 fibroblasts and myocardium-derived endothelial cells MHEC5-T were infected with 0.1 TCID50/cell MCMV-ΔM94-Δm157-rec-egfp (MCMV-ΔM94) or MCMV-Δm157-rec-egfp (wt). At indicated time points EGFP expressing cells were monitored. Scale bar represents 100 μm.

EXAMPLE 5

MCMV-ΔM94 does not Revert to Replication Competent Virus

A major safety concern is reversion of vaccine strains to replication competent viruses during preparation (Roizman et al. 1982 Dev Biol Stand. 52:287-304) or in the vaccinated patient (Iyer et al. 2009 Ann. Emerg. Med. 53:792-795). To exclude acquisition of the M94 gene through recombination via homologous sequences between MCMV-ΔM94 and the complementing cell line homologies were carefully avoided during virus construction. Replication competent virus indicative of recombination between the deletion virus and the M94 gene expressed by NT/M94-7 was never observed. In order to investigate the safety of MCMV-ΔM94 for vaccination studies in a highly susceptible mouse strain, 129.IFNαβR$^{-/-}$ mice were infected with MCMV-wt or MCMV-ΔM94. While all IFNαβR$^{-/-}$ mice died within 14 days upon infection with MCMV-wt, after infection with MCMV-ΔM94 all mice survived with no or only minimal weight loss (FIG. 2C). In conclusion, MCMV-ΔM94 could be safely produced and even immune deficient mice tolerated MCMV-ΔM94 infection.

EXAMPLE 6

MCMV-ΔM94 Induces Neutralizing Antibody and T Cell Responses

Poor induction of neutralizing antibodies that prevent viral entry is a problem in HCMV infection (Landini et al. 1991 Comp Immunol Microbiol Infect Dis 14:97-105). Therefore, the neutralizing antibody response to MCMV-wt and MCMV-ΔM94 was compared 12 weeks post immunization. Serial dilutions of sera were mixed with a luciferase expressing MCMV (MCMV-luc) prior to infection of NIH/3T3. The reduction of the luciferase signal reflected the neutralizing capacity of the antisera. Immunization with MCMV-ΔM94 induced a slightly lower amount of neutralizing antibodies than with MCMV-wt (FIG. 3A, p<0.05) whereas immunization with UV irradiated MCMV-wt abolished the induction of neutralizing antibodies confirming published observations (Gill et al. supra).

Figure 3:
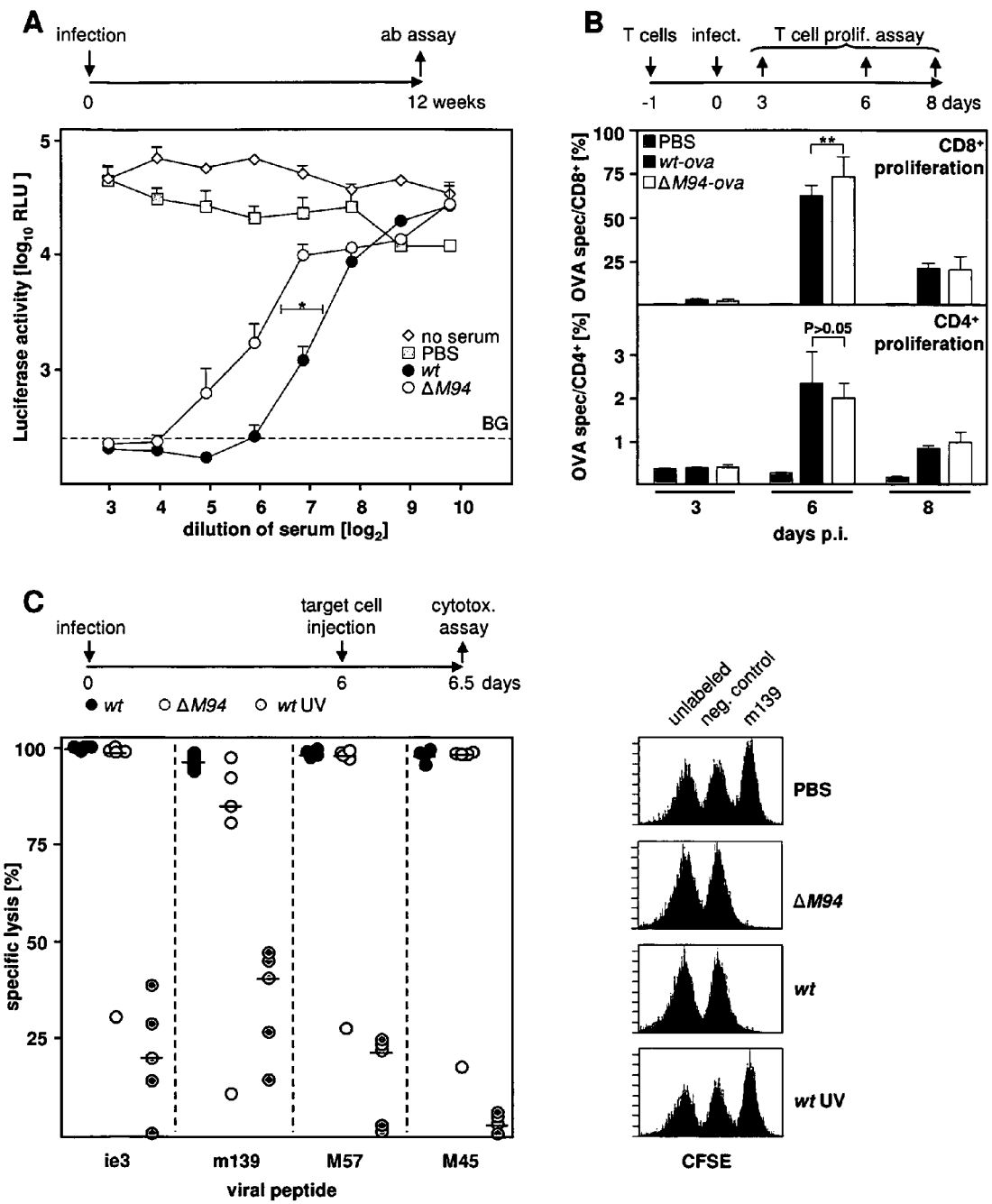
FIG. 3A is a diagram indicating virus neutralizing antibody response as luciferase activity as a function of dilution of serum.
FIG. 3B is a diagram indicating the percentage of adaptively transferred T cells at various time points.
FIG. 3C is a diagram indicating the percentage of specific lysis of transferred cells loaded with various viral peptides by $CD8^+$ T-cells specific for the viral peptides.

The results of this example are shown in FIG. 3. In FIG. 3A B6 mice were immunized i.p. with $10^5$ TCID$_{50}$ MCMV-wt (wt; closed circles), MCMV-ΔM94 (ΔM94; open circles) or mock infected (PBS; gray squares). Blood was collected 12 weeks p.i. and virus neutralizing capacity of the serum was determined using MCMV-luc. Neutralizing antibody levels of MCMV-ΔM94 immunized mice were significantly lower than antibody levels of MCMV-wt immunized mice using two-way ANOVA testing (P=0.04). Values represent the mean±SD of measured serum pools. RLU=Relative Luciferase Units, BG=background.

In FIG. 3B after adoptive transfer of $3×10^{50}$ T-I CD8$^+$ T cells (upper panel), B6 mice (n=5) were infected i.p. with $10^5$ TCID$_{50}$ MCMV-ova (wt-ova; closed bars), MCMV-ova-ΔM94 (ΔM94-ova; open bars) or PBS (gray bars). At day 3, 6 and 8 p.i. flow cytometrical analysis was performed on blood for the congenic marker CD45.1 and CD8. After adoptive transfer of $3×10^{50}$ T-II CD4$^+$ T cells (lower panel), B6 mice (n=5) were infected i.p. as above. At day 3, 6 and 8 p.i. flow cytometrical analysis was done on splenocytes for CD90.1 and CD4. Each bar represents the mean±SD of the indicated group; (**, P<0.01).

In FIG. 3C B6 mice (n=5) were infected i.p. with $10^5$ TCID$_{50}$ MCMV-wt (wt; closed symbols), MCMV-ΔM94 (ΔM94; open symbols) or UV irradiated MCMV-wt (wt UV; gray symbols). At day 6 p.i. in vivo cytotoxicity assay was performed using splenocytes labeled with carboxyfluorescein succinimidyl ester (CFSE) and the indicated viral peptides. Symbols represent the specific lysis activity against the indicated peptide in individual animals. The cross bar indicates the median of the analyzed group. The right panel shows an exemplary set of flow cytometric data.

Both CD4$^+$ and CD8$^+$ T cells play important roles in host defense against CMV. Antiviral CD8$^+$ T cells are effective in controlling MCMV during acute infection and mediate protection after immunization (Reddehase et al. supra). In addition, CD4$^+$ T helper cells are required for virus clearance in salivary glands (Jonjic et al. 1989 J Exp Med 169:1199-1212). In order to compare the level of CD4$^+$ and CD8$^+$ T cell responses induced by MCMV-wt and MCMV-ΔM94, OVA as a model antigen was chosen to be expressed by the vaccine. B6 mice were infected with MCMV-ova and MCMV-ova-ΔM94 one day after adoptive transfer of OVA specific CD4$^+$ or CD8$^+$ T cells. For MCMV-ova the expansion of OVA specific CD4$^+$ and CD8$^+$ T cells peaked at day 6 p.i., concordant with published data (Karrer et al, 2004 J Virol 78:2255-2264). Remarkably, MCMV-ova-ΔM94 also stimulated the proliferative response of OVA specific CD8$^+$ and CD4$^+$ (FIG. 3B) T cells to a degree comparable to the spread competent MCMV-ova. The amount of CD8$^+$ T cells was even slightly higher than with MCMV-wt (P<0.01).

This observation was to be confirmed for native MCMV antigens. B6 mice were infected with MCMV-ΔM94 or MCMV-wt. At six days p.i., target cells loaded with viral peptides derived from either m139, ie3, M57, or M45 (Snyder et al. 2008 supra) were injected and their cytolysis in vivo was analyzed (FIG. 3C). The cytolytic CD8$^+$ T cell response induced by MCMV-ΔM94 turned out to be comparable to MCMV-wt. In contrast, B6 mice injected with UV irradiated MCMV generated no or only poor lysis of targets. UV inactivation of MCMV-ΔM94 or MCMV-wt also abolished OVA specific T cell expansion and the virus neutralizing capacity of sera. Thus, viral gene expression appeared to be crucial for the induction of the adaptive immune response. Altogether, spread-deficient MCMV induced an immune response comparable to MCMV-wt.

EXAMPLE 7

Role of Viral Target Cell Types in CD8$^+$ T Cell Activation

The strong adaptive immune response against MCMV-ΔM94 was surprising, since MCMV-ΔM94 gene expression is limited to the first target cells. Induction of a specific T cell response is dependent on antigen presentation by infected cells and by professional antigen presenting cells (Villadangos et al. 2008 Immunity. 29:352-361). In order to assess the contribution of infection of different cell types in the generation of an efficient CD8+ T cell response the replication deficient MCMV was combined with conditional activation of a marker gene (Sacher et al. supra). MCMV-flox-ova-ΔM94 was constructed which expresses OVA only after Cre-mediated recombination.

Figure 4:
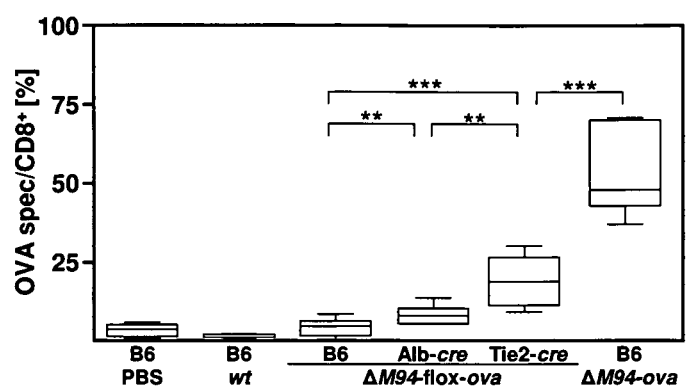
FIG. 4 is a Whisker blot indicating the percentage of adaptively transferred T cells in different mouse strains being infected with different virus mutants.

One day prior to i.p. injection of $10^5$ TCID$_{50}$ of MCMV-flox-ova-ΔM94 (ΔM94-flox-ova), MCMV-ova-ΔM94 (ΔM94-ova), MCMV-wt (wt) or PBS 3×10$^5$ congenic OT-I CD8+ T-cells were transferred i.v. into B6, Alb-cre and Tie2-cre mice. At day 6 p.i. a flow cytometrical analysis was performed on PBL for the congenic marker CD45.1 and CD8. Boxes represent the ratio of OT-I cells per CD8+ cells as a pool of 3 independent experiments and extend from the 25 to the 75 percentile. The lines indicate the median. Whiskers extend to show the extreme values. The P-values were obtained applying a two-tailed Wilcoxon rank sum test, (, P<0.01; *, P<0.001). The results are shown in FIG. 4

Endothelial cells (EC) and hepatocytes (Hc) are among the first target cells infected by MCMV in vivo (Sacher et al. supra). Whether these cell types contribute to CD8+ T cell activation was addressed by infecting mice that express Cre recombinase selectively in vascular EC (Tie2-cre) or Hc (Alb-cre). One day after adoptive transfer of OVA specific CD8+ T cells mice were infected with $10^5$ TCID$_{50}$ of spread-deficient MCMV-flox-ova-ΔM94. Hc are the main producers of infectious virus during the first few days of infection and are highly effective in activating a conditional marker gene by Cre recombinase (Sacher et al. supra). Yet, selective induction of OVA expression in MCMV infected Hc resulted in only weak proliferation of OVA specific CD8+ T cells (FIG. 4). In contrast, a significantly (P<0.001) higher proliferative response of OVA specific CD8+ T cells was observed upon OVA expression in EC. Therefore, infection of EC make a stronger contribution to the induction of an antiviral CD8+ T cell response than infection of Hc. As infection of C57BL/6 mice with MCMV-ΔM94-ova that leads to expression of OVA in all infected cells induces a higher proportion of OVA specific CD8+ T cells than expression selectively in EC (Tie2-cre mice infected with MCMV-ΔM94-flox-ova; P<0.01) additional cell types seem to be involved in antigen expression and T cell stimulation. In addition, the significant different T cell responses after cell type specific recombination in vivo prove that MCMV-ΔM94 is unable to spread from cell to cell.

Figure 5:
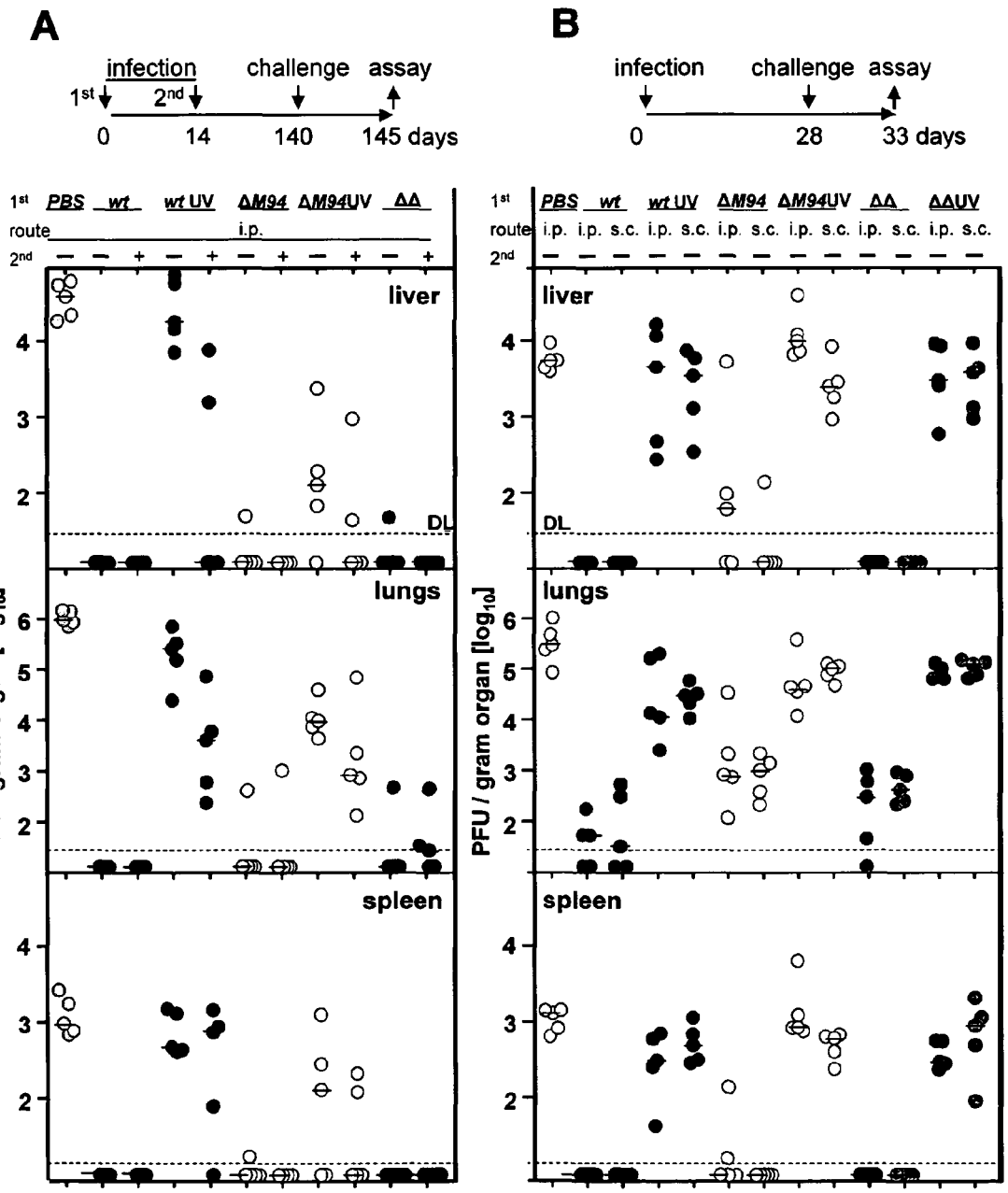
FIGS. 5A and 5B are diagrams indicating the challenge virus load in different organs of vaccinated mice.

The experimental details in connection with this example were, in addition to the ones outlined in Example 3, as follow and the results of this example are depicted in FIG. 5.

B6 mice (n=5) were immunized ($1^{st}$) s.c. or. i.p. with $10^5$ TCID$_{50}$ MCMV-wt (wt; closed symbols), MCMV-ΔM94 (ΔM94; open symbols), Δm01-17+m144-158-MCMV (AA; gray symbols) or PBS (light gray symbols). Virus preparations were UV irradiated before immunization (UV) as indicated. Optionally, mice were boosted ($2^{nd}$) two weeks later with the same dose, route and virus. Challenge infection was applied i.v. 20 (A) or four weeks (B) post prime with $10^6$ PFU MCMV-wt. Five day post challenge plaque assay was performed. Horizontal bars show the median of each group. Each symbol represents one individual mouse. DL=detection limit.

EXAMPLE 8

MCMV-ΔM94 Protects Against Challenge with MCMV-wt

In order to test protection of MCMV-ΔM94 against lethal challenge, B6 mice were infected with either spread-deficient MCMV-ΔM94, the attenuated strain Δm01-17+m144-158-MCMV (Cicin-Sain et al. 2007 J Virol 81:13825-13834) or MCMV-wt. A boost infection was applied 4 weeks later with the same dose. 20 weeks after priming mice were challenged i.v. with $10^6$ TCID$_{50}$ tissue culture derived MCMV-wt. Most remarkably, already a singular immunization dose of MCMV-ΔM94 was already sufficient to strongly suppress MCMV-wt replication by 10,000 fold in lungs, 1,000 fold in liver and at least 100 fold in spleen, whereas non-immunized controls had high virus loads in all organs tested (all P<0.01; FIG. 5A). Overall, the protection mediated by MCMV-ΔM94 vaccination was comparable to MCMV-wt or Δm01-17+m144-158-MCMV vaccination (all P>0.05). Due to the strong protection achieved already after one administration, a boosting effect could not be detected. However, there was weak protective effect after a singular dose when UV inactivated MCMV-wt or UV inactivated MCMV-ΔM94 virus was administered. Only after a boost with UV inactivated viruses the effect was slightly improved but still remained lower than that of a singular dose of MCMV-ΔM94 (P<0.05).

It was asked, whether the strong protection after singular administration of MCMV-ΔM94 could also be realized in a short-term vaccination protocol. In addition, the influence of two different application routes was tested. B6 mice were injected either i.p. or s.c. followed by challenge infection with MCMV-wt only 4 weeks later. Here, vaccination with MCMV-ΔM/94 resulted in about 100 fold reduction of challenge virus load in liver (P<0.05), lungs (P<0.01) and spleen (P<0.01; FIG. 5B) comparable to immunization with Δm01-17+m144-158-MCMV. MCMV-wt vaccination resulted in reduction of challenge virus load by 1,000 fold (P<0.01). Generally, there was no significant difference between the i.p. or s.c. vaccination route although s.c. injection appeared to induce slightly better protection in spleen (P>0.05) FIG. 5B) and hearts.

Summarized, vaccination with the spread-deficient MCMV-ΔM94 was able to efficiently protect immunocompetent mice against challenge with MCMV-wt after vaccination with a singular dose. Remarkably, vaccination with MCMV-ΔM94 was as efficient as vaccination with MCMV-wt concerning long-term vaccination, whereas the use of UV inactivated virus could not compete even after a second application.

EXAMPLE 9

Protection of Severely Immune Compromised Recipients

Type I interferons are key cytokines in the immune response against CMV and deletion of their receptor results in a mouse (IFNαβR$^{-/-}$) that is severely immunocompromised and at least 1.000-fold more susceptible to MCMV infection than the parental mouse strain (Presti et al. 1998 J Exp Med 188:577-588). Since spread-deficient MCMV-ΔM94 was proven to be well tolerated by IFNαβR$^{-/-}$ mice (FIG. 2C), it was tested whether MCMV-ΔM94 could even protect IFNαβR$^{-/-}$ mice against lethal MCMV-wt challenge (see FIG. 6A). B6.IFNαβR$^{-/-}$ mice were immunized with MCMV-ΔM94 or a sublethal dose of MCMV-wt. Both groups survived and mice immunized with MCMV-ΔM94 showed no significant weight loss, whereas MCMV-wt infected mice lost approximately 15% of their body weight. Four weeks later, mice were challenged by infection with a lethal dose of more virulent salivary glands derived MCMV (as described in Example 3). Most strikingly, the vaccination with both, MCMV-ΔM94 as well as MCMV-wt was protective and all animals survived (FIG. 6A).

Figure 6:
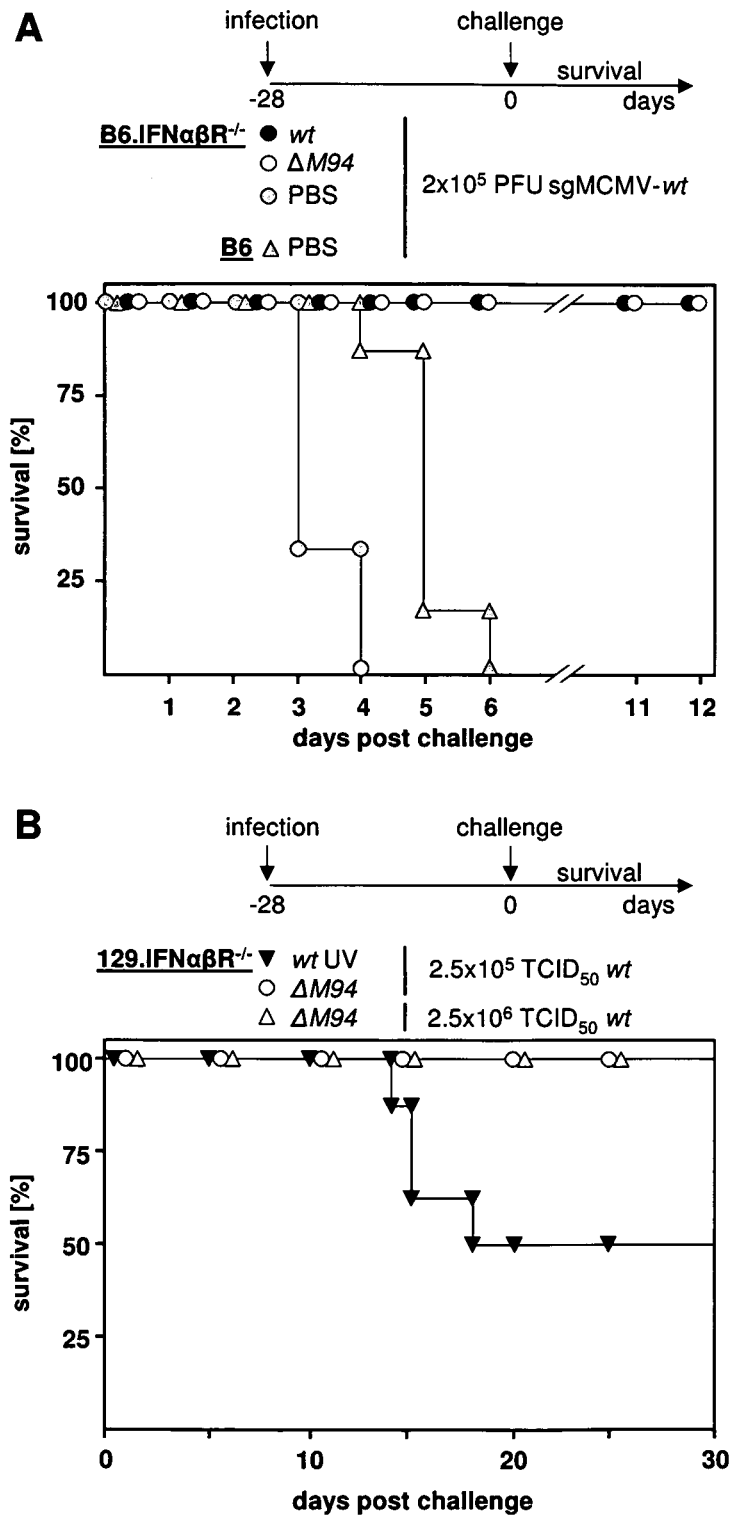
FIGS. 6A and 6B are survivorship curves indicating survival of vaccinated mice as a function of time.

The results of this Example are shown in FIG. 6.

In FIG. 6A B6.IFNαβR$^{-/-}$ (n=6) mice were immunized i.p. with 3×10$^5$ TCID$_{50}$ MCMV-wt (wt; black circles) or MCMV-ΔM94 (ΔM94; open circles). Control groups of B6.IFNαβR$^{-/-}$ (gray circles) or B6 (gray triangles) were treated with PBS. Four weeks later challenge infection was performed by i.p. injection of 2×10$^5$ PFU salivary glands derived MCMV (sgMCMV-wt) mice and survival was monitored.

In FIG. 6B 129.IFNαβR$^{-/-}$ mice 4 weeks previously immunized with 2.5×10$^5$ TCID$_{50}$ of MCMV-ΔM94 (ΔM94; open circles, n=8), or UV irradiated MCMV-wt (wt UV; closed triangles down, n=8) were challenged with a lethal dose of MCMV-wt (see FIG. 2C) and survival was monitored. A 10 fold higher dose of MCMV-wt was applied to mice immunized with MCMV-ΔM94 (n=7) (open triangles).

B6 mice profit from an Ly49H-dependant activation of natural killer cells resulting in a strong innate immune response stimulated by the MCMV protein encoded by m157 (Sun et al. 2008. J. Exp. Med. 205:1819-1828.). 129.IFNαβR$^{-/-}$ mice do not express Ly49H and are even more susceptible to MCMV infection than B6.IFNαβR$^{-/-}$ mice. 129.IFNαβR$^{-/-}$ mice were vaccinated with MCMV-ΔM94 and challenged 4 weeks later with a dose of 2.5×10$^5$ TCID$^{50}$ tissue culture derived MCMV-wt (FIG. 6B). In line with the earlier data (Cicin-Sain et al. 2007 supra), vaccination with UV inactivated virus mediated only partial protection and could delay death for a short period. MCMV-ΔM94 vaccinated mice survived the lethal challenge even with a dose of 2.5×10$^6$ TCID$^{50}$. In summary, vaccination with MCMV-ΔM94 is able to protect even highly susceptible immune compromised mice against lethal MCMV challenge.

EXAMPLE 10

Maintenance of the MCMV-ΔM94 Genome In Vivo

One argument against the application of attenuated life vaccines is their ability to establish a latent infection that bears the risk of reactivation (Iyer et al. supra). On the other hand non-productive reactivation episodes might result in endogenous boosts of the antiviral immune response (Snyder et al. 2008 Immunity 29:650-659). Thus, it was intriguing to test whether MCMV-ΔM94 genome is maintained in vaccinated hosts. Quantitative PCR analysis on total DNA extracted from lungs, a key manifestation site of CMV disease (Balthesen et al. 1993 J Virol 67:5360-5366), was performed. Twelve months p.i. genomes of MCMV-ΔM94 could be detected in all mice tested (FIGS. 7A and B) proving that the genome of MCMV-ΔM94 is maintained. Interestingly, the genome numbers detected in lungs one year after infection with MCMV-ΔM94 and MCMV-wt were not significantly different (P>0.05). This finding proved that at least some of the first target cells are not lost after infection either due to virus-induced cell death or elimination by the immune response. In summary, these data also provide first evidence that virus spread is not necessary for long-term genome maintenance and that first target cells of MCMV-ΔM94 may be able to contribute to a more sustained immune response.

Figure 7:
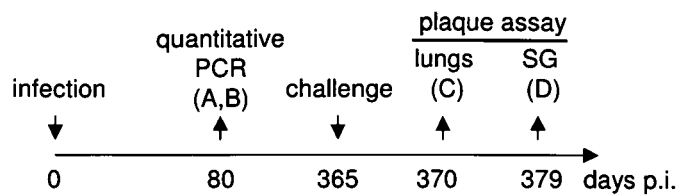
FIG. 7A is an agarose gel showing the result of a PCR detecting viral gene M54 in lungs of infected mice with either wild type or MCMV-ΔM94.
FIG. 7B is a diagram indicating the result of a quantitative PCR detecting viral gene M54 in lungs of infected mice with either wild type or MCMV-ΔM94.
Figure 7:
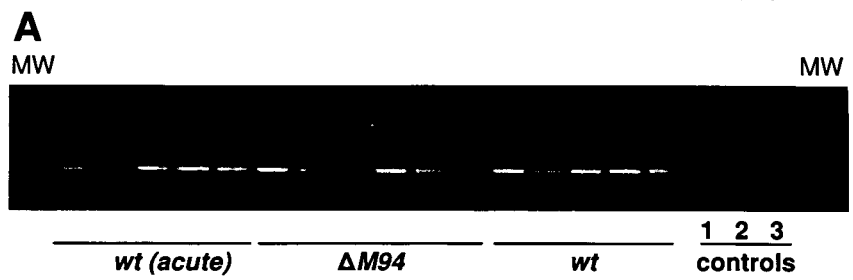
Figure 7:
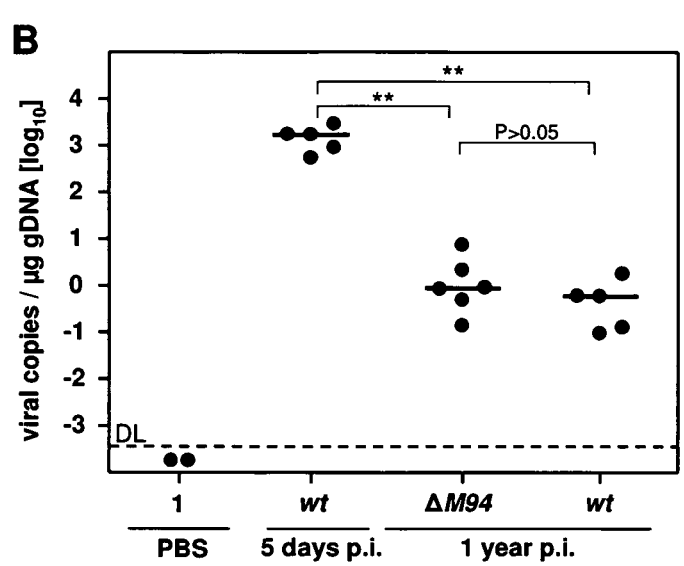
Figure 7:
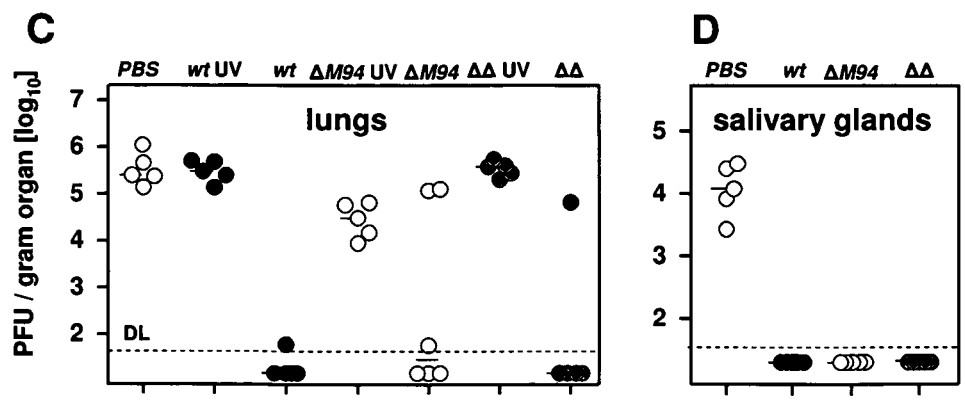

The results of this example are shown in FIG. 7.

B6 mice were infected i.p. with 10$^5$ TCID$_{50}$ MCMV-wt (wt) (n=5) or MCMV-ΔM94 (ΔM94) (n=6). Twelve months p.i. total DNA was extracted from lungs. (FIG. 7A) PCR analysis was performed obtaining a specific 246 bp fragment of the polymerase gene M54. As controls DNA from lungs five days after infection with 10$^5$ TCID$_{50}$ MCMV-wt (wt acute) (n=5), PBS (1), no template (2) or the BAC plasmid pSM3fr (3) were used. (FIG. 7B) Quantitative realtime PCR analysis was performed and viral M54 gene copies were calculated per μg genomic DNA. Each symbol represents one individual mouse. Horizontal bars show the median of each group. Genome copy numbers of MCMV-wt (wt) and MCMV-ΔM94 (ΔM94) are not significantly different (P>0.05). Both groups are significantly different compared to acutely infected lungs (wt acute) (**, P<0.01). MW=molecular weight marker; DL=detection limit. (FIG. 7C and FIG. 7D) B6 mice (n=5) were immunized i.p. with 10$^5$ TCID$_{50}$ MCMV-wt (wt; closed symbols), MCMV-ΔM94 (ΔM94; open symbols), Δm01-17+m144-158-MCMV (AA; gray symbols) or PBS (light gray symbols). Virus preparations were UV-irradiated before immunization (UV) as indicated. Challenge infection was applied i.v. one year post prime with 10$^6$ PFU MCMV-wt. Plaque assay was performed (FIG. 7C) five days post challenge with lungs and (FIG. 7D) 14 days post challenge with salivary glands (SG). Horizontal bars show the median of each group. Each symbol represents one individual mouse. DL=detection limit.

EXAMPLE 11

Vaccination with MCMV-ΔM94 Prevents Replication of Virus in the Respiratory Tract From epidemiological studies it was suggested that saliva is an important route of transmission of HCMV (Pass et al. 1986 N. Engl. J. Med 314:1414-1418.). To test whether the vaccine MCMV-ΔM94 is able to block virus replication in salivary glands and lungs C57BL/6 mice were immunized with MCMV-ΔM94 or control viruses and received twelve months later a challenge infection with 10$^6$ PFU MCMV-wt i.v. (FIGS. 7C and D). A single application of MCMV-ΔM94 was sufficient to suppress challenge virus replication by more than factor 1,000 in lungs in 4 out of 6 animals (FIG. 7C). Further, no challenge virus could be isolated from salivary glands 14 days after challenge (FIG. 7D). This implies that shedding of virus from the respiratory tract via saliva and therefore horizontal transmission via this route is abrogated by vaccination with spread-deficient MCMV.

EXAMPLE 12

Discussion

It is reported herein on the vaccination against a beta-herpesvirus using a spread-deficient vaccine. The vaccine induced a strong adaptive immune response comparable to MCMV-wt conferring protection even in highly immune compromised mice. This means that infection of the first target cells is sufficient for successful vaccination.

An intact immune system usually protects against HCMV disease. Hence, the antigenic capacity of the wild type virus is sufficient for the induction of a protective immune response. The inability of UV inactivated virus to protect efficiently against challenge infection demonstrated the need for viral antigen expression including nonstructural antigens (Cicin-Sain et al. 2007 supra; Gill et al. 2000 J Med Virol 62:127-139). As a consequence an ideal vaccine should exploit the full immunogenic but avoid the pathogenic potential of the wild type virus.

The alpha-herpesvirus field has pioneered the use of replication defective viruses as vaccines (Dudek et al. supra).

These vaccines were generated by the deletion of genes essential for virus replication and are thus apathogenic (Dudek et al. supra). Now, to construct a spread-deficient beta-herpesvirus vaccine deletion of M94 was chosen for the following reasons. First, M94 is essential for spread of MCMV and inferred from studies of HCMV it should be expressed with late kinetics during virus replication (Scott et al. supra; Wing et al. supra). Second, pM94 does not belong to the group of glycoproteins which comprise major targets for the neutralizing antibody response of HCMV. Third, M94 of MCMV is the homolog of UL94 in human CMV (Wing et al. supra) that in principle allows translation to the human pathogen. Finally, the deletion of UL94 of HCMV might even be of advantage because pUL94 induces autoreactive antibodies that are associated with systemic sclerosis (Lunardi et al. 2000 Nat Med 6:1183-1186). The SSc cross-reactive UL94 peptide is depicted in SEQ.ID:NO: 28. Interestingly, genomes of the spread-deficient MCMV-ΔM94 were detected in lungs after i.p. infection, showing that virus can disseminate either as free particles (Hsu et al. 2009 J Gen Virol 90:33-43) or associated to cells. Monocytes and macrophages were shown to be attracted to the peritoneal cavity after infection and transport the virus in blood (Stoddart et al. 1994 J Virol 68:6243-6253; van der Strate et al. 2003 J Virol 77:11274-11278). These cells could also release virus at distant sites to infect EC or other cell types, a process called trans infection (Halary et al. 2002 Immunity 17:653-664).

The spread-deficient beta-herpesvirus vaccine presented here, has a strong protective capacity similar to wild type CMV infection. The immune response of the vaccinee controls virus replication in all analysed organs preventing overt CMV-disease. The absence of detectable amounts of infectious virus in salivary glands of long-term vaccinated mice two weeks after challenge implies that also horizontal transmission to other individuals via saliva is abrogated. Because of this it is plausible that such an equivalent vaccine will protect against HCMV-disease, similar to the protective effect of a pre-existing infection. This is supported by the observation that women who were exposed to HCMV were at lower risk to give birth to children with symptomatic disease compared to non-infected women (Fowler et al. 2003 JAMA 289:1008-1011.). The seropositivity of the mother could not prevent infection but pathogenesis of the children. In addition, frequent exposure to different CMV strains could further increase immunity against reinfection (Adler et al. supra). It is therefore again plausible that a spread-deficient human CMV vaccine induces an immune response equal to natural infection which will protect against symptomatic human CMV infection without the risk for reactivation and pathogenesis.

The immune response to MCMV-ΔM94 reached a level comparable to MCMV-wt. Protection was similar to the recently generated vaccine Δm01-17+m144-158-MCMV (Cicin-Sain et al. 2007 supra) which lacks 32 viral genes but which is not spread-deficient in vitro. In Δm01-17+m144-158-MCMV immune evasive genes were deleted to increase the antiviral immune response and thereby to attenuate the virus (Scalzo et al. 2007 Immunol Cell Biol 85:46-54.).

It is within embodiments of the present invention that (a) at least one essential gene and (b) at least one immune evasive gene is deleted, whereby it is preferred that the deleted at least one immune evasive gene is selected from the group comprising genes encoding gene products affecting antigen presentation, interaction with cytokines, the complement system and humoral immunity. More preferably, the deleted at least one immune evasive gene is selected from the group comprising genes encoding gene products that down-regulate MHC I to avoid CTL response, gene products that evade the NK cell response, gene products that interfere with MHC II presentation, down-regulate adhesion molecules, gene products that interact with IL-1, gene products that activate TGF-β.

Infection of susceptible IFNαβR$^{-/-}$ mice with spread-deficient MCMV proved the safety of the vaccination concept. Furthermore, IFNαβR$^{-/-}$ mice were protected against otherwise lethal challenge, similar to other infection models (Calvo-Pinilla et al. 2009 PLoS One. 4:e5171; Paran et al. 2009 J Infect Dis 199:39-48). Although recent work revealed the capacity of MCMV to efficiently induce type I interferon (Hokeness-Antonelli et al. 2007 J Immunol 179:6176-6183), the efficacy of the spread-deficient MCMV vaccine in IFNαβR$^{-/-}$ mice implies that type I interferon-dependent immunity is not essential in the protection conferred by short term vaccination.

Interestingly, the spread-deficient MCMV induced an adaptive immune response with similar efficiency as MCMV-wt. The CD4$^+$ and CD8$^+$ T cell response was on the same level as MCMV-wt and the neutralizing antibody response was only marginally reduced. This slightly lower neutralizing capacity might be caused by the smaller number of infected cells and by the therefore reduced amount of antigen that is released after infection with MCMV-ΔM94. A lower number of antigen-antibody complexes might lead to less efficient affinity maturation creating antibodies of lower neutralizing capacity. Nevertheless, the neutralization of virus appears sufficient to control virus replication.

Why did the adaptive immune response to the vaccine reach a level near to MCMV-wt infection despite the inability to spread? MCMV-ΔM94 was able to establish viral genome maintenance as efficient as MCMV-wt. The classical definition of herpesviral latency includes the potential for reactivated gene expression with subsequent release of infectious virus (Roizman et al. 1987 Annu Rev Microbiol 41:543-571.). Although the term "latency" is formally not applicable to the situation with MCMV-ΔM94 in the absence of productive infection, there is no evidence that pM94 affects reactivation of gene expression. Because the protective effect of MCMV-ΔM94 rather increased than faded over time, the inventors believe that periodic restimulation of the immune response due to reactivation of gene expression contributed to the sustained protection induced by MCMV-ΔM94. Interestingly, virus infected cells are not eliminated by the activated immune response. This means that the first target cells that are infected by the spread-deficient vaccine are resistant to elimination. Similarly, cells infected with a spread-deficient mutant of the gamma herpesvirus MHV-68 were not attacked by the adaptive immune response (Tibbetts et al. 2006 Virology 353:210-219.). For MCMV-wt it was shown that T cells are activated against a highly antigenic virus epitope of M45 presented by professional APC but the activated T cells did not eliminate infected target cells in organs of C57BL/6 mice (Holtappels et al. 2004 J Exp Med 199:131-136). This protection was caused by m152, that is known to downmodulate MHC class I. The target cells that are protected from CD8$^+$ T cell elimination were not identified and it could be shown that at least some of these protected cells are first target cells of MCMV.

Endothelial cells (EC), hepatocytes (Hc) and macrophages are first target cells for HCMV and MCMV in vivo (Hsu et al. supra; Sacher et al. supra). In addition, EC have recently been identified as sites of virus latency (Seckert et al. 2009 J Virol 83:8869-8884), and at least liver EC are able to directly stimulate a cytotoxic T cell response (Kern et al. 2010 Gastroenterology 138(1):336-46). Using MCMV-ΔM94 constructs for conditional gene expression, substantial differences were noticed in the ability of EC and Hc to activate a CD8+ T cell response. In contrast to EC, Hc one of the most important first targets for MCMV during acute infection (Sacher et al. supra), induced only a poor CD8+ T cell response. This lack of stimulatory capacity is apparently not compensated by cross presentation through professional antigen presenting cells. Cross presentation was shown to be important for the induction of a T cell response against fibroblasts infected with a single-cycle MCMV (Snyder et al. 2010 PLoS One. 5:e9681). On the other hand, bone marrow derived APC, that are thought to be important cross presenting cells, seem not to be necessary for the activation of a CD8+ T cell response via cross presentation against MCMV infection (Kern et al. supra). In addition to EC also other cell types seem to contribute to CD8+ T cell stimulation as antigen expression in most infected cells led to a stronger T cell response than expression in infected EC only. Infected dendritic cells and macrophages were described to activate a T cell response against MCMV in vitro (Mathys et al. 2003 J Infect Dis 187:988-999) and are infected in vivo (Andrews et al. 2001 Nat Immunol 2:1077-1084). Therefore, it suggests itself that infected professional APC contribute to immune stimulation against MCMV in addition to EC. It appears noteworthy that the attenuated human CMV strains such as Towne and AD169 which are characterized by a 20-fold reduction of immunogenicity and the inability to confer immune protection (Adler et al. supra) accumulated mutations resulting in their inability to infect EC, epithelial cells, smooth muscle cells and macrophages (Hahn, G. et al. 2004 J Virol 78:10023-10033). Thus, it appears likely that the restricted cell tropism may in fact represent the cause for their failure as human CMV vaccines.

EXAMPLE 13

Spread-Assay of MCMV-ΔM94

The phenotype of MCMV-ΔM94 was analyzed in cell-to-cell spread. This was investigated by an in vitro spread assay as essentially described herein in Example 1 with the following mo modifications The results of this Example are shown in FIG. 9.

NIH/3T3 and NT/M94-7 cells were plated and infected with MCMVΔ1-16-FRT (dell-16) and MCMVΔM94tTA (Δ) at an MOI of 0.25 for 1 h and then washed twice with D-PBS. Cells were incubated for 6 h and afterwards washed four times with D-PBS. Equal numbers of non-infected cells were stained with 5 µM Carboxyfluorescein succinimidyl ester (CFSE) for 8 min and blocked by 2% FCS/D-PBS, then washed twice with 2% FCS/D-PBS, and subsequently seeded on top of the unstained but infected cells. Cells were fixed 48 hours post infection with 4% PFA in D-PBS for 10 min at 37° C. and washed and permeablized with 0.1% Triton X-100 for 10 min. After triple washing cells were blocked with 3% BSA/D-PBS for 1 h. Staining of immediate early gene products was performed by incubating fixed cells with a monoclonal antibody to MCMV immediate-early 1 in 3% BSA/D-PBS. After three D-PBS washes, cells were incubated with an Alexa Fluor 555-coupled anti-mouse secondary antibody (Invitrogen) in 3% BSA/D-PBS. Finally, cells were washed three times and imaged by confocal microscopy using a LSM 510 Meta (Zeiss). Virus transmission was determined by counting immediate-early 1- and CFSE-positive cells using the ImageJ Cell Counter plugin.

Figure 9:
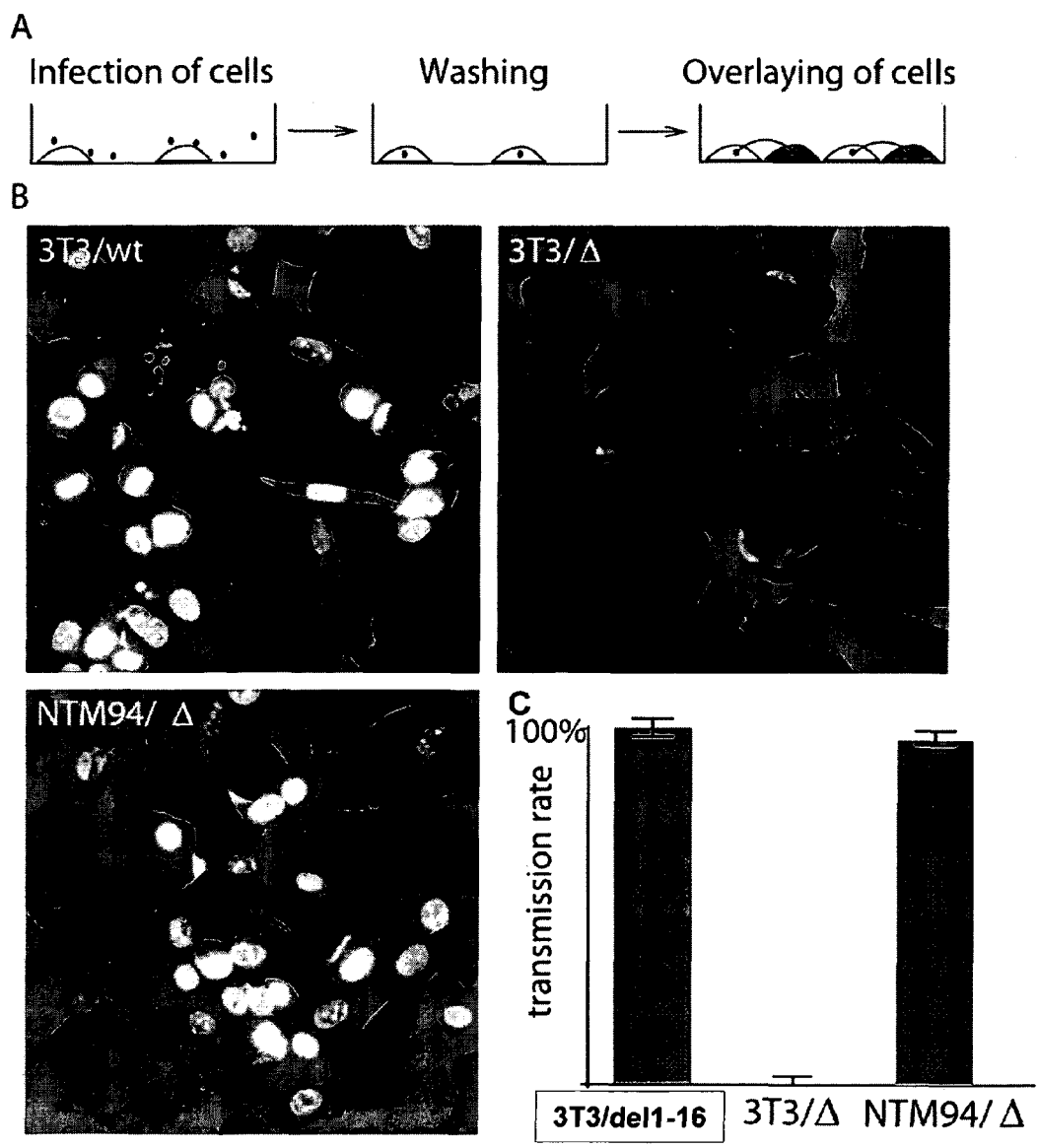

FIG. 9 shows that infection of NIH/3T3 and NT/M94-7 (NTM94) cells with MCMVΔ1-16-FRT (Mohr C A et al., Engineering of cytomegalovirus genomes for recombinant live herpesvirus vaccines; Int J Med. Microbiol. 2008 January; 298(1-2):115-25. Epub 2007 Aug. 16. Review) and MCMV-ΔM94, followed by removal of excess virus by extensive washes after infection. Next, CFSE stained NIH/3T3 were added and virus replication was permitted. After additional 48 h the culture was fixed and stained for immediate-early 1. This resulted in cells which were either immediate-early 1-positive, CFSE-positive or positive for both stains (FIG. 9 A). Stained cells were counted and cell-to-cell spread was determined by calculating the ratio between immediate-early 1-positive/CFSE stained cells to immediate-early 1-positive/CFSE-negative cells (FIG. 9 C). The spread rate of the MCMVΔ1-16-FRT was set as 100%. MCMVΔ1-16-FRT infection spreads rapidly throughout the cell culture as indicated by the large number double stained nuclei (FIG. 9 B). In contrast, the M94 deletion mutant did not infect the newly added cells. Only one double stained nucleus was seen after counting 416 immediate-early 1+/CFSE negative cells. Its ability to infect fresh cells was, however, restored to a transmission rate of 97% when the mutant was grown on complementing NT/M94-7 cells. It is thus evident that the effect of the M94 deletion on secondary envelopment of mouse CMV also resulted in a deficiency of cell-to-cell spread.

EXAMPLE 14

Propagation of Spread-Deficient Human CMV

Generation of the Trans-Complementing Cell Line TCL94/99-BP

Recombinant lentiviruses expressing a) UL99 coupled with EGFP (encoded by pCB-Ubic-UL99-IRES-gfp; SEQ.ID.No:18), b) UL99 coupled with UL94 mCherry (encoded by pCB-Ubic-UL94-IRES-mChe; SEQ.ID.No:17) and c) beta-lactamase coupled with puromycine resistance gene (encoded by pLV-Ubiqc-BLAs-IRES-Puro; SEQ.ID.No:19) were constructed and propagated by Sirion GmbH using ViraPower lentiviral packaging mix (Invitrogen) in 293FT cells (Invitrogen). $2 \times 10^6$ MRCS fibroblasts (ATCC CCL-171) were transduced by 5 TDU/cell (transduction units/cell) of each lentivirus by spin infection according to the manufacturer's protocol. The transduced cells were plated out on a 10 cm dish and were selected for 5 days with 20 µg/ml puromycin in OPTI-MEM 5% FCS. The tranduced cells were passaged (1:2) one time in the presence of 20 µg/ml puromycin and the double positive (mCherry+EGFP) cells were purified by fluorescence associated cell sorting and re-plated at density of $2.5 \times 10^4$ cell/cm$^2$. 48 h after confluency the cells were passaged (1:5) two more times in the presence of 20 µg/ml puromycin and re-sorted as above. After one more passage in OPTI-MEM 5% FCS+20 µg/ml puromycin the cells were aliquoted to $0.7 \times 10^7$ cell/vial and were deep frozen in OPTI-MEM supplemented with 10% FCS and 10% DMSO.

Construction of Spread-Deficient Human CMV

To generate a non-functional UL94 locus pTB40E-BAC4-FRT; SEQ.ID.No:20 (Scrivano L, et al., 2011. HCMV spread and cell tropism are determined by distinct virus populations. PLoS. Pathog. 7:e1001256; Sinzger, C. et al., 2008. Cloning and sequencing of a highly productive, endotheliotropic virus strain derived from human cytomegalovirus TB40/E. J. Gen. Virol. 89:359-368.) was introduced in GS1783 *E. coli* strain (Tischer, B. K. et al., 2010. En passant mutagenesis: a two step markerless red recombination system. Methods Mol. Biol. 634:421-430.). (a) Red-recombination was induced by electro-transformation of the synthetic DNA fragment LIFdel94; SEQ.ID.No:15 according to the standard protocol (Tischer, B. K. et al., supra) resulting in pTB40E-BAC4-delUL94-SZeo. Recombinants were selected by picking single clones after plating the transformants on LB agar plates in the presence of 25 µg/ml chloramphenicol and 30 µg/ml zeocin. The correct replacement of the BAC sequences from nt122630 to 123668 referring to SEQ.ID.No:20 with LIFde-IUL94, SEQ.ID.No:15 was confirmed by restrictions pattern analysis and sequencing. (b) To remove the zeocin cassette from the UL94 locus, a second round of Red recombination was induced in liquid culture of pTB40E-BAC4-delUL94-Szeo according to the standard protocol (Tischer, B. K. et al., supra) in presence of 25 µg/ml chloramphenichol and 2% of L-arabinose. Recombinants, which were coined pTB40E-BAC4-del94, were selected by picking single clones after plating of the recombinants on LB agar plates in the presence of 25 µg/ml chloramphenicol 1% of L-arabinose. The correct removal of the operational sequences were confirmed by restrictions pattern analysis and sequencing. (c) A next red-recombination was induced by electro-transformation of the synthetic mutagenesis fragment LIFdel99, SEQ.ID.No:16, as described above (see a) herein) resulting in pTB40E-BAC4-delUL94-del99-SZeo. Recombinants were selected by picking single clones after plating the transformants on LB agar plates in the presence of 25 µg/ml chloramphenicol and 30 µg/ml zeocin. The correct replacement of the sequences from nt 130670 to 131243 (according to the numbering of the BAC referred to herein as SEQ.ID.No:20) was confirmed by restrictions pattern analysis and sequencing. (d) To remove the zeocin cassette from the UL99 locus, a final round of red-recombination was induced in liquid culture of pTB40E-BAC4-delUL94-delUL99-Szeo as above (see b) herein). Recombinants, which were coined pTB40E-BAC4-del94-del99, were selected by picking single clones after plating of the recombinants on LB agar plates in the presence of 25 µg/ml chloramphenicol 1% of L-arabinose. The correct removal of the operational sequences from the UL99 locus were confirmed by restrictions pattern analysis and sequencing. 1. The description of the BAC modifications in the new way are the following:

M1) To generate a non-functional UL94 (or inactivate the UL94 gene) the nt sequence of pTB40E-BAC4-FRT (SEQ.ID.No:20) between nt 122630 and nt 123668 is replaced by the synthetic fragment delUL94S (SEQ.ID.No:34).

M2) To generate a non-functional UL99 (or inactivate the UL99 gene) the nt sequence of pTB40E-BAC4-FRT (SEQ.ID.No:20) between nt 130670 and nt 131243 is replaced by the synthetic fragment delUL99S (SEQ.ID.No:35). For the double mutant of UL94-UL99 this has to be done in addition to modification M1.

M3) To generate a non-functional UL50 (or inactivate the UL50 gene) the nt sequence of pTB40E-BAC4-FRT (SEQ.ID.No:20) between nt 58442 and nt 59622 is replaced by the synthetic fragment delUL50S (SEQ.ID.No:32).

M4) To generate a non-functional UL53 (or inactivate the UL53 gene) the nt sequence of pTB40E-BAC4-FRT (SEQ.ID.No:20) between nt 62129 and nt 63261 is replaced by the synthetic fragment delUL53S (SEQ.ID.No:33). For the double mutant of UL50-UL53 this has to be done in addition to modification M3.

Reconstitution of Spread-Deficient Human CMV.

$0.7 \times 10^7$ frozen TCL94/99-BP cells were plated on a 10 cm dish in OPTI-MEM 5% FCS containing 0.2 µg/ml puromycin and two days later the adherent cell were split and plated on 6 cm dishes at densities of $2 \times 10^6$ cells per dish. On the next day two 6 cm cultures were transfected with 2 µg of purified pTB40E-BAC4-FRT-del94-del99-DNA each by Lipofectamin 2000 (Invitrogen) according to the manufacturer's protocol. 24 h later the two culture were combined and plated on a 10 cm dish in OPTI-MEM 5% FCS. After 10 days the reconstitution of the recombinant TB40E-BAC4-FRT-del94-del99 virus was evident by plaque formation. After 14-16 days the most of the cells in the transfected cultures showed CPE the entire culture was harvested. The amounts of the viable viruses was determined by limiting dilution on sub-confluent TCL94/99-BP cell in 96 well plates using TCID50 (median tissue culture infectious dose) method as described in Mohr et al (Mohr, C. A. et al., 2010. A spread-deficient cytomegalovirus for assessment of first-target cells in vaccination. Virol. 2010 August; 84(15):7730-42. Epub 2010 May 12.). The spread-deficient human CMV reconstituted from TB40E-BAC4-FRTdel94-99, can be propagated using TCL94/99-BP cells after infection with 0.1 MOI per cell using standard protocols for propagation of human CMV as described by Scrivano et al. (Scrivano et al., supra).

HCMV lacking secondary envelopment complex, i.e. UL99 and UL94, is spread-deficient.

The phenotype of the UL94-UL99 double deletion CMV reconstituted from TB40E-BAC4-FRTdel94-99 was tested in cell-to-cell spread. This was investigated by infection of MRC5 and TCL94/99-BP cells as essentially described in Example 1 herein, with CMVs reconstituted from TB40E-BAC4-FRT-del94-del99 and TB40E-BAC4-FRT, respectively, followed by removal of excess virus by extensive washing after infection. Next, CFSE stained MRC5 cells were added and virus replication was permitted. After additional 72 h the culture was fixed and stained for immediate-early 1 expression as described in Example 1 herein. This resulted in cells which were either "immediate-early 1"-positive, CFSE-positive or positive for both stains. These cells were counted in each preparation. The missing increase of double positive cells in MRC5 after infection with TB40E-BAC4-FRT-del94-del99 is conclusive to a deficiency in cell-to-cell spread.

EXAMPLE 15

Immunization with Spread-Deficient Human CMV

After primary immunization with an additional boost with spread-deficient human CMV the human sera exhibit at least 64-fold higher neutralizing potency against endotheliotropic a human CMV strains such as TB40E or VR1814 assayed on endothelial- or epithelial cells (such as HUVEC [ATCC CRL 1730]- or ARPE-19 [ATCC CRL2302], respectively, than against the same virus assayed on human fibroblasts cell line (such as MRC5, ATCC CLL-171). In addition, specific antibody response is detectable against the gene products of UL130, UL128, or UL131A by Western blot (whereby it is sufficient that at least one specificity is seen).

The following deletions of the indicated genes result in recombinant human beta-herpesviruses which are spread-deficient:

| Effector complex | UL50 gene | UL53 gene | UL94 gene | UL99 gene |
| --- | --- | --- | --- | --- |
| NEC | + | | | |
| NEC | | + | | |
| NEC | + | + | | |
| SEC | | | + | |
| SEC | | | + | + |

The features of the present invention disclosed in the specification, the claims, the sequence listing and/or the drawings may both separately and in any combination thereof be material for realizing the invention in various forms thereof. It has to be acknowledged that the sequence listing is part of the instant specification.

The invention claimed is:

1. A recombinant human cytomegalovirus (HCMV), wherein said virus comprises a deletion of nucleotides 122631-123667 and 181653-189191 of SEQ ID NO: 20, and wherein SEQ ID NO: 34 is inserted into said virus to replace deleted nucleotides 12263-123667 from SEQ ID NO: 20.

2. The recombinant HCMV according to claim 1, wherein said virus further comprises a deletion of nucleotides 130671-131242 of SEQ ID NO: 20.

3. The recombinant HCMV according to claim 2, wherein SEQ ID NO: 35 is inserted into said virus to replace deleted nucleotides 130671-131242 from SEQ ID NO: 20.

4. A recombinant HCMV, wherein said virus comprises a deletion of nucleotides 58443-59622, 181653-189191 of SEQ ID NO: 20, and wherein SEQ ID NO: 32 is inserted into said virus to replace deleted nucleotides 58443-59622 from SEQ ID NO: 20.

5. A recombinant HCMV, wherein said virus comprises a deletion of nucleotides 62130-63260 and 181653-189191 of SEQ ID NO: 20, and wherein SEQ ID NO: 33 is inserted into said virus to replace deleted nucleotides 62130-63260 from SEQ ID NO: 20.

6. The HCMV of claim 5, further comprising a deletion of nucleotides 58443-59622.

7. The HCMV of claim 6, wherein SEQ ID NO: 32 is inserted into said virus to replace deleted nucleotides 58443-59622 from SEQ ID NO: 20.

8. An isolated host cell comprising a nucleic acid according to any one of claim 1, 2, 3, 4, 5, 6, or 7.

9. A pharmaceutical composition comprising the HCMV of any one of claim 1, 2, 3, 4, 5, 6, or 7, and a pharmaceutically acceptable carrier.

* * * * *

SEQUENCE LISTING

<160> NUMBER OF SEQ ID NOS: 35

<210> SEQ ID NO 1
<211> LENGTH: 57
<212> TYPE: DNA
<213> ORGANISM: Artificial
<220> FEATURE:
<223> OTHER INFORMATION: synthetic
<220> FEATURE:
<221> NAME/KEY: misc_feature
<223> OTHER INFORMATION: DNA

<400> SEQUENCE: 1
gtgggatcca ccatgtaccc ctacgacgtg cccgactacg ccacgtccag actatcc    57

<210> SEQ ID NO 2
<211> LENGTH: 34
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 2
actctagagt cgacttcaca tgtgctcgag aaca    34

<210> SEQ ID NO 3
<211> LENGTH: 71
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 3
aattcatgat aacttcgtat agcatacatt atacgaagtt atccggagat atccaccggt    60
ctggcggccg c    71

<210> SEQ ID NO 4
<211> LENGTH: 71
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 4
tcgagcggcc gccagaccgg tggatatctc cggataactt cgtataatgt atgctatacg    60
aagttatcat g    71

<210> SEQ ID NO 5
<211> LENGTH: 68
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 5

-continued

```
cgtggtcaag ccggtcgtgt tgtaccagaa ctcgacttcg gtcgcgttgc ttacaattta    60
cgcgcggg                                                              68

<210> SEQ ID NO 6
<211> LENGTH: 69
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 6
ccccgatatt tgagaaagtg taccccgata ttcagtacct cttgactaag aagccataga    60
gcccaccgc                                                             69

<210> SEQ ID NO 7
<211> LENGTH: 112
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 7
tgcttcccgg cggcttctgc gcgaccttcc agctgcaggt agaccacggc gacgtccaga    60
ctatccgtga aaagtttgag aagcatcagt agccgatttc ggcctattgg tt           112

<210> SEQ ID NO 8
<211> LENGTH: 77
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 8
catggatggg ttggttgatt tgtatgtctg ttggctactc acatgtgctc gagaagccag    60
tgtgatggat gatcctc                                                    77

<210> SEQ ID NO 9
<211> LENGTH: 8
<212> TYPE: PRT
<213> ORGANISM: Artificial
<220> FEATURE:
<223> OTHER INFORMATION: synthetic
<220> FEATURE:
<221> NAME/KEY: PEPTIDE
<222> LOCATION: (1)..(8)

<400> SEQUENCE: 9

Ser Ile Ile Asn Phe Glu Lys Leu
1               5

<210> SEQ ID NO 10
<211> LENGTH: 8
<212> TYPE: PRT
<213> ORGANISM: Artificial
<220> FEATURE:
<223> OTHER INFORMATION: synthetic
<220> FEATURE:
```

```
<221> NAME/KEY: PEPTIDE
<222> LOCATION: (1)..(8)

<400> SEQUENCE: 10

Thr Val Tyr Gly Phe Cys Leu Leu
1               5

<210> SEQ ID NO 11
<211> LENGTH: 8
<212> TYPE: PRT
<213> ORGANISM: artificial
<220> FEATURE:
<223> OTHER INFORMATION: synthetic
<220> FEATURE:
<221> NAME/KEY: PEPTIDE
<222> LOCATION: (1)..(8)

<400> SEQUENCE: 11

Arg Ala Leu Glu Tyr Lys Asn Leu
1               5

<210> SEQ ID NO 12
<211> LENGTH: 9
<212> TYPE: PRT
<213> ORGANISM: artificial
<220> FEATURE:
<223> OTHER INFORMATION: synthetic
<220> FEATURE:
<221> NAME/KEY: PEPTIDE
<222> LOCATION: (1)..(9)

<400> SEQUENCE: 12

Ser Cys Leu Glu Phe Trp Gln Arg Val
1               5

<210> SEQ ID NO 13
<211> LENGTH: 9
<212> TYPE: PRT
<213> ORGANISM: artificial
<220> FEATURE:
<223> OTHER INFORMATION: synthetic
<220> FEATURE:
<221> NAME/KEY: PEPTIDE
<222> LOCATION: (1)..(9)

<400> SEQUENCE: 13

His Gly Ile Arg Asn Ala Ser Phe Ile
1               5

<210> SEQ ID NO 14
<211> LENGTH: 25
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: DNA

<400> SEQUENCE: 14
aacgtacatc gctctctgct ggccg                                          25

<210> SEQ ID NO 15
<211> LENGTH: 940
<212> TYPE: DNA
<213> ORGANISM: artificial
<220> FEATURE:
<223> OTHER INFORMATION: synthetic
```

<400> SEQUENCE: 15

```
ttactgggtg ctgccgggcg gctttgccgt ctcttcgcgc gtcactcttc acggcctggc    60
ccagcgagcc ctgcgggacc ggttccaaaa cttcgaggcc gtgctggccc ggggcatgca   120
cgtggaggcc ggccggcagg agcccgagac ccccgggtg agcggccggc ggctgccctt    180
cgacgacctg tgatccggag gacgacggct cgtgtatctt gtgccaattg ctgttgctct   240
accgcgacgg cgaatggatc ctctgtcttt gctgcaacgg ccgttatcaa ggccactatg   300
gcggggtctg acagttcacg gggagaagaa acaagaaaca acaaaaaaaa agaggagat   360
ctgcggccgc tagggataac agggtaatcg atgttgacaa ttaatcatcg gcatagtata   420
tcggcatagt ataatacgac aaggtgagga actaaaccat ggcaaaactg accagcgcag   480
ttccggttct gaccgcacgt gatgttgccg gtgccgttga attttggacc gatcgtctgg   540
gttttagccg tgattttgtg gaagatgatt ttgccggtgt tgttcgtgat gatgttaccc   600
tgtttattag cgcagttcag gatcaggttg ttccggataa taccctggca tgggtttggg   660
ttcgtggtct ggatgaactg tatgcagaat ggtcagaagt tgtgagcacc aattttcgtg   720
atgcaagcgg tccggcaatg accgaaattg tgaacagcc gtggggtcgt gaatttgcac    780
tgcgtgatcc ggcaggtaat tgtgttcatt ttgttgcaga agaacaggat taacctcgat   840
taattaattg taacattacc ctgttatccc taccggtgtc ctaggcgggg tctgacagtt   900
cacggggaga agaaacaaga aacaacaaaa aaaaagagg                          940
```

<210> SEQ ID NO 16
<211> LENGTH: 719
<212> TYPE: DNA
<213> ORGANISM: artificial
<220> FEATURE:
<223> OTHER INFORMATION: synthetic

<400> SEQUENCE: 16

```
cgtgttagac cgttggagtc gcgacctgtc ccgcaagacg aacctaccga tctgggtcgc    60
caacagcgcc aacgagtacg tcgtcagctc cgtgccccgc cccgtcagtc cgtagaagta   120
actcataaac tttcaggtct cgcgtacgat tcgcgagtcg ggaatgtagg ataacaggg    180
taatcgatgt tgacaattaa tcatcggcat agtatatcgg catagtataa tacgacaagg   240
tgaggaacta aaccatggca aaactgacca gcgcagttcc ggttctgacc gcacgtgatg   300
ttgccggtgc cgttgaattt tggaccgatc gtctgggttt tagccgtgat tttgtggaag   360
atgattttgc cggtgttgtt cgtgatgatg ttaccctgtt tattagcgca gttcaggatc   420
aggttgttcc ggataatacc ctggcatggg tttgggttcg tggtctggat gaactgtatg   480
cagaatggtc agaagttgtg agcaccaatt ttcgtgatgc aagcggtccg gcaatgaccg   540
aaattggtga acagccgtgg ggtcgtgaat ttgcactgcg tgatccggca ggtaattgtg   600
ttcattttgt tgcagaagaa caggattaac ctcgattaat taattgtaac attaccctgt   660
tatccctaaa gtaactcata aactttcagg tctcgcgtac gattcgcgag tcgggaatg   719
```

<210> SEQ ID NO 17
<211> LENGTH: 9048
<212> TYPE: DNA
<213> ORGANISM: artificial
<220> FEATURE:
<223> OTHER INFORMATION: synthetic

<400> SEQUENCE: 17

```
actagtcggg gtcattagtt catagcccat atatggagtt ccgcgttaca taacttacgg    60
```

-continued

```
taaatggccc gcctggctga ccgcccaacg accccccgccc attgacgtca ataatgacgt    120
atgttcccat agtaacgcca atagggactt tccattgacg tcaatgggtg gagtatttac    180
ggtaaactgc ccacttggca gtacatcaag tgtatcatat gccaagtacg cccccctattg   240
acgtcaatga cggtaaatgg cccgcctggc attatgccca gtacatgacc ttatgggact    300
ttcctacttg gcagtacatc tacgtattag tcatcgctat taccatggtg atgcggtttt    360
ggcagtacat caatgggcgt ggatagcggt ttgactcacg gggatttcca agtctccacc    420
ccattgacgt caatgggagt ttgttttggc accaaaatca acgggacttt ccaaaatgtc    480
gtaacaactc cgccccattg acgcaaatgg gcggtaggcg tgtacggtgg gaggtctata    540
taagcagagc tggtttagtg aaccgggtct ctctggttag accagatttg agcctgggag    600
ctctctggct aactagggaa cccactgctt aagcctcaat aaagcttgcc ttgagtgctt    660
caagtagtgt gtgcccgtct gttgtgtgac tctggtaact agagatccct cagacccttt    720
tagtcagtgt ggaaaatctc tagcagtggc gcccgaacag ggacctgaaa gcgaaaggga    780
aaccagagga gctctctcga cgcaggactc ggcttgctga agcgcgcacg gcaagaggcg    840
aggggcggcg actgcagagt acgccaaaaa ttttgactag cggaggctag aaggagagag    900
atgggtgcga gagcgtcagt attaagcggg ggaaaatagc ggccgccaca atttaaaag     960
aaaggggggg attgggggt acagtgcagg ggaaagaata gtagacataa tagcaacaga    1020
catacaaact aaagaattac aaaaacaaat tacaaaaatt caaattttcg ggggatccca    1080
tggtggccct cctatagtga gtcgtattat actatgccga tatactatgc cgatgattaa    1140
ttgtcaacac gtgctgcagg tccgaggttc tagcgcgtgg cctccgcgcc gggttttggc    1200
gcctcccgcg ggcgccccccc tcctcacggc gagcgctgcc acgtcagacg aagggcgcag   1260
cgagcgtcct gatccttccg cccggacgct caggacagcg gcccgctgct cataagactc    1320
ggccttagaa ccccagtatc agcagaagga cattttagga cgggacttgg gtgactctag    1380
ggcactggtt ttctttccag agagcggaac aggcgaggaa aagtagtccc ttctcggcga    1440
ttctgcggag ggatctccgt ggggcggtga acgccgatga ttatataagg acgcgccggg    1500
tgtggcacag ctagttccgt cgcagccggg atttgggtcg cggttcttgt tgtggatcg    1560
ctgtgatcgt cacttggtga gtagcgggct gctgggctgg ccggggcttt cgtggccgcc    1620
gggccgctcg gtgggacgga agcgtgtgga gagaccgcca agggctgtag tctgggtccg    1680
cgagcaaggt tgccctgaac tgggggttgg ggggagcgca gcaaaatggc ggctgttccc    1740
gagtcttgaa tggaagacgc ttgtgaggcg ggctgtgagg tcgttgaaac aaggtggggg    1800
gcatggtggg cggcaagaac ccaaggtctt gaggccttcg ctaatgcggg aaagctctta    1860
ttcgggtgag atgggctggg gcaccatctg ggaccctgac gtgaagtttg tcactgact     1920
ggagaactcg gtttgtcgtc tgttgcgggg gcggcagtta tggcggtgcc gttgggcagt    1980
gcacccgtac ctttgggagc gcgcgccctc gtcgtgtcgt gacgtcaccc gttctgttgg    2040
cttataatgc agggtggggc cacctgccgg taggtgtgcg gtaggctttt ctccgtcgca    2100
ggacgcaggg ttcgggccta gggtaggctc tcctgaatcg acaggcgccg gacctctggt    2160
gaggggaggg ataagtgagg cgtcagtttc tttggtcggt tttatgtacc tatcttctta    2220
agtagctgaa gctccggttt tgaactatgc gctcggggtt ggcgagtgtg ttttgtgaag    2280
ttttttaggc acctttttgaa atgtaatcat ttgggtcaat atgtaatttt cagtgttaga    2340
ctagtaaatt gtccgctaaa ttctggccgt ttttggcttt tttgttagac gctagcctag    2400
```

-continued

```
cggatccgaa ttctgcagat atcaacaagt ttgtacaaaa aagcaggctt aatggcttgg      2460
cgcagcgggc tttgcgagac cgattccaga actttgaagc agttcttgca agaggaatgc      2520
atgtggaagc tggtcggcaa gagccggaaa caccgcgagt atcgggccgt cgcttgccgt      2580
tcgacgatct ttagtccgga ggacgacggc tcgtgtatct tgtgccaatt gctgttgctc      2640
taccgcgacg gcgaatggat cctctgtctt tgctgcaacg gccgttatca aggccactat      2700
ggcgtgggcc acgtacatcg gcgtcgtcga cgcatctgtc atttacctac cttgtaccaa      2760
ctgagcttcg gaggtccttt gggtccagcc agcattgatt tcttgccaag cttttagccag     2820 gtgaccagca gtatgacgtg cgatggtatt acgcccgacg tgatttacga ggtctgcatg      2880
ttggtgcccc aggatgaagc caagcgcatc ctggtcaagg gtcacggtgc catggacctg      2940
acctgtcaga aggcagtgac gctaggcggc gccggcgcct ggttgctgcc gcgtcccgaa      3000
ggctacacgc ttttcttta cattctgtgc tacgacctgt ttacctcatg cggcaatcgg       3060
tgcgatatcc cttccatgac gcggctcatg cggcggccca cggcctgcgg gcaggcgggt     3120
tgcagctttt gcacggatca cgagggacat gtagatccca ctggcaatta cgtgggttgc     3180 accccccgata tgggccgctg tctttgttac gtgccctgtg ggcccatgac gcagtcgctc     3240
atccacaacg atgaacccgc gacttttttc tgtgagagcg atgacgccaa ataccaatgc     3300
gccgtaggtt ctaagaccgc ggcgcaggtc acactgggag acggcctgga ttatcacatc     3360
ggtgtcaagg attctgaggg ccgatggttg cccgtcaaga ccgatgtgtg ggacctggtc      3420
aaggtagagg aacctgtgtc acgtatgata gtgtgttcct gtccggtgct aagaaccta      3480 gtgcactaaa cccagctttc ttgtacaaag tggttgatat ccagcacagt ggcggccgct     3540
cgagtctaga gggcccgcgg ttcgaaggta agcctatccc taaccctctc ctcggtctcg     3600
attctacgcg ccgcggccgc tacgtaaatt ccgcccctct ccctaacgtt actggccgaa     3660
gccgcttgga ataaggccgg tgtgcgtttg tctatatgtt attttccacc atattgccgt      3720
cttttggcaa tgtgagggcc cggaaacctg gccctgtctt cttgacgagc attcctaggg     3780
gtctttcccc tctcgccaaa ggaatgcaag gtctgttgaa tgtcgtgaag gaagcagttc      3840
ctctggaagc ttcttgaaga caaacaacgt ctgtagcgac cctttgcagg cagcggaacc     3900
ccccacctgg cgacaggtgc ctctgcggcc aaaagccacg tgtataagat acacctgcaa     3960
aggcggcaca cccccagtgc cacgttgtga gttggatagt tgtggaaaga gtcaaatggc     4020
tctcctcaag cgtattcaac aaggggctga aggatgccca gaaggtaccc cattgtatgg     4080
gatctgatct ggggcctcgg tgcacatgct ttacatgtgt ttagtcgagg ttaaaaaacg      4140
tctaggcccc ccgaaccacg gggacgtggt tttcctttga aaaacacgat gataatatgg     4200
ccacaaccat gaccgagtac aagcccacgg tgcgcctcgc cacccgcgac gacgtccccc     4260
gggccgtacg ggatcccgcc accatggtga gcaagggcga ggaggataac atggccatca     4320
tcaaggagtt catgcgcttc aaggtgcaca tggagggctc cgtgaacggc cacgagttcg     4380
agatcgaggg cgagggcgag ggccgcccct acgagggcac ccagaccgcc aagctgaagg    4440
tgaccaaggg tggccccctg cccttcgcct gggacatcct gtcccctcag ttcatgtacg    4500
gctccaaggc ctacgtgaag caccccgccg acatccccga ctacttgaag ctgtccttcc     4560
ccgagggctt caagtgggag cgcgtgatga acttcgagga cggcggcgtg gtgaccgtga     4620
cccaggactc ctccctgcag gacggcgagt tcatctacaa ggtgaagctg cgcggcacca    4680
acttcccctc cgacggcccc gtaatgcaga agaagaccat gggctgggag gcctcctccg    4740
agcggatgta ccccgaggac ggcgccctga agggcgagat caagcagagg ctgaagctga    4800
```

```
aggacggcgg ccactacgac gctgaggtca agaccaccta caaggccaag aagcccgtgc    4860
agctgcccgg cgcctacaac gtcaacatca agttggacat cacctcccac aacgaggact    4920
acaccatcgt ggaacagtac gaacgcgccg agggccgcca ctccaccggc ggcatggacg    4980
agctgtacaa gtaagtcgac ccggaccgcc acatcgagcg ggtcaccgag ctgcaagaac    5040
tcttcctcac gcgcgtcggg ctcgacatcg gcaaggtgtg ggtcgcggac gacggcgccg    5100
cggtggcggt ctggaccacg ccggagagcg tcgaagcggg ggcggtgttc gccgagatcg    5160
gctcgcgcat ggccgagttg agcggttccc ggctggccgc gcagcaacag atggaaggcc    5220
tcctggcgcc gcaccggccc aaggagcccg cgtggttcct ggccaccgtc ggcgtctcgc    5280
ccgaccacca gggcaagggt ctgggcagcg ccgtcgtgct ccccggagtg gaggcggccg    5340
agcgcgctgg ggtgcccgcc ttcctggaga cctccgcgcc ccgcaacctc cccttctacg    5400
agcggctcgg cttcaccgtc accgccgacg tcgaggtgcc cgaaggaccg cgcacctggt    5460
gcatgacccg caagcccggt gcctgagttc gcgtctggaa caatcaacct ctggactcga    5520
caatcaacct ctggattaca aaatttgtga agattgact ggtattctta actatgttgc    5580
tccttttacg ctatgtggat acgctgcttt aatgcctttg tatcatgcta ttgcttcccg    5640
tatggctttc attttctcct ccttgtataa atcctggttg ctgtctcttt atgaggagtt    5700
gtggcccgtt gtcaggcaac gtggcgtggt gtgcactgtg tttgctgacg caacccccac    5760
tggttggggc attgccacca cctgtcagct cctttccggg actttcgctt tccccctccc    5820
tattgccacg gcggaactca tcgccgcctg ccttgcccgc tgctggacag gggctcggct    5880
gttgggcact gacaattccg tggtgttgtc ggggaaatca tcgtcctttc cttggctgct    5940
cgcctgtgtt gccacctgga ttctgcgcgg gacgtccttc tgctacgtcc cttcggccct    6000
caatccagcg gaccttcctt cccgcggcct gctgccggct ctgcggcctc ttccgcgtct    6060
tcgccttcgc cctcagacga gtcggatctc cctttgggcc gcctcccgc ttagtactgg    6120
tacctttaag accaatgact tacaaggcag ctgtagatct tagccacttt ttaaaagaaa    6180
agggggact ggaagggcta attcactccc aacgaagaca agattccgga atttatttgt    6240
gaaatttgtg atgctattgc tttatttgta accggtgca gctgcttttt gcctgtactg    6300
ggtctctctg gttagaccag atctgagcct gggagctctc tggctaacta gggaacccac    6360
tgcttaagcc tcaataaagc ttgccttgag tgcttcaagt agtgtgtgcc cgtcgtttgt    6420
gtgactctgg taactagaga tccctcagac ccttttagtc agtgtggaaa atctctagca    6480
tctagagtat gcaaagcatg catctcaatt agtcagcaac caggtgtgga agtccccag    6540
gctccccagc aggcagaagt atgcaaagca tgcatctcaa ttagtcagca accatagtcc    6600
cgcccctaac tccgcccatc ccgcccctaa ctccgcccag ttccgcccat tctccgcccc    6660
atggctgact aatttttttt atttatgcag aggccgaggc cgcctcggcc tctgagctat    6720
tccagaagta gtgaggaggc ttttttggag gcctaggcta gagatcataa tcagccatac    6780
cacatttgta gaggttttac ttgctttaaa aaacctccca cacctccccc tgaacctgaa    6840
acataaaatg aatgcaattg ttgttgttaa cttgtttatt gcagcttata atggttacaa    6900
ataaagcaat agcatcacaa atttcacaaa taaagcattt ttttcactgc attctagttg    6960
tggtttgtcc aaactcatca atgtatctta tcatgtctgc tagccgggct tttttttctt    7020
aggccttctt ccgcttcctc gctcactgac tcgctgcgct cggtcgttcg gctgcggcga    7080
gcggtatcag ctcactcaaa ggcggtaata cggttatcca cagaatcagg ggataacgca    7140
```

| | |
|---|---:|
| ggaaagaaca tgtgagcaaa aggccagcaa aaggccagga accgtaaaaa ggccgcgttg | 7200 |
| ctggcgtttt tccataggct ccgcccccct gacgagcatc acaaaaatcg acgctcaagt | 7260 |
| cagaggtggc gaaacccgac aggactataa agataccagg cgtttccccc tggaagctcc | 7320 |
| ctcgtgcgct ctcctgttcc gaccctgccg cttaccggat acctgtccgc ctttctccct | 7380 |
| tcgggaagcg tggcgctttc tcatagctca cgctgtaggt atctcagttc ggtgtaggtc | 7440 |
| gttcgctcca agctgggctg tgtgcacgaa ccccccgttc agcccgaccg ctgcgcctta | 7500 |
| tccggtaact atcgtcttga gtccaacccg gtaagacacg acttatcgcc actggcagca | 7560 |
| gccactggta acaggattag cagagcgagg tatgtaggcg gtgctacaga gttcttgaag | 7620 |
| tggtggccta actacggcta cactagaaga acagtatttg gtatctgcgc tctgctgaag | 7680 |
| ccagttacct tcggaaaaag agttggtagc tcttgatccg gcaaacaaac caccgctggt | 7740 |
| agcggtggtt tttttgtttg caagcagcag attacgcgca gaaaaaaagg atctcaagaa | 7800 |
| gatcctttga tcttttctac ggggtctgac gctcagtgga acgaaaactc acgttaaggg | 7860 |
| attttggtca tgagattatc aaaaaggatc ttcacctaga tccttttaaa ttaaaaatga | 7920 |
| agttttaaat caatctaaag tatatatgag taaacttggt ctgacagtta ccaatgctta | 7980 |
| atcagtgagg cacctatctc agcgatctgt ctatttcgtt catccatagt tgcctgactc | 8040 |
| ctgcgcagtc caaaaaaaaa ggctccaaaa ggagccttta attgtatcgg tgggccctta | 8100 |
| gaaaaactca tcgagcatca atgaaactg caatttattc atatcaggat tatcaatacc | 8160 |
| atatttttga aaaagccgtt tctgtaatga aggagaaaac tcaccgaggc agttccatag | 8220 |
| gatggcaaga tcctggtatc ggtctgcgat tccgactcgt ccaacatcaa tacaacctat | 8280 |
| taatttcccc tcgtcaaaaa taaggttatc aagtgagaaa tcaccatgag tgacgactga | 8340 |
| atccggtgag aatggcaaaa gcttatgcat ttctttccag acttgttcaa caggccagcc | 8400 |
| attacgctcg tcatcaaaat cactcgcatc aaccaaaccg ttattcattc gtgattgcgc | 8460 |
| ctgagcgaga cgaaatacgc gatcgctgtt aaaaggacaa ttacaaacag gaatcgaatg | 8520 |
| caaccggcgc aggaacactg ccagcgcatc aacaatattt tcacctgaat caggatattc | 8580 |
| ttctaatacc tggaatgctg ttttcccggg gatcgcagtg gtgagtaacc atgcatcatc | 8640 |
| aggagtacgg ataaaatgct tgatggtcgg aagaggcata aattccgtca gccagtttag | 8700 |
| tctgaccatc tcatctgtaa catcattggc aacgctacct ttgccatgtt tcagaaacaa | 8760 |
| ctctggcgca tcgggcttcc catacaatcg atagattgtc gcacctgatt gcccgacatt | 8820 |
| atcgcgagcc catttatacc catataaatc agcatccatg ttggaattta atcgcggcct | 8880 |
| cgagcaagac gtttcccgtt gaatatggct cataacaccc cttgtattac tgtttatgta | 8940 |
| agcagacagt tttattgttc atgatgatat ttttatct tgtgcaatgt aacatcagag | 9000 |
| attttgagac acaacgtggt ttaaacaaat agtcaaaagc ctccggcg | 9048 |

<210> SEQ ID NO 18
<211> LENGTH: 8455
<212> TYPE: DNA
<213> ORGANISM: artificial
<220> FEATURE:
<223> OTHER INFORMATION: synthetic

<400> SEQUENCE: 18

| | |
|---|---:|
| actagtcggg gtcattagtt catagcccat atatggagtt ccgcgttaca taacttacgg | 60 |
| taaatggccc gcctggctga ccgcccaacg acccccgccc attgacgtca ataatgacgt | 120 |
| atgttcccat agtaacgcca atagggactt tccattgacg tcaatgggtg gagtatttac | 180 |

| | |
|---|---|
| ggtaaactgc ccacttggca gtacatcaag tgtatcatat gccaagtacg cccctattg | 240 |
| acgtcaatga cggtaaatgg cccgcctggc attatgccca gtacatgacc ttatgggact | 300 |
| ttcctacttg gcagtacatc tacgtattag tcatcgctat taccatggtg atgcggtttt | 360 |
| ggcagtacat caatgggcgt ggatagcggt ttgactcacg ggatttcca agtctccacc | 420 |
| ccattgacgt caatgggagt ttgttttggc accaaaatca acgggacttt ccaaaatgtc | 480 |
| gtaacaactc cgccccattg acgcaaatgg gcggtaggcg tgtacggtgg gaggtctata | 540 |
| taagcagagc tggtttagtg aaccgggtct ctctggttag accagatttg agcctgggag | 600 |
| ctctctggct aactagggaa cccactgctt aagcctcaat aaagcttgcc ttgagtgctt | 660 |
| caagtagtgt gtgcccgtct gttgtgtgac tctggtaact agagatccct cagacccttt | 720 |
| tagtcagtgt ggaaaatctc tagcagtggc gcccgaacag ggacctgaaa gcgaaaggga | 780 |
| aaccagagga gctctctcga cgcaggactc ggcttgctga agcgcgcacg gcaagaggcg | 840 |
| aggggcggcg actgcagagt acgccaaaaa ttttgactag cggaggctag aaggagagag | 900 |
| atgggtgcga gagcgtcagt attaagcggg ggaaaatagc ggccgccaca atttttaaaag | 960 |
| aaaaggggg attgggggt acagtgcagg ggaaagaata gtagacataa tagcaacaga | 1020 |
| catacaaact aaagaattac aaaaacaaat tacaaaaatt caaattttcg ggggatccca | 1080 |
| tggtggccct cctatagtga gtcgtattat actatgccga tatactatgc cgatgattaa | 1140 |
| ttgtcaacac gtgctgcagg tccgaggttc tagcgcgtgg cctccgcgcc gggttttggc | 1200 |
| gcctcccgcg ggcgcccccc tcctcacggc gagcgctgcc acgtcagacg aagggcgcag | 1260 |
| cgagcgtcct gatccttccg cccggacgct caggacagcg gcccgctgct cataagactc | 1320 |
| ggccttagaa ccccagtatc agcagaagga cattttagga cgggacttgg gtgactctag | 1380 |
| ggcactggtt ttctttccag agagcggaac aggcgaggaa aagtagtccc ttctcggcga | 1440 |
| ttctgcggag ggatctccgt ggggcggtga acgccgatga ttatataagg acgcgccggg | 1500 |
| tgtggcacag ctagttccgt cgcagccggg atttgggtcg cggttcttgt tgtggatcg | 1560 |
| ctgtgatcgt cacttggtga gtagcgggct gctgggctgg ccgggcttt cgtggccgcc | 1620 |
| gggccgctcg gtgggacgga agcgtgtgga gagaccgcca agggctgtag tctgggtccg | 1680 |
| cgagcaaggt tgccctgaac tggggggttgg ggggagcgca gcaaaatggc ggctgttccc | 1740 |
| gagtcttgaa tggaagacgc ttgtgaggcg gctgtgagg tcgttgaaac aaggtggggg | 1800 |
| gcatggtggg cggcaagaac ccaaggtctt gaggccttcg ctaatgcggg aaagctctta | 1860 |
| ttcgggtgag atgggctggg gcaccatctg ggaccctga cgtgaagttt gtcactgact | 1920 |
| ggagaactcg gtttgtcgtc tgttgcgggg cggcagtta tggcggtgcc gttgggcagt | 1980 |
| gcacccgtac ctttgggagc gcgcgccctc gtcgtgtcgt gacgtcaccc gttctgttgg | 2040 |
| cttataatgc agggtggggc cacctgccgg taggtgtgcg gtaggctttt ctccgtcgca | 2100 |
| ggacgcaggg ttcgggccta gggtaggctc tcctgaatcg acaggcgccg gacctctggt | 2160 |
| gaggggaggg ataagtgagg cgtcagtttc tttggtcggt tttatgtacc tatcttctta | 2220 |
| agtagctgaa gctccggttt tgaactatgc gctcggggtt ggcgagtgtg ttttgtgaag | 2280 |
| tttttttaggc acctttgaa atgtaatcat ttgggtcaat atgtaatttt cagtgttaga | 2340 |
| ctagtaaatt gtccgctaaa ttctggccgt ttttggcttt tttgttagac gctagcctag | 2400 |
| cggatccgaa ttctcactat agggagaccc aagcttggta ccgagctcgg atccaccatg | 2460 |
| ggtggcgaac tctgcaaacg aatatgttgt gagttcggta ccacgtccgg tgagcccctg | 2520 |

```
aaagatgctc tgggtcgcca ggtgtctcta cgctcctacg acaacatccc tccgacttcc    2580
tcctcggacg aagggggagga cgatgacgac ggggaggatg acgataacga ggagcggcaa    2640
cagaagctgc ggctctgcgg tagtggctgc gggggaaacg acagtagtag cggcagccac    2700
cgcgaggcca cccacgacgg ccccaagaaa aacgcggtgc gctcgacgtt tcgcgaggac    2760
aaggctccga aaccgagcaa gcagtcaaaa aagaaaaaga aaccctcaaa acatcaccac    2820
catcagcaaa gctccattat gcaggagacg gacgacttag acgaagaaga cacctcaatt    2880
tacctgtccc cgcccccggt ccccccgtc caggtggtgg ctaagcgact gccgcggccc     2940
gacacaccca ggactccgcg ccaaaagaag atttcacaac gtccacccac ccccgggaca    3000
aaaaagcccg ccgcccccctt gtccttttaa agtcgactct agagggccct attctatagt   3060
gtcacctaaa tgctagagct cgctgatcag acgcgccgcg gccgctacgt aaattccgcc    3120
cctctcccta acgttactgg ccgaagccgc ttggaataag gccggtgtgc gtttgtctat    3180
atgttatttt ccaccatatt gccgtctttt ggcaatgtga gggcccggaa acctggccct    3240
gtcttcttga cgagcattcc tagggtgtctt tcccctctcg ccaaaggaat gcaaggtctg   3300
ttgaatgtcg tgaaggaagc agttcctctg gaagcttctt gaagacaaac aacgtctgta    3360
gcgacccttt gcaggcagcg gaacccccca cctggcgaca ggtgcctctg cggccaaaag   3420
ccacgtgtat aagatacacc tgcaaaggcg gcacaacccc agtgccacgt tgtgagttgg    3480
atagttgtgg aaagagtcaa atggctctcc tcaagcgtat tcaacaaggg gctgaaggat    3540
gcccagaagg taccccattg tatgggatct gatctggggc ctcggtgcac atgctttaca    3600 tgtgttagt cgaggttaaa aaacgtctag gcccccccgaa ccacggggac gtggttttcc    3660
tttgaaaaac acgatgataa tatggtgagc aagggcgagg agctgttcac cggggtggtg    3720
cccatcctgg tcgagctgga cggcgacgta aacggccaca agttcagcgt gtccggcgag    3780
ggcgagggcg atgccaccta cggcaagctg accctgaagt tcatctgcac caccggcaag    3840
ctgcccgtgc cctggcccac cctcgtgacc accctgacct acggcgtgca gtgcttcagc    3900 cgctacccg accacatgaa gcagcacgac ttcttcaagt ccgccatgcc cgaaggctac    3960
gtccaggagc gcaccatctt cttcaaggac gacggcaact acaagacccg cgccgaggtg    4020
aagttcgagg gcgacaccct ggtgaaccgc atcgagctga agggcatcga cttcaaggag    4080
gacggcaaca tcctggggca caagctggag tacaactaca acagccacaa cgtctatatc    4140
atggccgaca agcagaagaa cggcatcaag gtgaacttca agatccgcca caacatcgag    4200
gacggcagcg tgcagctcgc cgaccactac cagcagaaca cccccatcgg cgacggcccc    4260
gtgctgctgc ccgacaacca ctacctgagc acccagtccg ccctgagcaa agaccccaac    4320
gagaagcgcg atcacatggt cctgctggag ttcgtgaccg ccgccgggat cactctcggc    4380
atggacgagc tgtacaagta agtcgacccg gaccgccaca tcgagcgggt caccgagctg    4440
caagaactct tcctcacgcg cgtcgggctc gacatcggca aggtgtgggt cgcggacgac    4500
ggcgccgcgg tggcggtctg gaccacgccg gagagcgtcg aagcgggggc ggtgttcgcc    4560
gagatcggct cgcgcatggc cgagttgagc ggttcccggc tggccgcgca gcaacagatg    4620
gaaggcctcc tggcgccgca ccggcccaag gagcccgcgt ggttcctggc caccgtcggc    4680
gtctcgcccg accaccaggg caagggtctg ggcagcgccg tcgtgctccc cggagtggag    4740
gcggccgagc gcgctggggt gcccgccttc ctggagacct ccgcgcccg caacctcccc    4800 ttctacgagc ggctcggctt caccgtcacc gccgacgtcg aggtgcccga aggaccgcgc    4860
acctggtgca tgacccgcaa gccgggtgcc tgagttcgcg tctggaacaa tcaacctctg    4920
```

```
gactcgacaa tcaacctctg gattacaaaa tttgtgaaag attgactggt attcttaact    4980
atgttgctcc ttttacgcta tgtggatacg ctgctttaat gcctttgtat catgctattg    5040
cttcccgtat ggcttttcatt ttctcctcct tgtataaatc ctggttgctg tctctttatg   5100
aggagttgtg gcccgttgtc aggcaacgtg gcgtggtgtg cactgtgttt gctgacgcaa    5160
cccccactgg ttggggcatt gccaccacct gtcagctcct ttccgggact ttcgctttcc    5220
ccctccctat tgccacggcg gaactcatcg ccgcctgcct tgcccgctgc tggacagggg    5280
ctcggctgtt gggcactgac aattccgtgg tgttgtcggg gaaatcatcg tcctttcctt    5340
ggctgctcgc ctgtgttgcc acctggattc tgcgcgggac gtccttctgc tacgtccctt    5400
cggccctcaa tccagcggac cttccttccc gcggcctgct gccggctctg cggcctcttc    5460
cgcgtcttcg ccttcgccct cagacgagtc ggatctccct ttgggccgcc tccccgctta    5520
gtactggtac ctttaagacc aatgacttac aaggcagctg tagatcttag ccactttta    5580 aaagaaaagg ggggactgga agggctaatt cactcccaac gaagacaaga ttccggaatt    5640
tatttgtgaa atttgtgatg ctattgcttt atttgtaaac cggtgcagct gcttttgcc    5700 tgtactgggt ctctctggtt agaccagatc tgagcctggg agctctctgg ctaactaggg    5760
aacccactgc ttaagcctca ataaagcttg ccttgagtgc ttcaagtagt gtgtgcccgt    5820
ctgttgtgtg actctggtaa ctagagatcc ctcagaccct tttagtcagt gtggaaaatc    5880
tctagcatct agagtatgca aagcatgcat ctcaattagt cagcaaccag gtgtggaaag    5940
tccccaggct ccccagcagg cagaagtatg caaagcatgc atctcaatta gtcagcaacc    6000
atagtcccgc ccctaactcc gcccatcccg ccctaactc cgcccagttc cgcccattct    6060
ccgccccatg gctgactaat ttttttatt tatgcagagg ccgaggccgc ctcggcctct    6120
gagctattcc agaagtagtg aggaggcttt tttggaggcc taggctagag atcataatca    6180
gccataccac atttgtagag gttttacttg ctttaaaaaa cctcccacac ctccccctga    6240
acctgaaaca taaaatgaat gcaattgttg ttgttaactt gtttattgca gcttataatg    6300
gttacaaata aagcaatagc atcacaaatt tcacaaataa agcatttttt tcactgcatt    6360
ctagttgtgg tttgtccaaa ctcatcaatg tatcttatca tgtctgctag ccgggctttt    6420
ttttcttagg ccttcttccg cttcctcgct cactgactcg ctgcgctcgg tcgttcggct    6480
gcggcgagcg gtatcagctc actcaaaggc ggtaatacgg ttatccacag aatcaggggg    6540
taacgcagga agaacatgt gagcaaaagg ccagcaaaag gccaggaacc gtaaaaaggc     6600
cgcgttgctg gcgtttttcc ataggctccg ccccctgac gagcatcaca aaaatcgacg     6660
ctcaagtcag aggtggcgaa acccgacagg actataaaga taccaggcgt ttccccctgg    6720
aagctccctc gtgcgctctc ctgttccgac cctgccgctt accggatacc tgtccgcctt    6780
tctcccttcg ggaagcgtgg cgctttctca tagctcacgc tgtaggtatc tcagttcggt    6840
gtaggtcgtt cgctccaagc tgggctgtgt gcacgaaccc cccgttcagc ccgaccgctg    6900
cgccttatcc ggtaactatc gtcttgagtc aacccggta agacacgact tatcgccact    6960
ggcagcagcc actggtaaca ggattagcag agcgaggtat gtaggcggtg ctacagagtt    7020
cttgaagtgg tggcctaact acggctacac tagaagaaca gtatttggta tctgcgctct    7080
gctgaagcca gttaccttcg gaaaaagagt tggtagctct tgatccggca acaaaccac     7140 cgctggtagc ggtggttttt tgtttgcaa gcagcagatt acgcgcagaa aaaaggatc     7200 tcaagaagat cctttgatct tttctacggg gtctgacgct cagtggaacg aaaactcacg    7260
```

-continued

| | |
|---|---|
| ttaagggatt ttggtcatga gattatcaaa aaggatcttc acctagatcc tttttaaatta | 7320 |
| aaaatgaagt tttaaatcaa tctaaagtat atatgagtaa acttggtctg acagttacca | 7380 |
| atgcttaatc agtgaggcac ctatctcagc gatctgtcta tttcgttcat ccatagttgc | 7440 |
| ctgactcctg cgcagtccaa aaaaaaaggc tccaaaagga gcctttaatt gtatcggtgg | 7500 |
| gcccttagaa aaactcatcg agcatcaaat gaaactgcaa tttattcata tcaggattat | 7560 |
| caataccata tttttgaaaa agccgtttct gtaatgaagg agaaaactca ccgaggcagt | 7620 |
| tccataggat ggcaagatcc tggtatcggt ctgcgattcc gactcgtcca acatcaatac | 7680 |
| aacctattaa tttcccctcg tcaaaaataa ggttatcaag tgagaaatca ccatgagtga | 7740 |
| cgactgaatc cggtgagaat ggcaaaagct tatgcatttc tttccagact tgttcaacag | 7800 |
| gccagccatt acgctcgtca tcaaaatcac tcgcatcaac caaaccgtta ttcattcgtg | 7860 |
| attgcgcctg agcgagacga atacgcgat cgctgttaaa aggacaatta caaacaggaa | 7920 |
| tcgaatgcaa ccggcgcagg aacactgcca gcgcatcaac aatatttcca cctgaatcag | 7980 |
| gatattcttc taatacctgg aatgctgttt cccgggggat cgcagtggtg agtaaccatg | 8040 |
| catcatcagg agtacggata aaatgcttga tggtcggaag aggcataaat tccgtcagcc | 8100 |
| agtttagtct gaccatctca tctgtaacat cattggcaac gctacctttg ccatgtttca | 8160 |
| gaaacaactc tggcgcatcg ggcttcccat acaatcgata gattgtcgca cctgattgcc | 8220 |
| cgacattatc gcgagcccat ttatacccat ataaatcagc atccatgttg aatttaatc | 8280 |
| gcggcctcga gcaagacgtt tcccgttgaa tatggctcat aacacccctt gtattactgt | 8340 |
| ttatgtaagc agacagtttt attgttcatg atgatatatt tttatcttgt gcaatgtaac | 8400 |
| atcagagatt ttgagacaca acgtggttta aacaaatagt caaaagcctc cggcg | 8455 |

<210> SEQ ID NO 19
<211> LENGTH: 12088
<212> TYPE: DNA
<213> ORGANISM: artificial
<220> FEATURE:
<223> OTHER INFORMATION: synthetic

<400> SEQUENCE: 19

| | |
|---|---|
| tggaagggct aattcactcc caagaagac aagatatcct tgatctgtgg atctaccaca | 60 |
| cacaaggcta cttccctgat tagcagaact acacaccagg gccagggtc agatatccac | 120 |
| tgacctttgg atggtgctac aagctagtac cagttgagcc agataaggta gaagaggcca | 180 |
| ataaaggaga gaacaccagc ttgttacacc ctgtgagcct gcatgggatg gatgacccgg | 240 |
| agagagaagt gttagagtgg aggtttgaca gccgcctagc atttcatcac gtggcccgag | 300 |
| agctgcatcc ggagtacttc aagaactgct gatatcgagc ttgctacaag gactttccg | 360 |
| ctggggactt tccaggggagg cgtggcctgg gcgggactgg ggagtggcga gccctcagat | 420 |
| cctgcatata agcagctgct ttttgcctgt actgggtctc tctggttaga ccagatctga | 480 |
| gcctgggagc tctctggcta actagggaac ccactgctta agcctcaata agcttgcct | 540 |
| tgagtgcttc aagtagtgtg tgcccgtctg ttgtgtgact ctggtaacta gagatccctc | 600 |
| agaccctttt agtcagtgtg aaaatctct agcagtggcg cccgaacagg acttgaaag | 660 |
| cgaaagggaa accagaggag ctctctcgac gcaggactcg gcttgctgaa gcgcgcacgg | 720 |
| caagaggcga ggggcggcga ctggtgagta cgccaaaaat tttgactagc ggaggctaga | 780 |
| aggagagaga tgggtgcgag agcgtcagta ttaagcgggg gagaattaga tcgcgatggg | 840 |
| aaaaaattcg gttaaggcca gggggaaaga aaaaatataa attaaaacat atagtatggg | 900 |

```
caagcaggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaaagaca   1080
ccaaggaagc tttagacaag atagaggaag agcaaaacaa aagtaagacc accgcacagc   1140
aagcggccgg ccgctgatct tcagacctgg aggaggagat atgagggaca attggagaag   1200
tgaattatat aaatataaag tagtaaaaat tgaaccatta ggagtagcac ccaccaaggc   1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag ttttgctgt    1860 actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atcggcactg cgtgcgccaa ttctgcagac   2040
aaatggcagt attcatccac aattttaaaa gaaaagggg gattgggggg tacagtgcag   2100
gggaaagaat agtagacata atagcaacag acatacaaac taaagaatta caaaaacaaa   2160
ttacaaaaat tcaaaatttt cgggtttatt acagggacag cagagatcca gtttggttag   2220
taccgggccc gctctagtcc ggaatcagtc ctgctcctcg gccacgaagt gcacgcagtt   2280
gccggccggg tcgcgcaggg cgaactcccg ccccacggc tgctcgccga tctcggtcat    2340
ggccggcccg gaggcgtccc ggaagttcgt ggacacgacc tccgaccact cggcgtacag   2400
ctcgtccagg ccgcgcaccc acacccaggc cagggtgttg tccggcacca cctggtcctg   2460
gaccgcgctg atgaacaggg tcacgtcgtc ccggaccaca ccggcgaagt cgtcctccac   2520
gaagtcccgg gagaacccga gccggtcggt ccagaactcg accgctccgg cgacgtcgcg   2580 gcggtgagc accggaacgg cactggtcaa cttggccatg gtggccctcc tatagtgagt   2640
cgtattatac tatgccgata tactatgccg atgattaatt gtcaacacgt gctgcaggtc   2700
cgaggttcta gcgcgtggcc tccgcgccgg gttttggcgc ctcccgcggg cgcccccctc   2760
ctcacggcga gcgctgccac gtcagacgaa gggcgcagcg agcgtcctga tccttccgcc   2820
cggacgctca ggacagcggc ccgctgctca taagactcgg ccttagaacc ccagtatcag   2880
cagaaggaca ttttaggacg ggacttgggt gactctaggg cactggtttt ctttccagag   2940
agcggaacag gcgaggaaaa gtagtcccct ctcgcgatt ctgcggaggg atctccgtgg    3000
ggcggtgaac gccgatgatt atataaggac gcgccgggtg tggcacagct agttccgtcg   3060
cagccgggat ttgggtcgcg gttcttgttt gtggatcgct gtgatcgtca cttggtgagt   3120
agcgggctgc tgggctggcc ggggcttccg tggccgccgg ccgctcggt gggacggaag    3180 cgtgtggaga gaccgccaag ggctgtagtc tgggtccgcg agcaaggttg ccctgaactg   3240
```

```
ggggttgggg ggagcgcagc aaaatggcgg ctgttcccga gtcttgaatg gaagacgctt    3300
gtgaggcggg ctgtgaggtc gttgaaacaa ggtgggggc atggtgggcg gcaagaaccc     3360
aaggtcttga ggccttcgct aatgcgggaa agctcttatt cgggtgagat gggctggggc    3420
accatctggg gaccctgacg tgaagtttgt cactgactgg agaactcggt ttgtcgtctg    3480 ttgcggggc ggcagttatg gcggtgccgt tgggcagtgc acccgtacct ttgggagcgc     3540
gcgccctcgt cgtgtcgtga cgtcacccgt tctgttggct tataatgcag ggtgggcca    3600 cctgccggta ggtgtgcggt aggctttct ccgtcgcagg acgcagggtt cgggcctagg    3660
gtaggctctc ctgaatcgac aggcgccgga cctctggtga ggggagggat aagtgaggcg    3720
tcagtttctt tggtcggttt tatgtaccta tcttcttaag tagctgaagc tccggttttg    3780
aactatgcgc tcggggttgg cgagtgtgtt ttgtgaagtt ttttaggcac cttttgaaat    3840
gtaatcattt gggtcaatat gtaattttca gtgttagact agtaaattgt ccgctaaatt    3900
ctggccgttt ttggcttttt tgttagacgc tagcctagcg gatccgaatt ctcgaaactt    3960
aagatgcacc cagaaacgct ggtgaaagta aaagatgctg aagatcagtt gggtgcacga    4020
gtgggttaca tcgaactgga tctcaacagc ggtaagatcc ttgagagttt tcgccccgaa    4080
gaacgttttc caatgatgag cacttttaaa gttctgctat gtggcgcggt attatcccgt    4140
attgacgccg ggcaagagca actcggtcgc cgcatacact attctcagaa tgacttggtt    4200
gagtactcac cagtcacaga aaagcatctt acggatggca tgacagtaag agaattatgc    4260
agtgctgcca taaccatgag tgataacact gcggccaact tacttctgac aacgatcgga    4320
ggaccgaagg agctaaccgc ttttttgcac aacatggggg atcatgtaac tcgccttgat    4380
cgttgggaac cggagctgaa tgaagccata ccaaacgacg agcgtgacac cacgacgcct    4440
gtagcaatgg caacaacgtt gcgcaaacta ttaactggct ccggaggcgg cggctccggc    4500
ggcggcggct cgagcggcgg cggcggatcc ctacttactc tagcttcccg gcaacaatta    4560
atagactgga tggaggcgga taaagttgca ggaccacttc tgcgctcggc ccttccggct    4620
ggctggttta ttgctgataa atctggagcc ggtgagcgtg gtctcgcgg tatcattgca     4680 gcactgggc cagatggtaa gccctcccgt atcgtagtta tctacacgac ggggagtcag    4740
gcaactatgg atgaacgaaa tagacagatc gctgagatag gtgcctcact gattaagcat    4800
tggtgagcag atctgccac tagtgagtcg tattacatcc atcacactgg cggccgcaaa    4860
ttccgcccct ctccctcccc ccccctaac gttactggcc gaagccgctt ggaataaggc    4920
cggtgtgcgt ttgtctatat gttatttcc accatattgc cgtcttttgg caatgtgagg    4980
gcccggaaac ctggccctgt cttcttgacg agcattccta ggggtctttc ccctctcgcc    5040
aaaggaatgc aaggtctgtt gaatgtcgtg aaggaagcag ttcctctgga agcttcttga    5100
agacaaacaa cgtctgtagc gaccctttgc aggcagcgga accccccacc tggcgacagg    5160
tgcctctgcg gccaaaagcc acgtgtataa gatacacctg caaaggcggc acaaccccag    5220
tgccacgttg tgagttggat agttgtgaa agagtcaaat ggctctcctc aagcgtattc     5280 aacaagggc tgaaggatgc ccagaaggta ccccattgta tgggatctga tctgggcct     5340 cggtgcacat gctttacatg tgtttagtcg aggttaaaaa aacgtctagg ccccccgaac    5400
cacggggacg tggttttcct ttgaaaaaca cgataatacc atggccaccg agtacaagcc    5460
cacggtgcgc ctcgccaccc gcgacgacgt ccccgggcc gtacgcaccc tcgccgccgc    5520
gttcgccgac taccccgcca cgcgccacac cgtcgacccg gaccgccaca tcgagcgggt    5580
caccgagctg caagaactct tcctcacgcg cgtcgggctc gacatcggca aggtgtgggt    5640
```

```
cgcggacgac ggcgccgcgg tggcggtctg gaccacgccg gagagcgtcg aagcggggc     5700 ggtgttcgcc gagatcggct cgcgcatggc cgagttgagc ggttcccggc tggccgcgca     5760
gcaacagatg gaaggcctcc tggcgccgca ccggcccaag gagcccgcgt ggttcctggc     5820
caccgtcggc gtctcgcccg accaccaggg caagggtctg ggcagcgccg tcgtgctccc     5880
cggagtggag gcggccgagc gcgctggggt gcccgccttc ctggagacct ccgcgccccg     5940
caacctcccc ttctacgagc ggctcggctt caccgtcacc gccgacgtcg aggtgcccga     6000
aggaccgcgc acctggtgca tgacccgcaa gcccggtgcc tgagttcgcg tctggaacaa     6060
tcaacctctg gattacaaaa tttgtgaaag attgactggt attcttaact atgttgctcc     6120
ttttacgcta tgtggatacg ctgctttaat gcctttgtat catgctattg cttcccgtat     6180
ggctttcatt ttctcctcct tgtataaatc ctggttgctg tctctttatg aggagttgtg     6240
gcccgttgtc aggcaacgtg gcgtggtgtg cactgtgttt gctgacgcaa cccccactgg     6300
ttggggcatt gccaccacct gtcagctcct ttccggggact ttcgctttcc cctccctat     6360 tgccacggcg gaactcatcg ccgcctgcct tgcccgctgc tggacagggg ctcggctgtt     6420
gggcactgac aattccgtgg tgttgtcggg gaagctgacg tccttccat ggctgctcgc     6480 ctgtgttgcc acctggattc tgcgcgggac gtccttctgc tacgtccctt cggccctcaa     6540
tccagcggac cttccttccc gcggcctgct gccggctctg cggcctcttc cgcgtcttcg     6600
ccttcgccct cagacgagtc ggatctccct ttgggccgcc tccccgcctg gaattaattc     6660
tgcagtcgag acctagaaaa acatggagca atcacaagta gcaatacagc agctaccaat     6720
gctgattgtg cctggctaga agcacaagag gaggaggagg tgggttttcc agtcacacct     6780
caggtacctt taagaccaat gacttacaag gcagctgtag atcttagcca ctttttaaaa     6840
gaaagagggg gactggaagg gctaattcac tcccaacgaa gacaagatct gcttttttgct     6900 tgtactgggt ctctctggtt agaccagatc tgagcctggg agctctctgg ctaactaggg     6960
aacccactgc ttaagcctca ataaagcttg ccttgagtgc ttcaagtagt gtgtgcccgt     7020
ctgttgtgtg actctggtaa ctagagatcc ctcagaccct tttagtcagt gtggaaaatc     7080
tctagcagta gtagttcatg tcatcttatt attcagtatt tataacttgc aaagaaatga     7140
atatcagaga gtgagaggcc ttgacattgt ttaaacccgc tgatcagcct cgactgtgcc     7200
ttctagttgc cagccatctg ttgtttgccc ctcccccgtg ccttccttga ccctggaagg     7260
tgccactccc actgtccttt cctaataaaa tgaggaaatt gcatcgcatt gtctgagtag     7320
gtgtcattct attctggggg gtggggtggg gcaggacagc aagggggagg attgggaaga     7380
caatagcagg catgctgggg atgcggtggg ctctatggct tctgaggcgg aaagaaccag     7440
ctggggctct agggggtatc cccacgcgcc ctgtagcggc gcattaagcg cggcgggtgt     7500
ggtggttacg cgcagcgtga ccgctacact tgccagcgcc ctagcgcccg ctcctttcgc     7560
tttcttccct tcctttctcg ccacgttcgc cggctttccc cgtcaagctc taaatcgggg     7620
gctcccttta gggttccgat ttagtgcttt acggcacctc gaccccaaaa aacttgatta     7680
gggtgatggt tcacgtagtg ggccatcgcc ctgatagacg gttttcgcc ctttgacgtt     7740 ggagtccacg ttctttaata gtggactctt gttccaaact ggaacaacac tcaaccctat     7800
ctcggtctat tcttttgatt tataagggat tttgccgatt tcggcctatt ggttaaaaaa     7860
tgagctgatt taacaaaaat ttaacgcgaa ttaattctgt ggaatgtgtg tcagttaggg     7920
tgtggaaagt ccccaggctc cccagcaggc agaagtatgc aaagcatgca tctcaattag     7980
```

```
tcagcaacca ggtgtggaaa gtccccaggc tccccagcag gcagaagtat gcaaagcatg    8040
catctcaatt agtcagcaac catagtcccg cccctaactc cgcccatccc gcccctaact    8100
ccgcccagtt ccgcccattc tccgcccat ggctgactaa ttttttttat ttatgcagag     8160
gccgaggccg cctctgcctc tgagctattc cagaagtagt gaggaggctt ttttggaggc    8220
ctaggctttt gcaaaaagct cccgggagct tgtatatcca ttttcggatc tgatcagcac    8280
gtgatgaaaa agcctgaact caccgcgacg tctgtcgaga gtttctgat cgaaaagttc     8340 gacagcgtct ccgacctgat gcagctctcg gagggcgaag aatctcgtgc tttcagcttc    8400
gatgtaggag ggcgtggata tgtcctgcgg gtaaatagct gcgccgatgg tttctacaaa    8460
gatcgttatg tttatcggca ctttgcatcg gccgcgctcc cgattccgga agtgcttgac    8520
attggggaat taattcagcg agagcctgac ctattgcatc tcccgccgtg cacagggtgt    8580
cacgttgcaa gacctgcctg aaaccgaact gcccgctgtt ctgcagccgg tcgcggaggc    8640
catggatgcg atcgctgcgg ccgatcttag ccagacgagc gggttcggcc cattcggacc    8700
gcaaggaatc ggtcaataca ctacatggcg tgatttcata tgcgcgattg ctgatcccca    8760
tgtgtatcac tggcaaactg tgatggacga caccgtcagt gcgtccgtcg cgcaggctct    8820
cgatgagctg atgctttggg ccgaggactg ccccgaagtc cggcacctcg tgcacgcgga    8880
tttcggctcc aacaatgtcc tgacggacaa tggccgcata acagcggtca ttgactggag    8940
cgaggcgatg ttcgggggatt cccaatacga ggtcgccaac atcttcttct ggaggccgtg    9000
gttggcttgt atggagcagc agacgcgcta cttcgagcgg aggcatccgg agcttgcagg    9060
atcgccgcgg ctccgggcgt atatgctccg cattggtctt gaccaactct atcagagctt    9120
ggttgacggc aatttcgatg atgcagcttg ggcgcagggt cgatgcgacg caatcgtccg    9180
atccggagcc gggactgtcg ggcgtacaca aatcgcccgc agaagcgcgg ccgtctggac    9240
cgatggctgt gtagaagtac tcgccgatag tggaaaccga cgccccagca ctcgtccgag    9300
ggcaaaggaa tagcacgtgc tacgagattt cgattccacc gccgccttct atgaaaggtt    9360
gggcttcgga atcgttttcc gggacgccgg ctggatgatc ctccagcgcg gggatctcat    9420
gctggagttc ttcgcccacc ccaacttgtt tattgcagct tataatggtt acaaataaag    9480
caatagcatc acaaatttca caaataaagc atttttttca ctgcattcta gttgtggttt    9540
gtccaaactc atcaatgtat cttatcatgt ctgtataccg tcgacctcta gctagagctt    9600
ggcgtaatca tggtcatagc tgtttcctgt gtgaaattgt tatccgctca caattccaca    9660
caacatacga gccggaagca taaagtgtaa agcctgggt gcctaatgag tgagctaact    9720
cacattaatt gcgttgcgct cactgcccgc tttccagtcg ggaaacctgt cgtgccagct    9780
gcattaatga atcggccaac gcgcggggag aggcggtttg cgtattgggc gctcttccgc    9840
ttcctcgctc actgactcgc tgcgctcggt cgttcggctg cggcgagcgg tatcagctca    9900
ctcaaaggcg gtaatacggt tatccacaga atcaggggat aacgcaggaa agaacatgtg    9960
agcaaaaggc cagcaaaagg ccaggaaccg taaaaaggcc gcgttgctgg cgttttccca    10020
taggctccgc cccctgacg agcatcacaa aaatcgacgc tcaagtcaga ggtggcgaaa     10080
cccgacagga ctataaagat accaggcgtt tccccctgga agctccctcg tgcgctctcc    10140
tgttccgacc ctgccgctta ccggatacct gtccgccttt ctcccttcgg gaagcgtggc    10200
gctttctcat agctcacgct gtaggtatct cagttcggtg taggtcgttc gctccaagct    10260
gggctgtgtg cacgaacccc ccgttcagcc cgaccgctgc gccttatccg gtaactatcg    10320
tcttgagtcc aacccggtaa gacacgactt atcgccactg gcagcagcca ctggtaacag    10380
```

```
gattagcaga gcgaggtatg taggcggtgc tacagagttc ttgaagtggt ggcctaacta    10440
cggctacact agaagaacag tatttggtat ctgcgctctg ctgaagccag ttaccttcgg    10500
aaaaagagtt ggtagctctt gatccggcaa acaaaccacc gctggtagcg gtggttttt    10560 tgtttgcaag cagcagatta cgcgcagaaa aaaaggatct caagaagatc ctttgatctt    10620
ttctacgggg tctgacgctc agtggaacga aaactcacgt taagggattt tggtcatgag    10680
attatcaaaa aggatcttca cctagatcct tttaaattaa aaatgaagtt ttaaatcaat    10740
ctaaagtata tatgagtaaa cttggtctga cagttaccaa tgcttaatca gtgaggcacc    10800
tatctcagcg atctgtctat ttcgttcatc catagttgcc tgactccccg tcgtgtagat    10860
aactacgata cgggagggct taccatctgg ccccagtgct gcaatgatac cgcgagaccc    10920
acgctcaccg gctccagatt tatcagcaat aaaccagcca gccggaaggg ccgagcgcag    10980
aagtggtcct gcaactttat ccgcctccat ccagtctatt aattgttgcc gggaagctag    11040
agtaagtagt tcgccagtta atagtttgcg caacgttgtt gccattgcta caggcatcgt    11100
ggtgtcacgc tcgtcgtttg gtatggcttc attcagctcc ggttcccaac gatcaaggcg    11160
agttacatga tcccccatgt tgtgcaaaaa agcggttagc tccttcggtc ctccgatcgt    11220
tgtcagaagt aagttggccg cagtgttatc actcatggtt atggcagcac tgcataattc    11280
tcttactgtc atgccatccg taagatgctt ttctgtgact ggtgagtact caaccaagtc    11340
attctgagaa tagtgtatgc ggcgaccgag ttgctcttgc ccggcgtcaa tacgggataa    11400
taccgcgcca catagcagaa ctttaaaagt gctcatcatt ggaaaacgtt cttcggggcg    11460
aaaactctca aggatcttac cgctgttgag atccagttcg atgtaaccca ctcgtgcacc    11520
caactgatct tcagcatctt ttactttcac cagcgtttct gggtgagcaa aaacaggaag    11580
gcaaaatgcc gcaaaaaagg gaataagggc gacacggaaa tgttgaatac tcatactctt    11640 ccttttcaa tattattgaa gcatttatca gggttattgt ctcatgagcg gatacatatt    11700
tgaatgtatt tagaaaaata aacaaatagg ggttccgcgc acatttcccc gaaaagtgcc    11760
acctgacgtc gacggatcgg gagatcaact tgtttattgc agcttataat ggttacaaat    11820
aaagcaatag catcacaaat ttcacaaata aagcattttt tcactgcat tctagttgtg    11880 gtttgtccaa actcatcaat gtatcttatc atgtctggat caactggata actcaagcta    11940
accaaaatca tcccaaactt cccacccat accctattac cactgccaat tacctgtggt    12000
ttcatttact ctaaacctgt gattcctctg aattattttc attttaaaga aattgtattt    12060
gttaaatatg tactacaaac ttagtagt                                       12088
```

<210> SEQ ID NO 20
<211> LENGTH: 233681
<212> TYPE: DNA
<213> ORGANISM: artificial
<220> FEATURE:
<223> OTHER INFORMATION: synthetic

<400> SEQUENCE: 20

```
catgcacacc aataaacttt tgcttttctt tttagccaat aatatgtttc cgtgtggttt      60
ttataggtta accacttatg gtgtaaagta ggatattcat agttattgaa acatgggta     120 cacaatgtaa cactaaacta ctatccgcac taatagcaac tgcaatcatc ctaactgcca    180
ttctagctcc ggtacttta catgaacaag aaaaggcatt ttaccgacaa cttttttgcgc    240 aaagtcaaca tgtaaaaaca cccatcacgg tagttcaggg agatacagtt taccttaacg    300
```

```
ctagtaataa cccctgcaac tattccagct tctggaacta tggcgattgc gaactttgtg    360
gatggaacgg atacatacaa agacaatatc acgaaaacaa atcgtgctct ccacgattta    420
catgttttaa tgacaccaaa ggtcttagac tacataacgt tacgtttagc gattcaggaa    480
catacacaga atacatgtac gactgtgatt ttccatgtaa cacgagtgac tatgaatatg    540
acatactaaa ctattttgac aattgtacta ctaccataaa cagtaccaat tatattatca    600
ccgtattgtc tccacgtcat tctaaacaca ccgatttgca cgtatccgct cacgccggtt    660
tggcagctgc catggtgaca gtaattataa tttgcgtttt gatctacttt aacgttccgg    720
caacccggag acacagacta cgaactagaa ataacgttaa ccacatactg taattacaaa    780
gtatcgacgc tagtttattc aggataaatt tgtgctactt tgtgtagctc tcaaaaattg    840
taaggcccca cttttccact ccgtcatgaa agatcgtaat aagctactca tatgtattat    900
ccttattttc accatgtgcc tcatctgtct ttattttaaa cgccgttgta ttcctactcc    960
atctccagac aaggcagatc tgcgagtgga atttccttcg ttatctccgt gtgtcggcat   1020
acaatgcgct tcacgggaag atgcgtgata catagcgtac ccccagacgg tacggcttat   1080
gagaacacaa ttgaaggaaa gtacaggttc ctgttgatat gttattacag aaggtcacgg   1140
aacacaaacg ttttctgcgt gtgttttat aaaagagcgt ctcgaagcag cttgagccac   1200
actacggtcc agatgacgag cgtgatcaaa aatatgccgc gcagtagtcg aaagccgtac   1260
tgagcgtgcg aggcgggtag ggtgccgaac gacggatatg cgtcgtcatc atctttgact   1320
ataaggatcg cgaccgaatc ttcggacatg gtaaaagcca cccactgtgg ctggtatgta   1380
gcgtatccgg tttggaatcg ttcggctccg gctcggggga tagtgaggaa ttctcagggg   1440
acgatatggg acccaatgac tggataaaag aagggttttt cccagtaaga tgatccccgt   1500
atcacatgag atctggatat gtataaatga ggagtgaaat aggcaagggg tatcagacac   1560
cggccccgtc atgcagccgc tggttctctc agcggaggaa ctatcgtctc tgctgatttg   1620
caaatacatc ccaccttaag cgacgagtcc ataaagcatc gttatccggg tacggtgaaa   1680
gtgacccgga ttgcaccacg tccctttttt gttttgcat cgtttatcgt caccactagt   1740
gcaatatttt tatcgtaagg ctgaaagagt atcgttatga tgcttagaat gtggagatta   1800
ttacagatgg tactgcttgc cacgtactgt tattatgttt ttgcgaattg ttcaatcagc   1860
acgacgactg ctcctgtgga atggaagtct cccaaccgtc agattcccaa gaatattacc   1920
tgcgctaatt actcagggac cgtcggcggt aacgttactt ttcagggtct caagaataaa   1980
acggaagact ttttatcttg gctactcggg tctggctata agtctatttg ctcgttcttc   2040
ccacaactcc ctggtgattc taatgagcag cattacagat atgaagtaac caacctcacg   2100
tacaattgta cctatgaccg cctaacgtta ctgaatctaa cgatggaaaa cagcaggaat   2160
tactatttca gaagagaaga tgcgaattcc accttctact actcttgtta caacctgacc   2220
gtgtcctaga gaacgcacgt gaagttccac agagccgcgt ggctgtagct attgtttacg   2280
ttgcttttga aatgttaagc gtccctacga cgctaactcg ggggagtcca gggttttccc   2340
agtcacgacg ttgtaaaacg acggccagtg aattcgagct cggtacccgg ggatcttgaa   2400
gttcctattc cgaagttcct attctctaga agtatagga acttcagagc gcttttgaag   2460
cttggcgtaa tcatggtcat agctgtttcc tgtgtgaaat tgttatccgc tcacaattcc   2520
acacaacata cgagccggaa gacacaagac tgccactcca catacaacgt ggatcatacc   2580
cctggttatc attataacaa tcatcatttt aatttgtttc aaatttcccc agaaagcttg   2640
gaataaaattc acacaatacc gatacagcga tatgctcgcc gctgcttaaa gaatcaacgt   2700
```

```
cgaggaaacc aaaacgcaaa cataatggat atgtacgtgt attttcagc tcactgtttg    2760 aataccgtaa gaaaatgac gtacatatac gtaataatac aacagttgct catgttatgc    2820
ggcgcctgat taactatatc gtgagtcatg gcctttttcc atggtccgtc atgaccgcaa    2880
tgatacttta caggtattcc gaaacctgta tggaggtcac cgttaaagta ggtgatccgg    2940
tcaccctcgg aagtggacac ggttatcatc ctggccaaag agtacactgg tataatcatt    3000
catgtgtcgg catcggtaac ggcgaaaatg cgcatcctat ctgtacctac gaccctccta    3060
aacctggtaa acataagacg atgaaaacca ctccgccgcc attaccgccg ttgtacgaat    3120
gtcataattc tacattaagt atccttcatg taaacgtttc agatcccaaa aactactgca    3180
gacgaaaatg tccatcaaat ggtaataact gtgagtttcc cacgtgtttt cagttatcgc    3240
ttatttatag aacgacgacc accaaaaaac ccggacaaaa aactacgtca ccgagattaa    3300
gaaccacgcc aaagaaacat acacagcaca aaagatccac aggaagaacg tcacctaaag    3360
attataatgt tacaggtctg ccaaaaggct ttgcggactc gtttaccggt aacgcagagg    3420
cacatagagc caaagatgcc gcacacagcg catggattat cattgtcatc atcattatca    3480
tagtcgtcat tttatttctc ttcaagattc ctcaaagact ccgagaaaaa tgggacacca    3540
ggggatactt ttacaaagga accgacggcc tgcccactac ggactaattg tcgtgagcgg    3600
atggatatct ccggtttcaa acccactgtt tgaatatagg acagtccct acggaacctg    3660 agaacatgtg gaaattacct gtggtagaat gctgttcagg tacatcacct ttcatcgcga    3720
aaaggtactt tacctaacgg ctgcatgcat ctttggtggc tacatcagcc tccacgatgc    3780
ctgcataccg gtggttggca aaataggtac caacgtcacg ttgaacgcgg tagattttca    3840
tcccggtgat cacgttcgct ggtcttacgg tcccggtggg gcaggctaca tgctatgtgt    3900
ttacactggt agttggacag aatacaaaaa gccagacatc atttttaagt gtttatcaaa    3960
taacagtctt cttttaatta acgtaactgt aaattatacc aacacttacc gtaccttgac    4020
atcgttaaac aattgggttc acaatcaaca tcaccataaa tttcccggat ggaacttgga    4080
cacatgttac agtctcacag tgaacgaaaa cggtacattc cccactacca ccaccaaaaa    4140
acccactacg accacgagaa cgacaactac caccacaaca aagaaaacaa ccaccacgag    4200
aacaaccacc gccgccaaga agacgacgat aagcactacc catcataaac actccagtcc    4260
caaaaaatcc agcaccccta acagtcacgt agaacatcac gttggttttg aagccacagc    4320
agcggaaaca ccgttacaac caagcccaca gcaccaacac gtggctacac acgccctctg    4380 ggtttttagcg gtcgtaatcg ttattatcat cattatcatt ttctactttc gaataccgca    4440
aaagctgtgg ctgctctggc agcatgacaa gcacggcatc gtgctcatcc ctcaaaccga    4500
tctgtgagca agtcgcgtag gaaatgattg catgaaatca ctgtgaaacg ccaactccgt    4560
gccagctggc gcggcggaca ggcctttgac gtatttgaag ccaggcgcgc tctcgatacc    4620
gaaaggatcc gaggggggctt tccaaagccg acgtccctga ttcccttcat aaagctgttg    4680
accggcccta gaaagaccaa gagcatgctg tgggcccact gcggtcgctt cttgcgttat    4740
catctgctcc cgctgctgct gtgtagactg ccattcttac tccttttcca gcggccgcag    4800
tgggcccacg gcttggacat tgtcgaggag gacgagtggc tacgggagat acaaggagcg    4860
acgtaccagc tgtccatagt gcgccaagcc atgcagcacg ccggattcca agtcagagca    4920
gcgtcggtca tgacgcggcg aaacgccgtt gacctggacc gaccgccgct ttggtcggga    4980
tcgctcccgc atttgcccgt ctacgatgtg cgttccccgc ggccgttgag accgccgtca    5040
```

```
tcacagcatc acgccgtatc acccgaactg ccgtcgcgag acgggatacg ttggcagtac    5100
caagagctgc agtatctggt ggaagaacaa cggcggcgaa atcagtcgcg caatgcgatt    5160
ccgagaccct cgttcccccc tccggatcca ccatcgcagc cggcagagga tgcacgagac    5220
gcggacgcag aacgtgccga atcaccacat agtgcagaaa gcaccgtcag gcacgacgcg    5280
agtgagaacg cagtgcggcg acggcacgaa agacggcgct ataacgctct gacggtccgc    5340
agccgggact cgctgctcct gacgcgaata cgcttctcca accaacggtg tttcggacgc    5400
gggcgtctga gacatcccgc gggaagcggt cccaacaccg gcggaccgcg acccggcggt    5460
gcgggactcc gtcaactacg ccaacaactg acggtccgct ggcagctgtt ccgcctacgg    5520
tgccacggtt ggacacagca ggtctctagc cagatcagaa cccgctggga ggaaagcaac    5580
gtcgtgagcc agacgccac gcgagtacgt acgtggttcg tgaaaagaac cacgttttgg    5640
cgtcgcacgt gggttccggg acagaacccg gcggccgaag cgcaagaact ggccgtcata    5700
ccgccggcac ccacggtgct ccggcagaac gaggaaccac gtcaacagct acgggagag    5760
gagacaagaa attcaacgca cactcaacgt gaagaagtgg aggacgtttc gagagagggc    5820
gcgagagaag ggaatgatgg gagccgagca agtggaaacg acgagagaag gaataatgcg    5880
ggaagatatg atgatgatca tgaggttcaa gagccgcagg tcacttatcc agcgggacaa    5940
ggagaactga ataggaggtc acaggaggag aacgaggaag gtggaccgtg tgaatcgccg    6000
ccaatgacga caaatacgct gaccgtggcc tgtccgcccc gagaaccccc gcatcgtgcc    6060
ctgtttcgtc tatgcttagg actgtgggtc tcgagctacc tggttcgacg gcccatgacg    6120
atttagaata caccgagcca ttcctttatt tccccccatc cccggtcgct tatgcgtgtt    6180
aaacactacc aataaagata atctgccaat cgcaccttat atataatatg tggtcgcgtg    6240
tggtcttttt aaggagctct gaaacacaga caggtatggg cggtggtcgg ctgccgccgc    6300
tgtggctgcc gctactgatc gcctggagcg agtggggcaa ctgctgcctc gatgcgcctc    6360
cggtggtgcg ttcgccctgt ctgcagccgg tgcgcgaccg caaccgcgag cggaacccgg    6420
gctcaccgca gttgctgcct tacggcgacc gtctggaggt ggcctgcatc ttccccgcgc    6480
acgactggcc agaggtctct atccgagtcc acctctgcta ctggcccgag atcgtgcgtt    6540
cgctggtggt ggacgcacgc agcggtcagg tgttacacaa cgacgccagc tgttacatcg    6600
ccggcgggc ctggcgcttc gaggacggcg gcgcggcgca gcggctgagc ctctcgtttc    6660
ggctcatcac cgagaccgcg ggcacctaca cctgcgtgct gggcaacgag acccacagcc    6720
tggcgaccga ccacggcg ctggtggccg acatgcacga cctgcgccac tcggaccgct    6780
cctgcgacct ggctttcgga tcgcgctcac agacgcggta cctgtggacg cccgatccct    6840
ccaggttgcg cagtataaac tgcggttggg agggtgaacg gcaccgcgta gtccactaca    6900
tccccggcac ctcgggtttg ctgccctcgt gcgaggagga cgagcgcgaa ctgtgcgtgc    6960
ccttcatcag ccagagcatt gcggacaaca actgcagccg ccggcatcga gttgacggcg    7020
ctaggcggcg ctatcatcta cggagggatt actggctgac ggatccgaag atcgggttgc    7080
tggccgcggg atcggtggcc ctgacctccc tctgccacct gctgtgctac tggtgttccg    7140
aatcgtaccg gcgtctgaac accgaggagg aaagcgaggc ggcggaggaa actgccgcgg    7200
gagaagcctc tgcggtagcg gcggcggccg tctctgagga agagcagcgg cgggagtaaa    7260
cgaggagagc catgaagcgg atgattcgca gtcacggcag gaaaacggaa tgtcagatga    7320
cgggcgccgg cgagcgacgc ggctccgccg tcggtgcgcc catctgcggc agcggtaccc    7380
gacgcggcag cggcgccaac gaacgccgcg actccgacgt cggtcccatc gcccacagta    7440
```

```
gcggtaccag acgcggttcg gcgaatgaaa cgtccgcctg tacgcggacc gatcaccaga    7500
aggcggacat tgggctgtgg ttcatgtttc tggtttttgg actgtgttcg tggttggcga    7560
tgcggtatcg cgcacaataa attttgaatc gatgtcaagg aacgcgtgtt ttgtattta    7620 ttgggaatat tggcggggat aaaccggttt cggatgttta cccttaatct taccggggac    7680
ctcgttgtcc tctcctcctt cttcctcgga caccgggctc catgctgacg taggtaccga    7740
ctggggtcaa aagcctgggt acttatgagg agcgcgcaca aaggaccgtt aggcgccggc    7800
atggagcgtc gccgaggtac ggtaccgctg ggatgggtgt tttttgttct ttgcttatct    7860
gcctcttcct cgtgtgctgt tgacctgggt agcaagtcct ccaactcgac ctgccgcttg    7920
aatgtgacgg agttggcctc gatccatcct ggggaaacgt ggacgttaca cgggatgtgt    7980
atttctatct gctactacga gaatgtgacc gaggacgaga tcatcggcgt ggcttttact    8040
tggcagcata acgagtctgt ggttgacctg tggttgtacc agaacgacac ggtgatccgc    8100
aatttcagcg acatcaccac taacatcttg caagacggac tgaaaatgcg aaccgtccct    8160
gtgactaaac tgtacaccag ccgcatggtc actaatctta ccgtgggccg ctatgactgt    8220
ttacgctgcg agaacggtac gacgaaaata atcgagcgcc tctacgtccg attgggctcg    8280
ctatatccga gaccgcccgg atccgggctc gccaaacacc cctccgtaag cgccgacgag    8340
gaactgtccg cgaccttggc gagagacatc gtgttggtct cagccatcac tctgttcttc    8400
ttcttgttgg ccctacggat cccccagcga ctgtgtcagc ggctgcgcat tcgcctgccg    8460
catcgatacc agcggttacg caccgaggac tgaacggata accgcaaagg ccacgtgcaa    8520
cgttcacgct gctataagaa ggccatgtcc cccgtggacg ggtctctttg acacgagcgc    8580
ggcacgccgt tgccacgagc atggatcacg cgctcttcac acacttcgtc ggccgacccc    8640
gtcactgtcg gttggaaatg ttgattctgg acgaacaggt gtctaagaga tcctgggaca    8700
ccacggttta ccacaggcgc cgcaaacatc tacctgacg tcgcgctccg tgcggccccc    8760
agaggcccgc cgagattccc aaaagaagaa aaaggcggc cgtccttcta tttggcacg    8820 atttgtgctg gctgtttcga cgacttttct ttcctcggga ggactcagag ccactgatgt    8880
cggatccggc acggtctccc gaagaggagg agtaaacaac acacggctaa gaggatacat    8940
catcaaagaa gataggaggg gtcaaaacgc ggactgaaag tatataacgc cgatcatgtc    9000
cgaggaactg ttaataaaac gccatgatga caatgtggtg tctgacgttg tttgtgctgt    9060
ggatgttgag agtggtggga atgcacgtgt tgcgttacgg gtacacgggg attttcgatg    9120
atacatcgca tatgacgttg accgttgtgg ggattttga cgggcaacac ttttttacct    9180
atcacgttaa ttccagcgat aaagcgtcaa gtcgggccaa cggtaccatt tcttggatgg    9240
ctaacgtctc ggcggcctac cccacctacc tggacgggga aagagccaaa ggtgaccta    9300 ttttaaccaa aaccgagcaa aacctgttag agctggaaat tgcgttgggt taccggtcac    9360
agagcgtgct gacgtggacg cacgagtgta ataccacgga aaacggtagt tttgtagccg    9420
gttacgaggg atttgggtgg gacggggaaa ctttaatgga gctcaaggat aacctgacac    9480
tatggacggg ccccaattac gaaattagtt ggttgaagca aaacaaaacg tacatcgacg    9540
gtaaaattaa aaacatcagc gagggggata ctacaataca aaggaactat ctcaagggta    9600
attgcactca atggtccgtc atttatagcg ggtttcaaac ccccgtcacc cacccagtgg    9660 taaagggcg tgtccgaaac cagaatgaca acagagctga agcattctgt acatcttacg    9720
ggttctttcc aggggaaatt aatattactt ttatccatta cggtaataag gcgcccgatg    9780
```

```
atagcgagcc tcaatgcaat ccgctacttc ccaccttgga tgggactttc catcagggat   9840
gttacgtagc catcttttgc aatcaaaact acacctgccg cgttacacac ggtaattgga   9900
cggtggaaat ccccatcagc gttacctcac ctgacgacag ttcctcgggg gaggtccccg   9960
atcacccgac agctaacaaa cgctataaca ccatgaccat cagcagtgtc ctcctagccc  10020
tgcttttatg cgctttgcta ttcgcgttcc tgcactactt taccaccttg aaacaatacc  10080
tacgtaacct ggcctttgcg tggcgctatc gcaaggtccg gtcgtcatga ccagcaacgc  10140
cctgtatgag ctgtttcgac gtcggttacc gcgtgccccc gtcaacacgg tcatgtttct  10200
cacgcgacgc actcgtgatg ggttctgcgg tcggttgacg tccatcgcca cgaattccca  10260
ctacactatg ttcgtgttgg atcacgggtc cgtgcgcatc gagcgaccga gtcagtcaga  10320
agtggattgc gccagtttaa tggaaacgct gaagcggatt cggttacgaa attcgtgggt  10380
agcgtcagaa gacgagctag atgggagtcg cagggacgcg tgacacgaaa cgcgttcagg  10440
attaacgtag gttttcaaaa taacctacgt ccgtgagtga cgcggtttcg tgttgaaacc  10500
cgcgcccggt tcccacggtg gtttatgatg aaaccggcgt tggggatcta cgcggggttcc  10560
tcattcaacc tgcgaaaaga ggaagttgcg gtaaaaccac gtcaataaag acgtcaatga  10620
cacctcaatg ttgcgttgga acggtcttta tatatacaaa cgccgttatg ctcagtgtcc  10680
ggcaagatgc tcgggataca tgctatgctg gtgatgctga attaccactg ggcacaggtg  10740
acaacgaaca atgacgcccg aaataataat acagatacca tctttgtatc tctccttacc  10800
gggcccaacg gaattacccg cacagccgtt ggaggtttgt attcaaacta caccgaccta  10860
accgggacat tcaatttcat ccaaggcaac atatcagcta atgcgtccag tggagataat  10920
tggagcgtag ctaacctgac aaaaaactgc atcaaccgcg gtgagtctta cctgactacc  10980
ctctggcttt tgaactgtac tcaaaacgat acttattggt actctggaaa tgcttacaac  11040
tatacaaata acacctgtgg aagtacagtc tcgggatatc ttttgggcat gtgcgaacta  11100
tggaaaaagt gggtcggtaa tgatacttct cataacacca ccagaatcga gttgttaaaa  11160
aatgaaacac gctgcacgct gcccgctaaa cagtatatcc tcaacgccac ggtggaatgg  11220
tacaacaaat ctgaaggtga cataccaaag gaattcatga gttatgctat cctgagttcc  11280
gtggcggtgc ttacatgcgg acttcaggaa gcttatatac tcgacatgac tcgcagaatc  11340
acgtacttgt tctccatgtc ctgcatagga atcacaagta taatatccat catactcgcc  11400
tccttatcgc tgcttatcct catctgttac tatcgctgtg gccgacttct gatatgccca  11460
cgcggctttg aacgcttgcc agaattcacc gaggaagagg aggaaaaaga aaacttgtta  11520
acgcacaagg acattgaagt ccaggtgcct atccgcacgc ggcgactgct cgtcccttgg  11580
atccgggaaa gcaaaatgtg gacattacca cctccacttc ctccacgacc tcctcactta  11640
atagaattcc caccgtctcc tccgtcgtcg cctgagccca cgcacatggt aatctgcata  11700
ccatcatgac ggactttgga ctgagcccca agcggtacgg actatatatt ttccacaagt  11760
ctacactgaa cttgagcaca caaatactga caatagactg gatatataga cttttatatg  11820
atccctgtac agatgtaaat aaaatgtttt tatttaaaac tggtcccaat gttcttcggg  11880
aatcatgggt tggggacggg ggacgcggta gggagcaaaa ccgggtacat ggggggggaac  11940
atcgtccagc aatagcacca gcggattggg tagggggttgc tgcggaggtc ggtcgatgac  12000
gatgtcgatc tccatcggca gatccggcaa catctcttcg tctccctcac cgaccagcac  12060
tcggcgctgt tctggatgta tatgattctg gaaaagcctc cgacgagctc gcggcgcgta  12120
gaaagccaag cggcgcaagg gccggcgagc ccgaaagtcc atgcgcacag atggcatgag  12180
```

```
tccttgagtg acggtggtga gctggggaac agggctacct cccatcgcga cggtgacagt   12240
ggatccatga gagaggcgcc gcacgctgca tgactaaata ccgtgaatcc cctgacgtcg   12300
tctttcgtcc agaacgcgtc atgttggggg cgaggcgtaa accgtcgagg ttgaaaaacc   12360
gcgtatctgc gacccgtccg gactacgttg tttttcagaa gcggccacat gacctcgaga   12420
tgtcgtcacc caaggtattt aacggcacac agccagacgc gttcgtcagc agcgacgccg   12480
acaagacctc agcatggctc ggaggctatg gatcttgagc ttactagccg tgaccttgac   12540
ggtggctttg gcggcacctt ctcagaaatc gaagcgcagg taaacggaat ctggggaatt   12600
caacacaggt aagaaataca aaaaaataac gtgattgtga acgcggttat cgtgtttttg   12660
cagcgtgacg gtggaacaac ccagtaccag cgctgatggt agtaatacca cccccagcaa   12720
gaacgtaact ctcagtcagg ggggtccac caccgacgga gacgaagatt actccgggga   12780
gtatgacgtt ttgattacag acggagatgg cagcgaacat cagcaaccac aaaagactga   12840
tgaacacaaa gaaaatcaag ccaaagaaaa tgaaagaag attcagtaac agcagacccc   12900
aagggttaac gattatgttg actaccttgt tttttattaa aaagctgtaa ggttttgctc   12960
taaaaacacc ccgcctccgg tcttttttct tttgtattcg gcacgcgaaa cacggtttct   13020
tcccatagcc tgtctaacta gccttcccgt gagagtttat gaacatgtat ctcaccagaa   13080
tgctagtttg tagaggctat gcgggatgct gcggcggcgc gaccttccct ctccacccag   13140
ccccgtcaaa acacacgcga ctcgagcggt tcgtatgaaa aataaaaaac agctttttat   13200
ttacaggaac ggggaaaaaa aaaggcacac ggtccgtggg agacgcgggt tcacgcgtcg   13260
tcaaaaagtt ggtggtccac tccgtaagga caggtaggct tatttagctt ccgcatgctc   13320
ctggttccgt aataaatgcc gttttcgtgg cagcgtgtca tgccgcgagt cacaaactcc   13380
atcaaactgt cggccacgat gcaaacgtgc tgattgttgg cagcaaagac gcgcatacag   13440
tcgtccacga agaggttgat cacgtcgtag gggctcacca accagcctaa aggttccacg   13500
tggttactgc cgaccatgac cctccagtcg ttaatctcgc tccagtcgta cagccgaatc   13560
gtggagacgc gaatgacgct gtaatcaccc atgaccatga gtcggccgcg atacgtagca   13620
cgccactgcg cgaacgcgtg gatgtgcatg cagccggcca gcgctctaag cgaggcggtg   13680
tgcggcagct cctctgggac ggtgatgaag ttgcagcgtc gcaaaccgat gttgagaaat   13740
tcagtgatgc tctcggccac aaaggtcaac gagtcagagt agatgtggtc ggtccacagg   13800
tacatggcgc ccgaggcgcc caggtacagt tcagacggca cgttgtgatc gcccttgtgt   13860
ttaagaaagt tgtaggtgca gatgctgccg acgaaacgca gcggctcggg gcagcagagg   13920
tagctggcca gacgctgtgc atcccgtcct tcgtcgcgca ccaagcgcca gcgacgccgg   13980
ataacgaggc agcggtcttt gggccagacc agggccacgc gttgcccggg tttccacggt   14040
cgcgacgtct taggaggcct ccagcggtcg agcagattga gaaacagtc cttgattacc   14100 gacatcgcgg tcgcgcgtcg gtggacaaaa agaaatcggg ccgatccgga aaaaaaaaa   14160 aaacgacggc aaaacaccgc cgtgctcgag cgaagggtgg cggagggcca gaagaggcgg   14220
ccttgacggc gttggcagcg aaaaaattgg cacgcgagtc aaacgggaag tagcgtcggt   14280
gttttatgcc ccaagcagcg tcgtcgtcac tcgtggcgtc acagtcaacg gtgctgacgt   14340
cctttggggc agtcgggcac gcgatcgtag atgccgttgt ggccgctgaa acgtcggttt   14400
tcaaacagca ggttaagtcc cagacacatg aacgtgttga gattatctcc cacccggatg   14460
tagcggtcgt cgcgcacgtc gcaggcgtag acggccccgg tataggcgac gacgatgggg   14520
```

```
ataaggtcga cgggccagcg caagtgagga aagggcgcgt tctcgccctt gaggctgacg    14580
gttcccaggc cgagaacgcg cattccgaaa gcggttttga tgttgcgcag caagtgaccg    14640
ccttccacgc tgttttcgaa acacctgagg ttgcatagac gcagttccgt tcccggcggg    14700
tacgtcaacg gcatgaactg cccgtggtgg cggatgatga atcgcgccat ggtatccaaa    14760
ccgaggctcc aggcgcgcaa cagcgggcga aagtagcgct taaccaacga cgaggtcagg    14820
tagcgcatgc agtgcagggt ctcgacgcg cgcagcccga cgcgcgcaaa ctccatgagg     14880
ttgcgggcca ggtagtagac ggcggtgtcc tcgcgtacat agcaaaagac atagccctcg    14940
tccgagatga ggcacacggc ggtcttcttc tgctgatccg cgacaacac ggcctcgttc     15000 acgaagcgac ccacgaaggc caggcgcgtc tcgcagcaca ggtagtgact ccaagctttc    15060
acgtcctccg gtttgaagtc ctcgtccgtc tcgatctcct gcagcactag gttccagccc    15120
ggcggccaga ccacgggcaa cacctggcct gcgttgatgc gcacgtaagc ttccagacag    15180
cccaggccga actcggccgt gagcgccagg ctagccagat cgctcatgtg acgcgccgag    15240
tcagtgggcg agcccggggg cccgtcgcac accacgctcc gtcttcttgt cctcaccgcg    15300
gccagcgtgg cgaggacact ttccgcgccc gaggctgtat cttcggtttg cccgccggag    15360
ccggccctca ctatataacg tcccgcccgg gtctcctcca tgtatgcagg taagcaactg    15420
agccgaacgc acctcagcag acgagaggat gtcgtcgcgg cgtcgcagct cgtcacgtcg    15480
ctctggcgaa ccctcgacgg tgatttatat cccctcgagc aacgaggaca cgccggcgga    15540
tgaggaggcg gaggacagcg ttttcacgag cacgcgggcg cgcagcgcca cggaagatct    15600
ggatcgcatg gaggccggtt tgtcgcccta cagcgtctcc tcggacgctc cgtcgtcctt    15660
cgagctcgtg cgcgagaccg gcggcaccgg cgccgccaag aaaccgagcg aaaagaaacg    15720
atcgtcgtcg cgtcggcaac cgcagatcgc agcgggcgcg cctcggggct cgccggcgac    15780
acccaaggcc ggcaagtcgc ctaaagtctc gcgaccgcct agtgtgccct cgctgcccga    15840
gaacggcgcc ggcggcggtg gcgacgataa cagcagcagc ggcggtagca gcagtcgcac    15900
caccagtaac agtagcagaa gtaccagtcc cgtggcgcca ggtgagccgt ccgctgccga    15960
gggcgatgag ttttccttct gcgacagcga catcgaagac tttgagcgcg aatgttaccg    16020
ggtcagcgtg gccgacaatc tgggcttcga gcccagcgtg gtcgcgccgc agcacgtcga    16080
gtatctcaaa ttcgtgctgc aagactttga cgtgcagcac ctccgccgcc tcaacgaatg    16140
catacccatg ccggccttcg cgctcaccag cctcgtcgac cccgtcttaa acaacgtagc    16200
gcctggcgag cgcgatctca cgcgtcggat aatcacgcac gcggtgatca tcaactatta    16260
ctacgtggcg caaaagaaag cgcgccacat ggtggaggcc atacggacca ccgtgcgggg    16320
cgacacggta cgccgggtag ccgcgcaggt caacaaccag agccgttcgg ggcgtgcggc    16380
cgcgctagcg cttcactttc tcacgtcacg aaaaggagtg acggacggcc agtacgccac    16440
gtctctgcgg cggctggacg aagagctgcg gcatcgcggc acgcccgaat cgccgcggct    16500
caccgaggtc taccagacgc tacgcgatta caacgtgctc ttctataccg cccactacac    16560
ctcgcgcggc gcgctctatc tctatcggca aaacctgcag cggctcaacg agaaccaccg    16620
gggcatgctc cggctgcttt cggtcgaaga gatatgtgaa gagcacacgc tcaacgatct    16680
ggcgttccta gtaggcgtcg agcttatgat cacgcacttt caacgcacca ttcgcgtgct    16740
gcgctgctat ctccagcacc agctgcagag catctcggag ctgtgttacc tcatctatgt    16800
acaactgccg tcgttgcgcg aagactacg gcagcttagt gacgtgatct actgggccgt    16860
cagtcaaaac tacgactacg cgctctacgc gagcacgccg gcgttgtttg acttttttacg    16920
```

```
cgtcgtgcgt cagcaggacg ccttcatttg caccgactac gtgtactgcg ccctgcgtct   16980
gctggcctgt cccgacagac ctattatcgg tgacaccggc ggcagcagta gctcccaacg   17040
cctcgtaggc gagtttatgg tgcgcgatcc gctgttgcgc gacccgcgcg ccacccacct   17100
gcgccagaaa ctcatcaccc gcgacatatg cgtggcgcgt tgcaagcgc agccctcgag    17160
tcgacacatt ccggtcgaac acacgggtgt ctcctccgtc accctgctca aaatctttag   17220
ccaggtcccc cccgacgaac gcgaagaaga cacgttacgc gagatggctc ttaaagcgtt   17280
tatggaagcg aacggtaatc acccgaaca aatctgccga tccccaccac ccccgctgcc    17340
accgcgcgac tatcctcaac gcgacagcg ggaccgtcac cgtcgcgacc gccgcgacag    17400
cggggaatac tgttgctgat ggtgggacga acagcaggg cggaacagtt tatgatagaa    17460
agtcacagga aagtatgtgt tgtttttttt ttaatgtacc aagaataaaa agtgcgtcta   17520
cgaccaaagc ggtgtgtgga cgctcgtcct ctgtcttctc cggtttttttt ttatgtgtgt  17580
gtttttcttt tccttcctat tttgttacgg caacagcgct gatggcacgt tgccggcttc   17640
gaacatcgcg tcggtgattt cttgcttgcc cggcgtcaca cggtgacgca gcagcgcgcg   17700
gctcacgtag caggccgact cgcggatgac ctggccgtcg gcgtcgcgtc gcaggcccga   17760
gcggttgccg tgacgcagtc ggccctgcgc ggcgcgctcc acgtcttcaa agtagctgtg   17820
tagcaggccg cgctccagca gctgcggcag cgagtcggcg gcgcgcacca caaagttctc   17880
acggctgatc tcgtagcaca gcacgctgcc gtcggctgcc acgccggcca cgctgcggtc   17940
ccaactgaag aggttggcga gtccgatggt gccgatgacg cgcaactgac cctgggtcac   18000
caccagcagc ttccagtatt ctacgtcgcg cggggtgagg atggtctcct ccacgtcgca   18060
gacaaacaac gtgtagccgc gcggataggc cagatccagg tggcgaccgc gctggcggcg   18120
cataaaatcg tctaaattca aaccgccgtc gggtgcgcgc ctgctcgtca tcgccgcgcc   18180
tcgtcggtcg atgaccccac ggtgcttata acgcgccgcc gcggcttcat gtggcgtgac   18240
ctccgacctc gtgaggccga aaacggcgta catgaagacg ctcaaacttt tgaatgtggg   18300
cccggtagcg caccgagggc cccggggcgg cgacgacggc gggtccgagt tccagcgggg   18360
ccttgcggcg gcagcggttg gcgtggttgc tcagctcggc gtccgagagc gccgagctga   18420
actgcggcag ccgcgtgcga tcctgcggcg cgtccccgtg tcgcagcgag tgccagagca   18480
ggcgctggac gcgcgccgtc tcgggcgtcg gcggcgcgcg acagcccgg cgcagcttga    18540
aaacgtgcag gcacagcagc tcgcgcttga tgcgcagcga cacgctgcgg tagtcgggaa   18600
tccgctgcac cagctcgaga aagtcgcaga aggtctccac gaacgtgtcc tcggtgaagc   18660
gaatgcgctt cagatcgtgg acgtgtttgc gaaaccgcga cagttctcga cgttgcacgg   18720
ggttctgagc gagtcccttg cgcagcagcg cagcctcgcc tttaaacagc ctgatgagcc   18780
gctgcacgtc cccgctcaac atacgtatac acgccgtgta ctcgtgacgt atactggcgc   18840
gcagcagccg aatgatacgc agggccagca cggcgttgga ggccaggtac atggcgtagc   18900
cgcgacgcgg gttggcacag gcccagcccg cggggagcag aaagtagtcg tcgaccagcg   18960
tctgcgacca gtcggcgaag cccaggtcac gtgatacgct gtcctggacg cgggccacgt   19020
cgccggctgt gaggtggcgg atcgccggca ggtgaaacgc gcccaggtgt cgattgcgct   19080
ccagcctcag ctcggcgtgc tccaaacggg aatggtggga cgccaccgcg gagggcgaca   19140
aagaggagtg gtcgccgccg ccgtagttac cgttgtgatt accgccgtcg tcgcccgt    19200
cgccgcactc gcaaaaggcc gcgtagaggt ccttcaacgc cgcttcggct cgcgccataa   19260
```

```
acgtggcgtg gaaaaaaacg gcggcgcggt gcgtccggta cttgacgggc aacccgcggc   19320
acagggccgc cggcaggcag cggccgatga gttcgcgctc ctcgggctcc agaaacaggc   19380
acagggtgcc gtccaggcgc aggtacagct cctcggtcat cgagcatagc tgccgcaagt   19440
aatgggtgcg cgtcccaaag gtcttgtaat cgagcaacgt gcacaccacg tattgccccg   19500
tggccacggc cagagcgatg cgtttggcgg cgcgactgat ctctggcaag tactgcgcct   19560
cgtgcaccag acggcggaaa gcgcggcgt tgagccagcg aaaatgctgc ggatcgggcg   19620
gcaagggcac gcctcgaagc gcggcccaga cagcgaggtc cgactcgagc gtcagaccgc   19680
ggatgtcgta cttgccgtgc gccgtagcgc aggctgaatg gacaagacag ctgcggcgaa   19740
tgtacaccat ggcgtgcttg ggatgtttgg gcgccggcgt tttcttttc tgaccgccgg    19800 cggccgccag atcctcgggc gtgcgacaca acaggccggc gcgcacagcc tcctgtcgat   19860
tacgaatcgg cgtcaggtag gcgcgcagga actggtgaca aaactcctca tcatcacgac   19920
agtcgtcgag atactcgtac gtggtgagcg gatcgcgaaa taggcgctcg tcaccgtcgt   19980
catggtcttc tttagcctgc tcctccggct gctgggttgg cggtggaggc ggcggctgat   20040
ccacggggtt catgactgag aggaagaaga aggtggcggc gaagcgacgc ggagcgacgg   20100
cggtaaagcc agacaccggc tatatagcta gtcatcacag tctcctcctt cacgacgccc   20160
ccgtgccgct cacgctatcc agcacgctac ggcccgaaaa cacgtactcg ctgacgtcgt   20220
acgcgggcga tgtatggctg ctcaccggtt tcgcggcgac ggttgcgctc gagtccaacg   20280
gcgagaagca aaaacgccgt gggcaacgaa accagaagga gccctgacgg ataaaaccgc   20340
gcagcgtctc ggccaactta accagcatcg taccgtacag cagtacgtga atgccgccat   20400
gcgcgtccat aaatacggct ttgttcacgg gttccatcca tccgatgact acaaaatggg   20460
cctgttctag cacgccgatc acgaaattgt tggcctcgtc ggcctcggcc acgttccacg   20520
agccgaaagt gaaagtacaa gcgggcgagc cgcccaggcg gatcttgcta ccggcgtgga   20580
gctgacatac gcgcagcaga ttggcgcggt cgtgcagtat ctgggagagt tcgtacatgc   20640
ccgcaaaggt gtgcttaaac cacgcgccct ctacgatctc atccacgtag tcgcgctcaa   20700
agaagctgta cacggcaaag aggccgttct caaaaaactc gccgaacgag agccccagca   20760
cgtacacctt gtcctcgccg ggcaggtacg caaaggcgtg cccgtgcccg gagacccaga   20820
tctcgggcgc cgtgtttgcg tccggcacgc attcgtacac actgacgagg ccgataaagt   20880
acaagcggcc agcctggcgc aggcacgaga agcgccggta ggtcttgtga tcgcgcacca   20940
ccccaaagta ctgagtgtcg cccagcatga tgccgtgcag cggcggccag cacagcggga   21000
gccaacgacc cgccgtggcg cgcacgtagc gctgcaggtg aaccccgctc gcacgctcgc   21060
gcggcttcgg gcgcttgtgg gtccaggcat cacgcaggcc gcgccagatg ctgctgaact   21120
tgggctgccc gcgcagatag agcgacgaga gcgagtcaaa gtagcccacg acgagcctgt   21180
cgggagacac aagagcgcga aaatcaaacc tagaacgaca acggtgaaaa aaccgaccag   21240
aagcgcgtgt ctcaaacacg ctactttcgg ttataaaaac accgtcgccc tatttctggg   21300
cgtgtgtaca ctgatgactc acctacgctt tttgaacggc agtctcagct cgggattggc   21360
ctcgtacagc gagctgcggt ccacggggcc gatgctctcg taacgaaagt cgtcgatgag   21420
cagcgccagc cccacgcgca cgaagcccct gaggtcgcgc gccagccgca ccaacttatc   21480
ctgccccacc agcgccgcgt acacggtgcc cgtatcaccg cagagaatcc gcacgcggtg   21540
aaagaaggtc ttgtcctcgg cgccctcgat ttcgcccagc ggcatgacgg gctcgcgcgt   21600
gtacaacgaa cgttgaaagc ggcgcagcat cgaggccgag agccccagat cgcgcgccgt   21660
```

```
gcgcagcacc agggaatgct tctcgggcca gatgaggatc agttgcgcct cgcggtgcgc   21720
ctctacgtag gcgcaacgag cggcggtgtc ctcgcaggcc agcaactcgc ggaaagccag   21780
cagcgaacgt aggtagcggc cgcgagcgga ggcgcgcgag cggcggcaca gctcagcccg   21840
atggtcggga tgcaccaagg gcacgttggg ttgcagacgc gcgcagatgg attcgtgcac   21900
cgggtcgcag cgaatcatgc ccttggcaaa aaatccggcc agatccgagg ccaactcgta   21960
caggcagtcc tcttgcgcgt cgtaggcgaa cacggagccg tacgcgtcca cgaacacctg   22020
gtaccggcag gtggcgtgcg agaccgtgcc aatgagatgc agagctcgga attcgccgaa   22080
aaagtcgttc tggcagtgct ccagatcgat ctcggtcagc gagtgcggcg aatgctcacc   22140
cccgaccacg tagatgcact gcgagggcca gcccagcgat acgcacgaac cctcgaagcg   22200
ccgcaagtaa cgccgcaggc cctcatagtc gcgtcgcacg cacaggtcgg ccaagtcgcg   22260
cgtgcaaaag acctcgggta ccaagcagcg tttgcgacgc ggccgacgcg cgtgcccggg   22320
cagaggagga aggcgcgacg gcggcgacga cgaggaggaa gacgccgtgg ccgccgagca   22380
gcccttgcga cggccagaca tgccggcagt ccgcgacgat ccacaggaga caaaaaagca   22440
gaagcagcag tagtctcgac gacccgctcc accccgtcct ccacacgctc agccgcgact   22500
gagcgccggg gcgcgccgct acttgggttt ttatagccat ctgcccccg tctcgggcac   22560
ccgggagcga tctacggaga cctgacagca cttgggcaac acaagacagg gaaatacaaa   22620
gacacttta ataaaaaacg agactacttt gtgtgtgtgc tccgtaaact gtttattctc    22680
cccctccgtc tcgctctgga tgggctccgg gtccgtcaac acgcgacccg cgtggcaaaa   22740
ggcacgctgt tgacggcgcg agagcccgtc atgatagtcc atcatgcccc ggagatcgtg   22800
cacaaagcag ctgtcgccgc gcagaaaccg acgcagcgtc tccacgtgct gcagctgtcg   22860
gcgcgtatca ggagccgtca tcgctgatgt cgtcatcgcc ctgacaggcg cgtagatggc   22920
tccgcgagat catgcgcgtt ttcaaccgcc gtgacacatc aggtccatct tgagctggcg   22980
ccgggcctcg cgcaggtctc gcacgcgttg tgagcgggag gcgagttcgg cttcttgctc   23040
gaactcctgc tgctcactgt ccgagagggt gcgataaaag gcggcaaagt cctccaagtc   23100
ggctacatgc gccctgggtc tgacgctcca aagcgtacgc agtctgatga agcggaccca   23160
tcgagcgtca cggcacgccg tcttgaacgc agggcccggg aagagattct tctccccggc   23220
gcgctcgggc cggcgaggcc gacgcggttt atatacaccg tctcggacgg cgggacgccg   23280
agcccgcgcc gcggccgctc atccggagac ggcggaaacc gcggcgccgg aggaaacggg   23340
gaccggcaac gacggcggtg gcggcgacca gattatgggg gacaagccca cgcttgtgac   23400
cctgttgacc gtcgccgtgt cgtcgccgcc accgtcgtcg ccgctgccgc tcgtcagctt   23460
cacggagctg ctgttaccgc cgccgtccgt cgccgccgct gcggtggcgg caacagcgac   23520
gagcgaggtg ggcgagaaaa ccgcggagca agaggtagcg gctgcgggtc cggagaccgg   23580
gaatgagaga agagaaaaca gggaggacga aggaggggag acgaggacga cgggcaccac   23640
cgcggtcaaa aggtcgcacg acggtatccc tcgccaactg gcagagcgcc tgcggctgtg   23700
ccgccacatg gaccccgagc aggactatcg tctgccggcg caggacgtgg tgacctcgtg   23760
gatcgaagcg ctacgcgacg cggaccgcga caactacggt cgctgcgtgc gccacgccaa   23820
gattcaccgt tcggcctcgc acctgacggc ctacgagtcg tacttggtgt ccatcaccga   23880
gcagtacaac acgcctcga acgtgacgga gaaagcttcg tacgtgcagg gctgcatctt    23940
tctctcgttt cccgtcattt acaacaacac gcagggctgc ggctacaagt acgactggtc   24000
```

```
caacgtggtg acgcccaagg cggcgtacgc cgagctcttc tttctgctct gctccaccag   24060
cgagagctcc gtggtgctgc aaccgctcat caccaagggc gggctctgct cgtccatggc   24120
ggtttacgac gaggaaacca tgcggcagtc gcaggcggtg cagatcggtt ttctgcacac   24180
acaactggtc atggtgccct tcgtgccgca cgcctgcccg cattacgccg tgcctttcac   24240
gacgccggga aagccgggct gcggcggtgc tccgagcggc gttgcggggt tggaggaggc   24300
ggcgcccttt ggacgggtca gcgtcacgcg gcatggcgcg acgctgctgt gtcgcgtgga   24360
ccatctgacc tggatcagta agcgcgtaac cacgtacgga cacaaaaaaa ttacgcgcta   24420
cctcgcgcag ttccgcggca cgatggacga cgacgaggcg cgctacccg gcaggacga    24480
ggcgtggatc gcgtccaaaa acgtgcagta cgaattcatg ggtctcattt tcaccgtcaa   24540
cgtggattca ctatgcgtgg acgcggaaca gcgccaactg ctgggcaccg tggccacctc   24600
cttctgtcac cgcgtctcgg acaagatcac agcgcgcaac atgccgcgcg ccttttcctt   24660
ctacttgcta acgagcgcgc agcgcgggta cgacctgcga tttagccgca acccgtcact   24720
cttttttcagc ggcgacgcgc tcaactgtcc gcttctcaac gagcccaacg tgttttcgct   24780
cacggtgcac gcgccttacg atatccactt cggggtgcaa ccgcggcaga cggtggagtt   24840
ggacttgcgc tacgtgcaga tcacagaccg gtgtttcttg gtggccaact tgccacacga   24900
ggacgccttt tacacggggc tcagcgtgtg gcgcggcggt gagccgctca aagtcacgct   24960
gtggacgcgc acgcgttcca tcgtgatccc gcagggcacc cccatcgcca cgttgtatca   25020
aatcaccgag ggcgacggta acgtgtactc gtacaatcac cacacggtgt tcggcagat   25080
gcacgccgcc ggagcaacca cgttctttct gggcgacatg caattgcccg cggacaactt   25140
tctcacgtct ccccatccct gaccctccgt ccgtcctcct ttcccgacac gtcactatcc   25200
gatgatttca ttaaaagta cgtctgcgtg tgtgtttctt aactattcct ccgttttctt    25260
aatcttctcg atcttttgga ggatgttctg cacggcgtcc gacggcgttt tggcgccccc   25320
catgccggca gaacccggtt gcggccccgt accgctcttc tggggcgacg ataggtcgaa   25380
agccaccgtt ttcatgcccg tcgtgctctt gacgggggaa cctacggcgg cggtccccgt   25440
cgagcggcgt gattgcaaag ccgcgctcgc ccccggtttc aggatggagg gggaggccac   25500
aggcggcgca ttcgatacgc tgcttttggc cgtagacgac ggtgggtaaa cggtagttac   25560
tgcgggatac gtcggcgtgg tcgaggcggc ccggctggtg ccggacaggc gacccggcgc   25620
gctaccgctc acggggaccg agggcggtcg acctaccacc gccttgccgc ccaaagtagg   25680
tttcaaggaa ggaacaacac cgacgcggct gcccccggcct ttcaccggag acgggggggc   25740
actcttggcc ggggacggag aggctgacga aagcatggac agcggcgatg tggcggggga   25800
cacgatatca tcctccgtgg gcgataaaac ggacgccgaa gctgacggct gtcgagccga   25860
agaagcggaa gaggttcccg cgccagaagt cacgttcctt gatgacgtcg ttttagacga   25920
agccggttga ggttgcaaca gcgtggcggg taccgtcgac ggcgtgcccg acacctgttt   25980
ctctagcctt ccctgaaccg gtgtcgacgt caccgtctgc gctcgggcgg acgcgtgcgg   26040
cgtcgcgact cgcttgccca gcaccggttt ctggctcgtg gatgtcgtcg tcattggaga   26100
cgataactta gctttacgta ttctggacgg cgtcgactgc tcgggcgtct gactgggagg   26160
cgaaatgacg tcgttgtaat cggacgacgg tgttgtgtgt cccaggctga cgacggagcc   26220
ggtgtccgag gagtcgtcgt cttcctcctc gctgtcttcg accggtgact ctgcagtttg   26280
gtcccttaaa gcccaaacct catcagcggt gttctgagac gctgtttgtg tcaccgcggc   26340
gcgtggagtc gacggcctcc gaggggtggt ggacacggtg ttttgagaag ccgtggaagt   26400
```

```
cgtaggcatc ctgaagggat tgtgagccag gtgaggattc ctgagggccc acgcgcgttc   26460
gcgcggccag ttggcggggt tcatatcccc gggcaacggc gccgtcggag cccagggcga   26520
gttaccgttg accggggttt gggtacccgc gaaggtaggt gtcggggccg gagcgggggc   26580
cgtagaagga ttgacaggcg tcggcgtgag gatggcagcg ccggcgccag cagggacgtt   26640
aactccggcg ccgaacgtca acgtcggttg ctcgaacttg tacgcggtgg tgacgggcgg   26700
tttggcgctc gtctcggtat ccgtgatgtc caccagcgtg tcggtgaaac gcggatcttg   26760
acggttgggg ggatagccat ccgagctgtc ggaatcctcg tcgcccgaga aaagatcccc   26820
tctggtctcc gtgagcggcc tcacgtccca cgcgctgtcc cgacggaccc ttcccgggct   26880
ggccttggtc acctgcgggg agacgagact gaaagccgcg tgacgctgtt gttgctgcgg   26940
gatgttcaag ggaccactgg tcggtttctg actgcccgag gataacaggc cgctgaaaat   27000
gctggaaaca ccgccaccac tagcggcgcc cttgccgcta gttcccggtt tcttgatggg   27060
cgtaaagatg ttttctcgt catcatcatc gtcgtcgtcg tcctcatcgg cactggagcc   27120
aaagagcctc cgggaggcgc tcggtttacg tgccgggggc ggtggttgct gctgacgttg   27180
ctgcaggttc tgctgcctct cctcccaagc cttcagctgc tgtttctcac gctgcaccac   27240
ctcgtcgtcc acccgtttct gccgctcgcg acgcttttcc tcttcgtcgt aatagccgac   27300
ggccgccgaa cgggcagcgt gggcgtcggc ggccggtgcc agagaaccat gggcctcgaa   27360
gcggaacggt ttgtgtccct tccagggact agcgatccag ctccagccgt ccagcggctg   27420
cgtggggaca tgtttcttgg gtaccgacga gaaggctgaa ccgccgccga gcgagaggag   27480
attggcgtca tcatcaaact ccaacgacgg cgagcgcgcg cccaaaaagg tgtgcgccga   27540
ctgcgggaag ctgtccacgt agatatcaaa gtcctcgatg agcagctcca gcagcgtgtc   27600
ggccgagtcg ccgttttcca cggcgtgctt gaggatattg cgacagtagt tggaatcaaa   27660
ggaaaggcac atgcgcagct ccttgaccag cagcttgcag cgctcttgaa tgcgcgccag   27720
acatttgcgc tccagctcct cccaagacct tcgcacgttc atgatgagac ggcccgtgta   27780
cacgagcttg ttgacggcgt tgaccagcgc cgtgttggcg tgccggtcca ggttaaggtc   27840
gagcggtttc acacagaaca tgttacggcg cacaccctcc aggttttctt caatgcgctg   27900
cacctccgta tctttgaggt gcacaaaggc gatgggttcc gtctggccga tggctgtgac   27960
cagcgtctcg cgcaccgaca tcttggccag aatgaccgcg cttacgagcg cgcgctccac   28020
gatctcggca tcgtggcgca cgtccgtatc gaattcggta cggtctagca cagccaggtg   28080
gtcacgcgcc ttaccacgat caccgaacgg gtaagtgtag ccgcgacgcg ccacggccgc   28140
gcaacgcacc tcgaactcct cgagcaccga ggagaggtcg ggattgtgga acgcagctc   28200 gcggtagtat cccaaccaaa gcatgagctc gttgaacagc accgtacgcc ggtgcaggcg   28260 ttttttcgcca cattttttca ggatcttggg gtgtgcctcg agatccacgt cgggcttttg   28320
cgtgagatgg cgcagaaagt tgaccagggc caccacatcg cgccgctgta gaccgataaa   28380
ctgcaaactc atgctggctt ttctccagaa cccggaagcg tcgtcgcccc ggactgcgcc   28440
cgcggtctgc tattcgccca cgatggacac catcatccac aactcggtga gcgccccacc   28500
tagagggagg gggggtagtt taatagcgga ggcggatacg cggttttctt ttaagcgccg   28560
ctgacttgtt tcttctgttt tttcgccccg tgtgctgttc cgcccagacc cgcaacaaca   28620
ctcctccgca catcaatgac acttgcaaca tgacagggcc gctattcgcc attcgaacca   28680
ccgaagccgt actcaacaca ttcatcatct tcgtgggcgg tccacttaac gccatagtgt   28740
```

```
tgatcacgca gctgctcacg aatcgcgtgc ttggctattc gacgcccacc atttacatga   28800
ccaacctcta ctctactaat tttctcacgc ttactgtgct acccttttatc gtactcagca   28860
accagtggct gttgccggcc ggcgtggcct cgtgtaaatt tctatcggtg atctactact   28920
caagctgcac agtgggcttt gccaccgtag ctctgatcgc cgccgatcgt tatcgcgtcc   28980
ttcataaacg aacatacgca cgccaatcat accgttcaac ctatatgatt ttgctattga   29040
catggctcgc tggactaatt ttttccgtgc ccgcagctgt ttacaccacg gtggtgatgc   29100
atcacgatgc caacgatacc aataatacta atgggcacgc cacctgtgta ctgtacttcg   29160
tagctgaaga agtgcacaca gtgctgcttt cgtggaaagt gctgctgacg ctggtatggg   29220
gtgccgcacc cgtgataatg atgacgtggt tctacgcatt cttctactca accgtacagc   29280
gcacgtcaca gaaacaaagg agtcgtacct taacctttgt tagcgtgcta ctcatctcct   29340
tcgtggcgct acagactccc tacgtctctc tcatgatctt caacagttat gccacaaccg   29400
cctggcccat gcagtgtgaa cacctcacac tgcgacgcac cattggcacg ctggcgcgtg   29460
tggtgcccca tctacactgc ctcattaatc ccatcctgta cgcgctgctg ggtcatgatt   29520
ttctgcaacg catgcggcag tgtttccgcg gtcagttgct ggaccgccgc gctttcctga   29580
gatcgcagca gaatcagcga gctacagcgg agacaaatct agcggctggc aacaattcac   29640
aatcagtggc tacgtcatta gacaccaata gcaaaaactg caatcagcac gccaaacgca   29700
gcgtgtcttt caattttccc agcggtacgt ggaaaggcgg ccagaaaacc gcgtccaacg   29760
acacatccac aaaaatcccc catcgactct cacaatcgca tcataacctc agcggggtat   29820
gagctttcct gttactttat tcagaaagca ccagaacccg tcgccatttc ccctcatata   29880
cggtacacgt cccctgatc tgtcatcacg gtacacagat ttcgcccgac tgcggacgcc   29940
gacggccaat cgcgtggcgt aggagtggcg ccccggcttc attataacgc cacgtcggag   30000
cccctgcgcg ccacaacgcc gtccggcgca acttctgtct cggcacggta cgataaaaac   30060
aacgtcccccc ctcgacgttg ttttctccga gcggtgatcg ttcccgtccc tctcctccct   30120
ccgcggcccc cacggcggcg gcctgctcgc acggacctat actattaccg ccccaccgcc   30180
gtcgtcgtca tgaacttcat catcaccacc cgagacttct ccaacgacga ttcagtcctg   30240
cgagccgccg agatgcgtga caacgtggca ggctcgattt ccaaagcgta caagggcacg   30300
gtacgcgccg aaggcaagaa gaagctgctg ctgaagcact tgcccgtgcc gcccggcggc   30360
tgctcgcgcc gcaacagcaa cctcttcgtt ttctgcaccg agcgcgacta ccgcaagttc   30420
caccagggca tcgcacagct caagcgcgcg ccggccgaac tggacccccca cgagatccag   30480
caagtcacgg ccagtatccg ctgccgcctg cagcccagtc tccgcgagcc gcccacgccg   30540
gccgacgagc tgcagacggc tgtgtcgcgc gtgtgcgcgc tcttcaacca gctggttttc   30600
acggcccagc tgcgccacta ctgcgagcac caggacaagg tggtgagcta cgcgcgcgac   30660
gagttgacca aacgctgcgg cgaaaaatcg gcgctgggcg tggaggtgca tcaactggta   30720
gccttgctgc cacacgagcg ccaccgcgaa ctgtgccacg tcctcatcgg cttgttgcac   30780
cagacgccgc acatgtgggc gcgctccatc cgtctcatcg acacctgcg ccactacctg   30840
cagaacagct tcctacacct gttgatgaac tcaggtttgg atatcgcaca gttttcgac   30900
ggctgttacc acagcgaggc ctaccgcatg ctcttccaga tcggtcatac ggactcggtg   30960
tcggcggccc tggaactctc acacagcgca gcggccgggc cgcccgaggc cgatgagaac   31020
aacgacgagg gagaggagga cgacgacgag ctccgtcaca gcgacccggc gccgcttcac   31080
gagtccaaga agccccgcaa cgcccgccgt ccccgcacac gcatgccgcc tcacgagcaa   31140
```

```
aagcccgaag aaaacgagga ggaagaagag gagctgtttc cctcctgcaa ggcaaccgca   31200
gcattcctgc gggcagaacc ctccgtctcc aacgacgacg gcaacggcgg cgaacgctgc   31260
gacacgctag cgaccgccct gcggcattgc gccgacgaag aagacggacc tctagccagc   31320
cagaccgctg tgcgggtcgc cgcgacccccc tcaccttcag tcaccccagc ccttacccccc  31380 gtcacgtccc ccataacccc gttgtgtatt taacgtcact ggagaacaat aaagcgttga   31440
tttctcaagt tccgctctgg ttttggtttc gttttcaaag ggagcccat catggcccaa    31500 ggatcgcgag ccccatcggg cccgccactg cccgttctcc ccgtggacga ctggctcaac   31560 tttcggggttg acctgtttgg ggacgagcac cggcgcctgc tgctcgaaat gttgaccccag 31620 ggctgctcca actttgtggg gctgctcaac tttggcgtgc ccagccccgt atacgcgctg   31680
gaggccctgg tggacttcca ggtgcgcaac gcttttatga aggtaaagcc cgtggcccag   31740
gagattatcc gtatctgcat cctcgctaac cactaccgca acagccgcga cgtgttgcgg   31800
gacctgcgca cgcagctcga cgtgctgtac tcggagccgc ttaagacacg gctgcttaga   31860
gggctcatcc ggctctgccg cgctgcgcaa accggcgtca agcccgagga catcagcgtg   31920 cacctggggcg ccgacgatgt gacattcggc gtgctaaaac gagcgctggt ccggctgcac  31980
cgggtacgcg acgcgctggg gctgcgcgcg tctcccgagg ccgaggcgcg ctatccgcgc   32040
ctcaccacct acaacctgct gttccaccca ccgcccttca ccacggtcga ggcggtggat   32100
ctgtgcgccg agaacctgtc cgacgtaaca caacgtcgca accgaccgtt acgctgcctc   32160
acctccatca aacgcccggg ctcacgcacc ttggaggacg cgctaaacga tatgtatctg   32220
ttgttgacgc tgcgacactt gcagctgcga cacgcgctgg agctacaaat gatgcaggac   32280
tgggtggtgg aacgctgcaa ccggctttgc gacgcgcttt acttttgtta cacgcaagcc   32340
cccgagacgc ggcagacttt cgtcacgctg gtgcgtgggc tggaacttgc gcggcaacac   32400
agcagtccgg ccttccagcc gatgctgtac aatctgttgc agctactgac gcaactgcac   32460
gaggccaacg tgtacctctg cccgggatat ttacatttca gcgcgtacaa gctgctgaaa   32520
aagatccaat cggtctcgga cgcccgcgag cgcggcgagt tcggggacga ggacgaagag   32580
caggagaacg acggcgagcc gcgcgaggcc cagctcgatc tcgaagccga tcccacggcg   32640 cgcgaggggcg agctcttttt cttctccaag aacctgtacg gcaacggtga ggttttccgc   32700
gtgccagaac agcccagccg ctacctgcgc cgacgtatgt tcgtggaacg gcccgaaacc   32760
ctgcagatct tctataactt ccacgaaggc aagatcacca ccgagacgta tcacctccag   32820
cgcatctata gcatgatgat cgagggcgcc tctcggcaga cgggcctgac acccaagcgc   32880
ttcatggaac tcctcgacag agcgcctctg ggccaggagt cggaacccga gatcacagaa   32940
catcgcgatt tatttgccga tgttttcgc cgtcctgtga ccgacgcggc ttcttcgtcg    33000
tccgcgtctt cgtcgtcgtc ctcagcatct ccgaattctg tttcgctgcc gtctgccagg   33060
tcgtcatcca cacgaaccac cacgcccgcg tccacgtaca cctcggccgg gacttcttct    33120
accacgggtc tcttgctctc ctcttcttcc ttgtcggggt cacacggcat tagctccgcg   33180
gacctggagc agccgccccg gcaacgacgc gcatggtcca gcgtgaccct cttttcgccc   33240
tactcggtag cctacagcca ccaccgacgt caccgaaggc gacgcagccc accacccgca   33300
ccccgagggc cagcccacac acgcttccag ggacccgaca gcatgccgag cattagctac   33360
ggcagcgacg tcgaagaccc gcgggacgat ctggccgaaa acctacgaa tctctgaacg    33420 cggttttttcc tcttttttcta cgtgtctgtc tcaggacgag atgtcgatat caataaaaat  33480
```

```
accgtcgacg tggtttttcta acagtgtggt tttctttatt gaccagcgga gtacacagtt    33540
tacgagtaaa aaagacaggg aaaggttata taaaatgctg tattatatac aaaaacatgc    33600
acatagacaa acgggaccac cgtgctcgtc atcccctcct taatcagtta ttcatgtagg    33660
cgtgtggcgg ggtgagggc ggcatgccgt tggcggcgcc aggaataatg tgccgtcgac    33720
cgacgtcgca caccttgaaa cgccgtcggc gcacgcagcg gtcgcaggac gggatatccc    33780
agaggaagcc catgtaagtt tcggggtcct cgtcgtgaaa gcgtaggag agttcaaagt    33840
ggtgcaacga gcccgtccga gctcgcagct tctggcgaac accctccacg tcatcggtgc    33900
acagcgacag tgctgggctg tcacacaggg cctgaagctc ctgcggccac aggtgcgtgg    33960
ccagggcga gtccgtcgtc accagtttga cgcagtgcat caggttctcg gtgatggcgt    34020
cgtacaggcg actctcggcc tcctcgtgcg tcatcacgtt tcgaggcagc acagctcgt    34080
cgtcgtcatc ctcgtcaaac atgatcatgg ggtcaggggt ttttttggga tgttgacagg    34140
tgggtgtctt ttccagacgc acgatggcct cacgccggcc gctgaaacgg tggtttcggt    34200
gtcccttctt tcccatgacg caggtgaaca taaccacgtc ctcggccaaa cggtagacgg    34260
cgtccatggc ggggtcgtag ccgtagacga cgccgaaagt gtccaccaag acgtactggc    34320
gtacgaggaa ctctttgcgt tctggcacct cgtggcccag cgcgcccaac aactggtggt    34380
aacaggtgat gcgcggcacg gtacggatca tgagctccat ggtctggatg ctgccgcccg    34440
cgcggacgac gctgaaggat gttttccttga acttcataac ctctgtgttg tgggtccaga    34500
aggcgaaatg ggtgtcggga cactcatcga aagggtcgtc gatgctgtag aagcgtagc    34560
cccgcttggt cacctcggcc gacaggctct ccacgtcacc gcggtagagc atgacggcgt    34620
tccagtagtc gtcgtactgc accatgggcc gctggtagtc gcgcatagtg tggaagtggt    34680
cgcagtgacg aaagccatgc cgcagaaagt ccttcatggt ggccgccagc tcgtagacgc    34740
agtcgcgcag gtcatcgtag cagtagatgc caccgcgctg cccgatgagc acgatgagtt    34800
ggtaacgcat aaagcccgga ccctcgacga aaccaaaggg gtgcaggtac tcctgacagc    34860
agacgtaagc acctggtgga gaaatgagaa aaatccacgc acgttgaaaa cacctggaaa    34920
gaacgtgccc gagcgaacgt cctctttcca ggtgtcttca acgacgtggg gcttaccttg    34980
cgaacagacg gtgcccatct tgcccacgaa gggcccagg gcgctgcgcg aacggagctg    35040
gatgaagcag cgttcgggcc aggccacgtg cagccgggtg ccgcattcct gctccagaaa    35100
gtcgttgaga ccgttaaagt ccccggctcg gatggcgatg cagccgtagg ccatcagcgt    35160
gtcccgtagg tcgtccatga cggactcctc taccttcgct cgccgacgct gcgcttctcc    35220
agccaccgct gcggtcgaca gactccttcg tccgccttcg gagaactacg gcgcggcggc    35280
acggccttta tagacactat cagcgttgac gtcagacgat ccgatgaacg tcgttttttg    35340
tgctggaact tccctcgtcc cgacaaatgt agcggaaatc ttcaagcaaa tcgcgacgaa    35400
gtccgatgag gaggatgcaa aagaggctga gcaacgcgat gctgcccgcc gccacagtac    35460
atatgctcaa caacgcccag tgtcccaacg cgcgactttt ggctcggagc agagccgaac    35520
ggcggtttct ccacatcgtg gatagcgtga tccaatactt ccatccttca cattccggtg    35580
tccacatgaa aagcgacgtc acgttagttc ccgtaaacgt tgagtttctt tttttgtttt    35640
tcgtaagctt aagggttctc ctaagaaacc gcgggcacat gtcttgtaga aagatgtaat    35700
cactttccgc gtattttgtc agtattaaca tcacagtggt agtgttttcc aaagaagtga    35760
cgttactagt aacgttggtt tcctcccaat gtacgtgatga ttcaaacgga ctcgtatgtg    35820
ctaccgcttg caacacgtaa ctgtggccgg tgaagttgag catcaattgt cccacggtaa    35880
```

```
cattggtgtc atttgtaaaa cacgcgattt ctccgcgaac ttccgtgacg ttggtctcac   35940
gactctcgtt caacacacgc aggggaaacc agccttccag gtgatactga aaaccaaatt   36000
taagcatgac gctgtgccat tgccgtcgtg attggttaaa cgttacattc aagggtagtc   36060
tggcttcggt cccgacacag gggccgttgt agatttgcgt attattgcac gtgcagttta   36120
actgacagtt catactcgta gtgttggaag tgacgttaat gtccgtgccg tggtacgtac   36180
agcggaccga acaccgtgt cccgtgctcc aaaacagcgt caacaacagc cacacagaca   36240
cctacgtggg gacgatacgg gacttttat tgacggagac tcacgtttct accctcccct   36300
ttcccgtagg taaaaaccca cgtttatcac acacgttgtt tttacctgaa acccgcgcag   36360
cccgtggacg cgacaaaaaa ccgcggcact agaagaaaa tgaaacaagt atgtttatta   36420
agcagcatgt ggggctaata gggggataa ctgaggtata gcaactatga aaaaatacta   36480
caaaaaaaaa agctgaacat ggtcatctag cagcaaagtt ctccttctag accacgacca   36540
ccatctgtac cacgtcgccc tccccggccg tgtacgac atccttcacc acgaccggcg   36600
gcagcggcgg cgacgaggac aactcgctct cgatggaggc cgggacgaca gaggacgggg   36660
gggtggtggc ggcggaggac gaaggggtgg cggcggcagc ggggtcttct tccgacacgg   36720
gcgacggcag gctcggcggc gcggacagca cccgttgcgc cggggcgtga aaggctgag    36780 ccccggtggc ctggatgtgg gccaacgaat tggctcgcag cgagtcgcga tccacgaagg   36840
tcataggaat cttcccttcg cggatccgcc gctcagattc caggatggcg cgcacgtagc   36900
tgttcaccga tttggcaaaa gtgcgcggcc cctccgtatt cttgtcgcga cgcgcttcca   36960
gcacttgctt ttcgtagtcc agctggtgga agaccatcac cagatcgtcc atagtgtgcg   37020
cgtgctgacg gacgtgggaa cgcacctcca ccgggaacaa agcgttccaa tactccagca   37080
cgatggcacc gtgccagaac tgcgccatgc tgggcgccag gaaaaacagg ataccggagt   37140
cgtaggcgaa cacgtcccac ttgggcgtca tgaacaacac cagctgacgc gtgggccgca   37200
ccgaagcttc ctcccaggcc tcgatgaccc cgaacatgat gagctcctgg tccaacgggg   37260
ggcagtgtcg ctccagccaa ctgatcttgc tcaggttcat ctgcaaaaac tcgtaagagg   37320
ggtcgcagat gcacacgtag agacccgagt cgtgccgcag cctggctccg cgcttcatca   37380
gtttcctcac cgcgtagcga agcgccacct tgcccaacgc cgacgcctgg atcagtcccc   37440
ccacgtccat ctgcgtctgt cgccactcgg cctcgtccag caggctcatg atagcggcgg   37500
tgctatgcgt ggtcgtagtc atcctttcta tccttctcta tgaatagcag caatagcggt   37560 aaagtcccctt cttatactat cccggagtct gtggtttttt tgtttacccc tgcttactgg   37620
tgagactgct gggggccgtt gtgctgcagc agccgagctc gtcgccgccg ttgccacagg   37680
aaccggtgcc tccgcaggcc cttttttgagg gcctcgcagg cttctcgcgc aagtcctgag   37740
aggccctcgg cgtcgatggg gttcacctcg ggcgtccgag cctcgttttc ttcttcttca   37800
tcctcccttt cctcctccgt gtcctcccgc tctgtgtcct ccgttacgct ctcctccccg   37860
gcctcggcca agagcgcggc caccaagtcc acggaccgct cggtctccga gttctcaccg   37920
tcaattacgc catgttggcg gcgtaaccgg tgccagaac gccgggtgag cgcacatgct   37980 ttttctttc ttaaccaagg cgggagagga tcttcaaggc gttttcgctg gatccagcgg   38040
tagctaaagt accaaaaggc cagcaggccc acgctaccta acagattcac gtagactgga   38100
gacataatta aagaaagaag tgaaaccgcg gtgtgggtct cacgtcgtct tgaaacaccg   38160
tcttatatac atgaagatgc cggacatgac gcgcccaaga cacgtggggt tttcccctta   38220
```

-continued

```
ggcgacccgg tttcttaaga tgtttttcat cttcgcacgc gatgtactac atcaaagggt    38280
cggctgaccg accgcattga cgcagtttcc gagtacgcgc gtctcggagc acctgacggt    38340
gagccaccca gctcacgcgg ataggggaca acactgacgt gagggcgat tcccgtcact     38400
gacgggtgac aggaataaga cgggtgagga atttccacct ttttcttaag tgtgactctc    38460
cttacggtaa atcgcacctg tgacctctta accccctcct cctggtaccc aataacagtg   38520
aaaaacacac accacacgtc acgacaccga tcgattttct ttattcttag tgtgatgata    38580
ggtaagggca ctcgtgagga tgtgcaatta tcattatcaa gccttttca aggcgtagtg    38640
atgatcgttg ggcagaaccc ccaggctcct agcgatctgg gaatagaagg aggagaacga    38700
ccccagggcc agaatgccca cagtgtacat ggcccaggtc tccagaccga acgtggcggg    38760
tcgcagcttc agatggtagg ccacccgctc cgagagttgt gaatgctcgt tcagcaaca    38820
ggactgcaga tgggtgagtc caaaagcgct ttcgtttacg ccgcgcacgt gcaccgtctg    38880
ggccgggcaa tcctggtgtt gcgcgcgaaa atggtccagg caggagactc cgtctgcacg    38940
gcggcgagtg ttgttaccca cttcgatcaa cagcgtgtta acggcaagat gacgcgagaa    39000
cgcgacggcg tgttgttgg aggtctggcg gcagcagtac acgtcgagtg tcatgagggc     39060
catgtcgcct tggtggtaca cggcgtacgc ccaaccctgg aacacgagcg gacataacgg    39120
accgtgagcg gacgtcacgc cggcggttgt taccgtcgtc tcggcaggag aagataataa    39180
actcctgatc ctcatacaca ggagtccaag cgtcagaatt aaagtccgcg gagccacaac    39240
cgcgcaagtg aagccgatac gagtgttgct gaatttgttc attctgccga ctgttgccca    39300
cgagcgttcg gaggcggtgc cacaggctgt tggccattaa aaagtcctgg cccgaatgac    39360
gacgagacag agcccgaggc gaagaaaaag acgcccgtca tgaagacgta ggcaggggaa    39420
ttcccatatt tttatggctt cttttaaaag tctgtatccg actccatccg gcgcttttcc    39480
caaaccgtgg tctcctcgtc gtccgactcg gtacccagga ggtggtaagt cttttgccgc    39540
acgtagaaag ctttcaacgt ggagcaaaag atgagaataa agaccccaaa acgaaacaa     39600
accacgccga tcatgccgat gcagacgttc atgtcgacgt agccggcggt gctgttggca    39660
gtgcggcaaa agagtgtcat gtcgtacgtg cacaaaaaac aacacacacc acaggccagg    39720
tcgtagcgta gttattattc cgtagcagca atgatagtac agtcaagcac atgctctatc    39780
cccgttaccc cgatgatgag gaaaccccg ttgttgtatt ggcactgtcc cggttaatca     39840
ccacggtgaa caccacggcc aagaaaatga tccctaatat agcgaccact aagagagcaa    39900
aagtccattt ccagccgttg tcaaagtacg ccccgtggt gggatgcatg gtggcgggca     39960
tttccatcat atccatgtcg aacgtgtgtc gcggcgacgg cgaactaacc aggcagtacg    40020
ggggtcgata gggcggtggg ctgcagtcgg gtggtggcgg cggtggcgtg gaaaccgtcg    40080
tcgggcacag acccatggcc tgctcgtagg tgggggcgc gtcgtcgtga tcccggtcgc     40140
ggagcatcgg cgtgggctcc atgtcggtgg cagtgacggc gacggtggta actgtggtgg    40200
agacggtacc gacggcgtcc gcggttcacc ttcgagcaaa gagccccttc tttttgcgca    40260
aacgacggca aaacagttct ctgggacagc cggtggcgcg gtaagcgggt gccacgcttt    40320
cagggtgggt aaaacagtcg cggcaaagc agtaattgtt gcagaaccgc aagaacccga     40380
cgcgaaagaa gcccaggagt ccgcgcgcca gaaagtcgcg ctgccgcgtc tcgggatgca    40440
cgccgaagac ggcgccgctc tcgttcacca gtatggagat gtccaggcgc tgctgcgact    40500
ccaccggcac ggcccgcacc acaaataccg tgcagcacgtt cagcgagcac gtctctttta   40560
accagttgcc gtgggccgga tcctcgtaag tctggctccc gttcaagacg accgtcgtca    40620
```

```
gcgcctcatt accgtctcgc cagctgaaga tggaaccctc gcgcttcatg cacaggcgcc   40680
acagggccag caggtcgcgc gccaacatga actcgcgacc cacgtcgccg ccggtctcga   40740
agcggacata gcccagttct tcgcgcagcg gcgcgtagtt gcgcaggccc tcctgcacga   40800
agccgcggaa accggaccgc gacaccaggt acagcgattc caccacgggc gagtagacgt   40860
agacgcgacc gccttcgccg atgagtacgg gtagcggtgg gcggccgatg gcttcgcaac   40920
gactcacagt gcccaccggc agcaggaact tgtcgcagca caggaaggtc ttctccaaac   40980
ctttaatatt gagatgtcca aagtaaccaa cgcgtaacag gtcgcagtag gtgaagaacc   41040
aaccgtttgg ccagctgaga cgcagcaccg tgccgctgac gcgacgaacc agcttctgca   41100
ggtccttgcg agcgtcggag gtgacagaac agcggaaggt ctcgttgacc agctcgacag   41160
ccagcgcgtc ctccagcgtg cgttccttca tctgtcgtt gatgctctgg cggcgccgcc   41220
ggatttcgtc gaaacgggcc gcggaggcgg cgaccgacgc ggaggtcgtc cgaacgccct   41280
ctgtgacgct accgtccggc cagtcaagaa agctaaggct ggcgctgcgc cgcctaaagt   41340
gtccgatccg cgcgggacgt cgctgaggga cggtggctgg tctgctgggg cgggtacggc   41400
cgcgggtgtc cgcggacacg ttagttatac acggaattga gtcacgtggc acgttgccag   41460
ctgaaaccgc cgtcgtctcc gccggcgttt tctccatcac gggaccgcgc cgtgcgcgcg   41520
ttcccaggca cgcggcccgc gctctagccg cacttttgct tcttggtgtt agggacgaac   41580
tcgaacgtta cagaatcctc gctgtcgctc tcctctttcg cgtcgttgaa gtaattgccg   41640
gagttgcgat ccaaaccgcc gcctcctcct cctccgccgc cgcccgatcc acctttggac   41700
gtcaggtagc tggtgatctt gtgctgctcg tattttttcct tggaggaaag accgtggtcg   41760
tgatcaccgc cgccgccacc gctgctcatt ttccgcgtac cggaaccacc gccgccaccg   41820
cggtcgtgct tcttgccgcc accgccgcca cctcctccca gaccgccgag acccatgggc   41880
tcgttcatga gatcgttatc cagacccggg ccgtcgtcat gcagaccgcc ggcattggcc   41940
agcgaagaga ggctgccgcc accaccgccg ccgccacgcg acttgccgct gttcccgacg   42000
taatttttat cgaagggatc gccacgctgg aaaggttcct cggtgagaaa attctccacg   42060
gcgaacagac cgttgcggct ggccacgtac aacagcgtgt cgtgctccgt aactatacgc   42120
aacgtgcacg gcagttttggt gacggcgcaa ttgagcagcg tctggtagaa gttcttcagc   42180
tgcacgttga tacgcatgtt tttcacgccg tggaaactga cgcggttatt ggccgtgaat   42240
tccagctcgc tgccgtttgt caggatgaac ttgatggccg gcggaccggc gtgcaccaga   42300
atctgcacgg tgcccgtagg gcagggcgct ttttaacgt tacgcttgac gcgagtatgc   42360
ggcccgatcc acttaagcag gtcggccacc acgccgaaat ctagatccac gtgcacggcc   42420
gaattctcgc tttcgcgcac aatgtcttgg ccgtgcacac aggccgagct gaactccata   42480
ttgaaatcgg gcgcgcacat ggagatcttg gccgaaaggt ccgaaatgtc ctgcacgtag   42540
aacttggtca ggtccttgct ggaagtcagg tacatgaaat taccgagcag cggcgtggaa   42600
ttgttaatgg tcttgggctg aaacgacttg tcagtgatgt agaggcatga gctgttaaaa   42660 gtgattttttg acacgcagtg actgcgtacc gtttgcaaga taagcgacgg cgtgggcaag   42720
aaggtaaccg tggtgttctc cttgagcgca cggatcacag atcgcagctg ctggatagcc   42780
gtcttgtacg gcttcagccg cagcgccagc gtcggtggct ccgagagacg cgtcttgcga   42840
tccatcccgg acagcgtgca agtctcgact aaggagcggg cgcgagcgag cgaaagtttt   42900
atagagagca cacacgacga ccgggaacgc tgcgaagacg cccggcgtct aataatacag   42960
```

```
ccgcgccgag ccagcgggcc cccgactaag aggcacagta cttatatact ccgaccttaa    43020
agcgccagtg gtaccacttg agcatcctgg ccagaagcac gtcgggcgtc atcccagagt    43080
catagtagaa aaccagggcc acgcactggt ccacaaacac gctcaggttc acggccgcca    43140
tttccacgtc gttttggatc gccggcgccg cctggaacag acactgcgtc gccttgccct    43200
cctcctggtg ctgctccaac cacgcgtaat tcaccacggg cacgcgcaac ggcctccgca    43260
ccacggtggg gaagtaacac tcacggttgg gcgggcacaa tgaccacacc gtctcctcct    43320
cgaacacggt gccgcgcgaa gcccatactg acggcgtcac gccccacaga tgcgccacct    43380
cgtcgtcggg acccaccgcc agaaactgac agttgcgcaa tccgaactcg agcatgtcgg    43440
cgcgcagcgc ttcccagcgc gcgctggcga tggagagccg cggcaaccga tacaattcga    43500
aaatgaattt gccctcttga tagatggtgc gttcgaacca ttcgcagcgt ggcaaacccg    43560
acttgcacaa atcgacgcta gcgcgcaccg cggcaaagta catgtgctca aagatgcgct    43620
cgatcaagtc ccaagaggca aagtacgtaa accctaaccg cataagcgcc gtgtgcaggc    43680
cagccacgcc gatgtgcagc ggacgcagtt tttccagcgc gctctctacc caccattcgg    43740
acgccgacat tagcgcgtcc aagcgcgcgt tgccccaaac caccgcctcg gtcaccaact    43800
cacgcagcac gctcaaatca aagtaacgtc gcgtgttccc caaaaccacg tcgggtagat    43860
gcagcttctg ctcgtcgcta cgcgcaaaca cgcagcgagc cacgttcacc gtcagccgct    43920
gcaccggcat gtcacactcg ccaaagtggc acgacgccat atcgggactc aagcacggcg    43980
gcaggcacac gctgtcggcc ataatcgagt acttgactac gtgatggaca aagaccaccg    44040
aggcacggcc cttgagcgcg cacagcaaca tcttttcag aaaatcgtcc gtgttcacga    44100
ccaccttggg gcacgattgc tcgcagcgcg aatactcttt ctcgaaagcc gactcctgac    44160
ccaggtccga gagccgccgg gagacaggcc gcccgaacag cgagtagcgc tgctcacgcg    44220
cacggtagcg cttcattaac acgctaggca cgttgaaagc gtagcaaacc cccgtcaact    44280
ccgacgtgct ttctttgaga ataaagttga tcacgcggat agcagccacg tcccacatgt    44340
ccacaaacac acgtaccacg ggtcgatgca cctccttctc gcgtatcaaa tcgcagtatc    44400
cccccagaca acgaatacg ctgttcacat cggcgttaag tcgcgttacg ttcaccgaca    44460
cagaaacgcc gcaactcaag gtgctcatcc attcgcacat agccgcccaa ctggcgtcac    44520
gcgaaaaagg gtcggccgag atcagaaagt cgtactgcgg cacgcgatcg aaacccacgg    44580
tagacatggt gaaggtggac agcgacagct gcccatcgcg acagcgcttc aacaccgatt    44640
ccaacacctc gccctcgaaa cgcgcatcca gatggaaacg atagatgcgc gagtgcctac    44700
tgttctcgat agccgccgtc aacgccacgg cgatgcgcaa aaacacgccg cccggactct    44760
cgtcctgtcc gtgcagttgg cgacacacct tatccaaaca caaatggcc gcgtacaagc    44820 cccagcaacc ggccaattcc acaaaacgcg ccgtctcttc ggccagcttg ggtagatcct    44880
ccatgtgacg cagcacaaaa cggcgcaccg actcatcgca cagctccgaa gcgtaacaca    44940
gtggcgtgcg gctttcgcgc gcccagttgg ctttgaaata aaagcgaccc aacagcagat    45000
cgcaacgcgg cgagtgacga atcagacagg gaccgtggcg catgatgagc tgaaacagcc    45060
tgaaactgcc caaaccggca ctgtgtcgcg acacggtgtc catctcgcgc acaacgcgt    45120 tcctgtcaga cggcagctcc cgcgccggct cctgtacgcc acaaaagcga aacttgcccc    45180
aatagccgtg acaatgacac ttttgcccca tcaacatgcg cgtagcctgt atcggcggcg    45240
acactttgca gagcgaagcc ccgaaatcgt cctcctcctc gacactgtcc agctccatcc    45300
tggtcgcgcc ggtcggattg aaggtgctca gaccgctact cacgcgtcca ccacgactgg    45360
```

```
gcacggcggg accgctatca cgcgtcaacg acagcacaga cggcgtgccg tcgggagacg    45420
gcgactcggg acgccaactg acgacgccgc caccactcgt aaaacccgct acacacgcta    45480
cgccgctcga cacgttggta ttttcagcgg acgcttcctt gtcaccccg ggcagcggcc     45540
cttcctcgag ctcgctgtca tctccccgg tagtatcagc gacggcctct gccgacgatt     45600
cctccgtctc gatttccgcg ccgcggctcg gaatcctacc tggccggcac cgatacacgg    45660
gcaccgagga cacccgctgt tcctcgtccg cgtcagccgg agtcataagt ttacgaggaa    45720
aagaacaaag aaatcaggta gatttcaata aagtgtgtct atatggcacc gataactacg    45780
gtttataaag tctgtgtgcg ctgtgtttat tttttcttct gtgtctcctc ctcgtatgct    45840
gtcagcgccg ctcagacgaa ttctcgaaag tctcccaatt cgacgctaaa gttgtccaaa    45900
cggacgacga acagtttgag ttctttgtgt accaggaacg aggtgtgaat gtcgtcagcc    45960
aggcaccagc ccagcttttg tataaccccg gtacacagag ggatctggcg tgggcgcgtg    46020
atgcgacggt tgacaaagct acagcgctcg cgggcgaact ttccgcgtgc aacgtcgacc    46080
agggtctgcc aatgtgcgat gctggaggtg agcacgtaga tgccgggacg tgtttcgggc    46140
ccgtcatagt catagacgat gattaaatac acgtattgca gccgtccccg ggtctcttcc    46200
cacgtcaggt acatgtcttt cggtatcatc aacgcgaaca cctccgtttt gagcgtgttg    46260
taaaggtagc cgcgcatgac gcaggtgagc aacgaggtga tgcccagcga cggtcttg     46320
acgcagccca gcgtctcgag gcggcggtgc agcagatgcg ggcccaggtc cagccactgc    46380
agcgcggcgc gcgcggccga ggccgtgtac acgctttcga gcaggcagcg cgtgctggcc    46440
gagacgttgg aggcgcgaat gcctaacagg tagaggctaa tgtagaggtg tcgcggcgag    46500
tcgcaacccg tctccatgcg gatgagcagc gcgcccggct gcgcctcgaa ctctaccagg    46560
ccctcgggca cgaagaaacg cgccgtgagc gcctggtgat cggcgtggta gaggtagcgc    46620
accgatatag tatttacctc gcgtttggct ttgagcgccg tcactagttc attgtcctcg    46680
tcggccgggt cgcgcggccg tttggccacc gcgcgcgcgt ccatgatggc aaggcgcacg    46740
gtagatttca aaagttgat agagcagctg cgggcacggg ccacggacaa agcggaggcg     46800
ttaaataccg tgagccaatt ggagatcggc gcggtggatg cccaggacgt gaccgcgagc    46860
gccgtgcgcg ccttcgtggg tgcgttgccg agctcgggtt accactttgg cttcgtgcgt    46920
cagaacgtgg tcttttacct cctaagccac gccacggtac agacggcgcg cgacccgctg    46980
tacgccgccg agcagttgca cgaacagctg gaccgcttcc tgcgacacca gcacgacggc    47040
ggcggagacg aggaccggtt gccgttctac cacaacgggg ccacgctgac ggcttttccag   47100
aagctgttgc agaccctgcg cgagatccag accgtaatag ccgaacagag cggcggcacc    47160
gcggcggcg cggacttgat cgccagtaac aacgcgtcga ccgagcgccg cggcaagaag     47220
ggcggttcga gttccggggg ccagcagccg ctggttcgcc gggtgatcac gcagctggaa    47280
acggctgcca cggaggcgcg gccctacatc aattgtcgcg ccgtggccga actcctggac    47340
ctgacctacc agcggctcat ctactgggcc tgcacgctca tgccctacgt gttgtttcgg    47400
cgcgacaccg acaccgaact ggacacggtg cttctgatgc atttttttta cacacactac    47460
cgttcggtta acgcgatttt ggccgtggag tttcaaaact acgtcaagaa cagcgtgcgg    47520
cacatgagct ctttcgtcag ttccgatatc gacggcgacc agaagcccgg tgccgaacac    47580
atgcgtgacg tcagctacaa gctgttcgtg ggtaatctgc aggcgcgtga cgccagcggc    47640
ctcatgtttc ccattattag cacgcgcatc tccaccgtga acctttacct gtcgcccgaa    47700
```

```
cgtatgttttt tccacccggg tctgatctcg cgtctgttga gtgaggaagt ttcgccgcgc   47760
gccaacctag acgcttacgc gcgcgtgtgc gatcgcgtgc tggaagacca cttgcatacg   47820
ccgcgacgcg tgcagcggct actggatctg acgcagatgg taacgctact ggtggaactg   47880
ggtttcaatc acgatacctg cgcggcctac gcacaaatgg cgctgatcca gccggccagt   47940
cagaagagct cgctctttgt cagcgagatt cgcgagaaac tcatacagat tatctacaat   48000
ttttacacgt ttttcatgtg cctctatgtg tacagcccca cgttcctgtt cgaccaccgg   48060
cggcggttga ttttggagca gcatcgatcc acgttgatcg gctccaagga ggaactacag   48120
cacgtctgga gcaacgtgac gctgaacgtc aatacgcact ttgcggttca gtacacggaa   48180
gaagactttg aggcacatac gaagggtgcc acggaggcag agcgcgagta cctgtatcgg   48240
gacctgcaca gcaagtgggg cgtgcacctg tttaccttgc gtccgtctcg cggcgcggcc   48300
ggcgcggcct cgccttttgcc tccgcttgac ggcgtcacac gctccgacat cttacgcgaa   48360
tgcgcgctcg ttaatctgaa cgaaggccgc gtcaactacg cctccctgct agccttcagc   48420
catcatcccg agttccccag catcttcgcg cagttggtgg tggtaactga attttcggag   48480
atctttggta tcccgcaggg cctgtttcaa gccgtgggtt cgccgcgtct tttcgcgctc   48540
attcagctgt gtcgtgtatt gttgcccgag caggtgacgc tgtaccagaa cctggtctcc   48600
atttacaacc tgaccacctt tgtcaagcac atcgacgccg cggttttttaa gacggtacgc   48660 gattgcgtct tcgacatcgc cacgaccctc gagcacctca gcggtgtacc cgtcacgccc   48720
aatgtggacc tgctggccga gctcatggcg cgctccgtag cgcataacct gtacaccacc   48780
gtcaacccgc tgatagagga cgtgatgcgc agcagcgccg gcagtctgag aaactatctg   48840
cgacacacgc gactctgttt cggtctggcg cgcggccggg cgcgcctctc ggaggacggc   48900
gtgacggtgt acgtggaggt acagggtcag tacggactgc gcgtacctac cacgcgtttc   48960
gtagaacagt tgcgcgaact ggttcgccgc gatcggctgt tggccgagaa tctgcgcggc   49020
ttaaacgagc gcctgctgag tgttcgcgtg gcgtacgtc agatcagcag cgacacagag   49080
gaagtaagcc gacacgccaa gggtcaccgc acggtggccc agatgagcaa ggcgctcaaa   49140
aagacggcct ccaaaatcaa agtgttggaa acacgcgtga cattggcgct cgagcaggcg   49200
caacgttcca atggcgccgt cgttaccgcg gtgcaacgcg cgctagccgt ctttgacgta   49260
ctaagtcgcg agaacttgga acgccgcggc gcacagctct gtctgacgga agcgacgagc   49320
ctactgcacc gacatcgcgc gctagcgccg atgacctggc ccgcgggcac gggcgttgcg   49380
gcggcggcca agcggatcg cgccttacgc gagttcttgg aggcgccctg ggaatcggcg   49440
ccccaaccgc cgcgactccg catgacgccc gacaccgatc acgaagaatc gacggcaggc   49500
gcgacgtccg taccggaggt cctgggtgcg cgctacgaac ccgcacacct ggccgcgagc   49560
gacctattaa actggtacat cgtccccgta agccaggcgc agcaggacat cttgtcttcg   49620
atcgacccgc ccgccggctc gacatcggtg tccctgccgc cggcctcgcc atgaaagtca   49680
cgcaggccag ctgccaccag ggcgacatcg ctcgcttttgg agcgcgagcg ggcaatcaat   49740
gcgtctgcaa cggcatcatg ttcctacacg ccttgcacct gggtggaacg agcgccgtcc   49800
tgcagaccga ggcgctggac gccatcatgg aagagggcgc gcgtctggac gcgcggctag   49860
agcgcgagtt gcaaaagaag ctgcccgccg gcgggcggct gccggtctac cgactgggcg   49920
acgaagtgcc gcgccgcctg gagtcgcggt tcggccggac cgtgcacgcg ctctcgcggc   49980
ccttcaacgg caccaccgag acgtgcgacc tggacggcta catgtgtccg ggcatctttg   50040
actttctgcg gtacgcgcac gccaaaccgc gtcccaccta cgtactcgtc accgtcaact   50100
```

```
cgttggcgcg cgccgtggtc ttcaccgagg accacatgtt ggtctttgat ccgcacagct   50160
ccgcggaatg tcacaacgcc gccgtgtatc actgcgaggg tctccatcag gtgctgatgg   50220
tgctcacggg cttcggcgtg cagctatcgc ccgctttcta ctatgaggcc ctttttctct   50280
acatgctgga tgtggcgacc gtgtcagagg ctgagatcgc cgcacgtttg gtctccacct   50340
atcgcgaccg cgatatcgac ctcaccggcg tcgttcgaga aagcgcggac acggcggcga   50400
caacgaccac cgccgcacct tccttacctc cgctgcccga ccccatcgtc gacccgggct   50460
gccctcctgg cgtggcgccc agcattcccg tctacgatcc ctcgtcctca cccaaaaaaa   50520
cacccgagaa acgccgcaag gacctcagcg gtagcaaaca cggaggcaaa aagaaacccc   50580
cgtccacgac gtccaaaaca ctggccaccg cctcctcctc ctcagcgata gcggcggcct   50640
cttcttcgtc cgcggtacca ccgtcctaca gctgcggcga agggcccctg ccggccctgg   50700
gccgctacca acagctggtc gacgaggtag agcaggagtt gaaggctctg acgctgccgc   50760
cgttgcctgc caacaccagc gcctggacgt tgcacgcggc gggtaccgaa agcggcgcta   50820
acgcggcaac ggccacggcg ccgtccttcg acgaagcttt cctcaccgat cgtctccagc   50880
agctcatcat ccatgccgtc aatcagcgct cgtgtctgcg tcgcccctgc ggtccgcaat   50940
cggcggcgca gcaggcggta cgcgcctatc tgggcctatc caagaaattg gatgcctttc   51000
tgctcaactg gctgcaccac ggcctggatc tgcggcgcat gcacgactac ctgagccaca   51060
agaccaccaa aggcacgtac tcgacgctgg atcgcgcact gctggagaag atgcaagtcg   51120
tcttcgatcc ctacggacgt cagcacggcc cggcgctcat cgcctgggtg gaggagatgc   51180
tacgctacgt ggaaagcaag cccactaacg aactgtctca acgactgcaa cgtttcgtaa   51240
ccaagcgacc gatgcccgtt agtgacagct tcgtctgcct gcgacccgta gactttcagc   51300
gtctgacgca ggtcatcgaa cagcgacgtc gggtgttgca acgtcaacgc gaggagtacc   51360
acggcgttta cgagcacttg gccggcctca tcaccagcat cgacattcac gacctagacg   51420
ccagcgatct gaaccgacgc gaaattctga aagcgctgca gccgttggac gacaacgcca   51480
agcaggaact ctttcgcctg gcaacgcca aaatgctaga gttgcagatg gacctggacc   51540
gtctgagcac gcagctgcta acgcgcgtgc acaatcacat cctcaacggc ttttgccgg   51600 tagaggacct gaagcagatg gaacgcgtcg tcgagcaggt actgagactc ttttacgacc   51660
tgcgcgacct gaaactgtgt gacggcagct acgaagaggg atttgtcgtc atacgcgaac   51720
aactgagcta cctcatgacg ggcactgtgc gcgacaacgt accgctactg caagagatcc   51780
tgcagctgcg acacgcgtac cagcaagcca cgcagcaaaa cgagggtcgc ctcacgcaga   51840
ttcacgacct gcttcatgtc atcgagacgc tggtgcgcga cccgggcagc cgcggctcgg   51900
cgctgacact ggccttggta caggagcagc tagctcagct ggaagcgcta gcggcctgc   51960 agctacccga agtgcagcag cgcctacaga acgcgcaact cgcgctaagc cgcctctacg   52020
aagaggaaga ggaaacgcag cgtttcctcg acggactctc gtacgacgat ccgcccaccg   52080
aacagaccat caagcgacac ccacaattac gcgagatgtt acgtcgcgac gaacagacgc   52140
gtctgcgact catcaacgcc gtactgagca tgttccacac attagtgatg cgactggcgc   52200
gcgacgagtc gccgcgaccg acgtttttg acgccgtcag tttgttgttg cagcaactgc   52260 caccccgactc gcacgaacgt gaggatctgc gtgccgccaa cgccacgtac gcgcagatgg   52320
tcaagaaact ggagcagatc gagaaagccg gtaccggcgc atccgaaaaa cgtttccaag   52380
cgttacggga gttggtttac ttttttccgta atcatgaata tttctttcaa catatggtcg   52440
```

```
gacgactggg cgtcggacct caggtaacgg aactctacga gcgatatcaa cacgagatgg   52500
aagaacagca cctggaacgg ctagaacgtg aatggcaaga agaggccggc aagctcacgg   52560
taacttctgt ggaggacgtg cagcgtgtct tggcccgggc accgagccat cgtgtcatgc   52620
atcaaatgca acaaacgtta accaccaaga tgcaagactt tttagacaag agaaacgta    52680 aacaggaaga acagcaacgg cagctactgg acggctacca aaaaaggtg cagcaggatt    52740 tgcaacgcgt ggtggacgcc gttaagggcg agatgctctc caccatcccg caccaaccac   52800
tggaggccac actcgagctg ctcttgggcc tagatcaacg cgcccaaccg ctactagaca   52860
agttcaacca ggacttgctg tcggcgctgc agcagctgag caaaaaacta dacgggcgaa   52920
tcaacgagtg tctgcacggc gtgctgacgg gtgatgtaga gcggcgctgt cacccgcacc   52980
gagaagcggc tatgcaaacc caagcctcgc taaaccactt ggaccaaatt ttgggtccgc   53040
aacttctgat ccatgagacg cagcaggccc tgcaacacgc cgtccatcaa gcgcagttca   53100
tcgagaagtg tcaacagggc gatccaacta cagccatcac gggcagcgag ttcgagggcg   53160
actttgcacg ctaccgcagc agtcaacaga agatggagga acaattacaa gagactagac   53220
aacagatgac cgagactagc gagcggctag atcgctcgct gcgccaggat cccgggagca   53280
gctccgtcac gcgtgtaccc gagaaaccct tcaagggtca ggagctggcg ggtcggatca   53340 cgccccccgcc cgccgacttc cagcagcccg ttttcaaaac gctgctagat cagcaggccg   53400
acgcggcccg gaaagcgctc agcgacgagg ccgatctgct gaatcagaaa gtacagacgc   53460
agttgcgaca acgcgacgag cagctgagca cggcgcagaa cctgtggact gatctggtca   53520
cgcgccacaa aatgagcggc ggactggacg tgaccacccc cgacgccaag gcgctgatgg   53580
aaaagccgct ggagacactt cgcgagctgt tgggcaaagc cacgcaacaa ctgccgtacc   53640
tgtcggcgga gcgcacggtg cgctggatgc tggcttttct ggaggaagcc cttgcgcaaa   53700
tcaccacgga ccctacgcac ccgcatcacg gaagcaggac ccactaccgg aacctgcaac   53760
agcaagccgt cgagagcgcc gtgacgctag cgcatcaaat cgaacaaaac gcggcctgtg   53820
aaaattttat tgcacagcat caagaggcga ctgccaacgg cgcgtccacg ccgcgggtcg   53880
acatggtcca ggcggtggaa gcgatctggc agcgactgga acccggacgc gtagccggcg   53940
gcgccgcgcg tcatcaaaaa gtgcaggaac tgttgcagcg cttgggtcag acgctaggcg   54000
acctagaact gcaggaaacg ttggcgacgg aatactttgc gctgttacac ggcatccaga   54060
ccttcagcta cgggctggac tttcggtcgc agttggaaaa gatccgcgat ctgcggactc   54120
gttttgcgga actggccaag cgacgcggta cacgtctctc caacgaggga gccctgccca   54180
acccacggaa accgcaggcg acgacttcgc tgggcgcctt tacacgcggg ttgaacgcac   54240
tggaacgaca cgtccagctg ggtcaccagt atctgctcaa caagctcaac ggctcatcgc   54300
tagtctatag gctggaagac attcctagcg tgcttccgcc aacacacgag accgaccccg   54360
cgctgatcat gcgcgaccgc ctgcgtcgtc tatgcttcgc gcgtcaccac gacacctttc   54420
ttgaagtggt agacgtcttc ggcatgcggc aaatcgtcac gcaggccggc gagcccattc   54480
acctggtcac cgattacggc aacgtagcct ttaagtactt ggcgctgcga gacgatggcc   54540
gaccCctggc atgcggcgc cgctgtagcg gcggaggact caagaacgtc gtcaccacac   54600
gttataaagc catcacggta gccgtggccg tctgtcagac attgcgcact ttctggccgc   54660
agatctcgca gtacgaccta cggccctacc tcacgcagca tcagagccac acgcaccccg   54720
cggagactca cacgttacat aaccttaagc tcttttgtta tctggtgagc accgcctggc   54780
accagcgcat cgacacgcag caggagctga cggccgccga tcgcgtaggc agcggcgaag   54840
```

```
gtggtgacgt aggggaacag agaccgggcc gcggcaccgt gctgcgtctg agtctccaag   54900
agttttgtgt actcatagca gctctgtacc ccgagtacat ctacaccgtc ctcaagtacc   54960
cggtgcagat gtcgctaccc tccctcacag ctcacctaca tcaggatgta atacacgcgg   55020
tagtcaataa cacacacaaa atgcccccg accacctccc cgaacaggtc aaggctttct    55080
gtatcacccc cacccaatgg cccgccatgc agctcaataa actgttttgg gaaaataaac   55140
tggtgcagca actgtgccag gtaggccgc aaaaaagcac accatcccta ggcaagctat    55200
ggctctacgc catggccacg ctggtctttc cacaagacat gctgcagtgt ctgtggctag   55260
aactgaaacc ccagtacgcc gagacctacg cctcggtgtc cgaattggta cagacgctgt   55320
ttcagatttt cacgcaacaa tgcgagatgg tgaccgaggg gtacacgcaa ccgcagctcc   55380
ccaccggaga gccggtgctt cagatgatcc gcgtgcgacg ccaagacaca accaccacag   55440
acacaaacac gaccacagag ccaggacttt tagatgtttt tattcaaaca gaaaccgccc   55500
tagactacgc gctgggctcc tggcttttcg gcatacccgt gtgtctcggc gtgcacgtag   55560
ccgacctgct gaaaggccaa cgtgtattag tagcgcgcca cctcgaatac acgtcgcgag   55620
accgcgactt cctccgcatc caacgctccc gggacctcaa tctcagtcaa ctgctccagg   55680
acacgtggac cgaaacgccg ctggagcact gctggctaca agcccaaatc agacggctac   55740
gcgattacct cgctttcccc acccgcttag agtttattcc cctagtcatt tacaacgcac   55800
aggaccacac cgttgtacgc gtgctgcgac cgccctccac gttcgaacag gaccacagtc   55860
ggctggtgtt ggacgaggcc ttccccacct tcccgctgta tgaccaagat gataacacat   55920
ccgcggacaa cgtcactgcg tctggcgccg ctccaacacc gccggtacct ttcaaccgcg   55980
taccagtcaa tattcagttt ctgcgtgaaa accgccacc catcgcacga gttcagcaac   56040
cgccgcgccg acatcgtcat cgagcggccg cggccgcaga cgacgacgga cagatacatc   56100
acgtacaaga cgatacatca aggacagccg actctgcatt agtctccacc gcctttggcg   56160
ggtccgtctt tcaagaaaac cggctgggag aaacaccact atgtcgagat gaacttgtgg   56220
ccgtggcacc cggcgccgcc agcaccagtt tcgcctcgcc gcctatcacg gtgctcacgc   56280
agaacgtcct cagtgctcta gaaatattgc gactagtgcg attggacctg cgacaactgg   56340
cgcaatccgt acaggacact attcaacaca tgcggtttct ctatcttttg taaccgacac   56400
tgacagtagc gggcaataaa aacaagagga ttgttatggt ttttgatat aaaacaacgt    56460 gtcactttca cggtgattta ttcttgctat tacttttccc catgggctgt cagcgtcggg   56520 tgcgcgcacac ggctaccatg cgcaacaggt ccagcttaaa ggcgcacttg tcgttaaaca  56580
gactggacat gcgcgtatac ttgctcagca tggtggccag taccgggtgg gtggcctctg   56640
agatctcggt cggcaactcc aaaacgacgt tgacgacgtg acgtgtttt tcgtcccgct    56700 tgttggccac cgtgggtccc ggcgcggtgt tagacatggg gcaggccgtg gggggaggac   56760
gaggaggaaa tcgctgctaa accgccgcgc gcctgctgca caatgtggcc gccgacgtgg   56820
caggcggtct gtttaaccag cgcgcagccc cgacacagcg gggcgccgtc ttcgctttcc   56880
aaacagctgt cgcggtactc gcccgtctga cagcgcgcgc acagcaggcc gtgcccgtgc   56940
gaagtgaggc gcaggagacg cgggaccgtc acgccgcgta ccaccacagt ggagtcgcag   57000
gtgcgtgccg cgcagggcag aatgacgtcg aaagccagcc ggtgatcgta cacggcacaa   57060
gccgcgttga ggcccagcac ggctttccag cccacgcgta cgcagcgctg tccaaagagc   57120
gtctcggaga cgagctcgta gacgcgctgc cgcaccaccc gctgactgcc gcagagcgag   57180
```

```
cagtgtacga gctcggcgtg cgtgttgaag atgacgctct tttcttgacg gtcccgataa    57240
tagaacatcg agttgagcgg aaaattttgc tggcagtgta gcttttcctt acccaggttg    57300
aggcagtgtc cgcactgccg acagaccacg gccaccagcg agcgcgcgtc cagatggcgc    57360
tcgcacttga gtcgacacag acaccagagc ggcaggtcga tgacgctgcc gatgaggccg    57420
ccgcgcagcg cggcgctgag tgcaaagagg acgatcttgg tgggctctac gtgacgcgcc    57480
tgctgtccgg cgcccgcgtg tcctaccgcc gcagctgccg ccgtcgagcc tcctccgcgc    57540
gtctcgtcgt gcagacccag tgcccgcaac ggcaccaggt atcgcggaca cgtgtcgcaa    57600
aacgtctgca ccgcttgtcg ggccagtacg tagagcgggt ttccgcaggg taccttcccg    57660
gcgtgccggc gcaaggctgc gatgaggccc cgcagctgcg gcgaccgcgg ctgccgttgg    57720
tgacaccact ggttacggtg gtatacggcc aaatcagcgc gggcgtcgaa gcgcttggcg    57780
cgtagtagtg ctaggcacgg cgagctggtg gggtgaagca cgggcagccg aaggtccacc    57840
ccgaaaagga aacggtgaag gtcacctagc agcgaggcgg tgacaccgtc caacaacgcg    57900
tgcagccgct cgggcgggta gagccgcaga cggcgcagca ggtagtcggt gttgtagcgt    57960
tcgaaacgca gaaaagccat cgtgcggacg gccacggtgt gcagacagtc catgctgtag    58020
acgtaagcga gaaacacaaa gtagggcttg gtcataacca tacgctgaaa gagcgccgtc    58080
accgcctccc gctcggcctg ccgacacacc agccattcgc gcaggaagcg ttggtagaga    58140
cggtcgccca gctcgcgatt caaaaagcgc ttatccgtca cgaagagatg aaggacgcaa    58200
gaacgtggca cgtgatgcac cagctgctgc tggaggaccg ccgacgtctg cgccgcaaac    58260
tgcgccggtg gctgcgacgt ttctaccgcc gcttcctccg gctgcagcgc accgcggccg    58320
atcaccagct gcacatggaa atggtcctcg tgaacgcaga ggggcgcgaa gagacggcac    58380
agagcctggt ggaactcatc agtcgcggtg tgcggagcgt gtcggagacg acgattggcc    58440
atgaccgcgc cacagcagag ccagcaccag cagaagagcc agcaccagcg ggcccagagt    58500
cgcaaagcgc gcgggcagcc acggcccaga ctgcggtcgc gatggcccgg agcgcgctcg    58560
ccaccacgat gacggtgccc aacgataacc agtccgctcc aaggacggcg cgcacggcgg    58620
agacggcgga tgacggtgat gggtcgacac ccctcgccga cgactcacgt gctcctccag    58680
aggccgacgc gcggacccctc cgacgtcctg gcccgccgct gccgctgccg ccttcccttc    58740
tcccgccaga gccagcaact cctcctcctc ttcatcagcg tctccctcgc ttgcgcatcc    58800
gcatcgtccc ataccaggcct cacaacgaca caaccgccac gaccccgccg ccatgggtgg    58860
cggcggcggc cgaggcccgg cagcggcgcc gccagcggcg accatggtgg gagagcaact    58920
cggatgacga ggaggaggag gaggaggagg gggagatgcg ctccgagagg accgctttcc    58980
cgccgttcgc gtgagcgcgg ccgacatgcg ggcgcgccac agggacggac cgctgccgct    59040
gtgactgctt acggtgacgt ggttccggac cgccaacgac gtcgacgcgg cttctcttggc    59100 gtacagctcg cgcagcagat tctcgtactc gccctcgttt tcgggtccga aggcgataag    59160
ctcgatgttg aagaccgacg ctgaattgga tttgcgcacc acgcacttcg tcagcactcc    59220
gtaggccgag ggcttgatct cctcgatgtc cttgagcgtg acgatgagcg actcgttcac    59280
cttaagcaca ttgaactcac ctacgtgcg cgccggcgaa acgagcttga cgggcgctcg    59340
cacaaaacag cagagggaga cggcgcagcc agtgttttta aagataaaac aaggcacgtg    59400
gtctgtgcgg ctctcccagt agctgagcag atactcgaca caatagaccg tgtctgtctt    59460
gagcatggcg tcgcacaccg agtaattggg gttttttacag atgaggccgg catcggtgac    59520
gcgcagctcg ctgggaccca acttgaggat acgccgcgtg gcctgcacca gatcctgatg    59580
```

```
gagaaccttg ttcatctcca tcgcaccgac gccaccgccg atttatttac ccggcgccgg   59640 ctcgtcttt  ccctccagga ttccgttaat gtccataagc ttgctgacga tcgccgttaa   59700
tagttgcgtc ttctcacgga ggatctctcc gtgactgcag gtcgcgcagt cgccgtgcac   59760
gtacttgagg aaggcggcgt acttctgacc cgcgttcacg aaatttaagc gcgcgtccag   59820
agagggcagc aacagatcgt agacgcgcgg cagcatcggc tcgaactgta atagcagatc   59880
gtcgtcaaga tcgggtagcg cgtgtccgtc ttcaccgtcc tcgtcgtcac cacctccccc   59940
ctcgagccca ccgctcgtac cagccgcggg ctccgcgtcc tcgtcgatca ccagcggtcg   60000
cgtcggcacc ggagaatcca cgtcatcctg cacgtcgttt tcctcctctc cgtcgtcatc   60060
gtccagaaac ggcacccgct gcttagtcca ggacattctt tctccgcgtc ctcaatcagc   60120
ggcgccgatc gccatgaatc cgagtaccca cgtgagcagt aacggcccaa cgactccccc   60180
tcacgggccc cacaccacgt ttcttccccc gaccagcccg gccccgtcca ccagctccgt   60240
cgccgccgct accttgtgca gtccgcaacg acaggccgtt tcgcgttaca gcggctggag   60300
caccgagtac acccagtggc actcggactt gacaactgag ctgctatggc acgcgcaccc   60360
gcgtcaagta cctatggacg aagcgctggc cgccgcggcg gccgcctcat accaggtgaa   60420
tcctcaacac cccgccaacc gttaccgtca ttacgaattc cagacgctca gcctcggcac   60480
ctcggaggta gacgaactgc tcaactgctg tgcggaagaa accacgtgcg gcggcacgca   60540
atccaccgta ctcaccaatg cgaccaacac cactagctgc ggcggagccg tcgccggcag   60600
tagtaacgca ggaccccgccg gcgcttcggc gccctgcgac ctagatgcag aactggccgg   60660
cctcgaaacc tcggcggccg actttgaaca actgcggcga ctgtgcgcgc cgctggccat   60720
cgacacgcgc tgtaacctat gcgccatcat cagcatctgc ctcaaacagg actgcgacca   60780
gagctggctc ctcgagtaca gcttgctgtg cttcaaatgc agttacgcgc cccgtgcggc   60840
gctcagcacg ctcatcatca tgtccgagtt tacgcatctg ctgcagcagc acttttccga   60900
tctgcgcatc gacgacctgt tccgacacca cgttctcacg gtcttcgatt tccacctgca   60960 cttttttcata aatcgttgct ttgaaaaaca agtgggcgac gcggttgata acgagaatgt   61020 cacccctaaaac catctagccg tggtgcgggc catggtcatg ggcgaagaca cggtgcctta   61080
caacaagcct cggcgccacc cgcaacagaa gcaaaaaaac aacccttatc acgtcgaagt   61140
gccacaagaa ctgatcgaca cttctctaga acacagctca cctagccgcg accgctttgt   61200
gcagctgctt ttctatatgt gggccggcac cggcgtcatg agcaccacgc cactcacgga   61260
acttacgcac actaagttcg cgcgactaga cgcgttatcc acggcctcgg aaagagaaga   61320
cgcaaggatg atgatggaag aagaggagga tgaagaagga gaaaaaagag gtgacgatcc   61380
gggccgtcac aacggcggtg gcaccagcgg ggggttcagc gagagcacgc taaaaaagaa   61440
cgtgggtccc atttacctat gtcccgtacc cgcctttttt accaagaacc aaaccagtac   61500
cgtgtgtctg ctgtgcgaac tcatggcctg ctcctattac gataacgtcg tcctgcgcga   61560
gctgtaccgc cgcgtcgtct cgtactgtca gaacaatgtg aagatggtgg accgcattca   61620
gctggtattg gccgacctgt tgcgcgaatg cacgtcgccg ctcggcgcgg cgcacgagga   61680
cgtggcgcgc tgtggactcg aagcgcccac ctcgcccgga ggcgactcgg actatcacgg   61740
cctgagcggc gtcgacggcg cactggcgcg acccgacccg gtattttgcc acgtcctgcg   61800
tcaggcgggg gtcacgggca tctacaagca ctttttctgt gacccgcagt gcgccggcaa   61860
catccgcgtc accaacgagg ccgtgctctt cggacgcctg caccccaccc acgtccagga   61920
```

```
ggtgaaactg gccatctgtc acgacaatta ctatataagt cgacttccgc gacgtgtgtg    61980
gctctgcatc acactcttca aggcctttca gattacaaaa cgcacctaca aaggcaaagt    62040
gcacctggcg gactttatgc gcgatttcac gcagctgttg gagagttgcg acatcaagct    62100
ggtggacccc acgtacgtga tagacaagta tgtctagcgt gagcggcgtg cgcacgccgc    62160
gcgaacgacg ttcggccttg cgctccctgc tccgcaagcg ccgccaacgc gagctggcca    62220
gcaaagtggc gtcaacggtg aacggcgcta cgtcggccaa caaccacggc gaaccgccgt    62280
cgccggccga cgcgcgcccg cgcctcacgc tgcacgacct gcacgacatc ttccgcgagc    62340
accccgaact agagctcaag tacctcaaca tgatgaagat ggccatcacg ggcaaagagt    62400
ccatctgctt acccttcaat ttccactcgc accggcagca cacctgcctc gacatctcgc    62460
cgtacggcaa cgagcaggtc tcgcgcatcg cctgcacctc gtgcgaggac aaccgcatcc    62520
tgcccaccgc ctccgacgcc atggtggcct tcatcaatca gacgtccaac atcatgaaaa    62580
atagaaactt ttattacggg ttctgtaaga gcagcgagct actcaagctc tccaccaacc    62640
agccgcccat cttccaaatt tattacctgc tgcacgccgc taaccacgac atcgtgccct    62700
ttatgcacgc cgaggacggc cggttgcaca tgcacgtcat cttcgaaaac cccgacgtgc    62760
acatcccctg cgactgcatc acgcagatgc tcacggcggc gcgcgaagac tacagcgtca    62820
cgctcaacat cgtgcgcgac cacgtcgtta tcagcgtgct gtgtcacgcc gtctcggcca    62880
gcagcgtcaa gatcgacgtg actattttgc aacgcaagat tgacgagatg gacattccca    62940
acgacgtgag cgagtccttt gagcgctaca aagagctcat tcaggagctg tgtcagtcca    63000
gcggcaacaa cctatacgag gaggccacgt cgtcctacgc gatacggtct cccttaaccg    63060
cgtcgccgtt gcacgtagtt tccaccaacg gctgcggccc ctcctcctcg tcccagtcca    63120
cgccgcctca tctccacccg ccgtcgcagg cgacgcagcc ccaccactac tctcaccacc    63180
agtctcagtc tcagcagcat catcaccgtc cccagtcacc accgccgccg ctgtttctca    63240
acagcattcg tgcgccttga cactgtacgg cagaaaagcc ggctccaagt gcaagcgccc    63300
cggcagcacc atgtgcaaaa acttgtcctt gcgcgcagtt tcgccgccgg gaaagacggg    63360
cgacagcacg ttggttacag ccttgagaac ctgctcaaag tacttgtcgg cgtgaatggg    63420
cacgccgtgc tcgcgcacgt agctcggatc ttcggctacc tcgtagttgc acacgaccga    63480
cggtggtttc cgcgccctct tctttgccgg ctctcctcct ctcctgttgc tctcctctac    63540
cccgccgccg tcagcgtcgt cgtccgtgcc atcaatcgcg tccgaccggg aaaccacgcc    63600
ggtggttaca gaatcaccgt tgtcggagga accctgcggc gccgtccgga cacccgggcgc    63660 cgtcaggacg taaaagaccc gatccccgac cgagggtagc tcctcagaac gggccgccag    63720
tcgcttaatg acggcaatgt gcggcaagtt agattgacgg tacaacgaga tgtccttaga    63780
aagcaccgac gaaagcacca ggtcctcgac acgcacacgg tgcaggtaca gatcgtcgcg    63840
agcctgcacc agacggcgca agatacgcca gaaaccgcgt ggcacgccgt atttcttgac    63900
ttcatcgagt gagaggcgcg acaggcgcac ggctgcttcc gagacctcgc gatcctcaaa    63960
gagcagcgag aggacgtcac gcgtgacgcc cttgacgaac tcgcaagccg tcttgcgcac    64020
caaatccacg cccttcatgc tcaggcccga ggcgccctcc actttgccga tgtaacgttt    64080
cttgcagatc atcataagag agacgaagac cttttcaaac tccagcttga cgggctccac    64140
aaaaagacag gccgtcacgt agtgcgccag gctgggccca cgcgccacca gagcctgcgg    64200
cgtcaggcca cgaaagcgga caaacacgct gtccgtgtcc ccgtagatga cccgcgcctc    64260
cacccgccgt tcgtccgagc cccctgacga tgtttcgagc ccctccggta acgtgctgct    64320
```

```
ctcctccgaa tccccctccc gcgttcccac tacatagtct tcctgattaa aaaaattgtg   64380
caaaaaacac ggctctgaaa agttgtcttt gatgaaccgc gccgtgcgct ctagcatgtc   64440
gcgaccgatg cgcgtgatgc tggcggcgat gggcagacac ggcatcatgc cgttgaccac   64500
gcctgtaaaa ccgtagaaag cgttacacgt tactttgagt gccatctgtt ccttgtcgag   64560
cagcatacgg cgcacggggt cttgacactc gcgcatgcat tcgcgcacgg cacggcgctg   64620
cgaaacccac ttgttgagca gttccgaaag caccgagacg cgcaccgaag cacgcacaaa   64680
gcggtgagtc acgccgttct ctagcgtgac gctgtataca tcggcggggt ccacggggta   64740
ctcgccaccc ggcaccagca gggtggagta gcaaaggttg tgagccatga tgatggaagg   64800
atagaggctg gcaaagtcaa acacggccac ggggtcgttg taataaccca cctcgggctc   64860
aaacaccgtg gcaccctggt acgaaaccgc cgcagtaccg ccggcgccgt gactgtcgtt   64920
ggaaacgccg acgccgccac tactgccgga gccgacgctg aaaacgccga cgctgctact   64980
actgttactg ccagagccgg gtaaaacgcc gtcctgactc gacggcgcag attgcaaggg   65040
cggcgacatc tgaaacatag ccgccacaga acccgcgtcg ccgggcacgg cggcggtaga   65100
gatgatagcg gcgttaggtg acacggcaac actattcgtt tcgggcaccg tcgtacccttt   65160 gctgtagtgg ttgggcagga taaaatcgcg gcaggcgcac tcgtccagca gcgaggtgta   65220
gatacggatc tgctgtccgt caaagatgac acgccgcaac ggaattttag ccagccgcgc   65280
gatggccccg gcctcgtagt gaaaattaat ggtgttgaac agatcgcgca ccaatacggc   65340
gtcctgcaga cagtaacggc ctacctgggc gcggccctcg gcattagcca cgaaacaacg   65400
cgggatgtcc ttgtaggaca ggtcatcctt gcgttgccgc aggtaaagct cggccatagt   65460
gttgagctta tagttgggcg agttagtctt ggccatgcat acggggtaca tgtcgataac   65520
caccgaaccc gcaatataca ccttggtggc ggccgtgctg gccggattgt tgtgagaagc   65580
cgagggaaag gcggcggcgt actgccgctt aaaacccacg gcggggctgt gtaaaaagaa   65640
acggccgccc tgcgccgtag gcaacttgca gaagcgctgc gagtccacct tatacaggta   65700
ctcgaggcgc gtgaggatgt acttcaagtc aaaagagttg atgttgtaac cggtcacaaa   65760
ggccggcgcg taccgttgaa agaaaagcat aaagcccagc agcagctcgt attcggaagg   65820
gaactcgtag acgtccacgt ctgggcccac ctgcccgcag gtgccgatcg tgaagagatg   65880
aagacccgag tgcccaaaga tcacaccctc cgaagtgcag ccccggccat cgttcccgtt   65940
tgggatcccc tgatccacgg cggtgtttcc ccccgtctcg tagcacacgc acgagatctg   66000
aatgacaatg tcatcggact tctcggcgca gggaaaacca ccctcgccgc tcatgcactc   66060
gatatcgaag acaggcatc gatagcgcgg ccacgagctg tcgtcgggca cggccaccag   66120
gtcagagaca tcgcagtcga cctcgatatc acaagtcgac gcgcgaccct gctgccgcca   66180
gtcgtaacga ttcacggagc accagccgaa cgtggtgatc cgccgatcga tgaccaaacg   66240
cgtcagcgga tccacacgga cctcgtacac gggaaaaccc tgctccagca gatactcgcc   66300 gattttctg gccatggtcc agttgctgat agacacacac tgcaaatcgg gcacgggtcg    66360
cgtcccgtac ccgtagatcg aggttttggt ggccggcgtg acagacacgg cgtatggcgt   66420
ccgcggttcg ggcactagtt cgcccacgct ggcaatgacc tcacgcagcc tatcggtgtc   66480
gctgtactca cagtaaaagt agctgcgctg cccgaaaacg ttgacgcaga tactgtagcc   66540
gtgttctgtg gccccgaaga aacgcaacac gttccccgaa ggcaccagat gctgacgata   66600
gcgcggcgac acgttttcgg gcgagtcgaa gaagagcacg gcgtccgtct gatcgtaggt   66660
```

```
gtgaaaacga ataggtccca ccacgcgacc caccagggtc tcgcgccaag gacacggcca   66720
aaccatgtca tgactcaaca aatgtttaat ctctcgatag aacatgagag gcagccgtcc   66780
cgtcttatgc ttgatcaacc ccgtctgacc gtcgaacatg acgcctcgcg gcacgatctg   66840
caaaaactgt ttctgtggcg gccgcttgcc cgagccctgc gcggagccgg gctgcgaacg   66900
ctgacgccgg ccaccgcga ccgcaccgcc ggtcacgccg ccgctcagat acggggttgaa   66960 aaacatagcg gaccgtgaga ggctgacagc ttacgaagca aaatcacaaa gaaaatacac   67020
atgcagcacc tagatatcca gtttaacccc gtatatcaca agtctctgtg tcactttttt   67080
tgtctgtttt tttttttctc tcctggttca gacgttctct tcttcgtcag agtctttcaa   67140
gtgtcggtag ccgttttgc gatgtcgcag tcggtctagt aggttgggct tctgtcccct   67200
gtcctgcgtg ccagtctgtc cgtccaaaga atctgtaccg ttctgctgcg ctcgctgctc   67260
tgcgtccaga cgggccaggg ccagaagcat ctggtaagcc tgctcgttgg tgtaaggcgg   67320
agccgccgtg gatgcatcag acgacggtgg tcccggtcct ttgcgaccag aattataaac   67380
actttcctcg taggaaggcg gagcctgtaa cgacgtgtct ttggtgctgc ccgacgtcac   67440
ggtggtcccg tcgcggaca ccagataggg aaagaggttc tgcagcggct gcgtgcacaa   67500
acgccgctgt cgagtataga tcaaataagt gataatgact acggctatgg ccacgaggat   67560
gatggtgaac gctccgaagg ggttttttgag gaaggtggca acgccttcga ccacggaggc   67620
caccgcgcca cccacggccc caatggctac gccaacggcc tttcccgcgg cgcccaggcc   67680
gctcatgagg tcgtccagac ccttgaggta gggcggtagc gggtcgacta ccttgtcctc   67740
cacgtacttt acccgctgct tgtacgagtt gaattcgcgc atgatctctt cgaggtcaaa   67800
aacgttgctg gaacgcagct ctttctgcga gtaaagttcc agtaccctga agtcggtatt   67860
ttccagcggg tcgatatcca gggcgatcat gctgtcgacg gtggagatac tgctgaggtc   67920
aatcatgcgt ttgaagaggt agtccacgta ctcgtaggcc gagttccgg cgatgaagat   67980 cttgaggctg ggaagctgac attcctcagt gcggtggttg cccaacagga tttcgttgtc   68040
ctcgcccagt tgaccgtact gcacgtacga gctgttggcg aaattaaaga tgaccacggg   68100
tcgtgagtag cagcgtcctg gcgactcctt cacgttcata tcacgcagca ccttgacgct   68160
ggtttggttg atggtcacgc agctggccag gcccaagaca tcacccatga aacgcgcggc   68220
aatcggtttg ttgtaaatgg ccgagagaat ggctgacggg ttgatcttgc tgagttcctt   68280
gaagacctct agggtgcgcc gttgatccac acaccaggct tctgcgattt gcgccagcgc   68340
ccggttgatg taaccgcgca acgtgtcata ggtgaactgc agctgggcgt agaccagatt   68400
gtgcaccgat tccatgttgg ataaatgagt tgcattgttg ccatctgtac ttcttttggt   68460
tctattatga gtaagattca gactggagcg gttggccaaa cgttcgagtt ctaccagaga   68520
tttttgcttg ataccttgcc agaacactac caaaccacca gtggtttcaa agacggacac   68580
gtttccatat ttttcatatg tttgattgta tgaagtattg aaaatctgct gtaacttatt   68640
tatagcctca tcacgtacgc agtccagcgc agagtcggac atgttcacct cttgcttctt   68700
agataagaaa gtggcggtca ttttggcaga agaaaagtga tacgagtcct cggcttcgga   68760
acgaatggtg cgttccgagg cttcccagaa agtgagttga caagtgacat tcttttcgtc   68820
ctgtatatcc caggagatca ccgagtccgc acgttcaaga aaagccacca acctgtgggt   68880
ctctaacgca gaattcggtc ttccaaagtc ggagacgata gtgtagttcg gaaaatgaa    68940 aaacttgtcg gcgttttctc caaagtagct ggcattgcga ttggttccgt tgtagaaagg   69000
agaaatgtca accacgttac ccgtggaagt ggcgaaaaaa tgataaggat atttggagcg   69060
```

```
cgcagtagtg atggtcacca tacaattcag attacaggtc tcacgataga gccaggtgct   69120
gccgcggctg tgccattgat ccttgaccgt cacgtaacgg gtactgtggg tgttggaata   69180
atcgtcgggc attaattgca tggttttgtt ttcatagctg tccctatgat aagccacgaa   69240
aaccgtgcct gctataacgc ggctgtagga actgtagcac tgactgtggc tgttgatatg   69300
atgaatctcc cacataggag gcgccacgta ttccgtgttg ctgcccagca gataagtggt   69360
gtggatgtaa gcgtagctac gacgaaacgt caaaaccttc tggtagactc gtaccttaaa   69420
ggtgtgcgcg acgatgttgc gtttgtagac caccatgatg ccctcgtcca ggtcttcatt   69480
gatgggcttc atcgaggtgc agacgatatt acgttcaaag cgataagat ccgtaccctg    69540 ggccatagaa cacacgcgat aggggtactt ggtggtattg accccacca catctccgta    69600 cttgagggta gtgttgtaga tggtctcgtt aacaccatgg ctgaccgttt gggaagaagt   69660
tacgcgttga gagactgaac cggatcgaga gtgagcagca gacgtcgtac gagaggaatg   69720
gtgactgtga gtagcagaag ttccacgagt agaagatgag gaaaccgcag cacccagacg   69780
gacgatacac aagttaacgc agactaccag gcaccagatc ctggattcca tgttcgtcgc   69840
gggccaaatc cagcagcgat gaggcgcgtc gtggtctctt gcgtgttgcg cggaccctcc   69900
gggaaacgcc cgcggtcgag gaggaggggt acggacttgg cagccaaagt cggtccggct   69960
ccctgaaggc acccgagacg gccgcggcgg ccgtcagggt ggagggcttg gccacgggag   70020
ctgttggcac gtcgccactc tcatccggtc tggacagatg cctgtagagg aggagatata   70080
gatctttgga cttataaaga cttccttcgt gacgaagcag cagcggccac tctttgttat   70140
acgtgagaat cacatctctg tccgggtgca gttcgtcgcg caggcacgcg atcgagagtt   70200
gtttcccgaa agtttcatta tatagtgcga cggagagcac gagctcccgc acgtgcatcc   70260
acatctcctt ctgcagcacg tttaggtcct gacagtccga aaaattgaaa aaacccatgt   70320
acttcaccac catccactca ctgggataca cggtaccttc cgcgcatttg accaaatcgt   70380
ccttgacgtg gggtagtacg cccgcgttgt cgcaggcata ggccatgtcc acattgtgag   70440 agagggggata gcgatcggta cagtgtgtga agaggggccc gttacacaac tcgtagatct   70500
gctgacccag tagcgggagg gattccacag gcagactctt gtggatcagg ttattgacca   70560
catacaggtg ctcatcgtac gtgaactgat cccccacgtc caccacgtct tgatcctggt   70620
ggtattggct gcggtataga aacccattca tgagcttaga gataaagtcc agacacaagg   70680
gccccactag gttgacatcg atgagtttgc tagtcagacg ctcctgcgtt ttgatgcaac   70740
ggatcacctt gccatagccc acctctgaga ccttctgcag gtaggcgcgt ttgcgcacgt   70800
tcacctcgcg ggtgacgttg tggatgcggg aacgcgcgtc caccaagtcg agagcctcgt   70860
gttcgtcgca gttgcgcacc cgtaagccgt tctcgctgcc gtcgccgtcc tgccattcg    70920 cccctccccc tacagctttc ttgcctcctc cacgggcccg gccgccgcca ccgttattcc   70980
tctgactgtg agtactgctg ttgctgctgt tgctggccgt catcaaagtc gtaccgtcc    71040 ccgacatcgc ctcccgtcca cgcaggtgaa tagcctcgcc ctcggggccg tcgcccccg    71100 tgccatcggg cagcggacgt cgaatctcct cgagaatatg cttgattttg gtgtacatct   71160
cgttgctttc gtggagcttg ttgaacaccg gattgtcctc gaaagcttga atgctgaggg   71220
atgtgatgag gtcgatgatc ctgttggggg cggcaaagac cgaccccacg aacatgcgct   71280 cctcccgtc caacgccttt tccccgagca cgaagatgtc ctccacgtcc tccccgtaca    71340
gatggcgact gatgccgttc atgagcgccc ggcacagctg gtgatacaca tttagctgct   71400
```

-continued

```
ggatggtgat gcccacccgc ttgacgataa cctccgaggt acgggaccag taggtaaaat    71460
ccgacaagga atatattcgt tccggtatat ccgtaaacag gttgtactcc ctcagcgcct    71520
cctccgcctc ctggatgtag ctgtggtagg ccgatgaaga agagaatagg cttttgaggg    71580
ccgaaaggac tccagccaag tgggggatgc gcgttgtcag gtccagcagg tcctgctcca    71640
ccgtctggat attcacatcg gactggcttg acggacggtg gaccgctata tggttgcaca    71700
gcaagccctg cagccgcttg ttcagcgagc ggccctgatt cgggatgatg gtcaactcct    71760
cgtagcattg ggcgcatgtc gtcccttcga cgtacacttc ctgacgcgcc accggcgaga    71820
tgccgcatag gcgacggagg agctccagca gctgcgcgca gacctccagg ccggcctccg    71880
gcgccaggat cccgtacacg tagttcattt tgcacaggaa gcgctcgatg tcgttgagtg    71940
tggccagact gacgctgaaa cggacgttgt ccgtaaactg gagctccacg gtgtgatggc    72000
gatcgcagcg atccaaacgg aggacggtac ggtagaaggc cgcccggtcc ggctggcgcg    72060
agtaggccat cagcgcccga tccagcaaag ccgtatcctc gtgcagcgcc ttcagcagca    72120
tctccagata gagcgtcagc agcgaactct gcgtacgatt ctgcgccacc acctccgggt    72180
agatcttccg gtacagatac actatagccg ccgcgtttct cttgaacggc gtggactccg    72240
ccagtaacac gttcggatcg cagtacttta gacactccag ctccatggcg tattcgttgc    72300
atttcgaaca cactacgcat agtttctgta acaaattcat ctccatgact cgactcgctc    72360
acgtacgaga cgctgtcgtc cggtctggcg ccggccagag acatggagtc ggtgcacaaa    72420
taactcgcgg gccgctcgct atgccgactg acgttgacgt taatatataa cgacgtcgtc    72480
gacgagggtt ctgctcccga agctgttgcc gccgcttgcg gcgcaacctc ctccaccacc    72540
gccgccgccg gctcctccgc ctcgggcgac ggggctcgg agatgaccgg ctgtgtctga    72600
cactcctccc cttcctcagg cggcccgggc gccgacgcga atgtcggagt ttgccagcgc    72660
ggcggcggtc tctgtctctg gtgccgcggc gctaatcttc ggggctgttg ctgctgttga    72720
tgatgcgacg ccgtctgtcg ccgctgttgc ggcggtagct gatacggtgt cgcctggtgc    72780
tgctgtgtcg gtggctgctg ttgctgctgt tgttgcggtc tgaaaagcgg ccacggggc    72840
tgcgactgtt gctgctgttg ttgcgatgct cgtgactgcg gcggccgttg tcgcggcgtt    72900
tgctggcggt tacaaccggc tgcgtttggc cggcaataac ccgctgcccc cgccgccccc    72960
gctgctcccg ccgacgccgc cagcctcgtc ttcgccggcg ttcacgagaa agcagccacc    73020
tcccgtctcg ccgggcacgc cgaagcaaat ggagttgccc gcgacggact cgccgagaag    73080
aagaccgcca cccccgacgc cggacgccgc gccgacgcca ctgggcgcga agagcgccga    73140
caggtcgtgc acctccccc cggcggcgtc cgttaatcgc tgggcgtcgg cgtccagcac    73200
gcgtcgcaag ttctccagcg aaaagtcctc cacgccctgc tcctgcaacg cggcaaactt    73260
gtccatcagc gacgcggcca gcgcctcgca gccatccacg aagaagagca catcgtcgga    73320
cgcgggggatc tcctcgcgca cgctcagaat ctcgtacacg gccatcactt cggggtcgca    73380
atccaagttc tcgcgtcca gcgccagcat gacgcggttt tttataagat ccgcgtcaaa    73440
aagcacgttc tcgcggcgcg agcgtttgat gagcacgtcg gccagacgcg tagccaagag    73500
gtaacgctgg cgcatgaaac gataatcttg accgctcata gagctcacgt taaggctgcg    73560
ttccacaccg ttgcccgaaa agtagccgat ctgcccaaac tgatagatct ccttgctgtt    73620
gttgataccg gcatattttt ccacgctcac gggcacggtc accaaggaac gatgctcaaa    73680
aacgctccgt accaacgatt cacgcgccac agtagcggcc atgggcgccg gcacgcctgc    73740
ggtcttcaag cccttgacat gcaacgcaaa ttcggcgggc gacgagaaac gcggactagc    73800
```

```
acctaacacg tgaggaaact gcgcgtggtt ctgcgtcgtt aagcgcgtcg ttaacccgtg   73860
cagcgagcca atgtagtctt tgaagccgta gtagcagagg aatttgttat ggaaacggct   73920
ttccacgtaa ctcagcacac agtctggcgc cacatccagc agatcgtgct cctgatagtc   73980
agccgtcaca gccaccagaa atttgacgaa agcattgaac tcgcccatgt cacctatggg   74040
cacattcttg ggcaacgcgt tggaacagac cttctgccaa aactgtaagc aggggagacc   74100
acattcagga aagagtcgct cgtgatgtcg atacagcaga atcccaagc agcccttagc    74160 cggattacga cgcggaacgt gatcgcggcg aaaaaacacg ctacccgcgt tgcccttgcc   74220
cgcgcggtag atgggtcggt ttttcacccg caccatgatc aacgtgggta ccgacagccg   74280
cgagagcttg atctccatgg gcaccacggc gtacgtaccc tgcgcgtaca gcctaaagtc   74340
cagcaggcgg tcgtgatccg aattcttgga cgacttgatc tgcttggtga agagaaagcc   74400
cttgcgcgac gacgtggtgg agaacgcgcc gtgaatggat tgaaaatgct gcgtcatcca   74460
tttggatacc aagttggtgg tcaacggatt gtccacaatg tatgaggtag cggtaataag   74520
cgccacgttc tggatcacgt aaaagacgga tctgaaatag gcgtaggcca gcagcggctg   74580
gaaagccacg gcgtagggat tcagatccag gttgaaggcc tgcgtggcgc ccgccacctc   74640
gtcgcggctg ctcttgaggc gcacctccga aacgaaaccc agggcctcgt cgtccacaaa   74700
cttgttgagc gccgaaaaga cggccacaaa gtcgcttttg ccgtgcgcgc taaaggtatc   74760
ctcgcccgtc acggggtcga tgagccgcat cttgcggcag taatccaaga tgcgattgag   74820
ccgataggta cggtccacac tagcgcccag catgcgaccg ccgcgcccca tcattccccc   74880
ggaatccccg ccaccccac caccacgacc gccgcccaga ccgtcgctcg ggcccccgct    74940
cacgtctcgt ccaccacccc cgccagcacc gccgcccgga accccgtcgt cacctttgcc   75000
gtccaaaccc ccgtccttgg cgtcgacgtt gtaacgccga ccgaagctgc ccaaaatatc   75060
cacgtcgttg agaaaacgcg actgcacggt gatcacgcag ggctccttct tgggctgctt   75120
gggcaccacg ggcaagcggg tgcgcacccg cacgaaggcc gtctgataac acgtgtggca   75180
acaagtaccc ccacaggcct cgcacagccc cgcggcgcag cccaccaggt gattcgtgag   75240
cgtcgacgaa cccgacaagc ccgtgttata caccgagaca cgatttagat accagacgaa   75300
gcccgaaact agctgcggac acgtgccaca caccaacgcc aaatgctgcg gcccatagcg   75360
ttcgtccttg agcggcgcgc cttgaaactt gagcaccttg cgcgcgtcgt tgtagacgtc   75420
ttcgcaggcc gccgacaacc cgttggtgaa ctgaatagcc ttgagcaacg tctcctgact   75480
ggccgtaccg ccggcgctgg gatgccgcgc agacgactga agatacacca gcctgtgctg   75540
gtagagcacc gaattagcgc tgaagaccaa ggcggccacg tgcgtcgaga gatgcaactt   75600
gagctcggtc agcgcgcgga tcagatcgcg gtgatcggtt gcgttggtca ctaaaggcca   75660
ctcggaaaag agcatagact cggcaggttg gtaggccgaa tcgaaaaata ccgaggcaaa   75720
actgaaggcc aactcacaaa ccaccgcgtc actcagcatc agatgatcct tttccagact   75780
gctgagtcgc tggctcatgt accccaagta gcgcttatgt ggcgccagct tcaccgactg   75840
ctgactgtcg tgcacaaact gccgcaacgc cgcctcgatc agcacacgcg gctccgagaa   75900
gcgcagcgat tgacaccatg acgtgtacac gtagtagaaa agcgtctcgc ttacggccgg   75960
cacgtagagc cctcgcgcct ccacaaaagc gctgcgcgca tccagcgaga cctcgtcggc   76020
ttcggcgtca agctgcagcg aattaaagag cgtaggcggg tacaacggca cgcgcaccgc   76080
ctcgccgccg tgcagtcgca ccgtggtcgc ctcctccacg catggaatca gctgaccggc   76140
```

```
aaagagaaac tccttcaagc cgttgcccac caccacgtgc acagtcgtct cggacgcctg   76200
acagcccact gccgcgcaca acgccgccag atcggtaggc acgcgatccg cctcgggcgt   76260
gtaggcctcc aacgcgtact tctggcgggc gtcctcgcac agccgatgca cgtctccgtg   76320
atcctcggta aaagccacga tgccttgcgt atgatgaaag tagagcgcaa aaggacaaaa   76380
ggacgtgact ttcgtgagca ccccgccgtc gtaacaaagc acaggcgtgc gcacagagac   76440
gccgaaatcc gcctccaccg tgagcccgc caacagagga gcgatcacca cgctcgagga   76500
acggtcgcat agcgagagag tggccagaat ctcctgcgtt tctgcgttca acctgctgaa   76560
gtagagaaaa gccgcgggcc ccaccggcgc tagcgcggtt agttcctcgt ggctcatggt   76620
ggatgaacgg aagacaatgg ctacgccgcc actgagtgaa ttttatacca aggaaaagtt   76680
cagcacgtca tgtttgacgc acgacgtctg ataccaccac cgtggccacca ctgcggtctg   76740 gctgcggttg cggaccacca aaggcgacaa ccgcaacgat cccagcaatt cgtaagaaaa   76800
gctaaccgtt acggtcgggc agcctctcgc agccagaccg ctagccgacg cacccgcccg   76860
cgaaaatagc gtgatgttcg ggacggcttc gcgtcaccgc aaactaacgt cggtagtcgc   76920
gcacgtcgtt tatcatcagc acaccgtccg atcacaaccc gttttcccac tcagtcgcac   76980
aagcagcaca taaaacccc acacagggca catgaaaaca acgtccctag aaaacggtgt   77040
tttctgtcct accgtcaccg ggccacacag gcaaatcccg agcccgatcc ccgaaaacac   77100
cgtacggtgt ttgtggcctc caaaatcaca tcagctaaca aaccgtgaaa agtcacgttt   77160
cacgaacacg gtgtttctaa atcacaaaga accgcctgac ggtttacaag cagaaacacc   77220
gcaccacggt ggtacaagcg cggtggatct ggtctcgcaa cctcaatcgc cgctatcacc   77280
accgactttc gctgcgctcc gccgacaaaa cgccgtacaa gttacacacc ccaaaaacct   77340 gcgcgccctat gggcgccaaa cgtgtgtatt atctcaacgt cacaacacga cacaaaccgc   77400
gtaacgtggt ttcccgaaca cgtacgcggc acagacccccg acacgtact cgaagacctt   77460 acagtttacg agtcaataaa acaggaaaag atccgaactt taaaattgtg tatttttatt   77520
ttcccatccc cctcttttta ccaaaaaaca cattttttcgt cttgtaaaaa gtaactttcg   77580
cccattgcca tgaaacaccg tgatggggaa cggtgttgtg tgtcgactga cgtcactacg   77640
gcgatcagta tcgacgtcgt gtatacataa cggtgcccgg tgttttttatt cggggcgttg   77700 tcgcgtcttg atgtaatgta acctgaaacc gccgtgccta agaatgcgga agccagcgtg   77760
taatcataac ggggttttgg gtacaatctg acgacatctg gcggcgagcg tacaccatcg   77820
aatgtggcga tcgccggctc tacgtcacaa tgacgcaaaa acacactgta aaacccgcgt   77880
agacagcttt cctggtcaat gagcgccatc tggtgtcggc ataagaacag gcatcaaccc   77940
cgtggccggc gaggcggtga gcacttttgt tggtcacgtg accatccgcg caggaagcga   78000
ggcccgtaga accgcccaag aggcggtgcc agatgccaac gtcataatca caaggtgatt   78060
tgttacgtca cgcgcacacg cacgcgcgcg cgcggtagaa tacagcgatc catagtgaag   78120
ccacacccat tacgtgtagc catatccgct tacgtataca gacacacccc taggtacgcc   78180
accttatcta ccaatcacag aaacggatat aaaatgaccc ctccctagac tccaccccctt   78240 gtacggaaat tcagataggt tggaaccccgt tagggttcca ccgtcctcgg tgtacgtaca   78300
ggcttctccg tctaccggaa atatacacat gctgacgtag acgctactcc cggatacgcg   78360
tcataagcta ctggacccta gggggggagt gtctacaggg ctacgtgcac gcccccttac   78420
ttagggtatc cgcccctttc ctctgttttg gcctagtaaa cttaacgccg ccgcttctca   78480 cgtgaccct gacaagccta cgtcacactc gcgtgaccac acccactccg gatatacgtc   78540
```

```
atcccgtgga ttccggacat acggtgacgt agcgagcgta gcgagctacg tcacgtatgc   78600
atgcgtcatc tccggcggaa atcatctctg atgacgtagc gagcgaagcg agctacgtca   78660
tcagtccgtt ttacgtatac cggatgctag gcgacgcccc gtaggggcgg agcctagctt   78720
ccacccctag gatgcatacc ctatatagca taattcttct aacgaaacgt tctacgaaaa   78780
cggactggcg gaacgggaac caccgtaacc cccccccctc accccccccc ttctcctccg   78840
gaaccggggg gggcaaattt ttaccaaatt tgggcaacca tgatttccaa tgggacggcg   78900
tttccgtgcg catgcgcagt cggggcgagt ttttggttgt cagggcgttg ccacgcggat   78960
tatgggatgg tgactcgagt gcgcatgcgc cggggatgcc gcatggaaaa cctatatata   79020 aggagggtg aaccaggggc cccggtgcgc atgcgcgggc cagggcccgc gggagggtcg   79080
ccctgcgcat gcgccggtaa aattccagtg tgtgtgtcgt gcgcatgcgc cagtattttt   79140
ccactagagg cagtcagtgc gcatgcgtcg gtaaaattcc actagatgtg cgccgtgcgc   79200
atgcgccggt attttccac tgggcggccg cacctaggga gcgcgagccc cgtgccgggc    79260
atgggccgcg gcggtggaaa attaccgctc cgcccaccta ggcggggcat ctgaaaacct   79320
ataaaacccg gcgtgcccgc cgcccccccgg cgcagtccgc ggcagggttc cggccgtgct   79380
gcggtccgca cgctgcgccc gctcccgcct gcctcccgcc ctaccccccca ccctccccgg   79440 ccgaggcccg gcgccggtcc gtccgcgggc ccgtcccacc gccctggagc accatccggg   79500
gccgtgggcc gggcaccggg cgcggccgcc tccggacctc ggccgggggt ccctcccctc   79560
cccccgctcg accccccatc cgacggcccg gccgggctgg gacccccgca ccggggtccc   79620
ggttcccgtc cgcggcccgg gggacccga gcggggcgtt cccaccccca ccccgctcct    79680 cccccgggctc cggcccggga tccctcgctg ctcccggcga cctccgccgg cttcccggtc   79740 caccccgccgc ggaacggacg ggacccgggg tccgcgcccct tccctcccc ccacgggggg   79800 ctgggtcgcg gaccccggtt cctaggctcg ttccgcggtg ggcgaccggg gatcccccac   79860
ccagctcccc ttcccggccc gccccgctgg cttttgggcc cctccgggct ttttttttcc   79920
ggctgggtgt cgcggcggtc ggccgacgac gacggtaggt gggccgggtg gacggtggtg   79980
gggacgggcg acgcccggc tcgacggcag tcggtcccgg aaggttgggg gctgggggcc    80040
cggtcaggag cttcgggagc gggggtcgacc gcgacggctt ccgggtctcg cggcggctcc   80100
ctctcggcgg ctccggttgg gctccctcc cccctctcga gggtccggcc gccagtcgtg   80160
accgggggtc cctcggccta gccgccggct ctcggtccgc cttatcctgg gcgttggccg    80220
gtcccgtgac gctccctcc cccactgctc cccaaaaaaa ctccgcccga accgtcgcgg    80280
cttgctggcc ctgggcgtgg tccccactc ccctccccc atcggccgcc cagccggggt     80340
cggcgcctcg gaccccacca ggctgtggcg tgtgtgctgg ccgatgcggc ggcgagggtga  80400 ggtgtggccg gaagcgctcg gggtcgacgg tgggccgcca tgacacctca attgccgtca   80460 gtacgcccttt ccacaatcac cgtccccaca cgatggcccc ggcaggtcac caacgttgg   80520 ttcaggccca gtcgagtttt tccccggcac gaacgcacgt cccgtgggc tccacgcgtt   80580 ttccaccctt tcctggaggg gtccggaaca ccgtgaatcc acggggaggg tcccggcacg   80640
ggccgaggag accacgaccg tcccaccccgg cgtgtcgact cgtccgagac ccgggaaggg   80700
aacaggcccc accatttttt ttttcccttc tccgatttgc cgtggaaaac ccgtgaaccg   80760
atacgggtac agacggccga aaaaaaaatt cgagacaata cgacggcagg gcgtgatttt   80820
ctcccccatc cgacaaaacc gtgtccctca aaattcccca cctttctctg ctcaaatggc   80880
```

```
cccgaaactg taaaacaccg tttgaccgca ccccaaccgg cgccatcttg gtgaccttct   80940
cgacggttct ctcgctcgtc atgccgttct gagctccgac atggcggacg agagaaaatg   81000
gcgtcgagag cctaggagcg ttttcgctcc aggcgggtaa aaaaatagca cgataacttt   81060
tctgtgcttt ttttgagacg ttttagaaga gcttttttct gctcagcgaa aaatgatag   81120
ccctgaaaat ctcgacgagt ctggccgagc ggcgccatct tggaggaggg gcgagtcgcg   81180
ggcaccgcct cggtaccccc tggccgaggc gagtccgcgg tcgccgcctg ttccgtgatg   81240
ctacctagag ggcgctgtcg aggcgactct tcctgttttc gccctgaggg ctaacggtcg   81300
ctgacgtcaa accatctcgt gctcgctgag tcacatccgg ttgttgacaa gcgatggagg   81360
accgcaccca aagtgcgccc tctagtcatc gcgcctgacc cctttataa actgctcgaa    81420
gaaaagaaca ccttatgtga aaaaatacag aatgatgaca agttcatcca acacaaccgc   81480
tcaacaacgc catatctatc agtgtccaaa aactatcttc tatcctttga aactataaat   81540
gctgcctata tacatattta gtatccaaga ctcttaccac gtagacgaaa agaagtgata   81600
caatgatctt gacgtgtatc gtctatatcg tgctagatat attcagataa gacgcgcaaa   81660
ccatagattt ctcatcagta tcatgaaaga cctatagctc tatatacgaa cctagtcatt   81720
ttaggacagc cgccggagaa gccgacgagg gatcgggcgg gtgcagccag aacctcacgc   81780
ccgatcccgc ctccggtagg cgatttgcat ctgtttggta aaaagctcat aagtctgtat   81840
gtgacctata tatatattat acgctatgta caccgaactg tcgctgttgt ataagaagaa   81900
aaaactctcc atatttatat cgtctgaatt tttgcttgat agacacgtgt ttggaactct   81960
gtcccccac gttttcactg tgtataacaa aaatatgtgt ttctcaaaag atcttgaggt    82020
gtttgaaaac gggggaaacc tgcgtttggg tgcgctaagc cccggactgg gacgtagccg   82080
gcgtccggca cctatatttt tctatttttt tacaaaatat atgatgaacc aagaataaaa   82140
ctctagctct cgtctatttt taatatgctc tacttagaac ctttttaatg acagaatgaa   82200
ctccatgtta tacgctcttt atatagtttc tctgcactaa cctttaaaac cgtatccttc   82260
cctgttgtac aaatcatctt ttgatacaca atgatgacct gatatccctc catatatatg   82320
atcggatatt attccgttag acttgtcctc cttttttttc ctcatctcct atatctggag   82380
atatatgttg accaccaccg ccatgaccac caaaaagcta gccgtcacga ctagaaatgt   82440
gtaggattcg gactttccgt tcgagaagaa agagaccgcg tctctggacg ctcttttgt    82500
cggtctgaat cgacccggga tacgtaagag agcggcccta catcgggggg cgctcgagac   82560
cgacgacgtt ccatctgacc agaaaaaaaa aaggcacccc tcggtagcga cctctcacca   82620
tcgtttgccc gtccgcccgt ccttcgtagc catcatcatc atctcaggct ctatcggtac   82680
catcgttgtc atctgaaaaa aaaaactgcc tcacccacct gcgtaaaaac accatctttc   82740
cggaggtgcg gtaagacggg caaatacggt cgtgccgagg caaaaaaaaa cgcaccatcg   82800
acaccacacc ctcatgagca ccacctgtcg gtgttggtcg tcctccatcg ttctctacga   82860
acatctcgac gcccgggtga cggacgacgg caagacgtcc cggagaagac ggtgttctct   82920
cgggcggtac gctctctgga tctataatat ctatagtagc taaacgagac tgtgagtacg   82980
acgaaccaca tcatcttttt tttatgttgc ttctttagaa aatgactat gtcgacgaca    83040
ctcggcatca gccatctcgt gaaacacgct cgcttttcgt ctctccaagg aacactgggt   83100
ccgctgaaag ggaccgtgta ccgaccaaag caaaaaacac acacgtagta acatgatcaa   83160
ccacgtctga atgacacgaa aacacaatcg tataacgctc tattcatgga acgaacttgg   83220
aataaaaaaa accatcgcag gccagaggct aagccgaaac cgtccgggga agcgggcgcg   83280
```

```
agttttccga cttagccttt ggtgctcgtt gagcctcttt ttttttttct gattctctga   83340
agaatcaccg tcacagccct atgacgcgaa atcaattgct agaacataaa cgttctcaac   83400
aggtatgaaa tgaacaaact agatgatgct ataaccttat attgtgtgta tatagatagg   83460
tgtgaaattt gtaggataaa aagtgtcgtt gtatgatgca caacgatcgt gaaactggag   83520
actgtagctc tctaccgaat gcaaatacac aaatgacatc gattcccgtc cccacataaa   83580
gaaatgtgct ttactgtgaa agaatgaaga agattcttgt tcctcgtacg acggggccct   83640
cgctcgtcgt gcctcttccc ccctccggga gagggacgt cggggccctc cgtcgcaccg   83700
ggccgaagcc agtgaaatgt ttactacact gtcatcagaa tatatgatgt atattatttc   83760
ctccaaactc ctcaccatag ccaccaattc gcatcactta agaaagtagt agcaaccgcg   83820
gcggcggcga ccggccggtc gtcgtctcct cgtcctcaaa tgttgtacat gtgcagaaaa   83880
atgtgtaaat acgtgttatt tatcccatgc gtcttgtaca tagatatatg tttttatata   83940
cgctatttat actttatata tccttttgca taaccataga cagtcaagga ttttaatgat   84000
ttgctcatcc gcctttgagc catcgcttag gagttagttc ctctatgttc tcggcccacc   84060
ttttcgacta cagtagcaaa cccttgtact accaccccga taaaaaccac atcatcatcg   84120
tcaccacgac ctgaaaacga cacacgttcc cccccaatct tgggcatgtg tatatataaa   84180
gaatgggagg gagaggacgt ggggctcgag aagaaataaa cgccaagctc gattcgaacc   84240
aaaaaaccac atgtgtattg tgctttgttt tttttttttac ggtggggaa aaggaggggg   84300 ccgtcattaa cggaaaccgt gtatggggtc cggacacgaa cagtacacag cttatgggga   84360
aaaaagctca cagagagaaa aaaaacacca agctcaggca cgcgtacatc attatcatca   84420
tcggatatct caccacgggt catagtagta ccaaggagtg tgtgtaacac cattttttct   84480
tttctttgta acgggataag ggacagcaat catcacgcac aacacccttc actttttttt   84540
ttagtcatcc atatcatcgc tgtaacacag catgtcctcg taatcgggcg tctggcaacg   84600
cattaccacc gagtcgtctt cttgcggtac cggtggtggt ggcggcggcg gctgctgctg   84660
ggttgccgtc gtactgtgat taccgttggc ggactgcacc gggatgatgg gctgcttgtg   84720
gggaacctgg ggtggactgc cgccgtgaga aggcgacggc gtcatcaagt taagctcacc   84780
acggtgactc cggacaccgg cgaggggcgc cgggggactg ggagggaccg cggtcgtctt   84840
gtagacgacg gtgtccccgt gccgatccgt ggctcgtacc agatcttgac tgctagcgtc   84900
gtcactgtct tcgtcctctt ccagctcgcc ctcagagtag tgctgctgtg gttgcgacgg   84960
tggctgggcg ggaggagcgg cggcgatcat tggagaggga tgtcgatgac tcccttctct   85020
gtccttttta tcgtaggctg tcagcgttgc tgggtccgtc ctgctttcca tatttgcgca   85080
ttgctcatcg gtgggatgaa tttggtctcc tccccgctgt tgtccgccgg cagtggcgtg   85140
gttgctggcg gttgtcgttg tcgtaccggc aaagacggtg agatccaata gcgactgctc   85200
gtcgaaggga cagtacgcta tcatgaaacg ataggtgcc aacgcgcgtt ggatgcgcag   85260
ttcgcacatc tcgttctgac actcgtggca ctgcagggcg cctaggatca ggtccgagac   85320
agcgccgcag cggtaggtac ccatggcgtt gttagtatcg aactggtcaa aaaattgggg   85380
cgtaccggtg acttgcaacg cgcgacgcg tagcgagacg gccacgcgcg agaaagagca   85440
cacgtaggcc atggcgcggt gcatgggttg cgagaaggtc tcgggcggac gcttctgcag   85500
atcgcagacg tcgtcgcgta gccaggcgct catttgaccg ggcttcttga ctaaccgttt   85560
gagcgtgctg caatggtcgc cccagccgtc ctggtggtcc aggatgcagc ccaggtccag   85620
```

```
gttgttgagt ttgttgaaga gcagctgacg catgccgccc accgtctcca gatagggatc    85680 gtgcggggttg acgggtagcc cgtgcaagtg gtggtacttc atgtagctga gcgtttcgtc    85740
gatgatggcc agcaacgtgt gcaagttggg agcgttgtac acggcgaaga tcttttccac    85800
caccagcttg cgcagcaacg gttcctccag ccaatcgaac tgttgacgga tgtgcaacag    85860
gtagtcggtg tgcatgagct cgtcgtgtga cagcaggatg cgaccgcgcg gctgatgatc    85920
ttgcgggaag gcggtgggga ccttgagatc ggcggggtag ggtgccagac gtagactctc    85980
ggccgtgtag cgctgaaggt cgtagacggg cgaggtagaa ctcggtgagg tacccgacga    86040
ggcggcgccg cgctgcagac gcgctctttt tttcttttcg atcaaacggc tgagttgctg    86100
tagttcgtcc tcgtccatgg cgtccagttc gtcgtcaata agcgccagca tctgttgttg    86160
ttgcggtccg gcggacgatc cgtgatgatt attggctgag gaggggtgag aagaaccgaa    86220
agtcgtagga caactgggaa ctcggcgacg aagatgcgtc gaatcgccgc cgtgatggtg    86280
cggttcgccg tcatcgttgt cgtaagactt accgtagtgg gggtgaaggg gcaccgaggc    86340
ggacgcggcc acgcgtcgct tgaaagagga ggacgcccta tgtccgccac ggaagcccgc    86400
ggtgcccatg atgatgtgtc cgccggtgcc cccgagtgcg tggcgggagg agggtggaag    86460
gggaggagga tagtggtccg gatcgccttc ggtatcatcg tctttgctgt agcggggtcg    86520
tcgtgcgggg acgcagggtc ggtgatgatg cgaggcggcg ccgacggtat cttccgcgag    86580
atggtattcg ctggcggctg ctccgttccg tgtcgacggc gaggttggac ttcgctcgcg    86640
tcggaacttc cgtggcacgg gttcgtaatc cagacagaag cgccgtgcgc gacgggcgcg    86700
gcgttcgcgc tcgctcaggg aagataacga cggagcgtcg tgacgccgc gtgagtcag     86760 ctccatggcc gccgtcgcta ggaaggtcac gttcgggcac gctgatgtat atatagatga    86820
gaccgctgcc ggggggcggg tcaccggcgc cgtggaaagt gaggctcaga cggcggtcgc    86880
cggcggcacg ggcgcgtcgg gcggtctgat tttgatggaa atgtggacgt ttttggcgtt    86940
ggagtgacac ttttttggtga acagcggct ccagaggctg gcccagagcg cgtagctgtg    87000
ctcggtgcgc aggtcgatga acacttgcac ggtctcttgc gggttgcggt gcgtgtagtt    87060
gagacagcga aaatcccgcg tgcgcgcgcc gtcgcgccgc ttgacggcca cgcagcaggc    87120 gccgtgggggc tgaaagagga ggacgtgggg cgcagtaaac tgctcgctga cgtgcggctc    87180
gtagtgttgc gtgaggtgct cgagcagtgg cggccacacg cgggtgacga cgagccgctg    87240
caagtccgtg tcggaaatcg cagcggcagt ggcgccgtcg ccaccgtaca ggtgataggc    87300
gagcacctcg gtgagaccgc ggcgtcgata acgcgtcacg ttaagcgagc gcgtctcgat    87360
aaagttggct tcggtcgagg ggcagatttt gtcatgtacg ctgagaatga cgcgtggcgg    87420
cggcgacagg ggcaacgcgg gcaggtcgtg cggcgggtgg tggtgaagca ggttacgcag    87480
atccagttgg gcgcgcacaa agcctagcgg gtgttcgcgg taggcgtcgg gcacgatgaa    87540
cagcggcaac agacggcgat gcatgaaata gccgtcgtct tggtccattt tatacatgta    87600
gggcagacgt acagagcgtc catggtggta gatgcctgtg tctaggctgc tctcgggatg    87660
cgagatgggg tccagcagcg tgtgcagttc ggcgtcgaga cagacggcgt gattgagcac    87720
ctgcgccacg gcgcgtaaaa cgctgggatg tacggcgacg gtgcaggcgg gaacggcgt     87780 gatgatgcgc agccccagtt tgcccttgca gcggcagtaa gggggtgacg tgtcaacgga    87840
agacgttgtt ttttgaaaaa cgccgttatc tgggacgtta ttttgtcct ctttcccgtc     87900 ttcgtcttcc tctgtgtcgc gctcgtcccg gtaatcgaga tagtcgtcgt catcgaaaggc   87960 cgcgccggcc gcgtccacgg gcacgctgtt gggtgggcac gcgcttttga agaaatagac    88020
```

```
cgggtgccgg tcggggtgcg tgtagccaaa gaggctcgcc catacggtca tccagacgcg   88080
tcgtagtccg cgacataact caaagacggt gtgtcgcgcc agaccggaga cgccgtcgcg   88140
cagccgtaaa tcaaagtcgg ccacaaaatt gaagacgggc agacgttcgt tgaagacttc   88200
gtgtcgcgtg tagtagaact gtgtctcggg gctggtgctg gccacgtcgt cgtcgtgtag   88260
ccacacggtc tcggtcaggg cctcgtccga gaaacggctg tcgggtacgt gacggagcag   88320
gtcgcgcgga aagaggctgc gatgccaggt ttcggaggcc acggcgcaga agacgtgctg   88380
gtcattgggc aggtgtacgc ggtagacggg cagcggtcgc tccagcagcg gtgccagcgc   88440
gggctcgggt agcaggtagc gacgttgcga gtaacgcgtt agcgtgccgg tggtgtaggt   88500
ctgggctgtg cgcagcgagg cgcagagacg taataagccg gacagggagc gttccagcgg   88560
ggagaagaca gactcggaaa gcgtgttgat gcgttcgagc tggcgcgcca gctgcgtgga   88620
ggtgccgaag aagcccgcca ggtgcgtgcc gtcgatgcgg ccgccgtagc cggccagccc   88680
caggccgtgc gggctggtcg ccgagtgggg ggattcgtcg agacgcagta ggtgcgtctc   88740
cacgtagtcg tgtagaaagt tgtcgagcga gaagtatttt tgcatgacgt ccagcagctc   88800
ggtggaaagc cggcggccca gaaaacccgg ttcgcgcgtg cactgcgctt cgggcgccgc   88860
gtcagcgtcg taagccacca cgccgccggta ctcgagcaac cgcgcgcgtg ccagcgccgt   88920
gcggtaggcc aggtagacgt agtgcacgca gaccgtgtcg ggcagacgcg cacgttcgcg   88980
gaacgcgttg atctgcgtgt ccacctgctc tagctcggtg tagtcgcggc ggttgcgcgc   89040
tacggcgtac gccacgaaag cggacacgcg ctgacggaag ggcgagccaa gtagcagacg   89100
cgcgaactcg cccatggagg cgtgcgtggg gatgatggtg ccaaggtcgc gcgtgcagaa   89160
gctgcgcacg tactcctcca cggtggagat ggtgctgtac tggccctcga ataggtagta   89220
ggccatggtc agcagcacct ggccctcggt gtgcccgaag acgctgatga accacgaggg   89280
cgaggtgggg cagaggaaga cctggttgag atgacgtagc acggccgcgt ggtgaaagta   89340
caccaggtgc ttgaattcgc gcacctcgcc gccgtgttcg ggcgagagca cgggcgtgcg   89400
gaagagatgc cggtagagcg gttgcgtctc ggcctcgtcc agactggcga tgagcgccga   89460 gaggggggatg ggctggcgcg cggccaggta gcgcgagagc tgcagcgttt cgttgttcac   89520
ggcgaagacg ggcgccaccc gccgcgagtc cgagcacttt tgcgtctgta ggcagaaata   89580
aacacgtcgc gagacctggt gtttgaccag caggggaag acgcagtggt ccgtcggtgt   89640
ctgcgagagt acgttggcga ctatatgagc agaatcatac tctgttgcga acagaacgag   89700
cgtcatcgtc gcgccggcac gatgcagctg gcccagcgcc tgtgcgagct gctgatgtgc   89760
cgtcgcaaag ccgcgcctgt ggccgattac gtgctgctgc agcctagcga ggacgtggag   89820
ctgcgcgagc tgcaggcgtt tctgacgag aactttaagc agctggagat caccccggcc   89880
gatctgcgaa ccttttctcg cgacacggac gtggtgaacc acttgctgaa gctgctgccg   89940
ctctataggc aatgccagag caagtgcgcg tttctcaagg gctatctctc ggagggctgt   90000
ttgcctcaca cgcggccggc ggccgaggtg gagtgcaaga aatcgcagcg tatcctggag   90060
gccctggaca ttcttatcct caaactggtg gtgggcgagt ttgccatgtc cgaggccgac   90120
agcctggaga tgttgctgga caagttctcc acgatcagg cctcgctggt ggaggtgcag   90180 ccgttatgg gcctggtgga catggattgc gagaaaagcg cgtacatgct cgaggccggc   90240
gcggctgcga cggttgcacc accgacgcca ccggcggtcg ttcaggggga aagcggcgtc   90300
cgcgaggacg gggaaacggt cgccgccgtg tcggcctttg cctgtccctc ggtttcggac   90360
```

```
tcgctgatcc ccgaggaaac gggggtcacg cgtcctatga tgagtttggc tcacattaac   90420
accgtctcct gtcccaccgt tatgaggttc gatcagcggc tgctggaaga gggcgacgag   90480
gaggatgaag tgaccgtgat gtcgccgtca cccgagcccg tgcaacagca gccgccggtc   90540
gagcccgtgc agcagcagcc ccagggacgc gggtctcacc gtcggcgcta caaggagtcg   90600
gcgccgcagg agacgctgcc tacgaatcac gaacgcgaga ttttggatct catgcgacac   90660
agccccgacg tgcctcggga ggcggtgatg tcaccgacca tggtcaccat acctcctccc   90720 cagatacccct ttgtgggttc cgcgcgtgaa ctcaggggcg tgaagaaaaa gaaacccacg   90780
gcggcggcct tgctgtcctc cgcgtgaaca gcctggcacg ttttggaaaa cgtacgtgat   90840
cacggacacg acgagtacgg ggtttctcat agacgtactt tattaggtca gggatgacgg   90900
ggaggtttcg ggccgacgtc aaaaataacg tcattcgtgt tgacagggct ttctgcgtcg   90960
gagctctttt catcttcttc tgtctcgtcg acgtcatcgt ctaccggcga gggtgtccgt   91020
tgcagcaacg cgtgctcggg cgtgtgggtg aaaccgatgt cggggtggg cggcacgatc   91080 atctgtccta gggggtgact gcccaccggc agataggtaa agcggtgggt ggtaaaaacc   91140
gctttggcta cggtggtgtg tggggagatg cagacggtgg tgtgcgaagt gttgaccacc   91200
gtcacgccgg ccgcggtacc cgggagccag atggtgggtc ggatgatgag atccgattga   91260
ctaaactggc gcacgcccac tatgagggcg cagataccgg gcgcgtgcac gtaggccgcg   91320
tcaaaataga cggtttgcgt gtgacccgga ccgatcacca cgtctgacg ggtacgtaat   91380 gaaaagaaac ggtgttcgtt gggcggcggc aagttcatga gctgccaggg ttctggcaca   91440
aaacagggga aaacgccgat atcgccttcg atggtgcccg gaaagatgga ctgaaaagtg   91500
tcgttgaggt tgacgacatc caactgcggg acttgcagcc cggattccag cagctcgggc   91560
atgcaaacga attgcgcgtc caggcatttg taaaaggtaa tgccgaaaaa accttcgggg   91620
atatagaggc tgacgcccag cgaggtgggc actttgcgct cgcgtgatag ccaaatgatg   91680
tgtttattgt aaaaggccag ctgcgtgtgg cattgtttga cgatgaaact ggaaggcatc   91740
cacttgtagg gaactttgag cggcgacggt aatggcgacg atgcttcatc ttctcccgga   91800
tgctgctctt tgtcgtattt ctcctcgatc gattggggca gcgtaaatgt ggtttgaaaa   91860
tcgctatcgc tagcgaaacg cacgcagtaa cgcatgttga cggatttctc ggctaggatg   91920
atggagcctg atgacggtgc ggactcttcc ttcattatta acgtaggggt ctcccagaat   91980
cgctgaaaac gggagcgcgg cagccgcgac agtaccagtt gagagtcgat tcggtcggtc   92040
aacatcgtaa gcatcgtggc ggtggtgcga tggagtggaa cacactagta ctaggtcttt   92100
tggttttatc ggtagcggca agttccaaca atacgtcgac tgctagcaca ccgagtcctt   92160
ctagctctac tcgcacctca acaaccgtga agtcaacggc tgttgcgaca actagtacaa   92220
ctacggcgac aagtacttca tcgacgacta gtaccaaacc cggttccacc actcacgacc   92280
ccaacgtgat gagaccacat gctcacaatg atttttacaa tgcgcattgt acatcgcata   92340
tgtatgagct ttcactgtcc agctttgcag cctggtggac tatgcttaac gctctcattc   92400
tgatgggagc cttttgtatc gtactacgac attgctgctt tcagaacttt actgcaacca   92460
ccaccaaagg ctattgaggg tggatagatt tacagcccgg cggtgttccg gcggggtaag   92520
atttccatac gcgggtaatt ggaggctaaa gttacggatt ttatctagaa acagcagcga   92580
gtctagatag tcccataggg gatctataaa cgttttctga aacctcgtcg atggtgacgt   92640
aggtgtagtt tcgttattat cggaagccgt ttcgttttcc acggacatgg tttcgttgta   92700
atataaggag ctcatgtcaa gagtgccgta aatagtgtac ggtgtttcgt tacgaatcag   92760
```

-continued

```
tacgtgcgtg tttttcataa attctgacac ggcggtacgg ttacggtctg gtttacaaaa    92820
gggttcattc cgataccgca gagtagtata cacccatgtc gctagatccc ttaactgcgt    92880
ggccataatg gacttcataa agctgctatc aggacgataa gcaatcgtag atgtgggaat    92940
ccgctttgcg ctggtggtaa ccctataagt cgcgttagta gtgacgttga gagcggtaga    93000
cgttgtatag gaaaaatatg gcgtagtagt actctgagat tttttagtct ttttttctaa    93060
ttgttctttg actggcgctt gtttacgttt tagttttcgc atagtgtttt tcaacttggt    93120
gccgttaata tacttgggga cgcggaatag attccggctc atggcgttaa ccaggtagaa    93180
actgtgtgtg cagttgcgtt gtgcgtaacg tagaagtagg gcggttaaac ccaaaaaata    93240
aatcgtttga ctatctacgt taactttagt cggacccacg tacaatttgg tattccaacg    93300
tggtacattg aaaaacatgg ggttgaacgt ggtaaaatta ccgcagcctt gttcgccagt    93360
atcattacgt ttggaaacgt ttaacatttc ggaaagacaa gtcattgaag gcactgtacc    93420
acaagatggg ggtctgaatg ttatcgtttt agccgtatga ttgtactgtg agtagacgta    93480
tttggcgggt tttctaagct gggtactata aaaatcgaac cacagatagg ttatactatc    93540
gtttcgaatg ggacccgcta gaatgtagta ttgtggaaac tgggtcatat tcatagtaag    93600
atttttaacg tgttgcctag tcatattgaa gtattttgta taaggttccc tttctaattg    93660
ttttaaaatc tctaacttga atttatctag ttttgcttg cctatcgtag aaagtactgt    93720
acctaaccag taacgtcccg gtggtctaac gaccttacag tttattatag aaaataacag    93780
gacagtcagt gatataataa agaataattt agaaatgctt ctcatgtctt cttttctccc    93840
catgacagag gaggaaaccc cgcaccgtcc gtctgccttg tggtttggct tgcctgcgtg    93900
tactcactgc tgattctggt cgttttgctg ctcatctacc gttgttgcat cggcttccaa    93960
gacgacctag tctcccgcac cttggctgtg taccgagctt gtatccaggg cccgatatgt    94020
aaccagaccc acaacagtac ctcgtaaata aagacgcaca gacctcacgc acatagtacc    94080
atcacaccgt gtggcgtgta ctttattaca acgagcaaga gtgcccctaa gtgttggggc    94140
ccgtaccgtt ttagaaggtt ttgtgtgaat gtctttaact tctctgtcct ttttctcgta    94200
aactgtcagg tcctagagtc agcatgtctt gagcatgcgg tagagcagat agatgccgat    94260
gatggccgac aacgcgtaga cggacatcat gaggagacgg ctgtcggtgg cgtccacgac    94320
gacgtcagtt acttccagga ccgtaccgtt tttcaacagc atgaggtagt gagttcgtgg    94380
agatgagacc accacttcgt tgtagggatc cagggcaaaa aggacgtcgt ccgagtcgtg    94440
catgtacatg atattaatga cgccttgcgt gtcgtcgtat tctagtaagg cgctttggca    94500
gaaggcgcag ttttctagcg aaatgttgag cgccgctgtg atgctgtgtg tggtgtgcat    94560
gttgcgcgtc agttcgcatt tactttgact gtccgtctgg gtgatgatga ggctctggcc    94620
tacgacggtg gtggagacag ggtaggagat acctttgatc aggtattggt ttgttacgac    94680
gtagctgacg tgttcggaga cggtgagcgc ggagaaggat tcgcctagtg gcagacaaaa    94740
caggtcgggg aaggtttcca gcgtgcttgg ttgcatggta gataggatgg agagggcggc    94800
gggaacggta gcggggacgg tggcatcggg gaagagacgc gtaaggcgtt cgagcgagtg    94860
atcgcgtcgc ccgctactgg aacagggtgt gtacaggtcg ctgaggtatt cgtggtgcgg    94920
atgagctagc aactgcgtaa agtgtgatag ctcggccaat gaacagaggc ccgtttctac    94980
gatgaagatt tcgcgtctct ccgtcgtatg caccagcatg gagtggacga ggctgcccat    95040
gaggtagagt tcttggcgcg cgaaggctga aagaaaagag gccaggtgcg ttttgtgtaa    95100
```

| | |
|---|---|
| ttgtagggca aagtcggcga tctgtcgtag tgcccactgg ggaatgagat gttgctgatt | 95160 |
| ctgtttagaa agtatgtaga ccaggcgtac gaggctggtg atgtcggtga tctggtccgg | 95220 |
| cgtccagagg gctcgtttgg ccaggtccac ggccgtggga tatagcagca atgtggtgcg | 95280 |
| tggtggtgtt tgtgagaggc aggtgatcat aaattcttgt atttgtaaga gtgcggcctg | 95340 |
| gcggtctagg gcccgtggga tggagatttc ggtgccggcc tcttcttgtc gggctgccgc | 95400 |
| gaacagtgct aatgcgtagg caaaggccat ttctaccgtg cggcggtcca gcatttgaca | 95460 |
| tcgaccgctt ttgagtacgt ctacagcgta acggtgaaag ctgttacgta gcagtgcgct | 95520 |
| gaggtccagg tagttgaagt cgagtgcggc gtcgagaaag tccgagtctt tgagatagga | 95580 |
| gtgacggttc agttgagttt tcttaactag taccaggagc tcgtgttttt cagtttgtcg | 95640 |
| tagtataaag ttgtcgcgtt gatagggcgc tttgaagagt acgcgtggaa gatgaccgaa | 95700 |
| gataagcagc atgggtgtgt cgtcgtctat ggataccgta actacgaaga agtcctcggt | 95760 |
| cagtgtgatt ttaacgtaac gtagttcgtc catgaggtaa aagccctggt gcagacaggg | 95820 |
| cgtaacggtg ctgaaaagca gatcgtgtcc atcaaagagg atacaggtct ggttaaagtg | 95880 |
| tggccgatgt agtcccgagg tggtgtgcga tcccttccag tcgtgtggag tggtttgggg | 95940 |
| tggcatccag acgtgaggta ttgacagatc aatgggcggt ggcacggtgg tgggctgctg | 96000 |
| acccaggctg tcttgtgcct tcagctgctg cgaaaaagat cggtagctag ccaggtcttt | 96060 |
| ggataccaat gcgtaggtgt taagtctctg ttggtatctt tctagggttt cggtcagatc | 96120 |
| tacctggttc agaaactgct ccgccagagg acccgcaaaa agacatcgag gcatatggaa | 96180 |
| tacatagtat tgattatagc tttggaaaaa gttgaaactg atggcgtttt ccctgacgac | 96240 |
| cgtgctgtta cggaggctgc tgttgtaggt gcactgggtg gtgttttcac gcaggaaacg | 96300 |
| gatgggtctc ccataggtgt tgagtagtag gtgaaacgcg tgagggtcca gcgcttcgga | 96360 |
| tgcggcgtct gcgccatatc gttgcgaagg taggtgacta aggaggtaga cggcgaagac | 96420 |
| ggtgaggtag aaggggaggc cgggccgcat agcgcggccg cgccgctggg ttcagcggcg | 96480 |
| tgatccaggt ggtggttggc gttacacccg agagaaggag aaaaaggatc ccaggaagga | 96540 |
| gcacccgggt gcggcgctac gggttacaaa agtcgcgtct tcgtctattt aatacgatgt | 96600 |
| cattggccgc tgcgaaggga gaagagggga cacgcgaata agccatgccg tccgggcgtg | 96660 |
| gggacgacgc tgatttgacg gggaacgctc tgccggagatt gcctcacgtg cgtaagcgga | 96720 |
| tcggtaagcg caagcacctg gatatctacc gtcgcctgct gcgggtcttt ccctcgtttg | 96780 |
| tggcgcttaa ccgcctgttg ggaggtcttt tcccacccga gttgcaaaag taccgtcgcc | 96840 |
| gtctttttat cgaagtacga ttaagtcggc ggattcccga ctgcgtgttg gtgttttttac | 96900 |
| cgccggactc tgggtcgcgc ggcatcgtgt attgctacgt gattgagttc aaaaccacgt | 96960 |
| actcagacgc cgacgatcag tccgtgcggt ggcacgccac ccacagtctg cagtacgccg | 97020 |
| agggcctgcg ccagctcaag ggcgcactgg tggactttga ttttctgcgt ctgccacgcg | 97080 |
| gtggcggtca ggtttggagc gtggtgccca gtctggtttt ttttcagcaa aaggccgatc | 97140 |
| gcccatcctt ttatcgggct ttccgctcag gccgttttaa cctgtgtacc gattctgtcc | 97200 |
| tggactatct agggaggcgt caggatgagt ctgttgcaca cctttggcg gctacccgtc | 97260 |
| gccgtcttct tcgagccgca cgaggaaaac gtgctgcgct gccccgagcg cgtgcttcgg | 97320 |
| cggttgctgg aggacgcggc ggtggcaatg cgcggcgggg gctggcgcga ggacgtgctc | 97380 |
| atggaccggg tgcgcaaacg gtatctgcgt caggagctga gggatctggg tcacagggta | 97440 |
| cagacttact gcgaggatct cgaagggcgc gtgtccgagg cggaggcgct gttgaaccag | 97500 |

```
cagtgcgagc tcgacgaagg accgtcgccg cggacgctgc tacaaccacc gtgtcgtccg    97560
cgttcgtcgt ccccagggac cggcgtggca ggagcttccg ccgtcccaca cggtctttat    97620
agtcggcacg atgccatcac gggacccgtc gccgccgcgt cagcggccgc cggtgcttct    97680
tctacctggc tggcgcagtg cgccgagcag ccgttgcccg ggaacgtacc taactacttt    97740
ggaatcacgc agaacgatcc ctttatccgc tttcacaccg attttcgcgg cgaggtggtc    97800
aacaccatgt tcgagaacgc ctccacttgg actttctcct tggtatctg gtactatcgg     97860
ctcaagcggg ggttgtacac gcaaccacgg tggaaacgag tgtaccatct ggcgcagatg    97920
gacaactttt ccatttcgca ggagctgctg ctcggcgtgg tcaacgcttt ggaaaacgtg    97980
acggtgtatc cgacgtacga ctgtgtactc tccgatttgg aagccgccgc ctgtctgcta    98040
gtcgcctacg gacacgcgct ttgggagggc cgcgatccgc cggactccgt gacggcggtg    98100
ttgagtgagc tgcctcagct gttaccgcgt ctggccgacg acgtgagtcg tgagattgcc    98160
gcttgggaag cccccgtcgc cgcgggtaac aactattacg cgtatcgcga ctcgcccgat    98220
ctacgctact acatgcccct aagcggtggt cgccactatc acccgggcac ttttgatcgt    98280
cacgtgctgg tgcggctttt ccacaaacgc ggcgttcttc agcatttgcc gggctacggg    98340
acgataacgg aggagctggt gcaagagcgt ctgtcgggcc aggtgcgcga cgacgtgctt    98400
tctctctgga gtcgacgtct gctggtcggc aagctgggtc gcgacgtgcc cgtctttgtg    98460
cacgaacagc aatatctgcg ttcgggcctg acctgcctgg ctggcctgct gttgttgtgg    98520
aaggtgacca acgcggatag cgtcttcgct ccgcgcacgg gcaaatttac gttggccgac    98580
ctgctgggtt cggatgccgt agccggcggc gggttgcccg gggggcgcgc gggcggcgaa    98640
gaggagggct acggggacg gcacgggcgg gtacgtaact ttgagtttct ggtacagtac     98700
tacatcgggc cgtggtacgc gcgcgacccc gcggtcacgc tgtcgcagct cttcccggc    98760
ctggctctgt tggccgtgac cgagagcgtg cgcagcggct gggatccctc acgtcgcgag    98820
gacagcgccg gaggtggcga cggcggcggc gccgtgctca tgcagctcag caagagcaac    98880
cccgtggccg actacatgtt cgcgcagagc tccaaacagt acggcgattt acgtcgctta    98940
gaggtacacg atgccctgct ctttcactac gaacacgggc tagggcggct gttgtcagtg    99000
accctgccgc gtcaccgtgt gtccactctg ggctcgtccc tctttaacgt caacgatatt    99060
tacgaactgt tgtactttt agtgttgggg tttcttccga gcgtggcggt gttgtaattt     99120
ccaccacgtg tcgctcgctg cataaagggc gaacgtcctc ggagagggta tattcgttcg    99180
gcgagagcgg gcggcggtgg tgggtatgtc cccttctgtg gaggagacta cctcagtcac    99240
cgagtccatc atgttcgcta ttgtgagttt caaacacatg ggcccgttcg aaggctactc    99300
tatgtcggcc gatcgcgccg cctcggatct actcatcggc atgttcggct ccgttagcct    99360
ggtcaacctg ctgactatca tcggttgcct ctgggtgttg cgtgttacgc ggccgcccgt    99420
gtccgtgatg atttttactt ggaatctggt acttagtcag tttttttcca tcctggccac    99480
catgttgtcc aagggtatca tgctgcgtgg cgctctaaat ctcagcctct gtcgcttagt    99540
gctctttgtc gacgacgtgg gcctatattc gacggcgttg ttttttcctct ttctgatact   99600
ggatcgtctg tcgccatat cttacggccg tgatctctgg catcatgaga cgcgcgaaaa     99660
cgccggcgtg gcgctctacg cggtcgcctt tgcctgggtt cttttccatcg tagccgctgt   99720
gcccaccgcc gctacgggtt cactggacta ccgttggcta ggctgtcaga tccctataca    99780
gtatgccgcg gtggacctca ccatcaagat gtggtttttg ctgggggcgc ccatgatcgc    99840
```

```
cgtactggct aacgtggtag agttggccta cagcgatcgg cgcgaccacg tctggtccta   99900
cgtgggtcgt gtctgcacct tctacgtgac gtgtctcatg ctgtttgtgc cctactactg   99960
cttcagagtc ctacgcggtg tactgcagcc cgctagcgcg gccggcaccg gtttcggcat  100020
tatggattac gtggaattgg ctacgcgtac ccttctcacc atgcgtcttg cattctgcc   100080 gctctttatc attgcgttct ctcccgcga gcccaccaag gatctggatg actcctttga  100140
ttatctggtc gagagatgtc agcaaagctg ccacggtcat ttcgtacgtc ggttggtgca  100200
ggcgttgaag cgggctatgt atagcgtgga gctggccgtg tgttactttt ctacgtccgt  100260
ccgagacgtc gccgaggcgg tgaaaaagtc ctccagccgt tgttacgccg acgcgacgtc  100320
ggcggccgtt gtggtaacga caaccacgtc ggagaaagcc acgttggtgg agcacgcgga  100380
aggcatggct tccgaaatgt gtcctgggac tacgatcaat gtttcggccg aaagttcctc  100440
cgtcctctgc accgacggcg aaaacaccgt cgcgtccgac gcaacggtga cggcattatg  100500
agcggcggcg ctgtacggca gcggggagaa aagtggcaga taaatcacgt caggttcaca  100560
cgtcgttagc cagcgtcggc atatgaaggg cgcgggcggc cagtacggcc tctgggctga  100620
gacaggacga ggcagggtga gaaagaggag gatgggggg accggggtgg tggtgctgct  100680
gctgttgtgg gtgcggacgg tgcgggtgcc gggacagcgt gccggcgaac gttctgtaat  100740
cttccataat aaaagtaaaa atgcccgtct cgtgtcgact ccgctggatc tcgaaggcgt  100800
cgggggtaat gcgcatcttg ccggtgccga tgagataaaa gtaccacatt ttttgacaga  100860
tgatgcgaat caagggttcg tacgcttcgg cacccagtg gcgcgtgaag aaggccgcca  100920
gacgaaacaa gcgtgtccg tagagcgtgc ctagggagaa gaggatgttg ccgttgcgcg  100980
ccaggtcttc ggggaaaacg accggcaggc cggtgtggcg ctgcacaaag cgcgtcagca  101040
gtccgccgct caagcgcggg tgacacaggc gctggctgag acgggcggcg cgcgtttcat  101100
cgaacacggc cgcctcaaag tccagccccg ggaaggcctg gcgcagttcg cggtacagat  101160
gaggccagta gggttgcggc gtcttgcgac taagcacggc gtggtccgag acacccaggt  101220
tgttcatggt ttcgcgcagt agcagcgttt cgagaccgcg gtgaaagagg aggacgcaga  101280
tgaggcgtac gatttttgagt tcttccaaac gcagcgagct cagcggctgt ccgcgcgaca  101340
tcttctcgct aatctgtaat attagatgat tggcgcaagt aaaggagaat tgcccgtgc   101400 ggacccgcgg gacggcgggg ttctcttcgt cgcgggccat catcgttcgc tcggtgagcg  101460
ggtagcgacg gtgaggacaa tgacgatgga cgagcagcag ccgcaggctg tagcgccggt  101520
ctacgtgggc ggctttctcg cccgctacga ccagtctccg gacgaggccg aattgctgtt  101580
gccgcgggac gtagtggagc actggttgca cgcgcagggc cagggacagc cttcgttgtc  101640
ggtcgcgctc ccgctcaaca tcaaccacga cgacacggcc gttgtaggac acgttgcggc  101700
gatgcagagc gtccgcgacg gtcttttttg cctgggctgc gtcacttcgc ccaggtttct  101760
ggagattgta cgccgcgctt cggaaaagtc cgagctggtt tcgcgcgggc ccgtcagtcc  101820
gctgcagcca gacaaggtgg tggagtttct cagcggcagc tacgccggcc tctcgctctc  101880
cagccggcgc tgcgacgacg tggaggccgc gacgtcgctt tcgggctcgg aaaccacgcc  101940
gttcaaacac gtggctttgt gcagcgtggg tcggcgtcgc ggtacgttgg ccgtgtacgg  102000
gcgcgatccc gagtgggtca cacaacggtt tccagacctc acgcggccg accgtgacgg  102060 gctacgtgca cagtggcagc gctgcggcag cactgctgtc gacgcgtcgg gcgatcccct  102120
tcgctcagac agctacggcc tgttgggcaa cagcgtggac gcgctctaca tccgtgagcg  102180
actgcccaag ctgcgctacg acaagcaact agtcggcgtg acggagcgcg agtcgtacgt  102240
```

```
caaggcgagc gtttcgcctg aggcggcgtg cgatattaaa gcggcgtccg ccgagcgttc   102300
gggcgacagc cgcagtcagg ccgccacgcc ggcggctggg gcgcgcgttc cctcttcgtc   102360
cccgtcgcct ccagtcgaac cgccatctcc tgtccagccg cctgcgcttc agcgtcgcc   102420 gtccgttctt cccgcggaat caccgccgtc gctttctccc tcggagccgg cagaggcggc   102480
gtccatgtcg caccctctga gtgctgcggt tcccgccgct acggctcctc caggtgctac   102540
cgtggcaggt gcgtcgccgg ctgtgccgtc tctagcgtgg cctcacgacg agtttatt    102600 acccaaagac gcttttttct cgctacttgg ggccagtcgc tcggcagcgc ccgtcatgta   102660
tcccggtgcc gtagcggctc ctccttctgc ttcgccagca ccgttgcctt tgccgtctta   102720
tcccgcgccc tacggcgccc ccgtcgtggg ttacgaccag ttggcgacac gtcactttgc   102780
ggaatacgtg gatccccatt atccggggtg gggtcggcgt tacgagcccg cgccgccttt   102840
gcattcggct tgtcccgtgc cgccgccacc atcaccagcc tattaccgtc ggcgcgattc   102900
tccgggcggt atggatgaac caccgtccgg atggagcgt tacgacgtg gtcaccgtgg   102960 tcagtcgcag aagcagcacc gtcacggggg cagcggtgga cacaacaaac gccgtaagga   103020
agctgcggcg gcgtcgtcgt cgtcctcgga cgaagacttg agtttccccg gcgaggccga   103080
gcacggccgg gcgcgaaagc gtctaaaaag tcacgtcaat agcgacggtg gaagtggcgg   103140
gcacgcgggt tccaatcagc agcagcaaca acgttacgat gaactgcggg atgccattca   103200
cgagctgaaa cgcgatctgt ttgccgcgcg gcagagttct acgttacttt cggcggctct   103260
ccccgctgcg gcctcttcct ccccaactac tactaccgtg tgtactccca ccggcgagct   103320
gacgagtggc ggaggagaaa cacccacggc acttctatcc ggaggtgcca aggtagctga   103380
gcgcgctcag gccggcgtgg tgaacgccag ttgccgcctc gctaccgcgt cgggttctga   103440
ggcggcaacg gccgggccct cgacggcagg ttcttcttcc tgcccggcta gtgtcgtgtt   103500
agccgccgct gctgcccaag ccgccgcagc ttcccagagc ccgcccaaag acatggtaga   103560
tctgaatcgg cggatttttg tggctgcgct caataagctc gagtaagaga gacgctatat   103620
ttagggcttc cctctctttt tttttctac accgtgatac cctaataaag tacaccgcgg   103680
ttattatcaa cgtctctgtg tttttattat ttagaaataa atacagggaa tggggaaaac   103740 acgcgggga aaacaaaga agtctctctc tagatgcggg gtcgactgcg tggggtgctg   103800
gaagtggaag cggtgctgat gggtgagggt cgtggcgcgg gcacggaccg caacgtgctg   103860
ctgatgtctg ccgcggtacg cacgtcgccg tccatgtcgc tgcgcagata agaggtaggt   103920
cgtaatgcgg cgtgttgcac gctcaccgtt aatggtacca agtcgtcaag gctcgcaaag   103980
acgtgccacg aggggatgac gagcgtgaga gccccgttgt taccgcttcg acgtctttgt   104040
ccggtcagga tcagtgcccg ggacagtccg gcttgggtgt ccgagtcctc gtcgccgctg   104100
gcctcctcga agccggcaaa catggcttcg gacagggggg tcggcgtcgg tgtggatgag   104160
aggtcatctt cgtcgtcctc ttcctcttct tcctcctctt cctcggtggg tggtaatccg   104220
ggggactgcg ggagaaactc ggagacggcg ccgcgcatga cgttgctccg tggaaagaga   104280
ccggcgcgca gctgcacctg gggacgcttg attttgtccg gtttaccggg tgtgagagtc   104340
caaaacccac ggcggaaaaa gtggatgcgg cctagcggct gtcggtgttc caaatgaacg   104400
gcctgatcgc cggtcagcgt gacgcgagg gtgattcgca cacgatcggg tagcgggccg   104460
gcttctatgg agacgcccgg gatgtttccc gggaaaaaga tggtgtcgtg agtctgattg   104520
gtctcgaaag cattctggat ctgcacgatg tactcgggat gtatgcgcgt cagcgtaaaa   104580
```

```
cttttgggaa tcaacagctg gaagccgttg tccggcaagc gtcgtaggtg cgggtacgga  104640
ttgtgtcgcg ccaccacctc ggcgcgatgc gtgtaaaccg aaaagtgcag aaacacgctg  104700
gtcggcgggt gcggtgagtc gtgatgcaga acagcatga tccattggcc tcgctcgtcc  104760
gtctccgttt tgtggatgta cgtattaggg tccgaacagg ccagctgctc cagggcgtct  104820
accaacgtca gcgggatagc gccggcgcga aaggcgaact ggctgacaaa gatctggccg  104880
gcctccaagc tgctgtcggt tctgcggcgc cagttcggcg ttacagtcag tcgcacggcc  104940
cagtagtgag ccgtgcggcg gatgatggcg cgcgcctcca ctcgcggccg attttcttcg  105000
ccgccgcgcc gctggctctg aaagaggtgc agtccgctga cgggtacgcg atccagcggc  105060
agcgcaaagg ccagcaccga gaccgtgttg ttttctgagc ctggcgtcag gcgtcgtggg  105120
ccaaagttgt tgaggtccac cagtagtcgg tcctgttcgc ccaccacgca gcggcccttg  105180
atgtttagat cggtcaggtc tacggtgtcg tgcggagatt tgttctcctg aaaacagcag  105240
agaaccgagg gccggctcac ctctatgttg gtacgcaggt ccaggagtcg tagacgaccg  105300
gcttccagcg agccgccttc cacgttggtg atgagccgaa gcacctggca gtgcaggcga  105360
ccaaagctgc cgctggcggc ttcggcctcg ctgatcgcgg ccgcttccga cgagggtccc  105420
tcaccgggcg aggacgatgc ctgagacatc gcgaaggcgg gatgggggga gggtcagggg  105480
atgcgcaaag gtgaacgggt cttcgtggga ggtcgggaag ggttccggca actgtcgcaa  105540
atatagcagc ggcgacaggt gtggcgccca aaagtcgcga gtctgagtgg acgtgggttt  105600
ttatagagtc gtcttaagcg cgtgcgcggc gggtggctca acctcgatgc tttttgggcg  105660
tcgaggcgat gcatggcccg ggcagggctt cttgccggtg gcggcgacgt ttgggttgcg  105720
cagcgggctg ccatacgcct tccaattcgg cgaagatgcg gtagatgtcg ttggcgtccc  105780
agaagaactc ctggtacttc agattctgac cctgaaccgt agccaccatg ggcaccaggt  105840
tgcgggccag gatgccggcc tgccagggcg gccaggtgaa cacggccgga ttgtggattt  105900
cgttgtcgga atcctcgtcg gtgtcctctt cgggcgcgac ggtggactcg gccttaaggc  105960
ggccgcgtgt cataacgccc gacgtgcacg ccgttgccga ggatgctgat ttgcgtttgc  106020
ggcccgcgga agtggaggcg cccgccatgg cgccgccgcc ggtgacgcgg ggcgtcttgc  106080
gctcggtggt tacgagttct tcgtcggagt ccgatccgct ggtccagacg tcgtcgtcgc  106140 cctgggcgg ccctcgtcg tgccggtccc aggtgtgtcg gtactcaagc ttgccctgga  106200
tgcgatactg gctggtgaag gtgggggtgct cgctgtactg aggcccgcgc tgcagcagca  106260
agtcgatatc gaaaaagaag agcgcagcca cgggatcgta ctgacgcagt ccacggtct  106320 cgcgtatcgc ttgtacctcc aggaagatct gctgcccgtt catcaacagg ttacctgaga  106380
tgctcaggcc cggatgctc ttgggacaca gcagcccaaa atgctcgtgt gaggtaaaag  106440
ccacatccag catgatgtgc gagatcttgc ccggtttgat tatcatattt ttgggacaca  106500
acaccgtaaa gccgttgcgt tcgtgggggc gcatgaaggg ttgcgggttg cgggtcatcg  106560
tcaggtcctc ttccacgtca gagcccagcg tgacgtgcat aaagagcttg ccggagggca  106620
cgtcctcgca gaaggactcc aggtacacct tgacgtactg gtcacctatc acctgcatct  106680
tggttgcgcg cgtgttctcc atggagcaaa ccagctcgtg cgcgcacacc acgtgccgca  106740
gtgccacgtc cttggtggga aacacgaacg ctgacgtgta gtagacgtcg ggctctttcc  106800
actggttctg ctgacgcgtc caggccagtc ccgagaccgt gagacgcgcc tgccacatct  106860
gcttgcccga cgcgtgaatc acagcgtcgg ctacgggcag gtgtcggtgt ttgcgctcgg  106920
ccgccgacgg gtagtggtgc acgttgatgc tggggatgtt cagcatcttg agcggcagcg  106980
```

```
cgtacacata gatcgacatg ggctcctggc tggggcagat gcttcggccc gtggggttgt   107040
gcacgttgac cgacacgttc tccacctcgc tgcccgtaaa gtacgtgtgc tgcacctgca   107100
gctgattgtc gccgcggtgg catggcgtcg agtcgggcgt gtactgcgac accaggatca   107160
gcgagggctg gctcacgcgt acgtggatac ccgtctgcag gagtcgcgtc tcgtgcggca   107220
gcaccggcgt atcgccgcga ctaaacacgg cttttcagcac gtgccccgaa atgggaccca   107280
gtacggatat catttcggga caacggcgac cgcgcgactc catgctgcct gcgcgtacgg   107340
gtgtaggcga ctgagcggcg cgccctctgc ggccgccgcc ttacataggc aggcgaccaa   107400
acgcggaacc cgaaataaaa acgttataca cagagacaac cgcggattat tgagtgtctt   107460 ttttattac aaaaaaaag aggcaaagcc ccaccgtcac cacaccccat cacacaccac      107520
caccgatttt ttttgtttta atcccgtatt gcgcggacgc ctagtgtccg ttttccatca   107580
ccagggtcct ctgtttagag atcgccgcag accatggcta gagtgacagg actcgttttc   107640
tctgtcgtat tttccgtaag cttacagtct tgcggttccg tctccgggga cgccagtcgc   107700
atgggcagca ggtcctccag cgcgatggaa gcgcccagca ccgagagctg ctgttgcgac   107760
ggcgaatggg acgtggaccg cgagtgtagc gtggatttga cttggtgcgt cattgctgac   107820
aggcaaccgc gattcagcgt atgctttgac gagataaaat agaggcgtcc caggagcgcg   107880
tcccgtggga acgtggcgcc gttctcgtcg cttaccagta cggttaattc caaccaggag   107940
cgcggtagcc agaccgtaac gggcattttg agtccctgac ggttgtgtgg tacaaaaaca   108000
cccagataag gcccgtaaaa gcggcggtag atacgtaacg tgtgcgagtt tttcagcgtc   108060
aattcgtaag ggacgcgcac ctccagtccc tcgtccgccg cgccggagcg tggcggtaca   108120
aagtaaggca gtggcgcgtc cgaaaagaag ggtcgtcgca ccgtttcgcg tcgcagccgc   108180
aggcgaaacg ccactgggtc ggctggcgcc tcggtgcggt cgcaggtcac gttgaaacgt   108240
aacatgccgt cttggtatag cgtgagtgac gacagcgtca ggtccggcgg tgattcgttc   108300
gggtctagct ccaatcgtcc aaagacggag ggtcccaatg tcttggctgt ggtttccgag   108360
aggcgcgccg agatacggct ggtgagtcca cgcggccccg agatgccgcc ttccactcga   108420
tgccagcaca gcgcgtgtcg tacgcgcacc gtcagcgtgg gcgtcagatc cgtgtccgtt   108480
gattccgcgg aaatcgcgtt ctccgttacg ttgtttatat ccagcgtcgg ctcgaacgtg   108540
agttctggca gatgcagcgc cagacagtcg tgtaacgccg tgtgatgcgc ggctttacgt   108600
cgtagcggta gccgtttcag cagcggcgtg atgatacgga gcgcgaagag attgagtgat   108660
aagcgcacga tggccatgcg cgtcagttgt tggtcaatta ccgagcgcag gatatggcag   108720
cctgggcgtg cgggaaagag agagaaggcc gggcgcacgt cagaatcctc gttagagacc   108780
acgcatagaa tgccgcgttc acgatcgtcg ttgcggtcat cctcgtcctc ttcttctttc   108840
ttctcttctt tttcctttt tttctcgggc tcgtgggaag ccgccgtttc ttcttcttgc    108900
gacgtcgcgg gggcggtttg agactcgccg ttcgcttccc ccaattgcag cggcgtagag   108960
agcagaatct ggaagggatc ccgcaattct tcgggtcgga ggtcgaggtg caactggatc   109020
agatggtagg tgccgcggtg cacccgaggc tgacggatgt cgtgtttatc cgtcagtgtg   109080
aggatggtct gcggtgagcc gctgtgcttg tccagctcgt ccggcgtttt caggagaaga   109140
ctgtcgtcgt cggtactggc gacgcccatc atggtcgtgg tggtagtggt ggagaggaaa   109200
gtgagcggcg cgctcgacag agctcggcgt tggcggcggc atttgccgct gtgtcggctg   109260
ctattgctgc caacgccacc gccgccgcct cgtctggctc gtggccggcg ggcccgattc   109320
```

-continued

```
cgaaggttgg ggtcgacgcg tggcatgctt ggtgtctgcg ggcgcgagag ggccggctca    109380
gcctttaaat atgcaggtcg cggatttgtt atcgggtgaa acgtcacaca ccgtgaagac    109440
gacctgttcg cggatgaggt catccagctg tcgcagcatg acgaaaagcg ccgacagccg    109500
cgcgatctcg tcgtcgggcg acacgtgctg tggccgcgcg ggcgtgcgcg gctcgccgac    109560
gctgcgctcg cggtccagcc gcatcagcag ctcctggcac ttgacgagca gcatggagct    109620
gtcctctagc gccaacttgc gcacgtaggt catggtcagc tccgaggcta ggttagccac    109680
catggacatg gagaggcagg cggtcttcat gtcgatcagc aggtgctggt cgatgaccgg    109740
atcggggatg gtgaaggtgg cgtcgcgaaa agtaatggtc tgcagctgct gcacggcagc    109800
ctttacctcc tcgtacgaac ggtcgagcga gaagaggccc atgatgagta gtcgctggtt    109860
gatttccagc gccagtggca tgggtacgat ccagggcagc accagctccc actggcccag    109920
cgtcagcagg ttctcgcgcg ccagcggtcc gtggaagagc ggcggcagca cgcatagcgc    109980
gtcgcccttc tcccaagtca cgggtcccgt gttgaggacg tgtagagca gtccgtgcgt    110040
cggtacgtgt aggaggatct ggttgccttc tacgcgccgc atcaacgtca gcgtcatatt    110100
gcgcagcagg ccgcgcagtc gtacgtagcc gcgggtgtga tctacgaact ggtgtaggcc    110160
cagctggtag tgcttgatga gatgtagacg ctgcggaatg ggcacaacgg ccgctactag    110220
tttggtcagt ttgcctacgt cggcgatgct gagcttgtgg tcgaaagtgc agaagatgtt    110280
ggcctccatg gccgccatag cggcggtgaa atcctggccg cgacggagga gaagcggaga    110340
cgaacaacgt ctgcaccggg cgcggcgtca gagcgagcgt ggcgcgtccg ggcccgcgtt    110400
tgcgtctagg tgacccgccg ctaacctgcg gtcgtcgccg tcctcctcac cggacggcct    110460
cacgagttaa ataacatgga ttgctgcagc gggatgattt cgcctacgac gtagttacca    110520
aagtgcgttt cggacgtagc aaaagccccg gcgccaccct tgagtttggt ctccatcagc    110580
gccagcgtgg tggtgctgag gatcggtagc gcttcctgcg tcagacggca cgggttttcg    110640
atgagttgtt ccgtgccttc gacgcagacg tactgcgtgt ccgtgtcgcc gcggatgcag    110700
tccttggcgc gtagcaggta ctcgtcgatg gttttgaaga gcgttttgtt ggccgcgata    110760
atctcttctg tgttaaagta ctgcgcgcag gggctgtaga atttggagtt gtagcctaga    110820
cgttcgcgat gtcgggtgtt gtagagtacg tcgctcagac agccggcttg cgaggcccag    110880
gggtgtgtg tggccgcgaa agtctgtgcg tccgcttcgc gatggtcgta gatgccttg    110940
gtggcggcct ccgtgtcgta cggatcgacg gccagcatgc aggaggcacg cccgcgcggg    111000
ttgttgggga tcttaaagta attaacgtcc atcgtcaccg gcgtaaggat tagttcgcac    111060
gcggcctttt gtccgtgcac cgtggcggcg gcattgcgct cggacatgct gccgaacgtc    111120
agcatggaga tggtctccgt atctaacagt tgcggtcgtt ctacgccggc cgcgtgccgg    111180
atccagcggt ccacctcgtc gtgccggtac acgttcatag ggaagacgcg aaagaggtcc    111240
tgcacgcgga cgcccatgtc ggttcgcacg cggtttacgt aggctacaca ggtatttgac    111300
gtgtaaccca gacccatgtc tacggtgtta atgttctgcg tgacgtggta cgtggtgctg    111360
atgtcgcgtt cctccttggt cacgataggg ttgttgatga taactgacgt gcacgacttg    111420
ccgctgtaga gcagcatgtc cacctcgaag gtgtcggtgc gtacgccgt gagtgcgaat    111480
cccgggtgga tgtgcgcctt ggtctgcagc accagtgaaa ctggtgagat tttgtataac    111540
atggcggcca gcgtcatgac tgagtgcaac acgttgggac aggtggccga gtaacgcgaa    111600
aagggcgagc gcagccagtt gtggtactcg tgtgcgaagg ctgtgggtag cgggaaacca    111660
ccgtcgtgac ggtgatagtg cgggaactcg gtcacgtagc gtttaatgtc gtcgctcaac    111720
```

```
gctgcgcaga tggtggggtt tgagtagaaa cggtggaaag gtacgggtag gctgtactcg   111780
atcaacgtct taggcgccgt cacgacgcag cagccgttgt aaagcacgtg ctgacgtgag   111840
ataaagtccg gcaggccctg acgctgcgcg tggtccagag gcgcgcgtac ttcgagcacc   111900
ttgacgtgct cgcccacgaa ttgcacggcc aaaaacagtt cacgacaggc ctgcagcagc   111960
ggcgtatgcg cgtcggtggc gacgtcctcc accagctcgg tcagcatctc gcctacggct   112020
tgacgttgcg ccgctatcga gtcttcgggg gtgacgccgc ttgtgctctc tttcgacgtc   112080
gtacctgacg tggagaccgc ggtggcggcc ggcatcagga gaaacgccgg tcggtaaaag   112140
aggtctacta gcagcgtctt gaggttgagt cccaggccgc aggcccggtt gttggtcatg   112200
gcgggcatga ggcagagata aagaccttt tgtaacgtcc attcgtcgtc ggtggcacgg   112260
taatcgtcca caaacagcgg ctcgtcggca tccatggcgc ccaaacgcgg tacgtccgaa   112320
acgccgtggt gtcgcgcctc gatgttggcc gggttcaacg gttgccggtc ggctactacc   112380
tgtacgcctt ccatgttacg cggcaggtgc gtaacgaagg ggggccacag ccggtggtcg   112440
tgcagcgcgt tcacgtaagc cgatagcggt tcctcagcca gttgaccgtt gttaagtccc   112500
ggcagcgctg agatgcgcgt caccagacgc agcacggcga tcagattgcg gtagtgaaag   112560
agcaactgcg gtggtagagc gccatcagcc aggtgttcgg cgatcaacgt caccagcgca   112620
tagctgtgcg caaaaaccag cagctgacgt gtgtgaaaca tgttgacgat acaacgtgct   112680
acgaaagtgc ggattagcaa aaaagcgtcg acgttgccgt gtaccagcac gtcaaccagg   112740
tagcagagct cagggtaatt ggggcttgtc acggtggttt taaaaagtcg caacgtgtct   112800
tcgtagtcgg gtggtggccg cagtcgcatg tgttccatga tctcccaggt gcgcagttcg   112860
tggaaggggc ccggtgccag tccatctggc aaattaccga tgacgatacg cggtgtacac   112920
agcgccaccg tttcgctgtt ttcctggcag tgcgtaaagt cgaagaaggg gtgcagctcg   112980
gtgtagagcg tgatgttgcc cacctttgtag aagtcggtga ccacaaagtc ctgcttcatt   113040
tcgttcaccg tgcgcgggac ctcgcgtcgt acgcggtaaa aatgcggtat gcggcgcgcc   113100
gcaccgccca tgggttcctg ctgaaaacga cactcgagca gtcgttgcat ggcgggttcc   113160
gagggcggtc cgcgttccgt gaaggtctgt agacagggcg cgggctcgtg cagcaccggg   113220
tggcacagcg tcttgagcgc gtccacaaag tctatctttt gtacggcacg gtcccggttt   113280
agcaggtagg ccgtggtggg caacgcgttg cgaacggtgt cgttaagctt aactttgctt   113340
tctaccgtgg tgtaaccgcg atcctcgggc agatacagcc ctacgggaa gaaaaacgtc   113400 aggtccacgt tacgttctag cggatctttg gtatcggtgt ttttgtagac gcgccgcaag   113460
ttttccataa tcaccgtttt ttcgcccagt cggatcacgt ccatgctcag cggcgttaag   113520
ctgtgcgccc cggcctgcga aagcgagtcg ttgggcaaat gcggttggcc cgaagtcaga   113580
tgagccttgt acgagttgaa atcggccagg atcgagtgat aggatatggc agtgacggca   113640
ttttcgggac tgagtacaaa attgccgtag gtggccggcg ccgagaccgt ttctttggtg   113700
atgtggcttg agagcagcga catgatgatc tgcataacgt tggctgtgct taccatcacg   113760
ccgctgatct tggcccccga gctcgtggtg tacgtggtgg ggttgtctag gatgctatcg   113820
gtggccgctt cggccagacg cgtgaggaac ttgagcacat agtcgcgatc gcgcgtgcga   113880
ttcagcaaaa agagcgtggc cagcatttttg gccttgaagc tctgcaagat gttgcttcgc   113940
tggatgcggt tcagcgcctg tcgcgccagc gtggcgttct ctaccagcgt ctgcaccaca   114000
aagtacggcg gcgccttgcg tagcagtgtc tgtaaaaagc tgtgaatcaa gccgcgttcc   114060
```

```
atggcgtcgg ccgtgttttt cagcgcgcgc agcaccgtgt gcatagcttc cacgttgagg   114120
atcttgtcca ggatggtgcc ttcgaacgtc tcgcgcagat acgtgaggca ggctgcgctg   114180
agctcaaagg ggatggtgat gggggatttt tcactgtatt tggtgaccat aatggtggtc   114240
tgacgactgg tgggcaaacc ggcgccgctg gccacacgcg gcacctgcac gtggaacagc   114300
atttttcccg tagtcagttt attgaggtcg tggaacttga tggcgtgcgc cgccgcggcc   114360
aagccgctgg tcaaaaaata aacccattcc aggcgattgc agaaggtgcc gaagatggct   114420
tcgaagtgaa tattgtaacg ctcggggtcg tcgccgtagt agatgcgtaa ggcctcgaac   114480
atctcctcgc cggcgctggt cttgacgtgc gtcagaaagt cagtgggaat gcctacttta   114540
ggcaggagct cgagcgccga ccagttctcc atcgcggcgg cggcgtgagc gcgaggcgtc   114600
ggagctcggg gaaagcagcg cgacccggat aatggccggc gctgcgccgc gccgcctcgg   114660
ctgtgacgct ctaatagtcg tcggcggctc cgctacgccg cgccgggttt tacacgtccc   114720
cgtgcacgtt cgcgcctgca acctcaccca agagctatca acgggcgagg acgcccgctt   114780
ctgtcgtccg cgacccgtta acgtcgaacg ggtgcgcgct gttttttgcgg ctctctaccg   114840 tgcctgtccg atacacgtga ggaccgagcc cgagcgtgtc aagctggtac tgggtcgtct   114900
gttactggga cccgtggccg taccctgttt ttgcgacggt gaagtggagg ccacggtga    114960 acatctggta cctacgacgc agttttgtcg cgggccgctg ctctacgtgc accgacgttg   115020
ttgttgcgga tccgtgaccg ccgggcgcgc gctgtcctac cacgttctcg aaaaccacgt   115080
ggccacgcat gtgctacgcg gattgctctc gctgacggaa tggaatcgag aattgccgag   115140
cctcttttgc gactgtcctg gcggcggtgg cgcctcggga accgaggaac gctacgctat   115200
ggcctgcctg ccgcgcgacc tcagcctgca cctggacgac tatccttacc tgatggtgga   115260
aatcggacgc gtactcagtg tcagcgaggt agacgactac gtaaccgccg tctccggcta   115320
cctgggcgag gccgcggcgc cgcgcatcca ggttcactac aagctgctct ttggactcaa   115380
cgtgcgtccg caagcgccgt gcgcgttgga cgctacacgc gacttttttc tactggagct   115440
gcaaaagctt tggctgggcg ttgaatatca ccacgaagtg acgtcggagt ttttcggtcg   115500
cgtgctggct cagctgcatc gcgaccgcgc ccgcgtcatg atggcgcttc gcttgcccga   115560
gcagacggtg tgccacctga gcaccttcgt tctcagtcgc ttcaagcgac aggtactgta   115620
cttcaagtta caggtgagct acggcaagtg ccggactggc cacgctgaca gaagtggggg   115680 aggggggaaac ggtggaaatc agggacacca caacctactg tgttatcgac gccttagcgt   115740 cacgttttgcc gacacggaca cggtgtggag aaaccttttc tacgtttatt atgaactagc   115800
tcgggatctg gggtcccatg ggacggggaa ccgacccgta aaccgcggtt acggtgtttc   115860
ttgcgctccg aggacgtcgc ggctatcacc gtcagaatcg acggtggttt cggcgaacgg   115920
acacgcgctg tcttccaccg cgctcccgac gacgagcgcg ggtcacaagc tgtcactgcc   115980
gcgcgacccg gccgccgatc gcgttcgacg ttacgtgtgc atcatctcgc gtctcatgta   116040
cgctcggtac ggggagagat ggcgtaaaca ccgtcaacgg cggtcggaga cgggagaaga   116100
ggaggaggaa gagacgctgg aatcgggggga gactgacgcc acgccgccat ttgactttac   116160
ggggcagcag ctgcgccggg cctatcagga acaccgacgt cgtaaacatc tagccgtgca   116220
gcgttacgcg ccgtgccgtc gtaagctcat cggcgggatg gagtttgccg aggtgacggg   116280
cgtgagtctg gaccgcatcg ccgtcaacgc tttcaacacc aaccgcgtta tcaatatgaa   116340
ggccgcgctc tcgtccatcg ccgcgtcggg tctcggcgtg cgcgcgccgc ggcttccaa    116400 gaacatgacc cacagttttg tgatgtacaa gcacaccttt aaggagcccg cttgcaccgt   116460
```

```
cagcaccttt gtttccaacg acgccgtcta cattaactcg ctcaacgtca atattcgcgg  116520
ttcctacccc gagtttctgt actcgctggg cgtgtaccgg ctgcacgtta atatcgatca  116580
cttttttctg ccggccgtgg tgtgcaacag caactcctcg ctggacgtgc atgggctgga  116640
ggaccaggcg gtgatccgct cggagcgcag caaggtgtac tggaccacca actttccgtg  116700
catgatctcg catactaaca acgtcaacgt gggctggttc aaagcggcta cggccattgt  116760
gccgcgcgtc tcgggcgctg acctggaagc cattctgctc aaagaactct cgtgtatcaa  116820
gaacatgcgc gacgtgtgca tcgattacgg tctgcaccgc gttttcacgc aactagagct  116880
gcgcaattcg taccagatcc ccttcctggc caagcagtta gtgctgtttc tgcgtgcttg  116940
cctgctcaag ctgcacggtc gagagaagcg gctgcagttg gaccgcctag tatttgaggc  117000
ggcacagcgg ggtctctttg actacagcaa gaacctcacg cgcacacca agatcaagca  117060 cacttgtgcg ctcatcggca gtcgtctagc caacaacgtg cccaagatcc tggcccggaa  117120
caaaaaagtc aaattggatc acctgggccg gaacgccaac gtgctgacgg tgtgtcggca  117180
cgtggaagcc cacaagatcc ctcgcacgcg cctcaaagtg ttagtcgagg tgctgggcgt  117240
gttgcagagt atcagcggta cgccgcacac gcgcgaagtg atccaccaga cgttgtttcg  117300
attgtgctcg gcggccgcag ccacatcggg cctgtgttca tcccctcccc cattgtgtgt  117360
gtcctcatct tcctccgtcc cttctgtccc aacctccgtc agcgttgacg gcagttctga  117420
acccacgtcg ccgcgagcgc ggtttgcatc acgatgatgg aagccgcggc cgctgccgcc  117480
gcggcgtttc gtccggagga gcgtccgacg ccgggttggc acgacgcggc gttgttaatg  117540
gacgacggta cggtgcgcga gcacgcgttt cgcaacggac cgctgtcgca actgattcgc  117600
cgtgtgttac cgccgccgcc cgacgccgaa gacgacgtgg tttttgcttc cgagctgtgt  117660
ttttattgca gcggtcgttt taaccgcagg tcgtccgtct tctccatcta ttggcagaag  117720
catagcgatc tggtgtacgc gcttacgggc attacccatt gcgccaagtt ggtggtggaa  117780
tgcggtcagt tggggagtag taggctacgg tggcgcgacg gtgatgcgag tggtgaggag  117840
cgccggggag acgacgacag cagggacgag ctgtacgacg tgccgggcat ttatatgatt  117900
cgcgtcaacg acggcggcag caccggcccc agacacgtta tttggccggg taccagcgtg  117960
ctttgggcgc cggacgttgt gatcactacg gtgcagcgac gaatctcggc ggcgcgcgcc  118020
ctggtgaaca cgttccgcca atattttttt ttgctgaaac ggcgctcgca cgaggagctg  118080
gttctttgtc cgcccgagat ggaggagcgt ctagcgccat tgttgcagag tgccacgcgc  118140
ggtgattcgg acatgtttga cggtgtggtg gccagcgctt atcaccgttt gcgaatgagt  118200
aatattccgc gttcatccgc ccgtctgctg gagcactgcg tggggctggc gggtgctaag  118260
aagctgctct tgctcgacgt gccgcgtctg gagaactatt ttctttgtca agtctgtctt  118320
tacgagctgg acgaggacga gatgggcgag gagatgctgg gcatgttggc cggaaagccc  118380
gaggatgccg ccgtctcggg cgcaagcggc ggttttctgc tacatcgcaa gacgatgaag  118440
ctggccgcct gtctgtgttt gttgctcaat tcgctgcatt gcaccagga ggcgctggag  118500 gccttggatc ctccgccgcc gcgcgtcgag gagaacgacc ttgtcaacgt ggtgctgcgc  118560
cgttattatc gcagtcacgg cggcgtgcag gcgcggacgc tggcggcggc ccgggctttg  118620
ttagccgact acgctgaaac gttttcgcct ttggggagtt ttacgcgcct gggttacgat  118680
cgtctcgttt ctgccgatgc cggcgtcagt cgtcggcacc tggtggctct gctgcgtgcc  118740
tagctgaccc tgaaacggat ggcgtgtata tcgtcacaca ggtaggtggc catgatgacg  118800
```

```
gcgatgataa gatcgtccga gatacgattc tggcgcttgg ccgagtagcg tgccgtcgtg   118860
ccttcggcca gcgtgacgcg gtgcaggttc tgaatctgct ccagaagata ctcgatgggg   118920
tcgtggctca gcttgatggt gtaggagacg agctcttgcg aggctttgat gtagcccgag   118980
ttgaaacgcg agatgaactg ttctacggcc agcgccttgt cgcggcccat gaggtagaag   119040
ggctgttcga tgtggttctg gtcgggcgtg tggtagaaga gcacgcggat gagcgtgctg   119100
ctctgcacgc tctgtcggat gaggcaggcg atgcgcacgg ccgccgcctg gttggtgttg   119160
ccctccacgg cgatacgcag ttcgtccagg taagggtgca ggctcagcac cgagatgatc   119220
atatgcgccg cgcactcggc gatggctacc tcagaactct cggagaggtc gcgcaaaaag   119280
aaatgctcta ggccgtaaat gagaaactgg tgtcggtagg cgcctacggc cgccacgccc   119340
gtgcccgagg ccttgcggtt ggtggtgaag gccgggtcca gatacacgta aagcgtcttg   119400
ccgaaataat cgtaggcgtt ggtgttgagc gtgctgtaac gcaaaatgtc gaactcttcg   119460
cggctctgat ccgtgatgag cacggtgttc tgcgagattt tattggtacc gccgatgatc   119520
tcgtccatga aagcgcccgg cataaacatg ttggccgtct tgcgcacctg cgagttgagg   119580
ctgatgaagg tgggcttgtg cagtcggtag caaggacacg ccgtggcgtc gcccttctcc   119640
gtgaagctgt gcaggtgctc ttcgcacacg taagagacca cattgagcat gtcaaagggc   119700
gcattgttga ggcgcgtcaa gaaacacgtg gcgtcactgg tagtgttggt ggacgatatg   119760
aagatgatct tggtggtatt ctgggccagg aaccccagaa tggtgttgaa ggcctctttc   119820
ttgatgaagt gcgcctcgtc caccagcagc aagtggaagt tttgtcctcg gatgctctgt   119880
gtagagagga gacagaaaag ggactcttat gattacgcac gctcggctgg aagcctacag   119940
agtcggggtg gggccggaca ggtgagccag gtgagccgcc aggtgaggcg ggatcgccgt   120000
gtgccaaccg ggctgcgacc tgaaaaccgg aaccaatccg ccgacaccgg cgccgcgtga   120060
cgcgcgccca taaaaacgaa agtgtcgtcg tcgcgacccg ccacagccgc catgaactcg   120120
ttgctggcga aactcaaccg actggggtc gcgcacgcca ctacggagga tgtttttatc   120180
tttgtcgacc gcctctttca acactttttcc ttccttttcc aggccgagga gtcaggcccg   120240
cgccgcttgg aactggtcgc gtccgtgttc gagcacctga cggtgagtg cgtcaacgac   120300 atcctggacg cctgcagcca cccggacgtg aacgtcgtgg agacaagcaa cacctgtcgt   120360
ccctgccctt ctcctgttcc ctccgccccc aaaactgtca gcgacgctca gacgtcatgt   120420
gcgacgcctc gggcgcctgt gacatgaggc acgtccagaa cgcgtttacc gaggagatcc   120480
agttacactc gctctacgcg tgcacgcgct gctttcgcac gcacctgtgt gatctgggca   120540
gcggctgcgc gctcgtctcc acgctcgagg gctccgtctg cgtcaagacg ggcctggtat   120600
acgaagctct ctatccggtg gcgcgtagcc acctgttgga acccatcgag gaggccgcac   120660
tggacgacgt caacatcatc agcgccgtgc tcagcggcgt gtacagctac ctcatgacgc   120720
acgccggccg ttacgccgac gtgatccaag aggtggtcga gcgcgaccgc ctcaaaaagc   120780
aggtggagga cagtatttac ttcacccttta ataaggtttt ccgttctatg cataacgtca   120840
atcgtatttc ggtgcccgtc atcagccaac ttttttattca gcttatcatc ggtatctact   120900
caaagcagac caagtacgac gcgtgtgtca tcaaggttag tcgtaagaag cgtgaggacg   120960
cgcttctgaa acagatgcgt tccgaatatg gaaacgcacc tgtattcgga tctggcgttt   121020
gaggcgcggt tcgctgacga tgagcaattg cctctacacc tggtgctcga ccaggaggtg   121080
ctgagtaacg aggaggccga gacgctgcgc tacgtctact atcgtaatgt agacagcgct   121140
ggccgatccg cgggccgcgt tccgggcgga gatgaggacg acgcaccggc ctccgacgac   121200
```

```
gccgaggacg ccgtgggcgg cgatcgcgct tttgaccgcg agcggcggac ttggcagcgg   121260
gcctgttttc gtgtactacc gcgcccactg gagttgctcg attacctacg tcaaagcggt   121320
ctcactgtga cgttagagaa agagcagcgc gtgcgcatgt tctatgccgt cttcactacg   121380
ttgggtctgc gctgccccga taatcggctc tcaggcgcgc agacgctaca cctgagactg   121440
gtctggcccg acggcagcta tcgtgactgg gagtttttag cgcgtgacct gttacgagaa   121500
gaaatggaag cgaataagcg cgaccggcag caccagttgg ctacgatcac gaatcaccgt   121560
cggcggggcg gactgcgtaa taacttagac aatgggtcgg atcgccgttt gcccgaagcg   121620
gctgtggctt ctctggagac ggccgtcagt actccatttt ttgaaattcc gaacggagca   121680
ggaacctcct ccgcgaacgg cggcggcaga ttcagtaacc tggagcagcg ggtagcgcgt   121740
ttgttgcgcg cgacgagga attcatctat cacgcgggtc cattggagcc gccttccaag   121800
atacgcggtc atgagttggt gcagctgcgc ctggacgtaa atccagacct catgtacgcc   121860
accgatccgc acgaccgcga cgaggtcgcg cgtacggacg agtggaaggg tgccggtgtc   121920
tcgcgtcttc gcgaggtctg ggatgtgcag catcgcgtgc gcctccgtgt gctgtggtac   121980
gtcaattcct tttggcgcag tcgcgagctg agctacgatg accacgaagt cgaactatac   122040
cgggcgttgg acgcttatcg ggcgcgcatc gccgtcgagt acgtgctgat tcgcgccgtg   122100
cgcgacgaga tctacgctgt actacgacgg gacagcggcg cgttgccaca gcgtttcgcc   122160
tgccacgtgc cacggaacat gtcctggcgc gttgtttggg aactttgccg tcatgccttg   122220
gcgctctgga tggatcgggc ggacgtgcgt agctgtatta ttaaggcgct aacgcctcgt   122280
ctgagccggg gtgccgccgc tgccgctcag cgagctcgtc gccagcgcga gcgctcggcg   122340
cccaaaccgc aggagctgct tttcggaccg cggaacgaga gcggtccgcc cgccgaacgg   122400
acttggtacg ctgacgtggt gcgctgcgtt cgcgcgcaag tggatttggg cgtggaagtg   122460
cgcgcggcgc gttgtcctcg caccgggctt tggatcgtcc gtgatcgccg cggacgcctg   122520
cgacgttggc tctcgcagcc cgaggtgtgc gtgctctacg tcacgccaga cttggacttt   122580
tactgggtgc tgccgggcgg cttttgccgtc tcttcgcgcg tcactcttca tggcttggcg   122640
cagcgggctt tgcgagaccg attccagaac tttgaagcag ttcttgcaag aggaatgcat   122700
gtggaagctg gtcggcaaga gccggaaaca ccgcgagtat cgggccgtcg cttgccgttc   122760
gacgatcttt agtccggagg acgacggctc gtgtatcttg tgccaattgc tgttgctcta   122820
ccgcgacggc gaatggatcc tctgtctttg ctgcaacggc cgttatcaag gccactatgg   122880
cgtgggccac gtacatcggc gtcgtcgacg catctgtcat ttacctacct tgtaccaact   122940
gagcttcgga ggtcctttgg gtccagccag cattgatttc ttgccaagct ttagccaggt   123000
gaccagcagt atgacgtgcg atggtattac gcccgacgtg atttacgagg tctgcatgtt   123060
ggtgccccag gatgaagcca agcgcatcct ggtcaagggt cacggtgcca tggacctgac   123120
ctgtcagaag gcagtgacgc taggcggcgc cggcgcctgg ttgctgccgc gtcccgaagg   123180
ctacacgctt ttcttttaca ttctgtgcta cgacctgttt acctcatgcg gcaatcggtg   123240
cgatatccct tccatgacgc ggctcatggc ggcggccacg gcctgcgggc aggcgggttg   123300
cagcttttgc acggatcacg agggacatgt agatcccact ggcaattacg tgggttgcac   123360
ccccgatatg ggccgctgtc tttgttacgt gccctgtggg cccatgacgc agtcgctcat   123420
ccacaacgat gaaccgcgca ctttttttctg tgagagcgat gacgccaaat acctatgcgc   123480
cgtaggttct aagaccgcgg cgcaggtcac actgggagac ggcctggatt atcacatcgg   123540
```

```
tgtcaaggat tctgagggcc gatggttgcc cgtcaagacc gatgtgtggg acctggtcaa   123600
ggtagaggaa cctgtgtcac gtatgatagt gtgttcctgt ccggtgctta agaacctagt   123660
gcactaacgg ggtctgacag ttcacgggga aagaaacaa gaaacaacaa aaaaaaaaga   123720
ggacatggac tcgccacggt ttgtggcaag gcgtatatta tcatcatgga gctactcacg   123780
ttggtgttgt agcaactggc aaaaagcgcc gtgctcttgg cgccgcggtg gtcgatgctg   123840
atcacgttgt ccttgttctc gaccacgtag tcgcgcgcga aggtgtggcg gcagcggaac   123900
tcgacctctt tgagcacaaa ctgcgacacg tgcttttggt gcgccacgta gccgatgctg   123960
atgccgatca tgtgcttaag cagaaacgag ataatgggga tgatgaacca agtcttgccg   124020
tgacgtcgcg gcaccaggaa cacggtggct ttctgcttaa agatgtcgat ggaggtctgc   124080
gagaggaagt cgatctggaa ggcgtggatg aggtactgca gcacgcgatt ggccagcacg   124140
gggatcttgg tcacggctat aaaaaagatg acgtgtatca ataaattctt ttgaaacggt   124200
tcgagtcgga tggcttttgc gtcgccctcg acggcggtac tgaagccgcc gtcgagccac   124260 ttttttaaagt cggtcatgaa gttgttgatc tgctgaaact gcggatcgcg gtagagctcg   124320
gtcaacgcgt ccagcttctg gtaggaggcg cgctgctcct cggagcacgg gcgaaacgtc   124380
agttcatcga gcgcactctt gaggcgctcg tgaaacagca gctcgcgctg gctttcctcg   124440
ggcgagttgt agtcgcggtg gcggccgcag aaggccatga gcggcaggaa ggcctcgttg   124500
cacgagtggg ccagcccgag ttcggggtgc atcatctggt agcgcttgcg gcacagcgcc   124560
gccacattgg tgaaggccgt ggagatgcag gaggtggggt ggctcttgcg cttctgcagc   124620
tccgcgtagc gctcctggat cttggcggcc gaatctccgc gcaacatgat ggcggcggcc   124680
gtggtgcgag cggaggttag gcggcagcgg cgagaggaga ggaaaaagat ggcgtccgcg   124740
aggacgacgg aggatccacc cgaaaaccac gttgtcgcgg acgtggcttg tgggacgggc   124800
gccgtcactc gttcgtcttc gtcgtcccta gtggtgtcgt cttcctcggc gtcaggctca   124860
gacgaatctt cctccgcctc tcctctcagt ttccccgtct cctctccctc aactgccgtc   124920
aggtctccgg ggtccgccgg ggtttcgacg tccctgtgct cggtggaacg gatggtcgag   124980
ctgtcggcgc agtctccggc cgccgatttc tcggtctccg aggcttggcg tttcgaggag   125040
gccgtaaata tggcgctggt ggcctgcgag gccgtgtcac cttacgatcg ctttcgccta   125100
attgaaacgc ccgacgagaa tttcttgttg gtcaccaacg taattccgcg cgagtcggcc   125160
gaggtgccgg tgttggatag cagtagcagc ggtggcgata gcgggccgga ggacaaaaag   125220
aaaaacgtcg ggaataaaac cgcgggggaa aagaacggcg gtgggtctcg ggccaaacgc   125280
cgtcgtagac gacgcgctcc gaaaaacgac gccgccacgc cgtctttttct acgtcgacac   125340 gacgtgctgg agcgtttcgc ggccgcggct gagcctttgc cgtcgctttg tgtgcatgat   125400
tatgcgttac gcaatgctga ccgtgttacc tacgacggcg aattaatcta cggcagttac   125460
ctgttgtatc gcaaggctca cgtggagctg tcactctcca gcaacaaggt gcaacacgtg   125520
gaagctgtgc tgcgacaggt gtacacgccg ggcttgttag atcatcacaa cgtgtgcgac   125580
gtggaggccc tgctgtggct gctgtactgt ggaccgcgca gcttttgcgc gcgtgacacc   125640
tgtttcggtc gcgaaaagaa cggttgtcct ttccccgcgt tgttgcccaa actcttttac   125700
gaacccgtgc gggactatat gacctacatg aatctggctg agctgtacgt ctttgtttgg   125760
tatcgcggct acgaattcct tgcgccaacg ccgcaggcga cgacggcggg tggtggtggt   125820
ggtagtggtg gcggcggcgg ggccggcgct tgtacggtcg agacgagcgc gtcagcaggc   125880
cgggtcgatg acgccggcga cgaggtgcat ttgcctttaa agcccgtctc gctggaccgt   125940
```

-continued

```
ctcagagagg tgttacaggc ggtgcgcggc cgcttctcgg ggcgcgaggt gcccgcctgg    126000
ccggcctcgt cgcgcacctg tttgttgtgc gcgctctaca gtcagaaccg tctctgttta    126060
gatctcgcgc gtgacgaggc gcggaccgtg agttatagcc ccatcgttat ccaagactgc    126120
gccgcggctg ttaccgacgt cactttgagc cacatcttgc ccggccagag caccgtctcg    126180
cttttccccg tctaccacgt cggcaagttg ctggacgctc tctcgctgaa cgacgcgggt    126240
ctcatcacgt tgaatctatg acgtcggtca acaaacagct cttaaaggac gtgatgcgcg    126300
tcgaccttga gcgacagcag catcagtttc tgcggcgtac ctacggaccg cagcaccggc    126360
tcaccacgca gcaggctttg acggtgatgc gtgtggccgc tcgggaacag acccgataca    126420
gtcagcgaac gacgcagtgc gtggccgcac acctgttgga gcaacgggcg gccgtgcagc    126480
aagagttgca acgcgcccga cagctgcaat ccggtaacgt ggacgacgcg ctggactctt    126540
taaccgagct gaaggacacg gtagacgacg tgagagccac cttggtggac tcggtttcgg    126600
cgacgtgcga tttggacctg gaggttgacg acgccgtcta acaggtatag caatccccgt    126660
cacgcctctg ttcagatttt attaaaaaaa aaacacacca taacgacagt gtcggtgtgg    126720
tagctagtgc agccctagga acagggaaga ctgtcgccac tatgtcctcc gcacttcggt    126780
ctcgggctcg ctcggcctcg ctcggaacga cgactcaggg ctgggatccg ccgccattgc    126840
gtcgtcccag cagggcgcgc cggcgccagt ggatgcgcga agctgcgcag gccgccgctc    126900
aagccgcggt acaggccgcg caggccgccg ccgctcaagt tgcccaggct cacgtcgatg    126960
aagacgaggt cgtggatctg atggccgacg aggccggcgg cggcgtcacc actttgacca    127020
ccctgagttc cgtcagcaca accaccgtgc ttggacacgc gactttttcc gcatgcgttc    127080
gaagtgacgt gatgcgtgac ggagaaaaag aggacgcggc ttcggacaag agaaccagc    127140 gtcggcccgt ggtgccgtcc acgtcgtctc gcggcagcgc cgccagcggc gacggttacc    127200
acggcttgcg ctgccgcgaa acctcggcca tgtggtcgtt cgagtacgat cgcgacggcg    127260
acgtgaccag cgtacgccgc gctctcttca ccggcggcag cgaccctcg gacagcgtga    127320 gcggcgtccg cggtggacgc aaacgcccgt tgcgtccgcc gttagtgtcg ctggcccgca    127380
ccccgctgtg ccgacgtcgt gtgggcggcg tggacgcggg gctcgaagaa aacgacgtgg    127440
agctgcgcgc ggaaagtcag gacagcgccg tggcatcggg cccgggccgc gttccgcagc    127500
cgctcagcgg tagttccggg gaggaatccg ccacggcggt ggaggccgac tccacgtcac    127560
acgacgatgt gcattgcacc tgttccaacg accagatcat caccacgtcc atccgcggcc    127620
ttacgtgcga cccgcgtatg ttcttgcgcc ttacgcatcc cgagctctgc gagctctcta    127680
tctcctacct gctggtctac gtgcccaaag aggacgattt tgccacaag atctgttatg    127740 ccgtggacat gagcgacgag agctaccgcc tgggccaggg ctccttcggc gaggtctggc    127800
cgctcgatcg ctatcgcgtg gtcaaggtgg cgcgtaagca cagcgagacg gtgctcacgg    127860
tctggatgtc gggcctgatc cgcacgcgcg ccgctggcga gcaacagcag ccgccgtcgc    127920
tggtgggcac gggcgtgcac cgcggtctgc tcacggccac gggctgctgt ctgctgcaca    127980
acgtcacggt acatcgacgt ttccacacag acatgtttca tcacgaccag tggaagctgg    128040
cgtgcatcga cagctaccga cgtgcctttt gcacgttggc cgacgctatc aaatttctca    128100
atcaccagtg tcgtgtatgc cactttgata ttacacccat gaacgtgctc atcgacgtga    128160
acccgcacaa ccccagcgag atcgtgcgcg ccgcgctgtg cgattacagc ctcagcgagc    128220
cctatccgga ttacaacgag cgctgtgtgg ccgtctttca ggagacgggc acggcgcgcc    128280
```

```
gcatccccaa ctgctcgcac cgtctgcgcg aatgttacca ccctgctttc cgacccatgc 128340
cgctgcagaa gctgctcatc tgcgacccgc acgcgcgttt ccccgtagcc ggcctacggc 128400
gttattgcat gtcggagttg tcggcgctgg gtaacgtgct gggcttttgc ctcatgcggc 128460
tgttggaccg gcgcggtctg gacgaggtgc gcatgggtac ggaggcgttg ctctttaagc 128520
acgccggcgc ggcctgccgc gcgttggaga acggcaagct cacgcactgc tccgacgcct 128580
gtctgctcat tctggcggcg caaatgagct acggcgcctg tctcctgggc gagcatggcc 128640
ccgcgctggt gtcgcacacg ctacgctttg tggaggccaa gatgtcctcg tgtcgcgtac 128700
gcgccttttcg ccgcttctac cacgaatgct cgcagaccat gctgcacgaa tacgtcagaa 128760
agaacgtgga gcgtctgttg gccacgagcg acgggctgta tttatataac gccttttcggc 128820
gcaccaccag cataatctgc gaggaggacc ttgacggtga ctgccgtcaa ctgttccccg 128880
agtaaccggg acgcggaacg tgacggttgc cgaggggaaa ggcgacagag aaggtacaaa 128940
cccaccggcg ggaaaaatac tgaggcgccg ccatcatcat gtgggcgtc tcgagtttgg 129000
actacgacga cgatgaggag ctcacccggc tgctggcggt ttgggacgat gagccccctca 129060
gtctcttttct catgaacacc tttttgctgc accaggaggg cttccgtaat ctgcccttta 129120
cggtgctgcg tctgtcttac gcctaccgca tcttcgccaa gatgctgcgg gcccacggta 129180
cgccagtagc cgaggacttt atgacgcgcg tggccgcgct ggctcgcgac gagggtctgc 129240
gcgacatttt gggtcagcgg cacgccgccg aagcctcgcg cgccgagatc gccgaggccc 129300
tggagcgcgt ggccgagcgg tgcgacgacc ggcacggcgg ctcggacgac tacgtgtggc 129360
tcagccggtt gctggatttg gcgcccaact atcggcaggt cgaactcttc cagttgctgg 129420
aaaaggaatc gcgcggacag tcgcgcaact cggtgtggca tctgttgcgt atggacacgg 129480
tctcggccac caagttctac gaggccttcg tcagcggctg tctgcccggc gccgcggcgg 129540
cggacggttc gggtggcggc ggctcgcact acacgggctc gcgcgccggc gtctcgccgg 129600
gcatccagtt cggtatcaaa cacgagggct tagtcaaaac gctggtggaa tgttacgtga 129660
tgcacggacg cgagccggtg cgcgacggcc tcggtctgct catcgacccc acgtcgggcc 129720
tgctgggcgc ttccatggac ctgtgcttcg gcgtgctcaa gcagggcagc ggtcgcacct 129780
tgctggtgga accgtgcgcg cgcgtctacg agatcaagtg ccgctacaaa tatttgcgca 129840
aaaaggagga ccccttttgtg cagaacgtgc tgcggaggca cgacgcggcg gccgtggcct 129900
cgctgttgca gtcacacccg gtgccgggcg tggagtttcg cggtgaacgc gaaacccgt 129960
cggcacgcga gtttctgctt tcgcacgacg cggcgctctt cagggccacg ctcaagcgcg 130020
cgcgcccgct caagccgccc gaaccgctgc gcgagtacct ggccgatctg ctgtatctca 130080
ataaggccga gtgttcggaa gtgatcgtgt ttgacgccaa gcacctgaat gacgacaaca 130140
gcgacgggga cgccacgatc actattaacg cgagtctcgg cctagccgcg gcgacgccg 130200
ctggcggcgg cgctgatcac cacctgcggg gcagcccggg cgattcgccg ccgccgatac 130260
cttttcgagga cgaaaacacg cccgagctgc tgggccggct caacgtgtac gaggtagcgc 130320
gcttttcact gccggctttt gtcaatccgc gtcaccagta ttactttcag atgctcattc 130380
agcagtacgt gctcagccaa tactatataa agaagcatcc ggaccggag cggatcgatt 130440
tccgcgacct gcctaccgtc tacctggtct cggccatctt ccgcgagcgc gaggaaagcg 130500
aactgggctg cgagttgctg gccggcggtc gcgttttcca ctgcgaccac atcccgctcc 130560
tgctcatcgt cacgcccgtg gtctttgacc ctcagtttac gcgccatgcc gtctctaccg 130620
tgttagaccg ttggagtcgc gacctgtccc gcaagacgaa cctaccgata tgggtggcga 130680
```

```
actctgcaaa cgaatatgtt gtgagttcgg taccacgtcc ggtgagcccc tgaaagatgc   130740
tctgggtcgc caggtgtctc tacgctccta cgacaacatc cctccgactt cctcctcgga   130800
cgaaggggag gacgatgacg acggggagga tgacgataac gaggagcggc aacagaagct   130860
gcggctctgc ggtagtggct gcgggggaaa cgacagtagt agcggcagcc accgcgaggc   130920
cacccacgac ggccccaaga aaacgcggt gcgctcgacg tttcgcgagg acaaggctcc   130980
gaaaccgagc aagcagtcaa aaagaaaaa gaaaccctca aaacatcacc accatcagca   131040
aagctccatt atgcaggaga cggacgactt agacgaagaa gacacctcaa tttacctgtc   131100 cccgccccg gtcccccccg tccaggtggt ggctaagcga ctgccgcggc ccgacacacc   131160
caggactccg cgccaaaaga agatttcaca acgtccaccc accccgggga caaaaaagcc   131220
cgccgccccc ttgtcctttt aactcataaa ctttcaggtc tcgcgtacga ttcgcgagtc   131280
gggaatggga cacccgtggg tgtttctccg tgtgtatatt attttttttt gtgtgtgttt   131340
gcgcccccgt gtgtctaatg tgctgtttga aacacgtaaa gtagctggtg gaagaacaga   131400
taaaccttta ataaaaaaaa agtatgtgct cccgacccac ggtctgcgtg tctcttttt   131460 atgtccatgt ctccaagtct ggtgcgggtg cggcggggt caagcgtcct cgaagtcttc   131520
atcatcgtcg tcgtcctctt cttcgcggag gcgacggctt tccaagctgt cgtggtgact   131580
gagcgcagcg acttcttcgc cggaggctgt ggccagcgcc tggtacttga cactgccgct   131640
accgcgtccg cgaaagtagc ggacggcgcg acacgtcgta acatggccc atatgaaaaa   131700 gagcatgccg aacgaccagc tgatgccggt acggtaatcg tcgccgatgg taaaggcgcc   131760
gtactgcacg atggggtaga tgaggccgca gagtccgaag aaggcgccca ggtggtagcc   131820
gaattgcact ttgacgtatt gaaaaaagac ggcttcgatc agtaaaaagt agattatgga   131880
gatgatagcg tagaccacga agacggccaa caccatgtgg cctgtacgca cgaaaaagtt   131940
gtttccgaag ccgtagcaca gggccatggc taccacggtg gtgttgaaac caagtgccat   132000
ctccaccagg ttgacgatga gcgtgcgaaa ctgcaccgta cctttgagct tggggtgaag   132060
acgcgagaaa aaaagagcg agcgtttgaa gctgcggtac tgcgtgacca tgctcacgtt   132120
gaaaatggtc aagcagaaaa agtgcacggc ggccatgaag gcgatcatgc tgggcagccg   132180
aaatgacatg gtcagtgtga atagttggaa cgtgtccatg ctgaggatga agaggaaggc   132240
tgtgaggctg tcgcccatgt acgaaatgtc acgtgtcgac tggtttaggc tcatgccttt   132300
gtccttgcgc atgctgatct tgatccagca taccaggtag tagatggtca cggctaaaaa   132360
gacgagctgc atgaacacgg cgtagcacac cagctgcacc gagtctaaga aaagcatagg   132420
cgtgtgcagg tgcattacgt tgtaggccga catgttgagc ctttcaaagt ccacgacgtg   132480
atagtagacg caggggtagc ccaggtgcgg aaaattgctc agcaccagat gcacgctgac   132540
gttgacaaaa gtcagcacca tgaaaatgat agaagcgctc catgtccgtg tattcacctt   132600
atccacgtgc gaggggcca tggcgatagc ggcggcccgc tcgctcggga ggcgatgggg   132660
gcgcgccgat gacgacaggc tcgcgggtcg ttaaatacta cgatgggagc cgccgcggct   132720
cacgacgcgg tttgagcacg tccgggcggt cggcgaaaaa agaccccgcg ggccttcgcg   132780
actctcttct gtccgaggat gaccgctcag ccgccgttgc accaccgcca ccaccgtac   132840 accctgttcg ggaccagctg tcatctcagc tggtacggcc ttctggaggc ctcggtgcct   132900
atcgtacaat gtctgttttt ggatctgggt ggcggccgtg ccgagccgcg gcttcacacg   132960
ttcgtggtgc gcggtgaccg tctgccgccg gctgaggtgc gtgctgtgca tcgcgccagc   133020
```

-continued

```
tacgccgcgc tggcctcggc cgtgactacg gacgccgacg agcgccggcg cggcctagag    133080
cagcgtagcg ccgtgttggc gcgcgtgttg ctagaaggca gcgcgttaat ccgcgtgttg    133140
gcgcgcacct tcacgccggt gcagattcag acggacgcta gcggcgtgga gattttggag    133200
gccgcaccgg cactgggcgt ggaaaccgca gcgctgtcga acgcgcttag tcttttccac    133260
gtagccaagc tagtggtcat cggctcgtat cccgaagtgc acgagccgcg tgtggttacg    133320
catgccgcgg aacgcgtctc cgaagagtat ggcacccacg cgcacaaaaa attgcgtcgc    133380
ggttactacg cctacgattt ggccatgtcg tttcgcgtcg gcactcacaa gtacgtgctg    133440
gagcgcgacg acgaggccgt cctggcacgc ctctttgagg tgcgcgaggt gtgtttttttg   133500
cgcacctgtc tgcgtctggt cacgcccgtc ggtttcgtgg ccgtggcagt gaccgacgag    133560
cagtgttgtt tattgctgca gtcggcctgg actcaccttt acgacgtgct tttccgtggt    133620
ttcgctgggc agccgccgct acgcgactac ctggggccgg accttttga dacgggcgcc     133680
gcccgttctt tcttttttcc cggtttcccg cccgtgcccg tctacgcggt ccacggtctg    133740
cacacgttaa tgcgcgagac ggcgttggac gcggcggctg aggtgctctc gtggtgcggc    133800
ctgcctgaca tcgtgggctc ggccggcaag ctggaggtgg aaccctgcgc gctctcgctc    133860
ggcgtgcccg aggatgagtg gcaggtcttc ggcaccgagg ccggcggcgg cgccgtgcgt    133920
ctcaatgcca cggcttttcg cgagcgaccg gccggcggcg atcgtcgctg gctgttgccg    133980
ccgctgccgc gtgacgacgg cgacggtgaa acaacgtcg tggaagtcag cagcagcacc     134040
ggcggtgcgc acccgccgag cgacgacgct actttcaccg tgcacgttcg cgacgccacg    134100
ctacatcgag tgctcatcgt ggatttggtt gagcgcgtgc tggccaagtg tgtacgcgcg    134160
cgcgacttca atccctacgt gcgttatagt catcgactcc acacttatgc ggtttgtgaa    134220
aagtttattg aaaatctgcg ttttcgctcg cgacgcgcct tctggcagat ccagagtcta    134280
ctgggctaca tctccgagca cgttacgtca gcctgcgctt cggccggcct tttgtgggtt    134340
ctgtcgcgtg gccaccgcga gttttatgtc tacgacggct attcgggtca cggacccgtc    134400
tcggccgaag tgtgcgtgcg gactgtggtc gactgttatt ggcgcaaaact ttttggcggc    134460
gacgatccgg gtcccacctg tcgtgttcaa gagagcgcgc ccggcgtgct gttggtctgg    134520
ggcgacgagc ggttggtggg tcccttcaac ttcttctacg gcaacggcgg cgccggtggt    134580
agtccgctcc acggggtggt gggtggtttc gcggcgggac attgcggtgg cgcttgttgc    134640
gcgggctgcg tcgtcactca ccgccattct agcggcggcg gcggtggtag tggcgtgggc    134700
gacgcggacc acgcgagtgg cggcggtcta gatgccgctg ccgggagtgg tcataacggc    134760
ggtagtgatc gggtttctcc ctccacgccg cccgcggcgt taggtggttg ttgctgcgcg    134820
gccggtggcg actggctctc ggccgtgggt catgtcctgg gccggctgcc ggcgctgtta    134880
cgggagcgcg tgagcgtgtc cgagctggaa gccgtgtacc gcgagatcct ctttcgcttc    134940
gtggctcgcc gcaacgacgt ggacttttgg ttactgcgct tccagcccgg tgaaaacgaa    135000
gtaaggccgc acgctggggt gattgactgc gcgcccttcc acggcgtgtg ggccgagcag    135060
ggccagatca tcgtacagtc acgcgatacg gcgttggcgg ccgatatcgg ctacggcgtc    135120
tatgtggaca aggcctttgc catgctcacg gcttgcgtgg aggtctgggc gcgagagtta    135180
ttgtcgtcct ccaccgcttc caccaccgct tgttcttctt cttccgttct ctcctccgcc    135240
tgccgtccg tcacttcgtc ctcttcgggc acgcgacgg tgtctcctcc gtcttgttct      135300
tcttcgtcgg cgacttggct cgaggagcgc gacgagtggg tgcgctcgct ggcggttgac    135360
gcgcaacacg ctgctaagcg ggtggcttcc gagggcctgc ggttttttccg gctcaacgct   135420
```

```
taacgagtca cgtagggaa ctacgtgggt aagtgacgtg gatactagta aaaaaaagtg  135480
cgtcaaagtt ctcagcgtgt gacgtggata ctagtaaaag ggacgtcaaa gctcactacg  135540
tgttgcgtgt tttttttttct atgatatgcg tgtctagttc gcttctcact cttcctctcc  135600
ccgttcccag cgcggtggca gcttgggggg tgagggcaaa ttggggtagt tggcgttgag  135660
cacgtctagc aggcccaggc ccacgggcca accgtccacg gtcttacgct cggtcagctt  135720
gaggctaaac gagtgtgcct cgtcttgacc ggtaaggcgg aaaagaagc gtgctaccag  135780
ctgcaggcag gtatgccgcg tctgctggaa gagcacgaag gtagcgggca cgtactgcac  135840
aatgtgcggt tcttttttcct caaagagtag gtagagcgcg ctgcagatca gccgccgggc  135900
gctgtggtgc agcagccggc cgaagctttc gcgcacgttc accgcgtcca ggtactggag  135960
caggtcgtgc aggcacttgc gcgttaagtt gcaattttcc acgcatgaaa taacggtaca  136020
gagcgcgaag tgcagcaggt tgtcggcctt gacgatgccg cagcggtgtt tgagccgcag  136080
atccgagagc ctcacctgcg tgacggcgtc ttcggtctcg agcaaaaaca cggcggagta  136140
gcccagaaag gccgaggtgc acagcaactc gctgcggtac tcggccatgg aaaccagcag  136200
cccgtgctcc gtatgcagcc acagcttgtc gccgcgcacc gtaaagtcga gcacttgcgg  136260
ctccatgatc atcacattct gtctagtgaa atccgtatgg acctccagca cgccgcggat  136320
catcagggcc tccatttcga aatcggccga cacgctctgg gccgcgccgc tcctcgtctg  136380
ccgtgatcaa gcggcgcggc gcggaccttt caagcgttcc tgggccgccg ctcgaggcag  136440
ttccccttc tggcactccg cccgccgctt cgcggctcat ttggcgccgg cgcgccttct  136500
cgcggctgca aatcagctcc acgtatcggc aaaacttgct gtcgtcgtag gcggcggcta  136560
cgatctcgcc gaaggagagc tgcaggtagg cctcgggtac ggggtccagc gtgcccagcg  136620
ccaggatgtg acacagatag ggcagggtca cgcgctctac cgtgtaattg gagtagacga  136680
tggcctcttc ggcccctcga tgcgtgacca gacgccgcag gcgaaaggtg cggaaatact  136740
cgttttccca cagctgcgtg aggaagcgtt ccagcgactc ggtgccgggc acgaactgcg  136800
agaagaagct gttggccacc aggcggttgt cctccaccgc cagcggacgg aagggcgccg  136860
cgtcgcgcgc cttgcgcacg gcctccaaca cgggcaggtg gtacagttcg gcgtcgcgcg  136920
cgcccaggct catggagtcc tcgccgcg aggcgtagcg cgtgagcagg tcgcgcagct  136980
cgcgcacgcg attctcccag gtctggttga gcgtgcgcag gtcctggatc tcgtccacct  137040
gcgactggat ctgctcctcc aggcacttga tgacctgctt cttaaacagg tcgcggatgt  137100
cccgctcggc cgccgccggg ccgggtggcg gcggcagcag cccgacgtgg cccgcgggtc  137160
ctcccaccac ggcgccgccg ggtcccacca cgccgggtcc acctggacca cgcgcgggta  137220
gtagacggtt ttggtccacc agcgagggg tcaggtcctg tagaaaggac tcgacgcgt  137280
cctcgatgcc gatgcgcgat ttgctgtccg agacgttaag caaaaacttc ataatggact  137340
ttttggcgtc gctgccccgg tcgtgctgct ccatcatctc caccagcttc ttgcagttga  137400
gctcgtggcg gctggcggtc accactttca caggaaaggt attgagcaac tggcagatct  137460
tttggtggcg gcagagcccg tcgtagcgca gaatctcctc gtgcaggtgt gccaccggcg  137520
tggtgaacag cagcttgtcg cgctcataag ccagcggttc ggccgccacg tacaagcgga  137580
tgtgcttgcc gcgcagctgc gcctccagcc gctccgagcg caccttcttg aagacgcgta  137640
cctcgggcgc gttggctacg cgcacggcgc ccaggcgctc ggccacctgc agcagcagcg  137700
ccaggttagc ctgcagcagg tcctgcgcca gcgggtgtgt ctcggtggcc cgctgcacgg  137760
```

```
ccgcgcgtac aaattgcgcc cgctcggccg cctcgctcgg cttggtcttc acgtccagca   137820
gcggtaccag tcccaccgtt acgcaccaat ccacgtagag accatagtcg tcgttatcgg   137880
cgtactgata taaaatgtcg cggagcgcgc ccagcacgcc cgtttgcacg ctctggcgca   137940
acgaagcgct ccacaccaac agatactgct ccaggtcctc ttcgtccagc gcgcggtagg   138000
gaaacagcgc cgcgtgcaac ttccactcct cggccacgcg ccgcaccgtg atggtgtcaa   138060
agagcgtctt gcacactccg tagagcagct gcttgcgcag cacgcacggg tcgcgcagca   138120
cctggtgcat gctctggccg cgacacgtcc ccagaaagcc gtgcagcaac cgcaggaagc   138180
tcatcgtctg gcccgtgggg aaaatgtcga tgacggcctc gtcatccacg ccgcggccca   138240
cgcccaagta cgacgacgcc ttgatcctca acctctcgtc ggccgccaag atcgaacgga   138300
tcgtcgacaa ggtcaagtcc ctctcgcgcc agcgctttgc gcccgaggat ttttcgttcc   138360
agtggtttcg ctccatcagt cgcgttgaac gaacgacaga taacaacccc tctgccgcaa   138420
ctaccgccgc ggcaacgacg accgttcact cctccgcctc ctcttctgcc gccgctgccg   138480
cttcgtccga ggccggcggc acgcgcgtgc cctgcgtcga ccgttggccc ttctttccct   138540
tccgcgcgct gctcgtcacc ggcacggcgg gcgccggcaa gacttccagc atccaggtgc   138600
tggcggccaa tctagattgc gtgatcaccg gtaccacggt gatcgccgcg cagaacctca   138660
gcgcgatcct caaccgcact cgttcggcgc aggtcaagac catctaccgc gtcttcggct   138720
tcgtcagcaa gcacgtgccg ctggctgaca gcgccgttag ccacgagacg ctggaacgct   138780
accgcgtgtg cgagccgcac gaggagacca ccatccagcg cctgcagatc aacgatctgc   138840
tcgcctactg gccggtcatc gccgacatcg tggacaaatg cttaaatatg tgggagcgca   138900
aggccgcttc ggcctccgcc gcggctgcag ccgccgcctg cgaggacctc tcggagctgt   138960
gcgagagcaa tatcatcgtc atcgacgagt gcggccttat gctgcgctac atgctgcagg   139020
tggtggtgtt ttttactac ttttacaacg ccctgggcga cacgcgactt taccgcgaac   139080
gccgcgtgcc ctgcatcatc tgcgtcggtt cgcccacgca gaccgaggcg ctggagagcc   139140
gctacgacca ctacacgcaa aacaagagcg tgcgcaaggg cgttgacgtg ctctcggcgc   139200
tgattcagaa cgaggtgctc atcaactact gcgacatcgc cgacaactgg gtcatgttta   139260
ttcacaacaa gcgttgcacc gacctggact ttggcgacct gctcaagtac atggagttcg   139320
gtatcccgct caaggaggag cacgtggcct acgtggaccg cttcgtgcgg ccgcccagct   139380
ccatccgcaa cccctcgtac gccgccgaga tgacgcggct ttttctctcg cacgtcgagg   139440
tgcaggctta cttcaagcgg ctgcacgagc agatccgcct gagcgagcgc caccgtctct   139500
ttgatctgcc cgtctactgc gtggtcaaca accgcgcgta ccaggagctc tgcgagctgg   139560
ccgacccgct gggcgactcg ccgcagcccg tcgagttctg gttccgccag aacttggcgc   139620
gcatcattaa ctactcgcag tttgtcgacc acaacctctc cagcgagatc accaaggagg   139680
cgctgcgccc cgcggccgac gtcgttgcca ccaacaactc ctccgtccag gctcacggag   139740
ggggaggatc tgtaatcggg agcaccggcg gcaacgacga gacggcgttt tccaggacg   139800
atgataccac caccgcgccc gatagccgtg agacgctgct caccttgcgc attacctaca   139860
tcaagggcag ttcggtggga gtcaactcta aggtgcgggc ctgtgttatc ggataccagg   139920
gcacggttga acgtttcgtg gacatcttgc aaaaggacac gtttattgaa cgcacgccct   139980
gcgagcaggc ggcctacgcc tactcgttag tttcgggcct gctcttctcg gccatgtact   140040
acttctacgt gtcgccctac acgaccgagg agatgttgcg tgagctggcg cgcgttgagc   140100
tgcccgacgt gagttcgctc tgcgccgctg ccgccgccac ggccgccgct cccgcttgga   140160
```

```
gcgggggaga gaatccgata aataatcacg tcgacgcgga ttcttctcag ggcggccaga   140220
gcgtgccggt atctcaacgg atggaacatg gccaagagga gacccacgac atccctgcc   140280 tgtccaacca ccatgacgac tcggacgcca tcacggacgc cgaactcatg gatcacacca   140340
gtctgtacgc ggatcccttt tttctcaaat acgtcaagcc acctagcctg gcgctgcttt   140400
ctttcgagga aacggtgcac atgtacacta ccttccgcga cattttttctc aagcgctacc   140460 agctcatgca gcgtctcacg ggcggtcgct tcgccacgtt gccgctcgtt acctacaatc   140520
gccgtaacgt ggtgttcaag gccaactgtc agatcagctc gcagaccggc tccttcgtgg   140580
gcatgctttc gcatgtgtcg ccggcgcaga cgtacgcgct cgagggctac accagcgaca   140640
acgtgctcag tctgcccagt gaccgccacc gcatccaccc cgaggtggtg cagcgcggcc   140700
tttcgcggct ggtgctacgc gatgcgctcg ggttcctctt tgtgctcgac gttaacgttt   140760
cgcgcttcgt cgagtcggcg cagggcaaga gtctgcacgt gtgcaccacc gtggactacg   140820
gccttacttc gcgcacggcc atgaccatcg ccaagagtca gggcctgtcg ctcgagaagg   140880
tggccgtgga ctttggggac catcccaaga acctcaagat gagccacatc tacgtggcca   140940
tgtcgcgagt cacggacccc gagcacctca tgatgaacgt taacccgttg cgactgcccc   141000
atgagaagaa caccgctatc acccctata tctgtcgcgc gctcaaagac aaacgcacca   141060
cgcttatttt ttgacacaac accgtgtaag gaaaacgtga cttattgag cagggtaaaa   141120 accacgtaca agaaccacgt tgtctatccc caaaaaaaca cacccgtca gggaacacat   141180 cgcctataga tagcggcact ttacataaaa ccaccgtacc tgcatcacgg tggctcgata   141240
cactggaaat tcaataaaaa ccaccgtgtc tccgtgacgg tacttatcgg gtcagcgtct   141300
ttctcttgag atttctgttc gtaaacttat ccgtttcccc ggtccgcggt gtctcctcgc   141360
gaggctgaca gtctacgagt ggtatctaca agagaaagaa acccgggtgg gagcgacgcc   141420
gtcgctgggt atcaaccccg cggctgaccg tcgtccggta aaggaacaac ccgtcgtcgc   141480
aagccgggtt cgaccaagag aaaaaacccg ggtgcggggg gagacgggtc gtcctttggt   141540
tgttcgcgga cggcgtacat gccgcgtggg tcagtcgacg gcgtcgctcc gtgcggtcgg   141600
tcatcattct gcttcacata tatgggttgt ttgtgttttt tttataatga atacgcactg   141660
atcctatccg tgactgcgcg tgtggcagag aggatgcctt ataacatgta ttttgaaaaa   141720
ttgccaacag ctataatttc tctcatgtag cagaatagag accttttgtc gtcttttttgt   141780 ttgtcattac ttgttttcca gggaattaga gagagggaac cgcgcctccg gcggcggtgc   141840
ccgcggaccc cggcccctcc tcgcgtgcgc ggtgtgactg gttgagcgaa tgagcagcta   141900
ggcttggtgg tgctccgcgt gcgggggaga agacgattaa caacaaaaaa taagtggaag   141960
tggccggtgg gtctttgtcc gcgtgcgcgc ccatccgtcg ccgggaccga gcagaaagtg   142020
atgtggtggt acattgattt tttccttgac aggaaagaaa aaaagagtt ttgttttcct   142080 atgtgagagg agaaaggtat gtgaggagat gttcgatgat cgtatgttac agttatgctg   142140
taaggaagct tttatcgtgc gtcctgtttt tcatttgatg tatatgacac aattgaaacc   142200
tatcgatagg cgtatatcga ggattcatca attcttagaa tcgtcgtctt tttggctaat   142260
tggactttgc ccatgttggt tgtcattcgt ggcctgaggt catcgtcgtc cacgacgacg   142320
tgtctatagc gtgcggtgtg atcattgtgt cgagccagag aaagcgcgcc tcgcacgacg   142380
tttgcggatc ggctcgcggg tgtgtggaat tcctaagaac ataatcagct ggtcgtcttt   142440 cttttgatgtg ttgttgtcgt cgaggtcttg cttcgttttc tttttttcttt ttagtcgatg   142500
```

```
gaacttttct tcggtacggg ttcttgttat ggaagcttgt gttttcgaac atgaattcga   142560
aaaaataaaa aggcctatct tcgtttcaaa aaaaggacag atatcaatct tcttaactta   142620
tatcatggta aattcagaat cctatggtgt cttattatct ctaaagtagt caacattatg   142680
gtctaacttg tatttccctg acgagatata tatgatcctt ataacctggc tactatcatg   142740
aacaacaata tccttactta cagtcatctt cgtgagttaa tgaagtataa tatcggtcat   142800
ctatcaactt atctgctatg taacgtaccc ttttaggtat tttgcgtttc ttaacgagtg   142860
tacccgcctg tgtgaggcga aactctgaga agtctaccga gtcgagttac aagtcactaa   142920
aacacttaca cgagttatct atactaaaat cactatctat gttgtttgct tacctaatta   142980
ttatcctaca tgacgaagct acctcccaac gtaaggtagg gggagaggag acagaacaat   143040
aaaaagtaac taatgtttct tagaacttac ccgctaagga cttaccaaac tatattcacc   143100
aaaaaacaac agctacgtgt ttcatttgtt ttaatctacc gaagtaaaaa aaaaagatga   143160
ttagctatcc agaacctact tacttcttaa tgttttaact aaggatgcct atgggattgg   143220
aaaaaaaatc acagcaactt gctactaatc agttgacagc gaagagactc ataacaaaga   143280
tttctgggta atacggttat aataatgctt atggactaaa ggatacttgg aaaaaaagaa   143340
cgggctatga ctatagagat tcatcgagat atcaaacttc aaataggcgg ctatcattca   143400
tggttgtggt gactatatcg tggagaaaaa atgtgatcgt tagttagcta ggtgagactt   143460
acagctatcc atccgtctag ttttcgttg taatgatgat agtacgtcta tggtggtgat   143520 cgatttggt tagcaatttg ttcgtttaaa ggcttaatgt acttatgcta catgatgtat   143580
tattctttga ttcatcgttc ctcctaaggg ggtgtatgta tgtatgtact agtcgtatag   143640
tgttcctaac atcatgacta ttcagactat ggcttcatct atcgtgtcta aagttcactt   143700
attctactat tactatatat atgcactact atgtaactag gatatggtcc tataaggtgt   143760
cttctatcac ggtggcttgt ttatcgcttg gcggttacga gcaagagttc atcacggacc   143820
agccgtgagg cagggcacac gcgggtcggc ggcgatgatg tcccccgcga aggggacaac   143880
aaaaacaaga caagaggccg ccggccgcgg ccacggacgc gtagcggtta cacaatgttt   143940
ggttgagcgt tttgtttcat cgtcgtggtg gtggttttgt tgttctctgt atatatcgtg   144000
tggtggcttt atcgtcatca ttattatcat cattcttgtt tccatcatca cgatgagttt   144060
tctccgtttt cctctcctcc agtggtagtc gtgtatcatc atcaatcatc gtagtgacgt   144120
cgttgctgct gctgctcttg ccttcatggc ggtatttctc ttcctccccc ctaaccccat   144180
attaactcgt gagtgtgatg gttagagtgg ctgcttgttt ttttttcttt tctcttttgga  144240 acaacaaaag aggataaaga tggtcggtga atgtattatt attatcatca tcattatgat   144300
acggtcgcgg tcttcttctc cgatgacgaa acctgcgcac atcgaagaaa agacgagcgc   144360
gcgaaccgat agccgtccgt ctgggacgaa ggagaagatg atggggagag gaggagagcc   144420
ccagaagcca gagcgagaag ggagacgaca gacatacgtc gtcaccgtcc tctgaggag   144480 gcacggcggc gctgtttgtt gtttggatgc ttgattatat cctgttctat ggggtagatt   144540
attatcaata ggcttggttt tcaaaggtca gcctgtgtat tgtcgtgtct ttttttcgt   144600 tctcatgatc gcggagacca cacagacgtg cgcgtctccc aatggctagg cgttctttt   144660 aggtagtaat tttttgatct tttttttttc ttaacaagtc tggcttgatt tctttatct   144720 atgatcgatt cttctttttc tcgggggttg catcttccgt gaaagtaaag tgacactact   144780
ctaaatggta accatattat ctgttgatta ggagaaaaaa taattttttc gcacgaaatc   144840
gatcctaagt gaggtgattt acttgctatc acacgaaatg attctttgc tgctaacgta   144900
```

```
ctgaattttt taacagaatt gcttctccgt aactatttcc gcagattcag acagattgtc 144960
aaaaaaaaaa tacggcacag aaatagtggg tctgtggctt ttggttcgtg tacattcgcg 145020
tttgcgtgtc gagatttcta cggtatgttt attcttcctg cgatgatgta gggtccttgg 145080
tgtaagtagg atttcgagta tctctcttag agcgaacaaa ataatcaaaa aacaacagct 145140
aggaaatcga gggttactct acgataaagt gtctctacaa agtgaagaat gttacgttgt 145200
ggtggaataa taagactcgc gtgatcgatg agtgatcgag agcggctcga accttcttta 145260
agagctttgt ttagtgcaac tttaaattac aaggagtaga aagctgaaat gaatctatga 145320
aggtgctatt ctttgaatat cttactttgt acgcttcaca ttcgttattt ggatagagag 145380
ttgtctagag aaaatctgtg attctctatg agtgttattt ttattatcct tttggggact 145440
acgattttc ttcttctaca taccactact actcgtaatc acatacatgg acgaaaaaaa 145500
aattcgtcag gcagtagata ccagattctc cgacgttacg gcgtcttttt ttcttttgag 145560
agagtatctg ctgagattgt ccgtggtgta tctagtcgct attttttgttg ttactagtag 145620
ttttgcacac agtttattca gtatagtttt tcttcttgcc atgatcaatt gagcccacca 145680
ccttttttt aagagaggag gaatttcgtc ttgatctcca gccggagata acggcggtgg 145740
tggtggtggc gggagagact tcaaggcaat gaaaaaaaaa atttcgtttt gccatcaagt 145800
ggtgacgata acccgtcaga ttgataattg gttcctacag aaactattct aaccgcgaa 145860
gaaagaaatt gaaaaaaaaa attgacaaaa acatcataac ataaaggacc acctacctgg 145920
gacgcgcagt tgggtggcgg actgggcgg catgctgcgg cgatgctgtc ggtgatggtc 145980
tcttcctctc tggtcctgat cgtctttttt ctaggcgctt ccgaggaggc gaagccggcg 146040
acgacgacga cgataaagaa tacaaagccg cagtgtcgtc cagaggatta cgcgaccaga 146100
ttgcaagatc tccgcgtcac cttcatcga gtaaaaccta cgttggtagg tcacgtaggt 146160
acggtttatt gcgacggtct ttcttttccg cgtgtcgggt gacgtagttt tcctcttgta 146220
gcaacgtgag gacgactact ccgtgtggct cgacggtacg atggtcaaag gctgttgggg 146280
atgcagcgtt atggactggt tgttgaggcg gtatctggag atcgtgttcc ccgcaggcga 146340
ccacgtctat cccggactta agacggaatt gcatagtatg cgctcgacgc tagaatccat 146400
ctacaaagac atgcggcaat gcgtaagtgt ctctgtggcg gcgctgtccg cgcagaggta 146460
acaacgtgtt catagcacgc tgttttactt ttgtcgggct cccagcctct gttaggttgc 146520
ggagataagt ccgtgattag tcggctgtct caggaggcgg aaaggaaatc ggataacggc 146580
acgcggaaag gtctcagcga gttggacacg ttgtttagcc gtctcgaaga gtatctgcac 146640
tcgagaaagt agcgttgcga tttgcagtcc gctccggtgt cgttcaccca gttactttaa 146700
taaacgtact gtttaaccac gttgcgtcgt gacgttgttt gtgggtgttg ctaggcgggc 146760
tggaaagatg atgtataaat agagtctgcg acggggttcg gcgctctgcc ggctgcggcg 146820
gcactcgctc cacggcctcc gacgagcgtt gcgctcgcgc tttgcgccgc gcgtcatgg 146880
atctccctac taccgtcgtg cgaaaatatt ggacttttgc gaatcctaac cgcatcctgc 146940
atcagagcgt caatcagact ttcgacgtgc gccagttcgt ctttgatacc gcgcgtctgg 147000
tcaactgcgt ggacggcgat ggcaaggtgt tgcacctcaa caagggctgg ctctgcgcta 147060
ccattatgca gcacggcgag gcttcggccg gtgctaagac gcagcagggc ttcatgtcca 147120
ttgacattac gggcgacggg gagctgcagg agcacctgtt tgtacgcggc ggtatcgtct 147180
tcaacaaatc cgtctcctcg gtggtgggct ccagcggacc caatgagagc gcgctgctca 147240
```

```
ccatgatttc cgagaacggt aatttgcaag tgacttacgt gcgccattac ctgaaaaacc 147300
acggcgaatc ctccggtgga ggcggtggtt gcggcgccgc gtctaccgcc tccgccgttt 147360
gcgtgtcctc gttgggcggc agcggcggga ctcgcgacgg tccttctgcg gaggaacagc 147420
aacggcgaag gcaggaacag cgtcacgaag aacggcgcaa aaagtcgtcc tcgtcggccg 147480
gtggtggtgg aggcggcggc gctggtggtg gcggtggcgg cggcgggagc ggcggtcagc 147540
actcctcgga ctccgccaac ggactgctgc gggatccccg gttgatgaac cggcagaagg 147600
agcggcggcc gcctccctcc tccgagaacg acggtgagtc ccggccctcc tcgcgtcacg 147660
gtgctttccg agtggactcg tgagcccccc gtagcgcacg agcgagcagg cgagcggtgt 147720
tggtgcgctg gtggttgtgt ggatgataac catgtgcttt ttcgtgcgct atgtgtcgtc 147780
ccgtctgtag gctctcctcc cctccggag gcgaagagac aaaagaccac cgcacagcac 147840
gaaggccatg gcggcggcgg caagaacgag acggagcagc agtccggtgg tgctggcggt 147900
ggtggtggcg gcggcagcgg ccgcatgtcg ctgccgctgg acacgtctga agcggtggcc 147960
tttctcaatt actcgtcctc atcctccgcg gtctcttctt cctccaataa ccaccaccac 148020
catcatcacc accataacgc cgtgacggac gtggccgccg gcaccgacgg tgcgttactt 148080
ctacccattg agcgcggagc ggtggttttcg tcgccgtcgt cgacgtcgcc gtcgtcactt 148140
ctttcgctcc ctcgacccag cagcgcccac agcgcgggcg agacggtgca ggagtccgag 148200
gcggcggcga cggcggcggc tgcggggtta atgatgatga ggaggatgag gagggctccg 148260
gctgaggcgg cggaggcacc accgcagtcg gaggaggaga atgattccac cactccagtc 148320
tctaactgcc gtgttcctcc gaattcgcag gaatccgcgg cgcctcagcc tcctcgcagt 148380
ccgcgttttg atgacattat acagtcattg accaaaatgc tcaatgattg taaggagaaa 148440
agattgtgcg atctcccct ggtttccagc agactcttgc cagagacgtc gggcgggact 148500
gtcgtcgtca accacagcag cgtcgcgagg accgccgcag ctgtctccac agccggcgtt 148560
ggccccccag cagccgcatg tccgccactc gtcaccaccg tgttgtacc ctcaggttcc 148620
gtcgccggtg tcgcgcccgt tgccgccgca gtcgaaacac cagctgctcc tccccggccc 148680
gtgtgtgaaa tcaagcccta cgtggtaaac cccgttgtcg ccaccgccgc ggctgccagt 148740
aactcttcct cgtcttcttc ggctccactg ccgccgccac caccaccgcc gggcggacgt 148800
cggggtcggg cccggaacaa tacccgagga ggcggcggtg gtggcggtgg tagaaacagc 148860
cggcggcagg ccgcatcgtc gtcgtcctcc tcctctcgga gatcgcgacg gagaaacaac 148920
cgccatgagc acgaggacaa cgatcctctg ctccggttgt cgcaagtcgc cggcagcggc 148980
cgccggcgag ggccctcgtt cctcgaggac ggactcgaaa ttatcgatcc cagcgaggag 149040
gctgcgatcg ccgccgcctc gatcgcggcg ttttttcgacg attaaaaaac agagccgaga 149100
ccggaaaaat tatgaaacag gacgcgcttg gacatttggg tttccacccc tttcggtgtg 149160
tgtctatata tattgtggtc actgattttt ttttacaata aagagatgaga catcacagtt 149220
caccaccttg tctccccggt gtgtctatta tcatcaatca cccacagagt cgccagtcca 149280
tggtctctcg gtaatgcgtg tccagatacg cgttggccag tataaagtgg tcgttgccca 149340
cgaaggcgcg ggtggtgttg cgcggcgacg ggtggcagga cttgagtacc aagtgccgcc 149400
gtcggtcgat caggtactcg caggtgtgcg cgtcggcgcc ccacagcatg aacaccagat 149460
gctcccggcg ctctgacagc ctccggatca catggttact cagcgtctgc cagcctaagt 149520
gacggtgaga tccaggctgt ccgtgcacca cggtgaacac ggtgttgagc agcagcacgc 149580
cgcgtcgcgc ccaggcgtcc aggcaacccg aggccggacg ctgaaacccg tccaccgtac 149640
```

```
gcgccagttc gcgaaacacg ttgttgaggg agggcggcgg tggtcggcct gccagcgtgc    149700
cgaaggccag gccgctggcg ctgccgtcgc agtacgggtc ctggcccacg atcaccacgc    149760
gcacctgctc gggcggacac agatagctcc agcggtgtac gtgctcgggt gccgggtaca    149820
ccatctcgag ttgccgcgcg ccctccaccg ccgccaccgt gtcgcgcagc agcaccgtgt    149880
cgtggtcggg caagctgagg aagcggatcc agtcggcgct cagacaaaac acgcgagcct    149940
gctcgtcggg ggttaacaga gagcctttat tatcagcaat gttagcgagc atccactgct    150000
tgagggccat agcgcgagtg agccggcagg ttgacgcgcg tctgcttcag ctcgggcggc    150060
agtccggcgt agtatttatc taggtggcgt agcagcggcg ggtccagctg gtgacgcagg    150120
caaaattcct tcactgcgtt gtacaggccg taaagagcg tgatgccctc gggcgcggca    150180
gcggtgctca cgggcagacg cacggcgcgg ttggtacgcg tggcttcgtt gcgtatggcc    150240
accaccacgt taaagagaga cggtggcacc agctcgaagc ctaacacgtg ttccgtgaag    150300
atgctgcgcc cgtatgacag tcgcgtgagg tcgtagccgc ggcacaggtc gtccacgcac    150360
gtgtacacgg ccggcgagcc atcgccgcac tcgctgtagc cgcgcatcac cgtcatccag    150420
cgcggcgctg tgtccgagct caacagtgtc agcagggccc gcaattgatc cggattgttg    150480
tacagcaggg ccagagtgtc caggaaagca tcgtccaaca gcacggagtt ggcggcctcc    150540
ggcgtaacgg gacggtaacg gataagttgc gatagcgggc cattgcgccc ggtaacattc    150600
accaacggac gcagccaact ttcatacttg tcaccctgaa acacctcacc caacaggcat    150660
cggcgcgtta gttcgggaca ctccgcgggg actttctcgg cggcgtagg agcgacgctg    150720 acggcgactg aggaaacaat gggcagcaga aggcaacacc acagcagtac caccggtcca    150780
ggtgagaaag agaagccgca atccgggcgg cggcacatca agtctgcggc acgatgagag    150840
tgtgacggta aggagccagt tggcgccgaa agttggcgct caggtcttcg atccctaaaa    150900
cgttatatat tgcatccagc aggtgagcca ggctaaacgg attcacgtac caggtttggt    150960
tacccgcgac gatgacggcc agaccgtggg cgctacagtt ggagaggttc ctgggtacga    151020
aggtaactga gtcgatgtcg cgccacgggg ggaatgagac agacgactgg cgcacgctgt    151080
aatcacaact gtgattgacg tattgtagcg tgtaatttag gttgcactca gcctcgaagt    151140 agaggggaa ccacagttcg tcgtactcgt cgtcgtcctc cagttctggc tcttcttcat    151200
ccaccgcaat gtctacgctg ctctgagatt cctcttcgta caggatgatt gacaggttat    151260
ggctacaaag gtcctgggcg ggaggacgcg tgggagcgcg ggtggtggta atgttttcca    151320
ggtcaaaagt tggagtgtag tcggatgtta catccccgtt gttggaggtg gtagaagtcg    151380
cggccggtgt cacggtggta agtatggata cagaagggga gggggaagta acgttcgtac    151440
cgatggttgt ggtattatta ttccttgtgt ttcttgttcc agaaaccgtt gacgttgaga    151500
tgggaatcga cgtggcgctg gatgtcagat tgctgaccga ggaaaccgtg gtgggagtga    151560
tgacggtgtt actcgtggtt gaagtgacgt taggggaggt agtagtggta ccggtggtgg    151620
cgacggtagt gtttgtcgtg gcggcggcag cggtggtact ggtaacggtg gtcgcgttgg    151680
tttccaccgc ttcacacagt aagcaaaagc acagggccag gaaaagcaac cagccccgcc    151740
atcgccgccg ccgcttcatg aggtgggcag gcgaaagctg gtgaattcgt tgtacagcgg    151800
caagtggggc gccgcgatcg aagggtacgt caacaagctg acgttgatat taaatacgtc    151860
tggctgcttt tctacgatgg aagcgcacag ggttacggcg tcgaacaggt ctttcttggt    151920
ggcgcccgag acccacatct ggtatacacc cgtctcgtgg tacgaagtag agcgcggcac    151980
```

```
caccggacgg atgcagtcca gaacgcggtt gggatcctgg tgaaagaatt tgaacgtggc   152040
tacggcctgt ggcgtgtgcg gcatcgtctg cgtgatgagc tgctggcccg ctaacacggt   152100
gacgttgtgc aacttgagca gggcactctt gagggcctgg aaagcgttgc cgcacgaggc   152160
gctgatttgc agctgcacgg ccgtggagtc gtgcagccgc atgagacgtg acacctcttc   152220
gaagacgtac ttatacttac tggcaaagag tggcgcgtac cgacagtcgg ccggcaaaat   152280
gtaggtggcg ttgccgccgt tggtggccac ggcgggcgca gcggccgcgg aggccggcgt   152340
aaacagcgtc agcggccggt ggtggctggt aaggtcgatc atgggcggcg tggtgaccgt   152400
ggcggtggcg ggcatgacgg ggtttgcggc gacgggcact ccggccacag cggcggcagc   152460
ggcggccacg gcggcgctgg ccgagcccac acctgccggc agtcctccgc cacccatgac   152520
gccgccgggc agagcgtcgc ccagacagac ttccacagtg gcgggcgcgc tctcggcggt   152580
cagtacggtt tgccgatcga cctcgcgacg aaagctggtg aggaactcac tatgatccat   152640
ggccgcaggg cccgagatcc cgggattctg cgggtgctga ccgagtgcgg gccgagttat   152700
atggaagacg attagcttgg agcggagttt tgcgtcccta gctgacctgc ggatcagcga   152760
cgtgccatag ggatagactg tgagcggcgg ccgcaacggc ggggtcggcc gccgttcgtc   152820
gtcacggggc ggcgcgaggg aggaggaggt ggtggtgggt acgatcttga cgtggttaac   152880
gtcctgcccg tccgggggaa tacgcaaaaa accccgccgc ggcgctacca cgatggtgcg   152940
atgggtcttt ctcttgttgg ccggggccag ggacttgcag atgcgtgtgg agccgtagac   153000
gatctggacg tggtcctggg agaacatgac catcgccgcc aacgctcagc gggggacgg    153060 gttgggaaca cagaggctga ggggaaaccc cgtagaagtc agcgaaataa agacaacaca   153120
gcagccgctc ctctcgtttc gggccctacc actgcttgaa gtagggcacc gggtgtttct   153180
tttcttcaac gggctcctcc agtctcttat aggaccagtc ccgccggcgc gccagcatgt   153240
aggtcacgta caaaagaata attaccatga acaccaggaa agccagcacg ccgtaggcca   153300
gcagccggtc ctcgaacagc gggtcgctct tgataaacac gtaggtggtg gtaaaacttc   153360
ggcccgcgat ctggacgtgg agacgcacga cagtatacgt gccgttgagg tagaagacaa   153420
actcgcgtaa ccgttgtccg ttatacgtca cgttactaat attccacggc ggaatgagct   153480
ggtcgccctg atgcagatgc acggtgctgt tggggtgata gaggctgcta ccgttgagca   153540
agcagtgttc gtgttcctga agcagcacgc ggacccgcat cgtggtagcg ttcaagcgag   153600
tcccgtacac ggcgtaaatg ggataggtga aaaggtccca agtggcgttg tgatggcggc   153660
cccaactgaa gaaagagcac gtgtactcag tggtctcctg cggcctgagt cccgagataa   153720
gcagctcttg agcagtagcg ttgtaggaga gatgtagttt tcctgtggaa aaaattaatg   153780
agttgtttat tttgttagca ggttggcgag ggaggaaggg gaacaaaaca gaaaggtacg   153840
tgttacttac ctttatcgtt ggagggaaaa gcgctaagat atcccacctg agtgaaggga   153900
cccttgcagt ctgtccgtgc ataacaagta actgataaaa tgtctggatt tttggtatta   153960
ttcaacagga taactttgca ggtggcgttt agagacactt ggtcgtagct gtagctggct   154020
tcgcaattca cagtatacag gtgcccctct ttctgcgtcg tggctatcac ggaggtggag   154080
gcggacgagg tagaggtttg taccgtggtg gtgcagcag aactgacgtt gttagaggta   154140
cttattgacg tagtagacgt gacggtggta ttactagggg aagtgacggc gcttgtggtg   154200
ctacttttca ctcccgggtg catgtcgccc aagagcgcaa ctacgagcgc gatcgccagc   154260
acggaacaca tgttgccgtg tgacgagacg gcgtgtggac gagctatatg tggcaggagg   154320
tcgcgtcacc tcttgtgacg cctaaacgtc cagctccaga taaaagaggc gttaataatg   154380
```

```
aagactacaa aaaccacttg cgtcagtatg acaatcataa aggctcggtg attgctacgc   154440
ctaaagtacg cgggattatc caccagttca tccttctgaa caaagtggat gattgacgta   154500
ttggtgttac tatccgtatt gttgatcatg gatttgacta agaaagtctt ggcaccaaaa   154560
gtcccgttag agcccagca ggtgacgctg ctatttacat aagttccagg tgccccgct    154620
agcatgtatt tcagttggtg ggtataattt tttctgtcgt tatccatgtc attgctgtag   154680
ttgaccttgc tggtgagaaa gcgtgttttc aacggggtac ttatcatcat ccctgaggcc   154740
aaaaagggcg aattgcaagc tgtagtgtta caaaaaatag tcaagttagt gtcattgtgt   154800
tgatacatgt aagccatgct cacttcaggc tcataccacc cgatcccaat cgcggccgcc   154860
accgtcacca cgtcccatct ccccaaactt accaccgcca ccactaatag cgtcacccc    154920
gcacggtaca tagttaccct ctcgacgtcg ccggctgtca atgacgtgcc tgcgtcagtg   154980
gctatgattt atagcttttg gacacaaccg caacggatct gtcgtaatct accttccaca   155040
gggccgccgc gacgatgctg aacgacagga tcagacagac ggcgtatagg agtcctaggt   155100
cggcgtcgac gcggcaggtg cggatgtctc gcagggtggg tagatgggcg atgcacaact   155160
ccttctcccc ccgcccgtac atctcatccc gtatcagcag ccgtagcgtg cattgatgg    155220
tcagcggggt aaccaaagaa atcacatagg gatgtgtaca ggaagtgcag tgacgggtat   155280
ccgtgagatg taagtcatca ccctcctcac cgtcatcatg aaagaccagg actcgggtga   155340
gacgacccga tgaatactgg atctcccacc acagtctttg atccaacacc gagagggcgc   155400
aagagattct aagtctccct gggttgggtg agcagatgta agcccgtat ggtgcctctcg   155460
ccatcagggc tatacacatg agggggagaa ggacaagtat ccgggaccac ccgcacccc    155520
acatcacgag accagagaca gagatgtata aaaaaagcta cttttattaa acagcattct   155580
caccacacgt taatactgtc acgggaatc actatgtaca agagtccatg tctctttcca    155640
gtttttcact tactgagact tgttcctcag gtcctggatg gctgcctcga tggccaggct   155700
cagggtgtcc aggtcttcgg gagggtctc ggtgggctgc tcaaactgcc ccacggcgta    155760
ggccttcgcg gccgtctcgt agataggcag catgaaccca ccctggttgg tggagaagat   155820
gcgcaccatg acctgtttgg gaaacttttg catcaggggt aggcacaggt tgagagcgcc   155880
caacaggtcc acggggtgg cagcgtggat gatcatgttg cggtaatcgg aagaacgggg    155940
gcataattgg tgggtgtgca attctttgag gctccacgcg gctttgacgc cttcgttaca   156000
agcatcggcc gtgcgctgcg ccacttcggg tgggtgtgtc acaggcatgg tgtgctccat   156060
gaggaaggga gtggagaggg ccaggttgca catggtgccc aggcgacacc gcaccgcatc   156120
cacctcactc ttcacctcat gattgcgggt gtagatgatc tggatgccct tgttgttcac   156180
ctgcatggtt ttgcaagctt tgatggcctc atctaacacc tggtccatac tgggaatcgt   156240
gaagggcagg ttcttgtact caagagagcg attggtgttg cggaacatgc ggctcacctc   156300
gtcaatcttg acgcgacccc gccgagtctg cacgttgggt gtgcagaagg gggtgttctt   156360
atctttcatg atattgcgta ccttctcgtt gtccaactcg gagatgcgtt tgctcttctt   156420
cttgcgggt ccggtgctcg ccccgccgct gctctgatgg ccgcagctca gcagagagga    156480
ggaggccgcg ccaccaaaac cgccgcgccc atggtggctc gaggtcacgg atgctcctcc   156540
gccactgctg catttcatct cctcggactc actctccgag tccgaagccg aactgcagga   156600
ggaggaagac gaagaggaac tatcttcatc gggccggccc aagggatcgg gaagaggagg   156660
gtggttcatc tgggagagcg ggtgcgtggg agaggtcact cgcggcgtgc cgctgccggt   156720
```

```
ggaagggaa  gacgcggtag  caccgcgggt  ttcgacttct  tcaccctgtt  cttcctcgct  156780
atcagagatc  acgatacagc  cggcggtatc  gataatcttg  ttgcggtact  ggatggtaaa  156840
gtcgggctcg  ggcttgatgt  cttcctgttt  gatgaggggc  agcatgatag  gcgcgggagg  156900
cacgggcggt  ttaataatca  ccttgaaagg  acgcgtggtt  ttgcgcggtt  tcttacgcgg  156960
gctgagctcg  ggagtagcgg  atgccccggg  gagaggagtg  ttagtaaccg  cgacgctggt  157020
gggggtcggc  ttgttaagag  gggcgctgct  aacgctgcaa  gagtgggttg  tcagcgtggg  157080
gccggtgcta  ctggaatcga  taccggcatg  attgacagcc  tgggcgagga  tgtcacctga  157140
tggtgataag  aagacacggg  agacttagta  cggtttcaca  ggcgtgacac  gtttattgag  157200
taggattaca  gagtataaca  tagagtataa  tatagagtat  acaatagtga  cgtgggatcc  157260
ataacagtaa  ctgatatata  cacacaaatag tttactggtc  agccttgctt  ctagtcacca  157320
tagggtgggt  gctcttgcct  ccagaggtgg  tgggttcctc  agcaccatcc  tcctcttcct  157380
ctgaggcaac  ttcctctatc  tcagacactg  gctcagactt  gacagacaca  gtgtcctcct  157440
gctcctcctg  agcaccctcc  tcctgttcct  catcactctg  ctcactttct  tcctgatcac  157500
tgttctcagc  cacaatcact  gaggacagag  ggatagtcgc  gggtacaggg  gactctgggg  157560
gtgacaccag  agaatcagag  gagctagcac  cagcggtggc  caaagtgtag  gctgcaatag  157620
catcttcctc  atctgactcc  tcagcgatgg  cccgtaggtc  atccacacta  ggagagcaga  157680
ctctcagagg  atcggccccc  agaatgtact  gggcaaagac  cttcatgcag  atctcctcaa  157740
tgcggcgctt  catgacattg  ataacctcag  gcttggttat  cagaggccgc  ttggccagca  157800
tcacactagt  ctcctctaag  atatagcagc  acagcacccg  acaaaactca  cttaagagag  157860
agatggaccc  gtacatggtc  atcatacaag  cgtcactggt  gaccttgtac  tcattacaca  157920
tggtttccac  acatgtagtg  aggatatcca  taaatatgtg  atcaatgtgc  gtgagcacct  157980
tgtctctctc  ctcatccaaa  atcttaaaga  ttttctgggc  ataagccata  atctcatcag  158040
gggagcactg  aggcaagttc  tgcaatgccg  ccatggcctg  actgcagcca  ttggtggtct  158100
tagggaaggc  tgagttcttg  gtaaagaact  ctatattcct  gtagcacata  taaatcatct  158160
ttctcttaag  ttcatcctt  ttagcacggg  ccttagcctt  cagtgcaccc  cctaacttgt  158220
tagcggcgcc  cttggtcaca  tcatgcagct  ccttaataca  agccatccac  atctcccgct  158280
tatcctcggg  tacaatgtag  ttctcataca  tgctctgcat  agttagccca  atacacttca  158340
tctcctcgaa  aggctcatga  accttatcta  agatatctaa  ggcattctgc  aaacatcccc  158400
ccatcatatt  aaaggcgcca  gtgaatttct  cttccgtctg  ggtatatttt  ttcagcatgt  158460
gctccttgat  tctatgccgc  accatgtcca  ctcgaacctt  aatctgtttg  actgtggagg  158520
aggataacaa  cacatataag  tatccgtcct  cctgactcat  ttatcgctac  ctcgatgccc  158580
cgctcacatg  caagagttaa  tcttcactct  atctgacata  cacaagtaaa  tccacgtccc  158640
atgcaggtta  gtatatatca  catacatgtc  aacagactta  ccgagttctg  ccaggacatc  158700
tttttcgggg  ttctcgttgc  aatcctcggt  cacttgttca  aaggttttga  gagattcttc  158760
ggccaattct  gggaacagcg  ggtctcccag  gctcagctga  ctgttaacct  ccttccttaa  158820
catagtctgc  aggaacgtcg  tggccttggt  cacgggtgtc  tcgggcctaa  acacatgata  158880
aacaaagtca  taagcacatg  ggtcacatac  agaaaatatg  tatataacat  taaagatata  158940
acttttatt  aaaaaagggg  gaacacaagt  cccgacacgt  accgtggcac  cttggaggaa  159000
gggcccctcgt  cagggttgtc  agggtccatc  tttctcttgg  cagaggactc  catcgtgtca  159060
aggacggtga  ctgcagaaaa  gacccatgga  aaggaacagt  ctgttagtct  gtcagctatt  159120
```

```
atgtctggtg gcgcgcgcgg cagcaacgag tactgctcag actacactgc cctccaccgt  159180
taacagcacc gcaacgggag ttacctctga ctcttatcag aacacaacaa ctcagctgcc  159240
tgcatcttct tctgccgctg ccttaagtct tccaaatgcg tcagcggtgc aagcccgctc  159300
cccgagctca ttttcagaca catacccTac cgccacggcc ttgtgcgcca cactggtggt  159360
ggtgggcatc gtgctgtgcc taagtctggc ctccactgtt aggagcaagg agctgccaag  159420
cgaccatgag ccgctggagg catgggagca gggctcggat gtagaagctc cgccgctacc  159480
ggagaagagc ccatgtccgg aacacgtacc cgagattcgc gtggagatcc cacgctatgt  159540
ttaataaaaa ctgcgggtac tggggacggt gttgttgtat atgtgaattt gtaaataata  159600
aatgggaccc catcctgtaa aaatacagag tccgtgtcag tctctgaagg acagagtatt  159660
ggcatatagc caataaagag agttgtggca aagagccatg ttatggatta gtaatggaaa  159720
gtatcgtcac caatagggga gtggtcaata atggtcaata acccacacct ataggctaag  159780
ctataccatc acctatagca taaggaagcg ggggtgtata gacccaagc caaaaacagt   159840 atagcatgca taagaagcca agggggtggg cctatagagt ctataggcgg tacttacgtc  159900
actcttggca cggggaatcc gcgttccaat gcaccgttcc cggccgcgga ggctggatcg  159960
gtcccggtgt cttctatgga ggtcaaaaca gcgtggatgg cgtctccagg cgatctgacg  160020
gttcactaaa cgagctctgc ttatatagac ctcccatagt acacgcctac cgcccatttg  160080
cgtcaatggg gcggagttat tacgacattt tggaaagtcc cgttgaattt ggtgccaaaa  160140
caaactccca ttgacgtcaa tggggtggag acttggaaat cccgtgagt  caaaccgcta  160200 tccacgccca ttgatgtact gccaaaaccg catcaccatg gtaatagcga tgactaatac  160260
gtagatgtac tgccaagtag gaaagtcccg taaggtcatg tactgggcat aatgccaggc  160320 gggccatttta ccgtcattga cgtcaatagg gggcgtactt ggcatatgat acacttgatg  160380
tactgccaag tgggcagttt accgtaaata ctcctcccat tgacgtcaat ggaaagtccc  160440
tattggcgtt actatgggaa cccacgtcat tattgacgtc aatgggcggg ggtcgttggg  160500
cggtcagcca ggcgggccat ttaccgtaag ttatgtaacg cggaactcca tatatgggct  160560
atgaactaat gaccccgtaa ttgattacta ttaataacta gtcaataatc aatgtcaaca  160620
tggcggtcat attggacatg agccaatata aatgtacaca ttatgatata gatgcaacgt  160680
atgcaatggc cattagccaa tattgattta cgctatataa ccaatgacta atatggctaa  160740
tggccaatat tgatgcaatg tatatatcga tatccattgg ccatgtgcca actcgatgtc  160800
gcctctatcg gcgatatggc ctcatatcgt ctgtcaccta tatcgaaact gcgatatttg  160860
cgacacaccg aatcgcccaa gtcgccaaag tcgtctatcg ccatccccg taaacgatat  160920 aagcgctatc gccagatatc gcgtatgccc aaaaatcact tttggaaaaa tggcgatatc  160980
agttacacag aaactcacat cggcgacatt ttcaatatgc catattttca aatattgatt  161040
tttccaatat cgccatctct atcggcgata aacaccacta tcgcgcgaca tgaatttagt  161100
cggcgacaga aatctcaaaa cgcgtatttc ggacaaacac acatttttatt attcactgca  161160 gcatatagcc cattttagcg cggcacacat ccagccgttt gtgtttctta acgctctcca  161220
ggtactgatc caggcccacg atccgggtta tcttgtcgta ttccaggttg atccatcgat  161280
agggaacgct gccagcggcg cccagcaggt actgcgcctt gtcgttcact ttgccgcagc  161340
gtattcgccc gtcagcttcg aggtataacc tacaacacgg aagggggta caaaacgtga  161400 aattagactt ttttttttaa tgatgttttg tccctctctg tcttactctc ccataggctg  161460
```

```
taaggccctc gaggaagaga cttacggatt gtagttgcag ctcgtcagtt tgttgtgtac   161520
gacctggcgt gtcaatgaat gggtcatggt ggtgacgatc ccgcgaatct cagccgtttt   161580
ctcgggactg tagcagactt cgccgtccgg acaccgcagc ctgtgtattc atgaaaatct   161640
actctggcat tcccgaggat cgtcgatgga acatggctat cagaaacgtc gagagacaga   161700
tccagacgca ccacagaacg cagacaatca tgaaaatacg tacgcgacgg tgaagcgatt   161760
gcacattttg aaatcgtaac agcgttccgg cgggtggttg acgtttatga attcgcaaca   161820
ttcttctgcg cgtacccgcg gcacgcggct gtgatccaat aacagccaca acgccgtcaa   161880
gaacggcgtc aggttttggg gactcatgac gcgcggtttt caaaattccc tgcgcgcgcg   161940
acgggctcaa acgatgagat tgggatgggt gcagaaggtg taagtctggt tattggcctc   162000
ggtgaacgtc aatcgcacct gaaaagacac gctgtagtcc cggaagacgt gagcccagct   162060
ctccagcttc atcacacaca tctgataacg tgtgccatcg ttgacgacga agcgtagcag   162120
cttggtctgc ttgggcacca tgtgcgctcc aaaaatcttg gcgtcttcca cgctgatctg   162180
cacgtttccg tcgctcggtt ttgaagccgt tcggggcatc cgttggagga tggtctggtt   162240
gcgaccgctc aggtaccaga tcacctttt cacccaggtg gagcttctct ccaccaaggt   162300 ctggcccttcc cggttgtaca gcagatacag ggtctcgttg cgacactcgg gacccgttaa   162360
tacccgctgg aaccccgaga attgcaaggg ggaccgtggg ggcgagggat agataaaagg   162420
acagtaaaac gtcgccgcgt catgcggttt ggaatacgtc agtttagacc atagcgggga   162480
cggattctgg ttcgccgtta gcgttgacca cggagacgcc agacagggcg ttgcccaaac   162540
cgcgcacaga agcaggcagt gaaagtggtg acgaagcaga agccgtagca tattatttcc   162600
cgtgacgcag gctagttggc aaagagccgc acgctgaact cgaggctccg ggcgtgcggc   162660
gccagcgaac cggcggcgtt gaacgtggtc cttttgttgg tgccgccgcg acggttctga   162720
cgtctaaagt cgctgatgag caacgacacc tcggtcacgt tgattctgca agcacaggtt   162780
ccgaacgtca tttcacaccc catgcggtta cctgcccgtt acccgttcgc ccttaccttc   162840
ccgttgtcat acacctttag cgcgtatcct cacctcttga gcacgtcaaa gttgtccaag   162900
ccgtggctcg catcgtagtg gtagttcaac gtgaggtcca cgagctgttc cacatacttg   162960
taacgggttt ggtcgggcag cgcgcgagag cacgcgtccc agtaatgcgg tactcggtaa   163020 taatcgttttt tttctgcggt ctcccgctgg cactgaccca gcaccacggc gcacagacaa   163080
acagacagcc acacccgaca cagccgcatg ttgcagactg agaaagaaag ctttattatg   163140
agacatcata cacatagtat aggcgaggtg atgggcggg gaaagagttg gaaccgaaag   163200
ataaaaaaaa aaaagcctag tcgtactcgg gatctctgag cgagacgggt tgcatggcaa   163260 cttttcattag tttgggaatc tgccagctgg tgctgttcga aggttcttcc atttccgagg   163320
cggtcagttc atcgtacacc gagacgtagt acctgatggg gtcttcctca ttgtccgaga   163380
ggtgagattc gatggtcaaa ggcgagcctc tcccataatt gggattcacg aacgacgtgt   163440
ccaagttgcc atccttctg aaatagatga cgttctcagg atcatgtttc atgcgctcgc   163500
gggccgcgga cgcctcctcc tcctcgtccc agtcccgagt ttccaaccgc tgataagggc   163560
tcgaggaaca aaatccggcg gggatctgag aacctcgtcg gaaccgctg ccaaacgggc   163620 tgccaccgcc actgtcgtcc gtgtcgtcca acaggttgac ggcttcttcg tcggcgaaac   163680
gaaagcggcc cgggtgcttg caacacgagg agtaaactac cgcgatcagt accgctatga   163740
agctgaaaat ggaggtgcct gtcacgatgt agaagaggat agccagcact ttcatgattt   163800
cgtcattgcg cacgctgtga acggaagact cgtgggtggt ggtcatgttg atcccggtcg   163860
```

```
tgggtccgct actcgtggca ttgtcgacgc tatttctgct gctggtgcta gtagggactt   163920
ttgtgctgct ggtcacattc gtagcgtcgc tgaggtctat ctgaagcagc aacccgaacg   163980
cgaccagggc caggaatgtt gcgcgaaggg accccgcgg ggccggcatt ctcgagacgt    164040
ggcgacgtgg atttcttgct atgtccgcga acgacgtgtg acgaggacgt ggtttccgca   164100
agcctctacc gacgccgcga caccaggtag gttatcaaaa cgcgagccca tatcgccgcc   164160
atcattgtaa tcagcaatgt gttgaggtac tgcacgatga atctgtctag tgacaccagc   164220
caaccctctg cttttgcggg caagcgcgct ttcggtgaca gggtgtatcg tacgtagccg   164280
cgggtcaggc gcgcgttgta gcggtacacg cagaaatcta tccacaggcc aacgcccggc   164340
tgtagcttcg gatggtggat aatagcgcgg tgacgtacgc cgcggggctt tagaatctcc   164400
acctgtaagg ccatctcctc caggtagtgg gtctgactgc gacgcagcgt ccagttcatg   164460
taaaagtcgg tctcgccgtg tccggccacg aagaggctgc ttactaaatc gggcgccaga   164520
gctaggtcag gcgtatcaaa ttccactgcc aggcgacctg attctaacgg ttccacgatc   164580
cgggagagcg tctctagata tagagcaaag cgtaccacgt ctacctgcgg tgtaaaaaac   164640
tgctgtgggc gttcaccgtc gttgaccacg taggccacgt agaggccaac attttccacc   164700
acgggttcta gctgcaggcg gcacgtaaag cttagaaacg acggctgtac ggtttggttc   164760
ccgtgaagct gaagcgtcac ttccttgccg gggctcactg tgctgtaacg ccgcaccgag   164820
tcggtcatct gctccggatc ggtagaccag aagggcgtgc aatgcatact gtcccagtcg   164880
cgacacgcag cccagcctag ctcggtgaag ggtcgacgca cacccgaaaa agtgtgcttg   164940
aagaccaggg ggtcgcctcg gtagctcaat agccgaacat gcacatagtc gcggctagca   165000
ttgacagacg gcccgtggag ggccagcagg acgagcgtga acagcaagcg caacatgctg   165060
cgcgggttag gaaatgcggc gtgccggcca ccgcccgact cataaacact accagcatga   165120
cgtctcagat cacacaagtg acgaggagcg taccgcaaat cactagggaa aaggccagca   165180
gagcccgata gtcttgctct tcgcgaacga tctcgtccgg ttcctcacac tcttcgtggt   165240
ccacagaaga tgaggagcag gaattttcgt taatctctgc gaggatacta gtgctgtacc   165300
acaccagagc gcttagtgtg cccagagcta ccgcacggta aaatagggac atgatcacca   165360
gcgcagtctg aagtggtggt agttcaattt cttggcgtat ttccagagaa aggctttgta   165420
ggccgtaggg gctggccagg caccaaactc aatattggta gacactacgt cgtaaatgcg   165480
ttgttcttcg tctaagatta accgaaaaaa tagccggttg atgtgacgac gcacagcttg   165540
cgcgttagga ttgagacact tggtgccctt gtcctttaaa atagccagca cttcctgacg   165600
attgcagctt tcgctcgctg cgattggctt aagcagttga gttccgactg gcagggtatt   165660
caacagaatt tggttgttgc aacgacgcg cttgtcgtaa tcttccaatt ctaagagata    165720
gacgaatagg ggacacgtgg aaaataacac atatgcggtc aaatacaggt atcgtaccga   165780
taagactttg atgtgcgaat ttggaatcgg atggtgtaac catgtcaaaa ccatgtcgaa   165840
aacacattgt attacctttt tcgctatata cgtgatattg ccaactcgtt ttacaattta   165900
taaaaaatta tagtcgccaa ggcgggtgtc tattggtgtc acttttgtct tctatatgtg   165960
gtccattatc agagttttc tttataaaca ctttatgcca ccagttactt cgtttgccat    166020
caacccattt cgatagataa tgatcaggag acaaacatac aggtgtttgt cggggaggta   166080
ataaaaagtg ttgcgttttg tcgcatgtag gatctggagg tttatagccg acccaaaaaa   166140
cgccgaatac gggatgattt gaaccattgc tacaccgaca acgtagttcc acactttcca   166200
```

```
ccttatagca caacgcgatc aaaagaccaa acagactaaa aataaatcgc attataattt   166260
tattatctac gtcactatca gtaattcgta atatccggta ttcccggaaa atcactcaaa   166320
actacgtcca tgacacatca actcccgata actacctccc tttgaaatcg atcccccca    166380
cgtaccaatc aatcacacaa cacacaggtt taaaaatcga tcactcgtca attaggtttc   166440
aaaatcgata ccgtttatta tcaggaatct agactaattc tacaatgaca gctctgaatt   166500
tctctctcgt cttccttgtc aggttctcat catcagttat cacttccacc catcgaggag   166560
tcatcgtcgc tccaaaatcc tttggggtcg ctagttggaa aagtctctga cacgatccag   166620
gcacccccgca cccagtccga ctgatctagc ttgcggagca tctcaacagg catgagctgc  166680
agggccatgg ctgtcacggc actgtatcga tgtaacacta gggactttct ttgcgatgta   166740
gccatcaaca cggcgtatgc cccatagttc gcgtgatacg acgcatgatg ggttaaacgt   166800
tcccatccgg cagtgccgtc tcgggtccgt gcacacaaca gctgcacggc attatgatgc   166860
ttaaaattaa ccataacgct ggggctactg atgaaggagt agtaatgagc caggacgccg   166920
tacatcgaag gcagcaagaa agagtgacag cacaatagca ccgggctctt atgtaggcga   166980
cagcttattt ttcctgacgt cggcaaaaag tacctaaatt ccccacagat attcagacac   167040
ggttccgcaa agtgcttctt tttttagtgc aggaattgga aaaataata aaaaatatga   167100
acagctcatc tgtaattatc tgtgtgactt catcgtaccg tgatgtaaaa acaacaacag   167160
gaagcttaca gggtgcggta gaaaattttg ccgattgagc aacactgttg gcatctctca   167220
ctccgatagg cggctataag atagaaaatt aaaagtatga tacccacgag aaagatgaag   167280
agggacaacc aggctagagt atgacgacca cttttcccctt gtttgacggt tacatgtgcg   167340
gtatgatttt gtcgttgctt gtgatgttgg acgcctggaa cggacaacga cgtataattc   167400
ttagatgcgc atacggtgtt attagtggaa gtgcagttac gaattgtaac ctcagtgtca   167460
ctacactcag tgcaattggt acaattgtaa agccctgata catacgtacc gttagggcaa   167520
agtgtacatg ttgtactcgt atattgcgta cattgtcctg taacacgata tccttgttta   167580
catgggggac aacactgact tcctaattgc acttcttcgg gtttgcatat ttcagttttc   167640
cctatgcatg ccaatagcat actcagcaaa ataagcatca ccagaggctt catgcctcct   167700
accggaagaa taaaaataac tcatggggcc gaacggtatc atcctctccg cggtttgtaa   167760
tacgagatcg taaacgtaaa taatgacat aacttcacta acccgcatac tgcaaagtcc   167820
acctacgacg ctgaaagctt ttccaggaca caacaggata gtcagccatc ttcacaggta   167880
accagtttct agtcacagta tagcgagcct aagagaccgc acacggtccc tgctggaaac   167940
acataccact acatcgattt gtcgtgtcgt acaaccgtca agttttccga acttttatac   168000
acgccaatgg cgttaggact atgtgtgctg ctgtgattgg aggcttcgag agttatgtga   168060
cagctgtgat tacacctgtc gccaaggctg acagcgatta cccaggtaga gcacaatcac   168120
atagctgatg gacgttggtt gatccgttga ttcccatgga cattttaacg gcgacagtac   168180
agctcccgtt aaacattaga ttaatagacg ctagtggatg acagcatgtt attcgcccaa   168240
ttgtgatggt ggttatactt tcttgttttt tgctcatatg ctgtaaggtg ttcgaggatc   168300
gtggggagta tatgtgttaa atcggaatca tatttactga ccgcgccata cttcgtatac   168360
gaacctaacc ggcgtaaagt gttttccgat atataaactg gcgccattg tggctgtagc   168420
gcccataggt atggcatata cccacggtga tgttgtgtta ttcgtttttt gtgataaaac   168480
gtagtttatg tttaacgtgt gttccgtcac gttatgtgtg tcgttaaaag acggcgtctg   168540
tacagtatgg cttttgagttg tatcttgaat tgttattgca tttggaggtg tgtacagagt   168600
```

-continued

```
ggttgttgtg tgctgaggtg ttgttacgtt ttgaggcaca gttgtggtgt atacggactt 168660
caaggtgtag ttacggagtc tttctatgca ggtagtgttg agatatttgt gaatgctggt 168720
tatgttcgat tctgtgaggt taaagtgtgt actatttatg gcggtataat ttagacggtc 168780
ttgccatccc gaggatgtta gtgttaggta attcgtgttg tttacgtttg cttgatatgt 168840
ataggtaggt gtactgtttg tgaggtcgca agtgtgattt tcttgcagag attttatcca 168900
tcttgtgtga aaatattgag atacgcgatg aatgttttcg ctatctatat tgtaaagcgt 168960
ttcggtggta cttaggggtt gtttgctgta actcttattt tggacccagg atgtgaacca 169020
tgactccaat gtttgtatag taaggtgtcc tattaataaa gacgaactga ttcctaccgt 169080
aatgttatat cgcacaccta gggtgccgtt tacaaacacg gaaatgtttc cgttacaaac 169140
cacgttggca gatgaattag attccaggtg gtaacgatag gataatgacc gttcgctccc 169200
aacggatgac acaaagtatc cgaataacca acacgcccat tcaatccgca tattttaatc 169260
acactattca catttcacac actgcatttt ttaacatgtt attttttat tttatgcgtg 169320 ttctcacctc ttcatctttt taacaccggg gtaactatcg taagtcggta ggcgtcgata 169380
gccctcacca cctcgtcgtc cccttccggg cgtggggcac cagcgtccac agcactgcag 169440
gtaacacagg tagcatagga aacatacggt gaaaatactc caaaatccca aaaatgccgc 169500
gattccccga gtggcccagg gagacatccc ggtgtctatg tcggccggcg gtgctggcgt 169560
caccggtaaa aatttcggcg ggtgtggctg cgaacgtag cagtcgccgg ggagccggta 169620
acgctgtatc actgtccaac agcggtcggg ttcctcgtcc ggacatgcgg gtttccagca 169680
atcctcggcg tcggcgcggc cgatatagaa gtagttgcgt tgaaaccgc ggtacatccc 169740 gcagtcgtga ttccgtagac gccagggcgt cggcgaccag atctggtctc ccagcgagta 169800
acgacctaac gccggcgtgc agcaaggttc gtcgggccgg ctgagcgtct ccagttgcgt 169860
gagaattacg aagcgttgca tgatgaggcc gtggctgtag ttgcgcagca cgcattcgta 169920
catgccggcc gtgtccgtcg atacgttgaa agtcagcgag aatatttggc cgagatgcaa 169980
ttgcagaaaa ttccaagtgg cgtacggcag gcggtactgg agtccgttca tcagccgatg 170040
gcctttgacg gcgtccagga tgagctcgtc gctgccgtcg tgggaacgac agaaacgtgc 170100
gcgaatggag accatgggcc aggagtgtgt catgaccgtg cagggatgg tataacttgc 170160 tctccctcgg cgaccaacac cggcgccggc gacgtggtct cataattctc ggcccacatc 170220
ttttcggcaa tgtcagcggt ggcgaagggg aacgaagagg aagaatattc gaggagtcgc 170280
gggcagctca acagcaccca gaacagccac ggcagagttc ggagcgactc tcggcggcac 170340
atgatgattc tttctttccc ttttttcgcag agacgctgcg cgcctgctcc tgctccgtgt 170400
gtcggccgct caaacgtcgg gccggcgtgg tggtgaccac cgtgcgacgc agcttctcgc 170460
ccgggatgcc cgcgactgag cgtccggttt ttttgcaggt ctttttttgct gcctcctcct 170520 cgccgtcgcc gtcgcggccg acgtggtgga ccagcaccgc gcaggaactc tcgcgtcgcc 170580
ggcggtacgc gacctgtctc attgctacct cggatgttta agaaggaacg ttcatctgcg 170640
tcacagggtc tgatgaagct gccaagagtc gtggctgtgg cgcagcgcgt tctgtacggc 170700
gcgtttcacc gctttctgca tggccgctac cacgtcgggt gggagcggct ccggcggaag 170760
ctcgatgagc agttgctgcg agtctcggcg ctcggtgtcc gccgtttcgt cggacgtggc 170820
gtaaaaaacc gaggtggttg cccagtcgtc cacgctgtcg acggcctctg tcagtgccgg 170880
gttgtcaaaa ccgccatcgg acgcgggtga taaaagaacg tacgatgaca cgctgttagt 170940
```

```
acgactctcg tcgtcgctct gggaacgacg tgatggacga cggtagatga cctcgtcttg  171000
ccacgcgtcg aagcggtcgc agcagcgctg gatccaagcg cagcgaagca gcttacggaa  171060
cacgtcgttg ttccaaaagt agagcataaa gagaaagaaa agtagcgtaa taatgaagcc  171120
gaaaacgacg agggtcggca gggcactacc gccgctgccg ttttttgtgt cgtgcgggtg  171180
cacggtggta gtggcgttag tctgagctgg ggtcatgaca agtctgaaga gatgagagcg  171240
tgggtgctca tcaggaacag ttgaggtctc tccctaccga agccttagcc tccacggtgt  171300
tttatgatca acgtgtctac gaacgtcatt gtgaaagtga cgtctcaggc tttccgaaac  171360
cgcgtcagat tcaacgtggg tttcggttta gcctgcgtca ccgaggcgga ggtgaaatg   171420 agccgtcctg tgggggagtg tacgaccctg tagtgcccat gggtaacgtc gcgtcggaag  171480
aagtgaatgc ggcattggtg tacgcgtggg ttgttttgct ctctgactcg gaggaattgc  171540
cgcagcagct gcagatttta cgtactaacc aaaagcagca aaagcagcag gtaaataaga  171600
gaaggagtcc agataatgtc cagccgctag cggcaagcag cgcgagctgt ggtactgtcc  171660
agctactgcc gttagaggca ttaatacatg tcgatacggt cgtgttggcg gtagcactag  171720
tagattgact ggaattagag ctggtacctg tagtggtttc actcgccgat gcggcgagtg  171780
caaataaaat taatatccac agcatgttta ttactatata attgatatac gaacccgtct  171840
gtcgtaacaa tcagcgttat acacgctgta tcggcatcgt tttaccgaaa agtttatcgt  171900
aatgtaaccc gcgttgtgta cattcgtact gacagggaac ccccggtgat gtgcacatta  171960
tactctttca ttctggggtt tcccaatgac gtaaaaattt ccactacaca ataaaattac  172020
tgactcatgt gaaagtgtg cttttatta acagagcaga gggtttacag tagatatatg    172080
tttgccaggg ccaccgtttt ctaacaccga tcaccgccac cattaccacc cgttgaactc  172140
cacacccggg agccgcctga tcgcagggga ctcctcaccg tccatcgtcc gaacaagctc  172200
ccgccaccga tgctgccacc atcaccgaga gaaagaaccg cttgctgcag atacgcttgg  172260
gctcgcctcc gtgcggacgc cgtttcgtgc agacgctgag tagatcgagc agagaatgtc  172320
aaaacgacat taccgcgatc cgctccctc tttttttctt ttctcattca cgtgtattct    172380
tgatgataat gtaccatggc tacggtggtg aactgcgtcg cggatcccgt cacgggtttc  172440
aacagatcga cgtcggtcag cggcgccgtc accgccatgt ccggcggagg cacgctgttt  172500
ctctggttag cgacgtggac cgacgacgaa gacgatgaac ccgcgcggcg gtctgttatc  172560
cgcgacgacg cgtagctgca ctgggaagac acttcctccc aacggaccaa gatctcatcg  172620
ggccgttcgg agaaacggta tcgtctgtcc gactcccgcc gtacggcgcc gaggcccagc  172680
gacgacaggt ccgcgaaccg cgcgctcgtat tccccgtaca gctcgcaaca gcggatcagc  172740
cagcggtagc tcaaaaacat gcgcaccagt ttgaaggtgt cgtgccaatg gtaagctaga  172800
tagcagagaa tggccacgat cagcacgagc atcacgccga tgatgggtaa cccgacgttc  172860
agcggcagat cgtccatggt gaccgtcctc tgtccggatc tacgtcccag tctctctctt  172920
ttgtacagca ctcgcgcggg aacggccccc tcaaccctct tacgtagcgg gagatacggc  172980
gttctcccgc gggccactta cttgcacggt cgcttgaacg gcggcttgga ccgccacatg  173040
taccgcatcc atccattctg gcagcagcgc gttcgacgac gtcgtacgag tcgcggatga  173100
tgttaccccg ccagcacctc cgccggcaac cgcgtcgtcg ttgctatcgt cgccggtttc  173160
gggcgatgac agcgccggcg gcgcgggtct cgtctcgtcc accatttcca ccgtgtcgaa  173220
gcgacagccc ctgccgtagt acatggcccc gttcaacggc cggcgggccg ggtcgccgag  173280
ttccgggtcg ggcacatcca tggctcgccg tctgcttctc tgccgctcgt ggtgccgacg  173340
```

```
gcacttctca ggataatgac agccgcaaaa tagatcgtgg agcatgtctc gccaactgtc  173400
ctggtggtaa tatcttaagt acgcgatgag cgcgccgatg gccataatca taagcgtaag  173460
caaaacggca cagataacgt gaaacaccgc ggtcatccaa gtcgggcggc gtcggggacg  173520
cggtgggtcg gtttctctta cgccggcgtc actcagccac cacacccgta gtcgacattc  173580
ccagaaccgg tgaatgcgac tcagggcctt tcgacgccgc catttatttc caacgtccaa  173640
gtcccacgtc atttctggca tctccacgcc cttgactgac atactctctt tctctctctt  173700
agctgcggtg aaaaagaggg aaggcgtgtg ctgctataca actgtacaac ggacgcgctc  173760
gctgtttcgg tctcaggtca tctgcattga ctcggcgtcc ttcatgacgc tctgcaccgc  173820
cttttccaag agttcctcga tgtccgacca tcgaggaggc ggggctaact cggaaaccga  173880
cacgataggc agcgtggtcg gctccgtcgg cgtgcgggt cggggacagg gacacgagag  173940
tcccaccttc gagagattct ccagcccgac ggtgcgcggc agtctcggat ccgcggtgg   174000
cttttgtggc gtcggcgttt tcgggaaggg cctgggcgtc accggcggtg tccagccgac  174060
cggcttgggt ttcgtgggcg gcggtgtttt cttggtgggc ggcgtgctca ggttcttacg  174120
cggcgcgggt atcggcgtcg ggggcctgtg cgacgacagc cgcgtggtgg gggcccggac  174180
cggcggcgta ggcggccgct tcttgcgccc gggcggcgga ggtggcttcc aggatggcgg  174240
cggctgatgc agtaccgtgt cgacgctggc cgaggacgac aaagagctcg acgaggagca  174300
atgcgacgga gatcggccga tgctggtcgg cgttcccggc gtggatacgt cggggatctc  174360
gaatcgcgcc ggaggaaact cgggtttatc tatcggcaga ccatcctctc ctatgtagag  174420
cgacgtacac cgcggcacct gcggcgtcgg cgggtgggtg gccacccgca tgagcccag   174480
ttccagatcc agcggctcga cgacgtcttc tttcggaatt cgatagcagc acgcgcaggc  174540
accacgctta tcagaagcag cacccgggag ccggcctcgc gacgaagtct cgtcggatcg  174600
cttgcggcct cggcgctggg taaataagga aatggccagg accagggaag ccagtccggt  174660
accgccgagg agcccgacgc cgagccacag ccacaccatg atcttctctc ctgcttggaa  174720
tctcaaactc cgtgtcggga agggccggtg tacggacatt tatgccttgg atttctggaa  174780
acgtcatttt ttggcaagga atgtgtttat tgtccaaaca ctgaggaagg agatgtgagc  174840
caagtcggaa aattccttat cacaccgggg gcgggttacg ttccggtctg atgctgctgc  174900
tgttgttgta gagccgcggc catggccgcc tgcacggcag cttgtaccgc ctcggccacg  174960
ccgggtggca tctgcggcat ggcggggga gacgcgtcgg gcggaccgcc gggcatcgcc  175020
gtcggctgcg acggtggttg tgaactcacc gtcggctcgc acggaggttt gtccttcggt  175080
ttgctcttcg gtttatcttt cgccctacct ttcttcggtt tgggttccga tgtcggtgtt  175140
ggcggctgcg gtgggatgac gggctggtgg gactcctccg acggcggggg gacgaatact  175200
gtcggcgccg aaaccggggg actctcgact atctcgcaga tcaccctgtc gggatcgtcg  175260
ccgtgtccgg gacgccgtcg atgaccatat tgaaccatgt cgtaaatcat cgtctccttg  175320
taacacgctg aacagcagcg gctacaagga cccgaaatgc atttgcagct gcacttacag  175380
ctgcagctgc agtagcgcac ccatcggcag gtgaagacgt cgattacgga gtccttgaag  175440
aattcccggt aacggatgag atacgcgcag aggaaaatca tgaaaacaga acagccgact  175500
acggctgcga tgccgggtcc cgaaaacgta ttcggtgatc ctaccaaaca ccaaattccc  175560
agggccgcgc atgttatcca ggccacaata atcgtgggaa cgcccattg gcattgccac  175620
gaaggatcgt gcacgtcgca acccatcgct actgcgttct cccacaaacg ccatcgcact  175680
```

-continued

```
atttatccct acagcggctg ccgagtcacg tccgccggcg cccatcggcc gcggcgatct   175740
cctagtaaca ctcgtccgac acttccacca tctccagctc cgccggcggt tcggcatcct   175800
ccactagcgg cgtcgtctca tcttttccgc agcagcgaac gcacaccttc tccaggcaga   175860
acgccaccag ctgccgccga acgtaccaca agtacacgtg cagacctgcg aacaggacta   175920
cggaggtcat gaccaccacg acgcacacgg gaatccaagg atcgagattg tcgctggaac   175980
tcatggctat cgccaccggc gtgcccgcgt ctgtctcacc gccgctcgcc cgatgtcgcg   176040
cggcttgtta tacgctagcc cgtcgccgcc ttggggcacg gtgccctcct acccacgtaa   176100
cttcctccgt gacttaaagt cgcgtgtggt agatctcctg ttccgtggac gaaccgtccg   176160
gcaggatagc ggttaaggat tcggtgctaa ggccgtgtcg ccaacgtcga atgctacgtt   176220
gcaacagctt cgacggacgg ccatcctccc tctcatcgca ataataaaac accagcagcg   176280
cgcacgacgc gatcacggtg acacccatga ccagacccac gcagatagcc agcccgcta   176340
gcgtatccag cgccatcccg ttcgctcccg tcgtcgtctc ctgaacaaag caactccgca   176400
gtccccgttt tcaaccgttt ttgtttcctt cttcgcgact agatgttaac gcccgcggtc   176460
tttccggccg tgctctacct cctggcgctt gtcgtctggg ttgagatgtt ctgcctcgtc   176520
gccgtagccg tcgtcgagcg cgagatcgcc tgggcgctgc tgctgcggat gctggtcgtt   176580
ggcttgatgg tggaagtcgg cgccgccgcc gcttggacct tcgtgcgttg tctcgcctat   176640
cagcgctcct tccccgtgct tacagccttc ccctgaaacc cacgttaacc gaccgtcccg   176700
aaaacaccgg tgttaacaca ggaaaaaaag gaaccgcgca ggaaccacgc ggaacatggg   176760
acactatctg gaaatcctgt tcaacgtcat cgtcttcact ctgctgctcg gcgtcatggt   176820
cagtatcgtc gcttggtact tcacgtgaac caccgtcgtc ccggtttaaa aaccatcatc   176880
gacggccgtt ataaagccac ccggacacgc gccgcggcac ttgcctacgg cgctgctcca   176940
gggaaactcc tcttccttct gctcttcctc cttcaccgca gggatcgttt ccctcgacca   177000
gggacccacc gaagcaacta ccggaacaac ctggaggagt cgcggcatga cggcgcccaa   177060
gtgtgtcacc accactacct atctggtgaa gaccaaggag cggccctggt ggcccgacaa   177120
cgccatcagg agatggtgga tcagcgttgc catcgtcatc ttcatcggag tatgtctggt   177180
ggccctgatg tactttacgc agcggcaagc gcagagcagc aacggcggca gcagcggcta   177240
gacgagtctc tggcggctac agctccaggc gccgtagccg gccgcctgc cgatcgcgac   177300
gtcgtggacc atcgaacaga gactcacgcg tacgagaccc cgaggtacgc cacgcggtgc   177360
ctaacgcggt ataccacatc cgtacggtct gcagtgcggc gtacaacgtg tggaaaacgc   177420
gtcgcgtcgc agagtccgcc acgtccctgt cttgtcgctc cccaatcgtc tcccgcacac   177480
cccccgcggc acccaggggg cgggtgagcc aagcattgtt aaggccgttc tctgttccat   177540
agcccataaa ttgttgattc cggagctcgt tggcgcggaa atagccggat aagggagca    177600
acaaccgtcg gcgaaagccg tcccgctcat tcagtccggg tttcgcgtcc agtcggacgt   177660
gtgaccgttg ggcaacggaa cggcgtttca ctaccaaaat cgtatcgggt agtgtacgag   177720
acgtcggcgg tgcagaatgc gactcgcggc gtagctcgcc gtcgctatgc ggctcgtcgc   177780
cgtgtggcgc ggcctggccg gctgtctgcg cccagatctg ttggccttt ggttcctctg    177840
gctgctgctg cgtgtgtgct ttggcagacg cggtggcagt ttgcggtctg cggtaagtga   177900
ggatgttgcc gagcaagcgc acttgcggcg cgtgatcggc acgcgtgtta ttgtaggttc   177960
gttgccagat ggcaagtgct gtcaacagca gacgttgtgg gcggtcggtg tatttttgtg   178020
ggttgcggtg agagtcggca ctcggtgttt tgtgagtgat ctcaaccgtt tgtgttgctt   178080
```

```
ttagcagcgt ccaaaacagc gacgcgactt tggggatggc ctcgtgctca ccgccgcgga  178140
gagtgtcgcc ggacctgctc gtcagcagcg agctacgcag acggaatatc tggaggagag  178200
ttacgtgtgt cacaggagag cgcgggtctc cggcggtaac gacggcggtg tcgtcgacac  178260
gtgtgcggcc tgctgtgctc tgcggaaaag cgccggtctc ggagaccgtg gacgaaaaag  178320
agaacggagc agctaccgct ggcggcggcg gcgttaatgc tgccgttgat gttagacgtt  178380
gtgagtactc ggaaacagcg gtgaggcaga agctcgatcc ttcagggaac gacagtcgat  178440
gtgtggtagc cgcagcaggt gaggttgggg cggataacgt gttgcggatc gtggcgagaa  178500
cgtcgtcctc cccttcttca ccgcccacc caccctcggt tggtgtttct tttttcttgt  178560
gtcctgcaga tagttccacg gacagcgacg gcaagtccat aatcaccggt gtgcaagtgg  178620
tggaccacga cgaagatatc atcgcgccgc agagtttgtg gtgcacggcg ttcaaggaag  178680
cccttggga tgtggctctg ttggaagtgc cgcgttgggc gtggcagggc tggaagaggt  178740
ggcgcaacag cgagtctggg cgtcgatgga gtgctgggtc tgcgtcggct tccagcttgt  178800
ctgacttggc gggcgaggcc gttggagaat tggtgggatc ggtcgtcgcg tacgtgatcc  178860
ttgaacgtct gtggttggca gccagaggct gggtgtgcga aaccggtgtg gaagccgagg  178920
aggctatggc gcggcggcga cagcgcatgc tgtggcgtat gttctctcgt ggaggcgacg  178980
gcgaatgcag cagacggtgt tcgatggaga tggcgtgcga ggaagaaagc gccgtgttgt  179040
gagcagacga cgttggatgc gggacgtcgg agcacatggg ccatgtgtgg tggcagatgg  179100
cggtgtccac ttgtgcttgt cgcggcagtg cacagacgaa gcaacatgtc gctgtgaaga  179160
gatagagtgt gagcatagct gtatgcagcg ttgcgtgtag aagcgggggg attaagacgt  179220
taataaagag tagcggcggt tgtgataggg cgaccgctga ggcgagctgc gtgtgcgtgc  179280
cgtctgtgtt ccccgtcccc gccgcaagag tccccgtcc ccgccacgca acagcccgcc  179340
atcccgcaac tccccgtccc cgccgcgaaa ggccccgtc ccgtcctca ccaccgtccc  179400
cactcccgtc cccgtctccg caacgccccg tcccgccgc aaaaggcccc cggccccgca  179460
acgcatcgtc cccgccgcaa aaggcccccg tggccgtacc cgcacacccc ccgtccccgc  179520
cgcaacccc gtccccgtcc ccagcgtaac tcccgttact agcgccggcg cccagcacgc  179580
ccgaaaacac cgccgtcgcc gccccgaaaa gcgaagcgcc gcgcaaaagc tgcctagaaa  179640
cgccgcgcaa acaccgtaga aacacccgcc gccaaccccc gagcgcgcgc aacacccgt  179700
ccccggcgcc ggtccgcgaa acaaaaaaca ccgcgggacg acacgcaccg gcagtgcgca  179760
caaagcgccg gacacagcac gccgcaaacg cgctgaggac accgctgcgc ttacttatgt  179820
ccagagacac acgcaccgcc agcgcgcaga aagctccgtg gacaaaactc ccgcagccct  179880
gtccagccct cagtcctatt ccgcgaatcg gcgcgctgac ggtggcaaaa cctccctcag  179940
ccccgtcccc agcgtaactc ccgttactag cgccggcgcc cagcacgccc gaaaacaccg  180000
ccgtcgccgc cccgaaaagc gaagcgccgc gcaaagctg cctagaaacg ccgcgcaaac  180060
accgtagaaa cacccgccgc caaccccga gcgcgcgcaa caccccgtcc ccggcgccgg  180120
tccgcgaaac aaaaaacacc gcgggacgac acgcaccggc agtgcgcaca aagcgccgga  180180
cacagcacgc cgcaaacgcg ctgaggacac cgctgcgctt acttatgtcc agagacacac  180240
gcaccgccag cgcgcagaaa gctccgtgga caaaactccc gcagccctgt ccagccctca  180300
gtcctattcc gcgaatcggc gcgctgacgg tggcaaaacc tccctcagcc ccgtcccag  180360
cgtaactccc gttactagcg ccggcgccca gcacgcccga aaacaccgcc gtcgccgccc  180420
```

```
cgaaaagcga agcgccgcgc aaaagctgcc tagaaacgcc gcgcaaacac cgtagaaaca 180480
cccgccgcca acccccgagc gcgcgcaaca cccgtccccc ggcgccggtc cgcgaaacaa 180540
aaaacaccgc gggacgacac gcaccggcag tgcgcacaaa gcgccggaca cagcacgccg 180600
caaacgcgct gaggacaccg ctgcgcttac ttatgtccag agacacacgc accgccagcg 180660
cgcagaaagc tccgtggaca aaactcccgc agccctgtcc agccctcagt cctattccgc 180720
gaatcggcgc gcttacggtg gcaaaacctc cctcagcccc gtcccgcacc ggcggcggtc 180780
ggggtgtgtc gggggcgcgg ctgggtggat gcgtgcgtgg ggtgggtgtc gggtgtgtca 180840
gggcgtgtgg cgggtgtgtc tgggtgtgtc gcgggcgtgt ggcgggtgtg ttggcggggt 180900
gtgtcagggg tgtgtcgggg tgtgttggcg ggccgtgtct gcgtgtgtgc cccggggtcc 180960
gcgaccccccc ccctcccctg ggcgatcgct tctgcgtgtg tcctcgacgc gggttgtgcc 181020
gtacttcgtc tgtcgtttcc cccgcggtcc cctagggact tcctcttttc cgcgtcttgc 181080
ccccctccc ttgcgccccc gagcttcctc tggccgttgt tttgcgtgtg tctgttcttt 181140
cctcttttcc gcgtcttgtc tctggccgtt gttttgcgtg tgtccccagg gacccgcgct 181200
gccgtcccct gggaacttcc tcttttcccc ggggaatcaa acagacacag acgcgcgtct 181260
gcttttcgcc gtgcgcggcg cacgtcgctt ttattcgccg tcgccggcct ccgcgaccgc 181320
cgtccccacc gcaccacacc gcaccacacg caactcttcg ccgtcgccgt ccacacacgc 181380
aacctcaaat ttcaccccccc cgctaaaaac accccccgc ccctcgggga cccagcacac 181440
ggcccggaat ggagggtaat gtttatggag taaaacacta ttgtccaggc cacatgcgtg 181500
tatgacttcc gcaccatccc gtactgcatg ttcacatgt acgcgctaga cgtgtaatcc 181560
actcgcagtt cggggacgca acgcagccag atcacatccc cttgcagtac cagacgcagg 181620
gctagttcta gagcggccgc cacggcgata tcggatccag acatgataag atacattgat 181680
gagtttggac aaaccacaac tagaatgcag tgaaaaaaat gctttatttg tgaaatttgt 181740
gatgctattg ctttatttgt aaccattata agctgcaata aacaagttaa agcggggttt 181800
gaacagggtt tcgctcaggt ttgcctgtgt catggatgca gcctccagaa tacttactgg 181860
aaactattgt aacccgcctg aagttaaaaa gaacaacgcc cggcagtgcc aggcgttgaa 181920
aagattagcg accggagatt ggcgggacga atacgacgcc catatcccac ggctgttcaa 181980
tccaggtatc ttgcgggata tcaacaacat agtcatcaac cagcggacga ccagccggtt 182040
ttgcgaagat ggtgacaaag tgcgcttttg gatacatttc acgaatcgca accgcagtac 182100
caccggtatc caccaggtca tcaataacga tgaagccttc gccatcgcct tctgcgcgtt 182160
tcagcacttt aagctcgcgc tggttgtcgt gatcgtagct ggaaatacaa acggtatcga 182220
catgacgaat acccagttca cgcgccagta acgcacccgg taccagaccg ccacggctta 182280
cggcaataat gccttttccat tgttcagaag gcatcagtcg gcttgcgagt ttacgtgcat 182340
ggatctgcaa catgtcccag gtgacgatgt attttttcgct catgtgaagt gtcccagcct 182400
gtttatctac ggcttaaaaa gtgttcgagg ggaaaatagg ttgcgcgaga ttatagagat 182460
ccgcgtcacc ttaatatgcg aagtggacct gggaccgcgc cgccccgact gcatctgcgt 182520
gttcgaattc gccaatgaca agacgctggg cggggtttgt gtcatcatag aactaaagac 182580
atgcaaatat atttcttccg gggacaccgc cagcaaacgc gagcaacggg ccacggggat 182640
gaagcagctg cgccactccc tgaagctcct gcagaagctt cgaattcgag ctcccgggta 182700
ccatggcatg catcgataga tcgcagcctt aattaaggat gcatgtttaa actcgacagc 182760
gacacacttg catcggatgc agcccggtta acgtgccggc acggcctggg taaccaggta 182820
```

```
ttttgtccac ataaccgtgc gcaaaatgtt gtggataagc aggacacagc agcaatccac 182880
agcaggcata caaccgcaca ccgaggttac tccgttctac aggttacgac gacatgtcaa 182940
tacttgccct tgacaggcat tgatggaatc gtagtctcac gctgatagtc tgatcgacaa 183000
tacaagtggg accgtggtcc cagaccgata atcagaccga caacacgagt gggatcgtgg 183060
tcccagacta ataatcagac cgacgatacg agtgggaccg tggtcccaga ctaataatca 183120
gaccgacgat acgagtggga ccgtggtcc agactaataa tcagaccgac gatacgagtg 183180
ggaccgtggt cccagactaa taatcagacc gacgatacga gtgggaccat ggtcccagac 183240
taataatcag accgacgata cgagtgggac cgtggtccca gtctgattat cagaccgacg 183300
atacgagtgg gaccgtggtc ccagactaat aatcagaccg acgatacgag tgggaccgtg 183360
gtcccagact aataatcaga ccgacgatac gagtgggacc gtggtcccag tctgattatc 183420
agaccgacga tacaagtgga acagtgggcc cagagagaat attcaggcca gttatgcttt 183480
ctggcctgta acaaggaca ttaagtaaag acagataaac gtagactaaa acgtggtcgc 183540
atcagggtgc tggcttttca agttccttaa gaatggcctc aattttctct atacactcag 183600
ttggaacacg agacctgtcc aggttaagca ccatttatc gcccttatac aatactgtcg 183660
ctccaggagc aaactgatgt cgtgagctta aactagttct tgatgcagat gacgttttaa 183720
gcacagaagt taaagagtg ataacttctt cagcttcaaa tatcacccca gcttttttct 183780
gctcatgaag gttagatgcc tgctgcttaa gtaattcctc tttatctgta aaggctttt 183840
gaagtgcatc acctgaccgg gcagatagtt caccggggtg agaaaaaga gcaacaactg 183900
atttaggcaa tttggcggtg ttgatacagc gggtaataat cttacgtgaa atattttccg 183960
catcagccag cgcagaaata tttccagcaa attcattctg caatcggctt gcataacgct 184020
gaccacgttc ataagcactt gttgggcgat aatcgttacc caatctggat aatgcagcca 184080
tctgctcatc atccagctcg ccaaccgaaa cacgataatc actttcggta agtgcagcag 184140
ctttacgacg gcgactccca tcggcaattt ctatgacacc agatactctt cgaccgaacg 184200
ccggtgtctg ttgaccagtc agtagaaaag aagggatgag atcatccagt gcgtcctcag 184260
taagcagctc ctggtcacgt tcattacctg accatacccg agaggtcttc tcaacactat 184320
caccccggag cacttcaaga gtaaacttca catcccgacc acatacaggc aaagtaatgg 184380
cattaccgcg agccattact cctacgcgcg caattaacga atccaccatc ggggcagctg 184440
gtgtcgataa cgaagtatct tcaaccggtt gagtattgag cgtatgtttt ggaataacag 184500
gcgcacgctt cattatctaa tctcccagcg tggtttaatc agacgatcga aaatttcatt 184560
gcagacaggt tcccaaatag aaagagcatt tctccaggca ccagttgaag agcgttgatc 184620
aatggcctgt tcaaaaacag ttctcatccg gatctgacct ttaccaactt catccgtttc 184680
acgtacaaca ttttttagaa ccatgcttcc ccaggcatcc cgaatttgct cctccatcca 184740
cggggactga gagccattac tattgctgta tttggtaagc aaaatacgta catcaggctc 184800
gaacccttta agatcaacgt tcttgagcag atcacgaagc atatcgaaaa actgcagtgc 184860
ggaggtgtag tcaaacaact cagcaggcgt gggaacaatc agcacatcag cagcacatac 184920
gacattaatc gtgccgatac ccaggttagg cgcgctgtca ataactatga catcatagtc 184980
atgagcaaca gtttcaatgg ccagtcggag catcaggtgt ggatcggtgg gcagtttacc 185040
ttcatcaaat ttgcccatta actcagtttc aatacggtgc agagccagac aggaaggaat 185100
aatgtcaagc cccggccagc aagtgggctt tattgcataa gtgacatcgt ccttttcccc 185160
```

```
aagatagaaa ggcaggagag tgtcttctgc atgaatatga agatctggta cccatccgtg   185220
atacattgag gctgttccct gggggtcgtt accttccacg agcaaaacac gtagcccctt   185280
cagagccaga tcctgagcaa gatgaacaga aactgaggtt ttgtaaacgc caccttttatg  185340 ggcagcaacc ccgatcaccg gtggaaatac gtcttcagca cgtcgcaatc gcgtaccaaa   185400
cacatcacgc atatgattaa tttgttcaat tgtataacca acacgttgct caacccgtcc   185460
tcgaatttcc atatccgggt gcggtagtcg ccctgctttc tcggcatctc tgatagcctg   185520
agaagaaacc ccaactaaat ccgctgcttc acctattctc cagcgccggg ttattttcct   185580
cgcttccggg ctgtcatcat taaactgtgc aatggcgata gccttcgtca tttcatgacc   185640
agcgtttatg cactggttaa gtgtttccat gagtttcatt ctgaacatcc tttaatcatt   185700
gctttgcgtt tttttattaa atcttgcaat ttactgcaaa gcaacaacaa atcgcaaag    185760 tcatcaaaaa accgcaaagt tgtttaaaat aagagcaaca ctacaaaagg agataagaag   185820
agcacatacc tcagtcactt attatcacta gcgctcgccg cagccgtgta accgagcata   185880
gcgagcgaac tggcgaggaa gcaaagaaga actgttctgt cagatagctc ttacgctcag   185940
cgcaagaaga aatatccacc gtgggaaaaa ctccaggtag aggtacacac gcggatagcc   186000
aattcagagt aataaactgt gataatcaac cctcatcaat gatgacgaac taaccccga    186060 tatcaggtca catgacgaag ggaaagagaa ggaaatcaac tgtgacaaac tgccctcaaa   186120
tttggcttcc ttaaaaatta cagttcaaaa agtatgagaa aatccatgca ggctgaagga   186180
aacagcaaaa ctgtgacaaa ttaccctcag taggtcagaa caaatgtgac gaaccaccct   186240
caaatctgtg acagataacc ctcagactat cctgtcgtca tggaagtgat atcgcggaag   186300
gaaaatacga tatgagtcgt ctggcggcct ttctttttct caatgtatga gaggcgcatt   186360
ggagttctgc tgttgatctc attaacacag acctgcagga agcggcggcg gaagtcaggc   186420
atacgctggt aactttgagg cagctggtaa cgctctatga tccagtcgat tttcagagag   186480
acgatgcctg agccatccgg cttacgatac tgacacaggg attcgtataa acgcatggca   186540
tacggattgg tgatttcttt tgtttcacta agccgaaact gcgtaaaccg gttctgtaac   186600
ccgataaaga agggaatgag atatgggttg atatgtacac tgtaaagccc tctggatgga   186660
ctgtgcgcac gtttgataaa ccaaggaaaa gattcatagc cttttttcatc gccggcatcc   186720 tcttcagggc gataaaaaac cacttccttc cccgcgaaac tcttcaatgc ctgccgtata   186780
tccttactgg cttccgcaga ggtcaatccg aatatttcag catatttagc aacatggatc   186840
tcgcagatac cgtcatgttc ctgtaggggtg ccatcagatt ttctgatctg gtcaacgaac   186900
agatacagca tacgtttttg atcccgggag agactatatg ccgcctcagt gaggtcgttt   186960
gactggacga ttcgcgggct atttttacgt ttcttgtgat tgataaccgc tgtttccgcc   187020
atgacagatc catgtgaagt gtgacaagtt tttagattgt cacactaaat aaaaaagagt   187080
caataagcag ggataacttt gtgaaaaaac agcttcttct gagggcaatt tgtcacaggg   187140
ttaagggcaa tttgtcacag acaggactgt catttgaggg tgatttgtca cactgaaagg   187200
gcaatttgtc acaacaccct tctctagaacc agcatggata aaggcctaca aggcgctcta   187260
aaaaagaaga tctaaaaact ataaaaaaaa taattataaa aatatccccg tggataagtg   187320
gataacccca agggaagttt tttcaggcat cgtgtgtaag cagaatatat aagtgctgtt   187380
ccctggtgct tcctcgctca ctcgagggct tcgccgtcgc tcgactgcgg cgagcctact   187440
ggctgtaaaa ggacagacca catcatggtt ctgtgttcat taggttgttc tgtccattgc   187500
tgacataatc cgctccactt caacgtaaca ccgcacgaag atttctattg ttcctgaagg   187560
```

```
catattcaaa tcgttttcgt taccgcttgc aggcatcatg acagaacact acttcctata  187620
aacgctacac aggctcctga gattaataat gcggatctct acgataatgg gagattttcc  187680
cgactgtttc gttcgcttct cagtggataa cagccagctt ctctgtttaa cagacaaaaa  187740
cagcatatcc actcagttcc acatttccat ataaaggcca aggcatttat tctcaggata  187800
attgtttcag catcgcaacc gcatcagact ccggcatcgc aaactgcacc cggtgccggg  187860
cagccacatc cagcgcaaaa accttcgtgt agacttccgt tgaactgatg gacttatgtc  187920
ccatcaggct ttgcagaact ttcagcggta taccggcata cagcatgtgc atcgcatagg  187980
aatggcggaa cgtatgtggt gtgaccggaa cagagaacgt cacaccgtca gcagcagcgg  188040
cggcaaccgc ctccccaatc caggtcctga ccgttctgtc cgtcacttcc cagatccgcg  188100
ctttctctgt ccttcctgtg cgacggttac gccgctccat gagcttatcg cgaataaata  188160
cctgtgacgg aagatcactt cgcagaataa ataaatcctg gtgtccctgt tgataccggg  188220
aagccctggg ccaacttttg gcgaaaatga gacgttgatc ggcacgtaag aggttccaac  188280
tttcaccata atgaaataag atcactaccg ggcgtatttt ttgagttatc gagattttca  188340
ggagctaagg aagctaaaat ggagaaaaaa atcactggat ataccaccgt tgatatatcc  188400
caatggcatc gtaaagaaca ttttgaggca tttcagtcag ttgctcaatg tacctataac  188460
cagaccgttc agctggatat tacggccttt ttaaagaccg taaagaaaaa taagcacaag  188520
ttttatccgg cctttattca cattcttgcc cgcctgatga atgctcatcc ggaattccgt  188580
atggcaatga agacggtga gctggtgata tgggatagtg ttcacccttg ttacaccgtt  188640
ttccatgagc aaactgaaac gttttcatcg ctctggagtg aataccacga cgatttccgg  188700
cagtttctac acatatattc gcaagatgtg gcgtgttacg gtgaaaacct ggcctatttc  188760
cctaaagggt ttattgagaa tatgttttc gtctcagcca atccctgggt gagtttcacc  188820
agttttgatt taaacgtggc caatatggac aacttcttcg cccccgtttt caccatgggc  188880
aaatattata cgcaaggcga caaggtgctg atgccgctgg cgattcaggt tcatcatgcc  188940
gtctgtgatg gcttccatgt cggcagaatg cttaatgaat acaacagta ctgcgatgag  189000
tggcagggcg gggcgtaatt ttttaaggc agttattggt gcccttaaac gcctggttgc  189060
tacgcctgaa taagtgataa taagcggatg aatggcagaa attctgatga taagctgtca  189120
aacatgagaa ttggtcgaga agctaggcgc gcctgtttaa acatggatcc ggcgcccctt  189180
aattaacgtg ggagtctgat ccaacactga acgctttcgt cgtgttttc atgcagcttt  189240
tacagaccat gacaagcctg acgagagcgt tcatcgggc atgaagtacg cattacacaa  189300
actccatata tttgttacga tagaatacgg aacggaggag gctttcgcca cacctatcct  189360
gaaagcgttg cattctttat gataggtgtg acgatgtctt taccattccc acggctgctt  189420
tgcgtgatga tgacattcat catgtatttc cattcacaca tacctttgt gcatacggtt  189480
tatatatgac catccacgct tataacgaac ctaacagttt attagccctt gacaggatag  189540
gtcaaaagat tatatgtagg ttttccggta aaccgaattg tgatatttct ctgcaggaaa  189600
tagaacagcc tggtacctat aaaacggaca atgcagtact gtagcagcgt aaccaagtag  189660
gtccacatga acacgtacaa aattatggta agccatcgtt tttcatacca cagcctgtag  189720
ctgtcgtaca tgaatgagga cggtcgagga acccagggta gttgtaattg ggggcgacat  189780
tcgtactgtc cagaagacaa ttgcacgggt tcagtgaga tgagtacttt agcgatgtcg  189840
gcggggcgc tacgtttcac cgtgacggtg agaacttgac cgtcgttttg tatttcatga  189900
```

```
ggcacgttat acaagccact ggtatcatga aggatgacct ctgatgcgat gtgaggatta    189960
aattgtccct caaaccgcca aacgctggtc atgtttccac cgtcaattac gcagctgacg    190020
gtgtgagata ccacgatgtt ggacttaggt ttggggcta attgccttt tacaaattcc    190080 cttctgtatt gcaggtcctg ctgccactgc ttttccgtgc ggaaagtcgc catgtcttcc    190140
acacgtgtgg cgacgataga cgccaccaag gtagctacca gaagcagctg gatccgcatg    190200
gcattaccgt atgtcaatta gaaagttgag cggacacggt tatcgttcct ggcggatata    190260
agtatataaa cgcgagttag cctttcccgt ccgttttgta cacccgttcc ccacacaaat    190320
gacgaatacg accttttttt ttataaaaat aaaccacgtg tattatataa aaacatttac    190380
atagaaaaga gacacacgga tcaacataag gacttttcac acttttgggg tacacaggcg    190440
tgccaccgca gatagtaagc gctggataca cggtacacag tcctggccag cacgtatccc    190500
aacagcagca ccatcgccat ctgtatggcg atcacgaccc cgagctctaa gtgtctgtat    190560
tcatagtgta gtcgtcgcag gttatccact gaattcccgt aactgaaata acgtatatgg    190620
taccgaggct ggcaccacat gggtttgcat ttggtgcacg gcaccaaatg cagagtgaga    190680
tggtccaagt ccgtgggcac ccactggcgc aaacggaata cggcttcggt ggtctccacg    190740
aggcactccg gggcgtgcag acggcccccac tttcgtccgt gacggcccga ccagccgacc    190800
cgagccacta tccctttctc gggatagaac gtaccctgta cacgccacac agcgtccaac    190860
acgccgtcct tgacgacgca gctggcctga tagctggaca cgttgttaag cggcggaaag    190920
cgaaactgac gtgccggcgg agccacatag ttcggttcac cgtgttgtcg cggttcgtcc    190980
tccctatagt aatagtagtc gtcctcatag gggttgccgg cgtgagccag cgttacccaa    191040
cagcagccca ggccgacgag gaggcgcagc caccgcctca tggcggcttc gccagtcaat    191100
cgtctttagc ctcttcttcc cgtgaggtcc ttccggtggc gcggtgccga cctcggaccc    191160
agggacgtat ccacctcagg tacacacagc aggctacctg gacaccgaag ctgaacaagg    191220
ctacgtgttt cacaaactgc accagtacca catagaggaa tgtcaggtag cgtctctccg    191280
caaacagccg ttccaagtct gagggcgtta cccgcagcgg caaccagggc agcctggacg    191340
ccggccggca atggagcacg ctccggttac aggcactgca ggggtaaacg gttaacatca    191400
cgtaagagag tcgtgcgtcc acctgtggga gctcagtttc gtaacgtaga gccccgtcat    191460
tttccagctg gggtgcgccg accttgaaat gggtcgcgct ccgctcgtta ccccaggtgc    191520
cgtaggctct cggggccgta tcggagaagt tgccacgcac aagccaggcg gccacgagta    191580
ccccgtgctg gacgtaacat tcggacacgg aactggagac acggtagccg gacacgtccc    191640
caaaccgcgc agggtactgg ggcagacgga cggacttgct atttgacaac ggacagatac    191700
gagacgacga ggacgcagac gactcgtcgc tggaccacga caaccggagc gactccttgg    191760
agcggctcga gagtacactt actgcgatca gacaccagtg ccagaagaag gaacaggtgg    191820
acggggacca caggatcata gccgccggca ccgcggccgg ccgcaggaag ccgcccggcg    191880
cgtcgtctgt gtgcgggagc cgaaacaccg tgcctcttta tatcgtcccg acgtgacgcg    191940
agtattacgt gtcaggggaa accccgtca cgacgaacgt gatttgtaag tgacgcgggg    192000
tgctgacggg gttcggcccg agaggtgacg gagcgcctca cgtcagtatg atgtccgatc    192060
cgcgtcagcc ccgacgtggt tgtggtcacc gaaacccacg tttatatgga cgttgagagc    192120
agcgcctgac cacatgattc atcataccat ttctcggaat cgggcccatg ccgggaaagc    192180
acattccttt tcagtaaaca acaatgacat cataacaaat catttattc gcgaggtgga    192240 taataaccgc atatcaggag gagggatcgg gtgatgacgc aggccccgca gaacagtccg    192300
```

```
aaataaattt ttagtattgc cccatagtcg cctagatacc agaggtacgt caagttcatc    192360
aaaacgccca tcggcgtccc ggaatcgtat accgggcaca cgaagcgttc ataacaatcc    192420
cgggaggcga gtgttagggt agcagagtag tttcggggtc ggtttccttc cggcgacgac    192480
agttccgtgg gcagcagaat gtacagcgcc tcggtagctg tcgcggtgcc ttccacgagg    192540
atgggctgcc ggtgcctttc gtgattttcc ccgtcgtgta gccaagccga ggcccgcaaa    192600
gtcttaggcg aggggaattg tccatagagt ttcaccgcac ccttcagtac atggttctga    192660
ataacacagc cgcacgtgaa gtaggtaggt tctctcgtct cctccgtggc tgccgccacc    192720
actcccagcc accacaacag gcagatcgcc agagggttcc ggaggcttcc ccggcgtagc    192780
atggttttgg gttaaagcaa aaagtctggt gagtcgtttc cgagcgactc gagatgcact    192840
ccgcttcagt ctatatatca ccactggtcc gaaaacatcc agggaaaatg tcggtgcagc    192900
caacctttca catacagccc ccaaaacact tgaatcactg ccaccatcat cagcgtatac    192960
tgcgccgact taatcgtgag cgcgtagtac gccattagac ggcgatcttc gaacaatagt    193020
cgttcgatgt cctctaacga gctccacagg ggaacccaag gcacgaggca ccggggttcg    193080
cactctacat aataagtttg gcattggtgg caggggaaa agtagaacaa cacgagtttt    193140
gtgcgttggg gaacacgata gtcccggagc cagtaacgtt ttgcgacgag gctttcggag    193200
acgtcctcca ccgcgtcgg cactcgatcc gcgtagccct ccagcgtctg gtagtacacc    193260
cggggtgtcg gcgtgggcac ggacaggttc ccgcgcaggg tccacagagc ctccaatcga    193320
ccgcccgatc ggagcacgca gcgcgcctcg gaatactcta ctcggtactc cgaaacatcg    193380
ggcagaggcg gtaacggctc cgtctccacc aagggcggag gttcatcgaa aagagtcaag    193440
gataattcag gcatactacc cgcgaccggg gcccagaggg ctagaataag cattacaaga    193500
ttcattctgt cttacaaggg aaggctgttc ccctgtctag actcaaaagc tgtaaggctg    193560
tcttatagca tgtagtcttg cacgtcatgg ggaacagggt ggtgatctag tgacgtcggg    193620
agaacacggt gttttagggt gcgggggaca aaggacagta cgacagatta ggtgatagaa    193680 acgtttttt tttatttatg aaaaagccag tgtgccgtgc ggcctagggc cccggcgtag    193740
tttggatacc agatgggggc cgtcaggggt actaccacga gcagaaacat aatgacttgg    193800
tccatgtata gcagcatagc ggtgcgcagc aggtcgccgt ccgtgtagca atttgacggt    193860
gagcgataaa gcaccgttaa tgtgtcgcgg ataagcacga tcttgaggcc gtagatgaag    193920
ctcacagtca gtgctaaaat gatgcgctgg tatggttccc aggactgcac ggcgatgaag    193980
agccagagta tgggaagcat gaagcttagc aaacagagga tggctaaccg tcgttgcatg    194040
ttccaggcca taagccaggc taggcccgta caccagacgc agagcatgga tgacaggaca    194100
taggcctgga ttaccacggt gcgatcgaaa cacagcccga tggtgacac ggatatcgta    194160 gtgagggtgg tatataccat gaccagcatc agggtcccgg gtcggcgccg acgttccagc    194220
cagtacgcgt ggcaacgcag agcgcagggt agcagtgtgc tccagaaggg cagtgtatcg    194280
cgcaggtagg gggttgtcac gcgccacggt atgagcatga aaaggatggt agtggctatg    194340
gtggcgctgg tctggaacac gacggtgccg tagagacgta ccatccagag aaagtgttga    194400
acgctccgca gggtgtcttc atctttggtg attacggtga ctcgacggat cggcggtggt    194460
gacggcggcg acacgggtgg gggtttctct ttcttatggc cgagtggctc gccttggtga    194520
aactggatct gtaccatgac gggtgctcga cgaacagtcg tcggggcttc aggtacccgg    194580
caagttttat agagaaaggg ggacgatggg tggtggctac gagccaccgc caccttcgca    194640
```

```
atacgaggat ctgaaggcgg caaagacggt cgtccagggc aggcgccaga ggttgggact    194700
gagcacgatc agcgtgattt taaacatggt caccagtcct acgtagatta gcagcgagcc    194760
gcgtaacgtc tgagcagccg gcagttcgtc gcggatgtaa cgcgtgccgt agaaagtcac    194820
ggtcatcata aggaagacga tggcgccgta gccgtagagt agaatacgct gatgatggaa    194880
cacggtctgg tcgccgataa cccaaagcgt gatgaaaaaa acgctggtga gcacccgtga    194940
gcatatgagc tcccaacgct taacgcgaaa gctgtcccca accatgacag cgccggtgca    195000
agctatccac agcgtgagga ccagtgtgta gtcgatgagg atggcgggca ggtcggagca    195060
ccaggtgtag aaaatcgtgg taacggagag gaggcctacg tagcccatgg tcaataccac    195120
gtcgtcgggg tgccttttcgc cctgtatcaa gaccaaacac cagagaaggg agggggcaaa    195180
aaccagcagc agaggggaag attcatgttg acatatgttg tgggaatcgg ggatacccag    195240
ccaaatcatt ccgcagaaag ccgtactgat ggcgatgtga aagaccacta ggcgtagac      195300 ccggacgagg acagcaaaac ggcgcagcca cataaggccg tggtgcagct gcaggaggga    195360
agcccattgc ggcgaatgta gcgacggcag cggcgggtcc atgaggcggg tgatgcgccc    195420
gagtgaacgg gtgagcgtct cggtggagtc ttcttataaa ccagcgggtc tcaagcaacc    195480
ctgctctgga acgtcgcggt ggtgctgttg aggatgacgc tgagcgtgcc gttgtcgatc    195540
agataatgat gataggtgcc gagcttggcc aggtagctga acatttggtc ccagcgtgcc    195600
gaccacacca cgggcgtgag catcaggagt gtggtgtgat agattagtgt ttcggtggcc    195660
taaagtatca gcgagctgcg gatgacgtgg ttcacgggca ttttggtggc gatgtagcgc    195720
acgtcttgga aaaggacggc caggatgcag cccacgaaca cggtgtagag acacagcaaa    195780
gtcttatgta accaggtgta agtagaagcc aggacgctga ccatcaccgt caaaagtgtg    195840
gaggtaaaaa gcgcgtcacg ccacacggag ctgagacggt gctcccaagc cacgccgttg    195900
caggccacga acaacgtcca cgttaggatg aggctagaaa tgccgatggg cgctgtggcg    195960
cacaggttga gcccggcggt ggtgaacgag agaagcgcca catacagcgc aaacaccagg    196020
ccgttgctgg ggtgtctgtg atcggtgagc tccagcgcgc ccagaaccaa tactggtgtg    196080
cagctaagca atagcggcga gggatcgtcg ctgcactcgt agcccagcga ggggtaaccc    196140
agccaaacca gcgcgctaat gagtacgctg aaagcggttt ccagcgtcag caatccgtag    196200
acacgcatga cgatcgcggt ccgccgtagc caacacacgg cattttcgga aactgtggac    196260
gctgtttccg aataccggga ggagatcgtg cttccctctt ccaaggatcg gaaagtagcg    196320
tccgtcgttt ccgcggacgc ggcttccctg gtacgctccg tttccgacga cgcggttttcc    196380 cgctgcgtgg aaactgtctt catgtcggga ccgcagcgcc cggcggcgta tccgcaaggt    196440
ctcgaagcta cagcttgtca gaggaaaagt aggtttgcaa aaaggtgcgc agggtcatga    196500
ttctcagcac catcagcaga gtgaaaacca gactgagaaa caccttgacg gccgccaaaa    196560
gcgcgcgttc cagcggcgtc tcgtagcgta cagccagggc cgcttcgtgg aaatgcgaga    196620
cggctagaca ggtaatgagc acgctgaagg acaagacgat cttaaagcac caggaccaac    196680
cacgcctcaa gatgaccacc acgattgccg tgaaggtcaa cgtgatcaaa gcatggacga    196740
ccacgatctg acgcggacg gtacgttcgg gagccaacaa cgctacgccg gtgcagctga     196800
gaaaggccag taaggtgaac aacgcggccg agatgaccaa cgtaccgtcc aggcagagac    196860
atatcacgat caacgcggc acgtgaagca gcgtgtaaaa gagcagaacg ccgatattgc     196920
tgggatgcga tgtttcgtaa cagtgaatga agatcactga cgtgacgggt atgacaaaga    196980
cgaggctggg cgaggactcc gtgagacaca gacgagaatg gtgaaaccac gtcgcgggcg    197040
```

```
ccgcgtagca gaaggcgctc aacaacgcgg tcaagccggc cagctgccaa cccacggcgc  197100
cataggtgtg cagcgccacg cggcaacagt cgacccaagc cagactgcgg gtcgccagcc  197160
gggtctcttg gatcccgggg ggcacgtaga tgaccgtgcc atcggtgggt acttgaaacc  197220
cttttctct tctcatggtg cgctgcgttc tctggaaacg gctgctctgt ccgaaaacca  197280
gttccgaacg aaaatctagg gcgagagggt ggacaacggc gtcgacgacg aagcatggga  197340
caggtcgttc ggcgttaacg tcatcgcgtc ggacgacggt agttctaaga gacgtagatc  197400
gctcagcagg tcctgacagt tgcggattcg caagatcaga aaaaaaggg aaatgaacgt  197460
aataaagagc tgtagcgacg tatgcgccac atcgcgtggc ataagaacgt gacggacgaa  197520
aaggacctgc tgcgaaaagt gaccggcgaa gataaggccc accgtgctgt agaagcccaa  197580
aagcagccgc aggggccaag tccagggccg cgtgaagacg atgagaacgt tgaccagaaa  197640
gaccacgacc cagacgccgt tgatgagggt aaattgatcg gacagggtgc agttgtcgcg  197700
acagatgaag actacttccg cgcagagcaa ggtgatgacc aacgtgagca caaacgacgt  197760
caacacctcg cggggctcct ggcaggcaca cgtgacacct agcgccggga tgtgcgccag  197820
gaggccggca gtaatagca ccagctgtcg gaacggacga cggcagcgcg ggtgccggtt  197880
tcgctgagcg agaaccggtc gctcatagcg gaaatacacg aagagcgcgg aggccacagg  197940
caccaggagg agcacctcgg gcgcccagac aacgtgacaa ggaaagcccg gacgcgactt  198000
gagagtcgct gtagggaaga ccagagagaa gctacccaag acggccaccg ccgcggagat  198060
ttggaagagg agcaagccgg cgattcggac gacaacctcg aagcgatgca cccagcccag  198120
cacggccacc acggccgctt catcatagtc gtcgttgttg ccgctgtcga acagccgccg  198180
aaacacgatc tgtcgctggg tcgcggtggg aaagcgcaga cccatgacag ccggaggcta  198240
tatgaccgcg cgtctaagac gcgagatccg tgggggggact tttagatgtt tgggcggccc  198300
gcagttctaa caggcttgat tggtggagac ggccggcgcg gcgggtgggg gaaacgacga  198360
gttttccgt tacgccatgg ttcgcgtgag gtttctctgt acctcccgca aaaggtcaca  198420
gcccgaaatg gaggccgcgt tggtggcccc ggtggcgcgt gacgataacc aggtcatcca  198480
agcgatgagt ttgtctaatg agtcctcggt ggtgaagagg atgagaatga gcaggtacag  198540
gtacaccagg ttctcataga gacacaaggt gagcaggtcg gcctcggacc acgcgatctc  198600
aaacaggcgc gtggtgtcaa agaccgtgac gaccagcatg aagctgagcg ccatggcgta  198660
atagcccaaa aaaagtttgt gccccaacgg tacgggctgc aggtaaagtg cgatcaagaa  198720
cgcgataacg ccgatcacaa acagcgtgac gatgacctgc catcgacggt gattatggcc  198780
ggctagaccc gtgacgcagc tgcagaggct aaaaagcacg caagccaaga ggcccgagaa  198840
ggtcaccagc gtagaggagg agcaggcgct ggccacgatc accgaaagcg tcgtgagcac  198900
gctataaatg gtgagcaggc ccgggctcgg cggcgacgtg aacgatcctt catcgcgttt  198960
gccgtgcagc agggccaaac agatggtggg caccatcaaa ctcaagggcg gcataaagcc  199020
ggtgcaacag agaaagacgg tgcctttaag atgcggaaaa gccagcacca ggcccagaca  199080
gagcaagaag gtgcaggtgc cctgcacggc cacggtgctg tagacccgca tacaaagtaa  199140
aaagcgacgt acgtcgttcg tcgagacgga ggaaatcata atgactccgc gcgagggtcg  199200
cgggggtggg ggcgcccagg ccgtcccggt ggcctctgag ttcggagaca tgacggcggt  199260
ggctatcaaa aggcgcgtat gagaaaccgt ttatagagtg taatagaatc accgtcattc  199320
ccacacggcg ttcccccata aagtcacgtc acactcgagt aagcgtgaaa aagctttatt  199380
```

```
gttgaataaa aaacacgagt acaacaccga gttgcggtgt cctgtctgtc tactgggtgg   199440 gggggttca tcgtctgtct ctagagggaa ggtggggaac gtctaagcga gcggagcgt    199500 gtcatctccc ccatcttttt acaacaagct gaggagactc acgccgtcga tgcgtccgcc   199560
gtgtttctcg gcgtactgct gcacccgac gtggccgcta agatggcga cgctcatgtt    199620 taggagactc atgacgatgg tgtacaacac gacgctgaca catacgctgt ttttagacaa   199680
cgttccacgc tggtagatga gatccagggt ctcgtaaata agcacggccg aagcggcggt   199740
caccaccagg acgtagagtc cgctgtagat cttgctgacc cacagcacgg gcgaaaagta   199800
aagcaatagg taaaagacga tgacggacca gccgtagcca atcccgatga ctttccagcg   199860
cgtgggattg ttgccggcca ggtaggtgag accgctgcag agaacgaaaa agaccatcac   199920
cagggcaaac gacagaccga tgacgcgcct ttctccgcaa aagcccgtgc acacggtgat   199980
gccggtgttg atcagcaagc acgccaccgt gagatgagca aaattggtgg tgtgtgggcg   200040
aaactcggcg aaaccgcgta gcatagccag cgtggacacg ggtacgatgg aggatagggc   200100
tggcactatg ccgttggcgc actgtccctg cacatcgggg aaggcgagcc aagccagcaa   200160
gcagaccgtg agggtacaag ccagctgcca cacgagcccg tgatagacct ccatgagcag   200220
cttaaagcgt ttcaaccatt ggaagagctg ctgttcggcc accagcgcgt ggctgcgatg   200280
gagcggcacg atggtgaccg tcggcgactc atggtgttcg gaaaccgagg cggtgtcgcc   200340
catgctgccg cttacgaccg ctgtcggtct aaggtaggcg tcgatgaaac agtccgtctt   200400
atcagcaccc ggttaccgcg gatttgattg acgtcacgag tgtggtcaaa ccgtggcggc   200460
accctgtatc cgaccgtcg tcatgggctc cacaaccaga gcctcagaag atggtacatg    200520
ccgatgaata aagccacatt ttcgacatag aggcgtagcg agggctgaaa actctccggg   200580
aaagaactct gacaggtgat cagggacaga tcgtgaatta gcatcagcgt caccgtcaac   200640
agcgtcgtcg cgtgtaaacc gagaaagaac ggggccgcgg cccgcagcag ccaaagtccc   200700
agcgccgtag cgcagagcag agacaggacc gacggtagcc acagccgccg gagagacgcg   200760
ccaggatcgc aacccaaaag cgaggcccc aggcagctga gatctaccgc cagggcgaga    200820
agagccgcgc cgacaaaggc ctgcggcgac ggctggcaca tcagcaaggt cagaaaggct   200880
agcgcgtgcg gcaggcagta agccaacagg agtgggagtt tgcggggaca acggtcgatc   200940 gacgaccgc gtagcagcag gaacaggcag ccgacgggca cgacgaggct gagatgagaa    201000
agcggcggtg ggtcgtcgtc ccgtccccgc tcgcatagct cggccaccgg tggcggcatg   201060
agccaccagc tgagcacgct gagggcgacg gtggcggtaa gctggaaggc gacgaggacg   201120
gaggcgcgca gccataccgc cagcctctct aggtagggga ctacctcctc gacggtccat   201180
tctagcggga cgacatgaag catggcgaca agcgcggctg ctgtgaaaac gggcgcggtt   201240
ttataggcat taggacttcc ccgtcgtact ggcggctgtc aaagtcccgt tgtccaaagg   201300
cgcgccgtcc gaaagactaa tccaacgggg acccgagagc atgagcaaca acgtgagaaa   201360
gatggccatg ctgtccaggt agagacagac ggcgtgacgg atgcattggt taggtgggca   201420
gaaaaagatg accatgagac tgtcgtaggc cagaataccc aaaaagaagc tgatagagaa   201480
ggcgcacaac gtcaccacta tcttctgcag ccaatcggcg tcgcttagca gagcgagcgt   201540
gaggaacgaa agcagcatca ccacgtagac gcagctgatg catttccagc gacgtcggtc   201600
acggccacct agaaacgcca gccccgtaaa ggagataaac aacgccaggg tcatcacgta   201660
ggaacctact agtacgcggc tttcagagca catttggaag atggccgccg tcaggctgtt   201720
ggccaacaga tagatgaaaa gcaccgtggc gttactaggg tgttcgttgc ccaacgtgta   201780
```

```
cgtgatgaac atgcagacga tgggcacgag cacggtgaga aagaagctgt agttctcgac   201840
gcaaaagttg cggttttgtg ggaacccaa ccaaaaaacg cttcccaagc cgaagctgaa   201900
agccagctga aagatgaaga tggcgtacac gcgcagccat acggtgaact tttgaacca    201960 ctcgagagcc tccatgcggg agagcagcag cgcgttagcc tcctgcgcct gcatggtggc   202020
gacggtctcg gcacaaagcc gctgcggcgc acctaccctt ctcttataca caagcgagcg   202080 agtgggcac ggtgacgtgg tcacgccgcg gacacgtcga ttaggagacg aactggggcg    202140
acgccgctgc tgtggcagcg accgtcgtct gagcagtgtg ggcgctgccg ggctcggagg   202200
gcatgaagta gagcacggag acaaagaggt acatgaggtc catgtacaag cagagcgcgc   202260
ccgggatata actctcatac tcgatgtcgt gcaggatgtc ctgcgtatcg cacaccaccg   202320
aggtcacgat gacggccaaa ccggctatca tcaccaggat ctcacttacc gcctcggaa    202380 aaagagaaaa tacggcgaac agtaagagaa tcagcgtgga tgcgcccgtc aatagggaac   202440
gctgtaattc cacgtcgcgg gcaaacagat acgtagcgag cgtgaggaaa caaaatagcg   202500
tcactgtggc caccatggca taaatgactg aacgatgact aaagtggaag cctgacgccg   202560
tgacagccac gctggtaagc aacgtgtacg tcagtaagat ccatacgttt ttgggaaagt   202620
tgggctcggc ccaacgcaac agacctaggc acacgatgga gatcattaag caagacagcg   202680
tcagacgcac gctggaaaag agctgctcca gccggtgcgg caacaccagc cagcaaaagg   202740
cgcagacgct cataaggatg aggcattgca cccagataag gatgtagatg cgcagcagga   202800
agaccgaccg ggctatctgg acctgaccgc ggagcgacat ggcggcaacg ccggcggtta   202860
tcgccgagat tcgtctaaat acacgaagcg aactagaaaa cgcacacacg tgatttgcaa   202920
aaagaaagca gctgccggct tattatttta ttaaaaattt atctgtgcag aatcataagt   202980
ttatgatgaa taaaaacggg gaaagggaat ctgcttttag ggacccgggt ctggtccgtc   203040
gtctcccatc tggtcgggtt cggggatggg gacctgtttc agcgtgtgtc cgcgggcgtg   203100
catggctttt gctcgccggc cgcgctgtaa ccaggcctct ttctctgtgg tcggcgagtc   203160
ttccgacggg tagggaacct gggagtccat cgcttcaggc ccaccgctcg ttccctcgac   203220
cgtcgtgtcg tcctcgtttt cgctattaca cggggtttct ggagtatcgc ctatacggtt   203280
ggcgattctc cggggcggc cgctctcgtc ctcgtcgctg ctatcgccgc ccggtaattc    203340
gacgccgcat tcgttgtacg gagcgcggca catgggcggc ggaaagagct tgggcatgcg   203400
aaagcagcgt tgtccatcca cggtctgcgt ggtttcatcg ttatcctccc ataatccccc   203460
ctgtagcgcg ggcagcgttt cgacgctgtg agaggggaag gcccagttct ggttgtcttg   203520
cagcgcgccc gtgggcagta ggtccgtgcg gccccatgcg ctgctgttgt tgggtacctt   203580
gtcagtgccg cgagtaggtc gcagaaacca gtccagagcg ctctctagct gcgagcgtgt   203640
gatggtgccc agtgcgccgt gccagcgcag cacgtctctt ttcagcgtgt ggtgacagac   203700
gggcagctcc tccaaccgac actcgccgcg caatccgcgg tcgaagcggc agagaccacg   203760
cagtttaagc agaccgcact tgagaaacat gtgaaaatta tcggcaatgc gatacaggtc   203820
tgagtcctcg atcttgtgta ggtagaccac gccaaacttg tcgagcagca ccaggccgct   203880
gggcacaaaa ggcccgtagg ccaggtaata gcccacgagg ccgacgacgt accactcgca   203940
gcacaagcgt tgacgaataa agttcagaag atcgcgaaag tccgcggccg gcatgtggtc   204000
aaaaggtctg caggcgcgca ggccctcgat ggagccaagc atgagcaacg gctccacctc   204060
ggtgcgaccc ggcgtgcgga tgaccaggtt gagaccgctc atttcgcggg ccgtcttggc   204120
```

```
cacggccgca gcgtcagtgg ggtcggtgca gaggaatttt tgcacatgat agcgcggttc 204180
ggtggtggcg aacggcgttt gtgggtgccg atacacatat tcgcaccaga gtaagccgtt 204240
cttggaaaag gctttgatat cactggccac ctcgtagagc ccgtcggtct cccagtcgta 204300
gacgtagacg tgtgccgtaat gacttagcat gagcacacag ggcagttcct gcgcctgctt 204360
ggtgtttcgt gttagatcgc tgtcgggtgg acgtacggct aatacaccga cggcttccag 204420
ggtgtcatcg cagcagagat agtcggcggc cagagaacgt gcgtaaatct gcgggatagc 204480
ggcctgttcg cgcatcacta ggaaccagtt ggcggggttg cgcagtgcta cggtggttcc 204540
ctggtgacgc tgcacgtagg ttctcagcgc cggaggatcg tactggcgca gatagaggcc 204600
ttgcagcatc gataacgtct tttgaaagac ggtgtttcta aattggaaaa cgccgtagtc 204660
gcagcggata gcatcttcgc agcgctcgtc gcgctgtcgg agataggtgc cccaggcttc 204720
ggcggcggct ttggtgagta gggacatgcc ggcaaagccg tctcgacagc gaatcggata 204780
aagcgcgctg cgcgaaagct taatatagga gcagcgtcag acgaatcgcg gctggtggcc 204840 cgggggtgg gacgcgccgc ctacacaaag tgctcccgaa aatcgaaact cttgacccac 204900
tccggagaca aatccgtatt cagattgatg cgtcgcgctt ccacttcggc ttccgaaacc 204960
tcggcctccg tccggtaggc gttaacgata cgctgaccca ggtgccaacg ctctttctct 205020
gccaaacgcc gttgctcaaa ccattcgtct acgtccttga ggtcaaagac agtgtcctcc 205080
tcaaggtcaa agcctaggtc ttcccactcg tcgtcatcgc tctcgtgcc ggcggccata 205140 cgcgcggcaa ccgcgtcttc ccctcctctt cttt caacgt ttggtaccac gttgttttct 205200
tcgggttcca taggttctgc gccactgtcg tcatcgtcct ctccctgctc ctcatcgtcc 205260
gccaaggcgt cgtggattac ctccaggttc tgattgtcgg gtacgacgtg gttatcttcg 205320
tcgtcgtcgc gtggcatggg tggcggccga cggcggacga ccggcatggc gcggccgtcg 205380
tttccttcgt cttcctcttc accgtctccc agggaacgcg gtcgacggcg ttccgcgaag 205440
tcgccgcgga ccacgcgcgc ctgccagatg gtaaatgcgt cccaaccgtc ccagttattg 205500
agcatttcgg cgcggaaacg gtcgcctcga cagagccagc gaaactgccg cgcgtagtcg 205560
cggtctacgc cgctgtcgaa catggtaaag tgcagacgcg ccgcttcgcc catgtgtacg 205620
cagcctccgt tgcgttccag cctggccgcg cgccgcagac cgtgttcgta gcggcgacgc 205680
acgtacacct tcatgaggcc ggcgcgaaaa agttcctcta ggctgtcagc cagacggtag 205740
atttcaccgg caagacgctg caggggcggc gagcggtcca ggtgcgactt gacgatcacc 205800
acgtaaaaac gacagaaacg gtcgaagatg atgaggaagg acgtgtcaaa aaaaccacca 205860
gcgcggtagg agcccacggc gcccagcagg taccagcggc aacgcagttg cagcgtgacg 205920
tacatttcgc actcggccaa gcgggcggct ggcgctacct cgaagggcca gcagtccgtc 205980
aagcagccga aactggtcag gagtttcaac gttttggcat gacgcccagg tgtgtgaaag 206040
ttcacgtcgc gtccgtggtg ttccaccaacg caggcggcca acgcgtcggc gtcacgagcg 206100
tgacgcagca gcatcgctac cacgtcgtgc ggtacccgcg tagcaaacgg cgtctgtggc 206160
tgacggtaca cggcttcggt gtacatcata ccgtaacgcg ccagctcgtc cagatgacgc 206220
gcgcacaaca gcagaatctc ttgcgagggt tcgtagatgt agaggcgcgt accgccaccc 206280
atgcagagca ccagctccgt ttcttcgtag tgatcttcca ccatgatcac gcacttgcct 206340
agcacgataa ggcgttcggg gcaacaaatc acgtcgtcca gcaactggtc gcgtagctcc 206400
ggcatggtgc tgccgggccg cacctgcagg aaccagttgt gcggaatgcc gagcgacagc 206460
acctggtcga cgtggttacg gacccagtcg cgaagcacgt cggcgctgta ctggcactca 206520
```

```
aagatgccct gaaagtcgcc catgacccgc agaaaagttt cgtagcgcgt gtggcaatag  206580
aggaattcat cgtttcgcgt aaacgtggga gctccgtctt cccaacgtgt acgccacatg  206640
tcaaaagagg ccgccagcta gacacccag aaaagaagca gagaaggaga cttctttgtg   206700
cgacacgttt tattccgcgt cctccgctcg acgttcaaat ctggatgtac tcgcgcacac  206760
ccgtcaggct cttaaaggga aaagggtccg agtacgtcac taaccgcgac tgatgcacca  206820
gggcggtaat caccccgctcc cgccctcgc cgtcgacga acgcgtcgtc accaggcagt  206880
gcagccgcgg gcccgtatcg tcctgatgac cagcggcctc cgctcggct gcttccacac   206940 cgacaatgtc gggatccaac acgtagctct gcgagttggt gtcgtagcgg tgtagcacca  207000
acgtgttggg gtccagacgc tcccacgcgc cctcgtgcgg gtcaaaacgc tccgttaaac  207060
agagccagtc atactgctgc tgcagaatac gccgctcgcg ctcgcgtcgc tcatcgggca  207120
acgcggcgtc ttcgttgaag agaatgtccc gcttgtggtc tacggcacgc tcgtggtggt  207180
gcgggcacag atgacggtgt tccatacgcg tctgacgttg acgctcgcgc tcaaaacgcc  207240
ggtgtcgaaa gaccatttc agcaaccccca tgcggaaaaa ctccgtgatg gtgttggcaa  207300
cgcgccgcac atagtggttg gggtcgtcca tctggatggc gtacacggca ccgaaccagt  207360
ccagcagtac cagcacttcg gccacaaagc tgcgtcccgg tcgcggacgt cccgtcacgc  207420
ctagcacata ccacggcgtg gccagattag cacggacagc ccaccaccaa cgacggctct  207480
ccacctcggt gagcgcacaa aagggccaaa tgcggtgtaa ttgctgcacc gtttctcatca  207540 gccgcataat caccgtgccg taacccggtg tatgcaactt cacgtcgcaa cccaggattc  207600
gttcggccgt ggcgtacgag ccctcaggcg tggtgtcatt gagaaacaaa acatgcatgg  207660
tacgcgcgcc cttagggtat cgtcgcggaa caggtaccgt cattctccgc aaagtggtgt  207720
gaatcacgtc gcgatacgca atctccgaac gtgacacacc gtaacgtgcc agttcgtcca  207780
ggttgtgcga taccaacacc atgtactttt cacgagtgtc gtaggcgtag acgcgagaaa  207840
agcgacccat aaaaaccacg tacggggtag ccaccatgcc atcatggtga tcgcgacgtg  207900
gctcgggcaa caaataaca gcgtatccca acggcgtcag cggctcgcgg caacagatga   207960
gctttgacgc cgcctgtttg gcggcggtaa tgatcccgtc ctccgtacgt aacatcacat  208020
gccagccctt gggggaccc aaggacagac agcgtccctc gttacgatga acgtaacgcg   208080
tgatttccat tggctccagg caaaagaaca gttccttaaa atcccgcaac acttgtcggt  208140
ataacgccat gggatcctcg gccgccacag gcagcgcggg gagctccggc ggcataactg  208200
cagcgccgtc agggccagaa cccgcagccg gatccatcat tgcgcgacac tctcagccgg  208260
acaaccggcg tcactgacag aagccgagcc aaatacagag aaagcaacgc tacaccgtca  208320
ccccgctccc aagcgccgcg aaaagtgctc cgatttttca ccgtcgttcg cgacgttgat  208380
ttgcctcggt ctgagaaccg acctagcgtt cggaccggtg cgcagaaaca gccggcggtc  208440
cgagccactg agcggttcac agccccgcc gccgatagtt accggagaga cgttcgagct   208500
gcaggtacat cggcgctccc cgcttcgcca ccccgcgccc gccccagttt atactctccg  208560 acgcccgtc caacgcgcct gtggagggc aatcggaccg cgggagctct ccaagtggat    208620
gacaggcaca gccgggtgcc cgaccgtaaa gagccctcat ccacctgaac agaccgctaa  208680
ccgaaggacc ccgagtcgcg tccgtcggtc ccgacgtccg tcgtcatctg gctccctgct  208740
gttggctacc tctcggattt caaaaaagag cacgtgccga tgacggtgca caggaaagag  208800
ccaaagtgtc acagcgtcct tttttatttg tattcctttc ctgttttgta ctcgtaaact  208860
```

-continued

```
gttgatgttg tttttacatc caaaagggca agtaagaaac aggatgaggc atggtaggtt 208920
tgggcgcggg gcggccctcc agcacggcgg cccgggccgc ccggcgggtg agcacccggc 208980
gttgcgccgt atctatcttg tgtttcttct gtgtcttttt cctatcttgt tccgcgacgg 209040
cctctttcat cacgttcagc atgcgttcct cgacgccctc cagggggtcct ggggaggagg 209100
gagtcctagt gaggcttcca atgttgtttt gtggattttc ggtttcctct tcttggtcgt 209160
catcgtcgga cgtgtcgtct tcctcttgat cctcttcttc gtccgaatag tagacgcata 209220
gtccttggtt catcaggctg ggattcatca ggttctgacg gggaatccgc tgttgtagac 209280
gtttaaccgc ccgttccagg cgagagctca tgccgcacca gacgctgtaa cgccgcacgg 209340
gcccgtagcg ggctgtttgt tcgcgtacat gatcgttgag ctcttgccaa tattgtttgg 209400
cacactccag atcggaggtt tgtggatagt cgggtcggat ccgcggatcc caactgacat 209460
cggcggtgcc agagacttcg tccagactgt tacgcataga gcaccagtcg ggtcggacga 209520
taaacctgtc cttgcggatt aaccatttat aacgtagttc gtgatggcgt gtagaggccc 209580
gtacacgctc cacggtccca aagcggtccc agaagggaaa gttttcgtga gggcagcgac 209640
ccggcacttc cagacgttcg gcgtcgtcca cggcgtagtg aaaacgccgg ccggcctggt 209700
aaattttgag cagaccacg gttaacaaca tgtccacgct gtcagccaac cgccagatct 209760
cgcgccgaga cacgtcaaaa tagaaaaatt cgcaggctcg gtcgaccagg atcacgaaat 209820
cggcgtgaaa gacgccggag ggtagcgact cgcccaccac acccattatc atggtttcac 209880
agcataagcg gtccacaaag aacttcaaca ggtcgttgaa ttgctcagtc tccatacaga 209940
tgaagggcca gacgcctttg aggttctcgg cctggccgca gagcagcaac ggacgcgtca 210000
tctcgcctgg agtgcgcaga ggcacgcatt cgccgcgata acgacaggtc acacgctgca 210060
gttcgctgat gctgttgtcg tgcaggcgaa ggtcgcagat aatatgatcc ggttgcgtgg 210120
ttagcagcgg cgtgcgcatt tgctcgccgt agatggcctc gcagtgcaac agcccgtgtc 210180
gtgcaaaatc gtccagactg tgcgccaggt agtaaagcac cccgcgatcg cggtctagac 210240
accacacagt ttcgtaacgt cctagcagga gcaccagacg ggcctggcta gcggctcta 210300
tctcctctac gtagacaaaa aagtcgtcgt cgtctgagtc ctcgtcctcg gaagaggatc 210360
tcggcccatg tactctgggc aacacggtgg tcgaaaactg caggacgccc agggactcga 210420
gcgactcttc gcagcagatg agctgacccc agggcgtttc gggcccatcg gtgacggccg 210480
cgctgccaaa gatgtcctca aactctacaa aatctagacg ccatccgggt ggcgctgaga 210540
cgggaaggct aatgttcatg tcagcgtagc tacggactaa gtggcggatg tcctgacgcg 210600
agtcttgaca gagaatgagt tttcgtagac ccttgagggt tcgccgaaca acggcccag 210660
acgcgtagcg ataggactgg cgcatggtgc cgcggcgtgg agaggcactt ggcagcctat 210720
tttatggagt ttcttcaatg acgtggcttg ttcacgtcgt tcgtgggctg cggtcggcag 210780
ctccggtctg taaccaccc gaaaagactg acatcgacgt caaagactca cgtaatttgg 210840
aacatgtgca actgcaaagt gcgtcagaat agcacgtgac tttgggacat aaaaagtacc 210900
gtgagttata gacgtggttt ttgtgattga cacttacagc aggtaagaca agggacgata 210960
aaactgtatg tgaggaacct gggtgcttag acaactaacg tgttatgctt tttacaggac 211020
cgttcagcag gtaacactac ctgtaaggtg atgaccacct ctacaaacca aaccttaaca 211080
caggtgagca acatgacaaa tcacaccttg aacaacaccg aaatctatca gctgttcgag 211140
tacactcggt tggggggtatg gttgatgtgc atcgtgggca cgtttctgaa cgtgctggtg 211200
atcaccacca tcatgtacta ccgtcgtaag aagaaatctc cgagcgatac ttacatctgc 211260
```

```
aacctggcta tagccgatct gctgattgtc gtcggcctgc cgttttttct agaatatgcc   211320
aagcatcacc ctaaactcag ccgagaggtg gtttgttcgg gactcaacgc ttgtttctac   211380
atctgtcttt ttgccggcgt ttgttttctc atcaacctgt cgatggatcg ctactgcgtc   211440
attgtttggg gtgtagaatt gaaccgcgtg cgaaataaca agcgggccac ctgttgggtg   211500
gtgattttt ggatactagc cgtgcttatg gggatgccac attacctgat gtacagccat    211560
accaacaacg agtgtgttgg tgaattcgct aacgagactt cgggttggtt ccccgtgttt   211620
ttgaacacca aagttaacat tgcggctac ctggcgccca ttgcgctgat ggcgtacacg     211680
tacaaccgta tggtgcggtt tatcattaac tacgttggta aatggcacat gcagacgctc   211740
cacgttcttt tggttgtggt tgtgtctttt gccagctttt ggtttccttt caacctggcg   211800
ctatttttag aatccatccg tcttctggcg ggagtgtaca atgacacact tcaaaacgtt   211860
attatcttct gtctatacgt cggtcagttt ttggcctacg ttcgcgcttg tctgaatcct   211920
gggatctaca tcctagtagg cactcaaatg aggaaggaca tgtggacaac cctaagggta   211980
ttcgcctgtt gctgcgtgaa gcaggagata ccttaccagg acattgatat tgagctacaa   212040
aaggacatac aaagaagggc caaacacacc aaacgtaccc attatgacag aaaaaatgca   212100
cctatggagt ccggggagga ggaatttcta ttgtaattcg atcctctttc acgcgtccgc   212160
cgcacatcta tttttgctca ttgcacgttt cttcgtggtc acgtcggctc gaagaggttg   212220
gtgtgaaaac gtcatctcgc cgacgtggtg aaccgctcat atagaccaaa ccggacgctg   212280
cctcagtctc tcggtgcgtg gaccaggcgg tgtccatgca ccgagggcag aactggtgct   212340
accatgacgc cgacgacgac gaccacggaa ctcacgacgg agtttgaata cgaccttgga   212400
gcaacccctt gtaccttcac cgacgtgctt aatcagtcaa agccggtcac gttgtttctg   212460
tacggcgttg tctttctctt cggttccgtc ggcaacttct tggtgatttt caccatcacc   212520
tggcgacgtc ggattcaatg ctccggcgat gtttacttta tcaatctcgc ggccgccgat   212580
ttgcttttcg tttgtacact acctctgtgg atgcaatacc tcctagatca caactcccta   212640
gccagcgtgc cgtgtacgtt actcactgcc tgtttctacg tggctatgtt tgccagtttg   212700
tgttttatca cggagattgc actcgatcgc tactacgcta ttgtttacat gagatatcgg   212760
cctgtaaaac aggcctgcct tttcagtatt ttttggtgga tctttgccgt gatcatcgcc   212820
attccacatt ttatggtggt gaccaaaaaa gacaatcaat gtatgaccga ctacgactac   212880
ttagaggtca gctacccgat catcctcaac gtagaactca tgctcggtgc tttcgtgatc   212940
ccgctcagtg tcatcagcta ctgctactac cgcatttcca gaatcgttgc ggtgtctcag   213000
tcgcgccaca aggtcgcat tgtacgggta cttatagcgg tcgtgcttgt ctttatcatc     213060
ttttggctgc cgtaccacct gacgctgttt gtggacacgt aaaaactcct caaatggatc   213120
tccagcagct gcgagttcga aagatcgctc aaacgtgcgc tcatcttgac cgagtcgctc   213180
gcctttgtc actgttgtct caatccgctg ctgtacgtct tcgtgggcac caagtttcgg     213240
caagaactgc actgtctgct ggccgagttt cgccagcgac tcttttcccg cgatgtatcc   213300
tggtaccaca gcatgagctt ttcgcgtcgg agctcgccga gccgaagaga gacatcttcc   213360
gacacgctgt ccgacgaggt gtgtcgcgtc tcacaaatta taccgtaata aaaaagcgct   213420
acctcggcct tttcatacaa acccgtgtc cgcccctctt ttccccgtgc ccgatataca     213480
cgatattaaa cccacgacca tttccgtgcg attagcgaac cggaaaagtt tatgggaaa     213540
aagacgtagg aaaggatcat gtagaaaaac atgcggtgtt tccgatggtg gctctacagt   213600
```

```
gggtggtggt ggctcacgtt tggatgtgct cggaccgtga cggtgggttt cgtcgcgccc 213660
acggtccggg cacaatcaac cgtggtccgc tctgagccgg ctccgccgtc ggaaacccga 213720
cgagacaaca atgacacgtc ttacttcagc agcacctctt tccattcttc cgtgtcccct 213780
gccacctcag tggaccgtca atttcgacgg accacgtacg accgttggga cggtcgacgt 213840
tggctgcgca cccgctacgg gaacgccagc gcctgcgtga cgggcaccca atggagcacc 213900
aactttttt tctctcagtg tgagcactac cctagtttcg tgaaactcaa cggggtgcag 213960
cgctggacac ctgttcggag acctatgggc gaggttgcct actacggggg ttgttgtatg 214020
gtgggcgggg gtaatcgtgc gtacgtgata ctcgtgagcg gttacgggac cgccagctac 214080
ggcaacgctt tacgcgtgga ttttgggcgc ggcaactgca cggcgccgaa acgcacctac 214140
cctcggcgct tggaactgca cgatggccgc acagaccta gccgttgcga tccctaccaa 214200
gtatatttct acggtctgca gtgtcctgag caactggtta tcaccgccca cggcggcgtg 214260
ggtatgcgcc gctgtcctac cggctctcgt cccaccccgt cccggcccca ccggcatgac 214320
ttggagaacg agctacatgg tctgtgtgtg gatcttctgg tgtgcgtcct tttattagct 214380
ctgctgctgt tggagctcgt tcccatggaa gccgtgcgtc acccgctgct tttctggcga 214440
cgcgtggcgt tatcgccgtc cacttccaag gtggatcgcg ccgtcaagct gtgtcttcgg 214500
cgcatgctgg gtctgccgcc gccaccgtca gtcgcaccac ctggggaaaa gaaggagcta 214560
ccggctcagg cggccttgtc gccgccactg accacctggt cactaccgcc gtttctgtcc 214620
acgcggatac ctgacagtcc gccgccaccg taccagcttc gtcacgccac gtcactagtg 214680
acggtaccca cgctgctgtt atatacgtca tccgacatcg gtgacacagc ttcagaaaca 214740
acgtgtgtgg cgcacgctac ttatggggaa ccccggagc ccgctcgatc gacggctacg 214800
gttcaggaat gtacggttct taccgccccg aattgcggca tcgtcaacaa cgacggcgcg 214860
gtctctgaag gccaagacca tggagatgcg gttcaccata gcctggatgt ggtttcccag 214920
tgtgctgctg atactggggt tgttgacacc tccgagtaac gggtgcaccg tcgatgttgg 214980
acgaaacgta tccattcgag aacagtgccg ccttcgaaac ggtgcgacgt tctccaaggg 215040
agacatcgaa ggtaacttca gtgggcccgt cgtcgtggag ttggactacg aagacatcga 215100
tattactggc gaacggcagc gacttcggtt ccatctcagc ggactcgggt gtcctacaaa 215160
ggaaaatata agaaaagaca atgaaagcga cgtcaacggt ggaattcgct gggctctata 215220
tatacaaacc ggcgacgcca agtacggtat tcgtaaccag catttgagta tacggttaat 215280
gtatcctggg gaaaaaaata cacaacagct gttgggttct gatttcagtt gcgaacgtca 215340
ccggagaccg tccacgccgt tgggaaagaa cgccgaagtg cctcccgcga cccgcacgtc 215400
ttctacatac ggcgtcctca gcgcttttgt agtgtggatt ggatccggcc tcaatatcat 215460
ctggtggacc ggcatcgtgc ttctggcggc ggacgctctc ggacttggcg agcgttggct 215520
gaggttggca ctgtcccacc gggataaaca tcacgcatcg agaaccgcgg cgctccagtg 215580
tcaacgcgac atgttacttc ggcaacgtcg acgggctcgg cggctgcacg ccgtttctga 215640
aggcaaactg caggaagaga agaaacgaca gtctgctctg gtctggaacg ttgaggcgcg 215700
acccttccg tccacacatc agctgattgt gctgcccct cctgtagcgt cagctcctcc 215760
tgcggttccc tcgcagcccc ccgagtattc gtctgtgttt ccgcctgtat aaaaataaag 215820
agacgggagg ctgatcgcgg ccttcagcgt ctcatttgtc tttactctcg agtgcggtcg 215880
gtgtctcatc ggtgagacga ggccgccgcc cgacaagttc gatctcatgt cgctcttgga 215940
gcgcgaagag agttggcgtc gcgtagtcga ctactcgcac aacctgtggt gtacgtgcgg 216000
```

```
taactggcaa agccacgttg agattcagga ccaggagccc aactgcgagc agccggagcc 216060
cgcacactgg ctagaatacg tggcggtcca gtggcaggcc cgggttcgcg attctcacga 216120
tcgctggtgt ctctgcaacg cctggcgtga tcacgccttg cgcggccgtt ggggtacggc 216180
gtattcctcg ggttcctcgg cctcttcctc cggtttcgtc gcggagagca agttcacctg 216240
gtggaaacga ctgcgccaca gtacccggcg ctggttgttt cgccgccggc gagctcgata 216300
cactccgtct aactgtgggg aaagtagcac tagcagcggc cagagtagcg gtgacgagag 216360
taactgcagt ctacgcaccc acggcgtgta cacacggggt gaacaacact aatcgataag 216420
tcgcgtgtag gcgactggct acatcaaccg gatatctgcg gggatttaaa aagacgaccc 216480
gttgtcatcc ggcttagagc aaaccgtcct tttatcatct tccgtcgcca tggctatgta 216540
cacatccgaa tccgaacgcg actggcgtcg tgtaatccac gactcgcacg gcctgtggtg 216600
cgattgcggc gactggcgag agcacctcta ttgtgtgtac gacagccatt ttcagcgacg 216660
acccacgacc cgagccgaac ggagggccgc caattggcgg cgacagatgc ggcggttaca 216720
ccgtctgtgg tgtttttgtc aggactggaa gtgtcacgcg ttatacgccg agtgggacgg 216780
caaagaatcc gacgacgagt cgtcggcgtc ttcctcgggc gaagcgccag agcaacaggt 216840
ccccgcttgg aagaccgtgc gagccttctc gcgggcctac caccaccgca ttaaccgggg 216900
tctgcgggge acgcccccac cgcgcaactt gccgggatac gagcacgcct ccgagggctg 216960
gcggttttgc aatcgacggg aacggcgaga ggacgatctt cgcacgcggg ctgagccgga 217020
ccgcgtggtg ttccagttag ggggagtacc tcctcgccgt caccgggaaa cttacgtgta 217080
agaacacggc gtgacaataa acaacatagc gtaaatcccc gtgtgatgtg tgtgattgac 217140
gttcgggaaa catgtcccca tcatcagcgt cacaactgac gtgggttggt cactgacgtg 217200
caggatgtta cgcgagtcag agaatcgcat aagaacgggg tggtgagcgg ttcccacag 217260
gagtctctgg cgcaaaagca ccatgagcct caggttcccc gagagggcgg gttacgaaga 217320
actgggatac cgcccgcatg ccaaacgcgt gtgggtgcat gacccgttgg gattgacgcg 217380
gtttatcatg aggcaactca tgatgtaccc gctggtgttg ccgttcactt ttccgtttta 217440
cgtgccgcgg tcctagcacg tcagtggtga cgctgataat tgcaacatgg cccatgacga 217500
acccgcttgg gacgaacgtc aataccacgt caaaccaccg tgacttggct gaacgttgaa 217560
acataaagcc aaagcgccgt cggcacttgg cttcagagca gcgcctcggg gcgatgcgac 217620
ggcgatgaac ttagagcaac tcatcaacgt ccttggtctg ctcgtctgga ttgccgctcg 217680
tgctgtcagc cgcgttggtc cgcatggctc cggactcgtt tatcgtgagc ttcatgattt 217740
ctacgggtat ctgcagctgg accttctggg accagtggtg gcggggaatc gctcagtccg 217800
gacctggaga gagcaggcgg accgagccag agggaccttc gttcggcgtt caggccttaa 217860
tactagccac atcttacctg tcggcggcct gtctgggggc tccggtacct tacccgccgg 217920
cctgtatcgt cccgaagaag aggtgttcct cctcttgaac cgctgccatg gccactgtc 217980
aacgccgaaa agcgcttttc tggctgaggt tggtgtcgct aatgccagtt ttttatctcg 218040
cttcaatgtc ggtgattttc acggagcgtc atgggaaaac ggtaccgctc ccgatggaga 218100
gcccggggta tgctgaaatt cttcttaaaa ttacgtaaac gacgtcgtcc agtcgttgtg 218160
ccgcgattcg tacggttcat cgtctacgtc gttttgttca ccgtcgctgt gcaacgcgtg 218220
aaacaagagc gtgatgcgca ccttcggcgg tatgaagaac gattgcagaa aaaccgtgca 218280
cggcgtcggc agagttttcc gtgacttggg gcggtgggtc cgagctgcgg tatgggtcac 218340
```

```
ggcggcgtgc gtcttattga caaagatgcc gatgtgtgac taaaaaacgt cccagcccca 218400
gagcgatgtg tttcaataaa aattatgtag tatcatatta tgcgtgtcct ggttttttcat 218460 tttttggatg tatttgtcgc ataaaaggcg gtgggatgtg gggatgaaat atatccagat 218520
acgcagtttt gttatcctaa caaaacccgt gtcatgctaa aaacggtaat gcaggatgaa 218580
agtcccgtgg ggggggggg gaggcagaca gtagtcgttt ttgccgctgg gcgtacgcta 218640
tgcttgtatt tatgactata atatgtgcac tcgtgtgtcg atgttcctat tgggaagggt 218700
gtgaatgtag gaggtataaa aatggtggg atgcggagag gcatcgctag acacaggttg 218760
atcgttgtgc tagccccacc tgagcagcgt catgaataaa gcggtgatta agcgtgaaaa 218820
caccgtgagg gggggggggc aggacgcttg gtggcagtgg ccgttggata ccttacgtgt 218880
ctgtattggt acatttgcaa atcgtcgggt gcgacggtat agtttaacga taattatatt 218940
atgtatgcgc agtatacaat gccgtaaacc attgtaacac gaaacgttac aatgatggga 219000
aagatgccga taaaaaacac ataaaacaca taaaaggcat atacacgaat tactagttac 219060
acgtttgtct atgtgcgagt tcaaggacac ttgtataatg catatcccta taatcggatg 219120
tgtgttactc attcgtggcg ttgttatagt attgtgaaaa agaattctcg taagcatgtt 219180
gacaactgca aaataaaagc attttattga gcattgtaat ggtagtgtgt ggctacatta 219240
gaaaacgtga cgcgtcgcat gtcgcggcac aatctggcag cggggtcggg gtagggtacg 219300
gtgggaggca tgtacacaga tggaacaaaa gcagaagtaa cgtgagacgg agcatatagt 219360
ccagtatccg gcggttcctg agtagcacca cccatcaact gaatgccctc atgagtaaaa 219420
gtctgcgggc gacagccctt ggggaccgtt ggcatgggac gatcaatctc caaaccacag 219480
cgtaacacgg ttttcttcca acgtcgttga tagacgtcgt ttttacggtt actccccaga 219540
acccagaaag tctcgtccaa gtcgtaccag gagtcttccc cagggagacg tggcggtttc 219600
caatcctcat cgtcccgtcg caaagcacgt cccaaactgg cttggggagt caacggtggt 219660
tctgtgggtc gggtgtagcg cgagtgtttt cccttcatga gcgattcgtc ctccttgcct 219720
ttaggctttt tggtcttttt gtgtatcatc tggccgccgg cctccataac caccgtggcc 219780
aagtccagtc ccagagcttg agcgtcggcg cggcgtcggg cgtcttgcag atagtcttcc 219840
acatttgcac agatggccgg gtgtttggtg gctagggtga gcacctcagc ctcgccgcgg 219900
cccggacgta gcaaaaaagc taactgcccg tgcggctcgc gcgcccacag cgcggcgcgc 219960
gggtgcaggt gcagcgcgtc ccagcgcggc cgctcccact gctcgcggtc cagctcgggc 220020
agcagccgcc gcgcggcctc ggcggcgggc gccgactcgc gccccagcgc cagcgcgccc 220080
agcacgcccg cgcgcagaaa gtgcgacagc tccgccgcca gtgggtacac gtgcccgtcc 220140
agcgggcagt acccgaacac ggcgcccagc tcgtccagca ccaccaccag catggcgcgc 220200
ggtacggtcc ccgacgccgc cggacccacc atcgccgccg acccaccat caccgtcggc 220260 gccgccgctg ctgccgctgc cgccgcgtcc gccccgacca ccgcgtgcgc gtccgcgctt 220320
ggcacgcaaa tcgcgctccc gccggcggcg ccgtacggct gcggaggtaa agtcacagca 220380
gaccccacgg ctcccgctat cgcgcacggc gcgtccccgc cggcggcctc cgtctccgtg 220440
ccgctcgccc ccggcggcga cgtcgtcccc gccgccgtcc ctgtcgccgg cccgccgcg 220500 cagcccagcc accgcgacgg cagcaccgcg cccagcgcca gccagccgca gcacagacgc 220560
tggttcaggt gccgacgcac ggccgtcagc agcgacgcgg ggtgcggcgc cgacgcgaac 220620
ggctcgtact gcgccagctc ctgccacgcg cccagcagca ccatcggctg cagtcgcctg 220680
cccggcgtct gcagtgccac cgtcgtgccg gcccaccggc ggcgcagctc ccgtccgagc 220740
```

```
gccgtcgcct cctcggcgcg cagcaacgtc tggcgaagcg ccggctgagg cagcagcgtc    220800
gcgcgcgggg tgcccacgcc cagccggttg cagcggtaca gccgcaccac ctcgcccgcg    220860
ccgtgccgaa accactcgtc cgcgtcgcgc gccgccagga tcagcgtgtt gttcgccagg    220920
tcgtacacga acacgcggaa cccggcgccc agcgccaggt acagtccgtc ctgcgcgcac    220980
agaccctcgg gatggccggc cttgtcgccc accgtcgggt cggccgcggg gtccacctcg    221040 tgcaccacg tcgccaccag cacgatccac gcgtcccgcg cgacagctg acgcaggtcc    221100 gtcgcgccca cgccgttcat ctggctgcgc ggcgtcaccc gcgcgtagaa tccgtacggc    221160
cgtccgagcg gcagcagcgt gcccgcgtcg cgctgcgacc acttgcgcat ggcgcggccc    221220
gtgctgttgg ccaaaaacgc cgcgcgccac acggcgccca tggcctggta ttccagctcc    221280
gtcagcgcct ggcgctccac cggaatctga gacagcagca agcgctccgg gccgtgccaa    221340
aagttgctgt tgttgccgct acccggaggg gcgcccggcg gcccgcgggg ttctacccgg    221400
tggacggcgt gggccggtgt cgccgtaccc gcagcactcg tactagtccc cgctgttgac    221460
gtcgcttcca aagaagaaga acgagaggaa ccaacccccg aaggccctcc ggcttcgcgg    221520
ccgcgaccga ggggcggggg gcgcggcgac atgccgttgc gctgggccat ggccgccgga    221580
cacctccgac gtccactata taccaagcaa acccgcgtca gcgaccacgc cgtttacaca    221640
tgcggacgcc gcagtcgccc gtgtgccccg gccgacacgc atctggcttt tataggcagc    221700
gacgtgcacg gcgcttgctg gcgccgcctc gccgcgcagt cgggaagccc gtggaaatgc    221760
acccggcagc cgacgcgcca ctggactggc aaaggcagcc cgagcgagaa cccatctagg    221820
tggacgcccg acatccattc cgggccgtgt gctgggtccc cgaggggcgg gggggtgttt    221880
ttagcggggg ggtgaaattt gaggttgcgt gtgtggacgg cgacggcgaa gagttgcgtg    221940
tggtgcggtg tggtgcggtg gggacggcgg tcgcggaggc cggcgacggc gaataaaagc    222000
gacgtgcgcc gcgcacggcg aaaagcagac gcgcgtctgt gtctgtttga ttccccgggg    222060
aaaagaggaa gttcccaggg gacggcagcg cgggtccctg gggacacacg caaaacaacg    222120
gccagagaca agacgcggaa aagaggaaag aacagacaca cgcaaaacaa cggccagagg    222180
aagctcgggg gcgcaaggga ggggggggcaa gacgcggaaa agaggaagtc cctaggggac    222240
cgcggggaaa acgacagacg aagtacggca caacccgcgt cgaggacaca cgcagaagcg    222300
atcgcccagg ggagggggg ggtcgcggac cccggggcac acacgcagac acggcccgcc    222360
aacacacccc gacacacccc tgacacaccc cgccaacaca cccgccacac gcccgcgaca    222420
cacccagaca cacccgccac acgccctgac acacccgaca cccaccccac gcgcgcaccc    222480
acccagccgc gccccgaca caccccgacc gccgcggtg cgggacgggg ctgagggagg    222540
ttttgccacc gtaagcgcgc cgattcgcgg aataggactg agggctggac agggctgcgg    222600
gagttttgtc cacggagctt tctgcgcgct ggcggtgcgt gtgtctctgg acataagtaa    222660
gcgcagcggt gtcctcagcg cgtttgcggc gtgctgtgtc cggcgctttg tgcgcactgc    222720
cggtgcgtgt cgtcccgcgg tgttttttgt ttcgcggacc ggcgccgggg acggggtgtt    222780
gcgcgcgctc gggggttggc ggcgggtgtt tctacggtgt ttgcgcggcg tttctaggca    222840
gcttttgcgc ggcgcttcgc ttttcggggc ggcgacggcg gtgttttcgg gcgtgctggg    222900
cgccggcgct agtaacggga gttacgctgg ggacggggac ggggtttgcg gcggggacgg    222960
gggggtgtgc gggacggggg ggtgtgcggg gacgggggt gtgcggggac ggccacgggg    223020
gccttttgcg gcggggacga tgcgttgcgg ggccgggggc cttttgcggc ggggacgggg    223080
```

-continued

```
cgttgcggag acggggacgg gagtggggac ggtggtgagg acggggacgg gggcctttcg 223140
cggcggggac ggggagttgc gggatggcgg gctgttgcgt ggcggggacg ggggactctt 223200
gcggcgggga cggggaacac agacggcacg cacacgcagc tcgcctattt aacctccacc 223260
cactacaaca cacacatgcc gcacaatcat gccagccaca gacacaaaca gcacccacac 223320
cacgccgctt cacccagagc accaacacgc gttaccctta caccacagca ccacacaacc 223380
gcatgtccaa acttcggaca aacacgccga caaacaacac cgcacgcaga tggagctcga 223440
cgccgcggac tacgctgctt gcgcacaggc ccgccaacac ctctacggtc aaacacaacc 223500
ccaactacac gcatacccca acgccaaccc acaggaaagc gctcattttt gcacagagaa 223560
tcaacatcaa ctcacgaatc tacttcacaa cataggcgag ggcgcagcgc tcggctaccc 223620
cgtcccccgc gcggaaatcc gccgcggcgg tggcgactgg gccgacagcg caagcgactt 223680
cgacgccgac tgctggtgca tgtggggacg cttcggaacc atgggccgcc aacctgtcgt 223740
aaccttactg ttggcgcgcc aacgcgacgg cctcgctgac tggaacgtcg tacgctgccg 223800
cggaacaggc tttcgcgcac acgattccga ggacggcgtc tctgtctggc gtcagcacct 223860
ggttttttta ctcggaggcc acggccgccg tgtacagtta gaacgaccat ccgcgggaga 223920
agcccaagct cgaggcctat tgccacgcat ccggatcacc cccatctcca catctccacg 223980
cccaaaacca ccccagccca ccacatccac cgcatcgcac ccacatgcta cggctcggcc 224040
agatcacacg ctctctcctg tcccttctac accctcagcc acggttcaca atccccgaaa 224100
ctacgccgtc caacttcacg cagaaacgac ccgcacatgg cgctgggcac gacgcggtga 224160
acgtggcgcg tggatgccgg ccgagacatt tacgtgtccc aaggataaac gtccctggta 224220
gacggggtag ggggatctac cagcccagga atcgcgtctt tcgccgccac gctgcttcac 224280
cgatatccaa taaacccatc ccctcgccac gacgtctccg cgtatctttg tagcctcagg 224340
aatacgtccc cacgtccacc catcccaagc actccacacg ctatcacaga ccacggacac 224400
ggcaaaaaat gcatgcaaac ttctcattta ttgtgtctac tactctgtgt tgctacaggg 224460
agtgaagggg gtgaaggcaa agaaaaaaaa aagaacaaaa taatagatta gcagaaggaa 224520
taatccgtgc gaccgagctt gtgcttcttt tcttataagg aggcaaatat actagggaaa 224580
acataacaat aggaagaaac cgaggtttgg gagaaaagct gagataaaat agcgcatttt 224640
ccatacagag gttgttgttt ttgtggatcc taagaggttt caagtgcgaa tctcaaagtt 224700
ctcacgagaa tattgtcttc aagaatcgac aactgtggtc caagattttt ttttggtctt 224760
tttaggttct gcgagggaca tcacgatgga tcgttgcgat gaagtcacgc gtacgcctct 224820
ggtgtggcgc ggtgtcgtga caggagagtg tgttttcagt gcagagctgt cttgattcct 224880
atatccgagt atctgttttc tcgtaaggac ggtaatcttc tttggtgtaa gtacatctaa 224940
aagctgcaaa ctatatttta agggctgtct ctaggtgtac tttgatgctg gagtttttcg 225000
ctgtgttgat gtgaataaat ctactactac tattatatgc agaaagagtg attatgccga 225060
gacaagattg cattggctga actgtttcaa aaacgcctac actctactta tccgtaaacc 225120
taaggtaata ctatgtgtaa gttgtttttt tttcttttg tagtaaaatg gtgatacgtg 225180
caattaaaac tgtattccat gtttccatcc tttcatttca actttaaagg cggctttgag 225240
agcgaagaag tgcgaggata aaaatggatg actccttcgt gtccagggag tcgactactg 225300
caacgctgat tgattaaaag atggtctccg atgatgttgt tattgatcga atcatggtgc 225360
agaacgcgca cggagaggag cgtgtccgcc gccgggaagg tggtctcttt ctcttttctt 225420
ttttcaagaa atcttccatg tgtttatcgt agtgatcgaa atcgactgat ctcgggttct 225480
```

```
ttttgttggt ttcttttcgg ttaatcatgt attgttttct tttttttacag aaagatactt 225540
ttttcatgag caattcctcg cccggcgccg gcatgccgag gtggggccac tgcgatcagc 225600
ggcatgccga cgccgacccg gggatcttgg attcaccgtt ttctctcttc tctctctaca 225660
tacagaccgg gtggcaggag cggtaaggaa tcatcgtcgt ctttcattct tcgatgatta 225720
tggtaatact aaatcttatc taggagcata tacatctaag attggagtac tagtagtcgt 225780
ttgtggtttc tattttttt tatatttatc tatgacagtt tttctgtttt tcgttttgat 225840
aataatataa taaaaactca tggacgtgaa atctggcttg gttgtggtga tttcattctc 225900
attattgttg ttttctttcc gtcttgcgga tgaagatgtt gcgatgcggt tgttgttggt 225960
gttgctatac accgagagag atgatctttt tgttcttctg gttcatttcc tatgattgtt 226020
tggctgctga ccgacgcgtc aggatgtgca gggcatgcgg ggaatcagga ccggacacgg 226080
gataatttca tctacctata cggagatcgc ggtcctcgcc atgaggatcg cgacaggcgc 226140
gtcgaggggg gcaggaacac ccttgcggat tgacattctt ggtggtgttt cgttgttgtc 226200
ggtagttgtt gttgacgatg aggataaata aaaatgacct tgttttgtt ctgttttctc 226260
ttgttgggaa tcgtcgactt tgaattcttc gagttatcgg aaagctgagg tacccaaatg 226320
tctgtagctt ttttctttt accctcttgt ttatcatctg cgattcgtgg taggtaggag 226380
agggaaatga taatccgaga ttaaggaaag gagaagataa aaaaaaaaaa aataataaaa 226440
cagaagccga ccggccgccg acccgttccc caggaccagc ctacgaggaa cggataacgc 226500
ggtggcgacg gcagcggtgg tggcgctggg ggtggcggta gtggtgctgc tgatggtagt 226560
cgggacggag gagagacgat gcatacatac acacgtgcat gctgcatggg tggatggacc 226620
gaccgggaga cgcggaagag aaactcacat aaaaaggtga caaaaagagc ggttgaaaag 226680
agaaaacgag attcgaccag acagaagaga aggaccgggg cttggcgacc cttccacgac 226740
tgctgttgtc atctcggctc ctccgtcttc tccggccac gggcggctaa gtcaccgccg 226800
ttctccccat ccgtccgagc gccgaccgac cagccggccg attcgcccgc cggggcttct 226860
ggagaacgcc ggagcagcag cgatctgggg aagccgctaa accctgcgt ttttatatgg 226920
tagctctgcc gagcgcgggc tgacgcgttg agtaagcgga aagacgtgtg tgacgaaaag 226980
gggtcccatg gtatttcacg tgacgatgag gagatgcggt ttggagcaca tacggtttaa 227040
aaaaagggag ttgtcgtgac aagggctgag ggacctctgt ctccatgtgt gtataaaaag 227100
caaggcacgt tcataatgta aaaaagaaca cgttgtaaac aagctattgc tgtatcattc 227160
ggctgactat gcttcattcg gactgatttt cttttcctaa cggcgtaact taaagtgatt 227220
aacgtatgat atttgttccc cagagttata ctatagtcat catcctaaaa ttcagatata 227280
aggtgctaaa acaaatctat acgttgatcc tacacgttct acgattaacc aacagagacc 227340
aaccatgtct ctttaaccctc gcttgggccg ctaccgtctt tccaaaccag atcgtaacct 227400
ccttcattta cagacgtaac gttacacagc gttaaatgca catggctgca attacatatg 227460
ccaccgaccg atcccaacgt aaaattgttt acgcctgtca cggtacaaac cgtggtctca 227520
ttatgtttag ttccatccgt aagcttccaa gttgacgtaa gatcgtgttt tagatttgta 227580
ttttcaccaa cctttatact agaacttta aaactttcaa cttcaaggca taatgccaaa 227640
attaagcacg ttattagtcc ccccccccc accgaggaat gtgactggac cggttcttag 227700
cagctttggg agccatcttc aaggtggacc gcagctacag cgaaaccgag tccagtgacc 227760
gataaccacg tgcaaccctg cgtatgtacc agtccaagta cgtccggtca ttgttccaca 227820
```

```
caggaaatct aactaggtca acggacaaaa ccaaattgtc aatccaccat atgcacaaca 227880
caaaagcact gacgtttatt tgttgaatta tcaacgttac ttagttacaa taaggaacca 227940
tgtatccact tgaatgttgc ccaactgggt cttccccgtt atagtcatag cgttcccagg 228000
caaaagctaa cgccgaacct aatgcagtaa accgcgcttg cacccagaac cagcttatgt 228060
atcagccaca ataacatccg gttattgttt ccacaggaaa tcctaccagg caaagccccg 228120
cttgttttgt ttctaaccat cttgtttagc aactcgtaaa ctgtcagccc agcgacgtcc 228180
gtttggatca aaagccacgt atactgagac gctgtttcta cccgtttccc catcccgcca 228240
ttcccgggca acccacccaa gtcccgacaa ccaaccacca acagaaaaca tacacagacc 228300
accgggagtt cagttaaaga tttcatcagg tttatttttgg ctgctgctag tcttttgctt 228360
cttagaaaaa aaatacccat atagagaaat aatgatagtt tgacaacaca tatggcaggg 228420
atttcttctt catcaataag atatgcaatt cccccaggga gagactttca acaattgaat 228480
ttacaaaaac aaaattacat caggagaaag agaggataca ttaataaata tattatatct 228540
ggtgtatata ctgaatgctg ctggttcata aggtaacgat gctactttt ttaattccaa 228600 gatgattttt cttttgttagt cttttgttga cttgctggtt cctaaaagtt cgcaaaaacg 228660
attgtgtgaa gattttatga cgttggttga ctagttcatg agattctgct gtacgtgtga 228720
tggttattcg ctggttcgtt ctaagatgag tatcgtactg tgtctgcgat ggtcgtctct 228780
tactggcatt ctctcggctg cctcttgctt tcatgattga aaaggaaaaa aggactccga 228840
gggcgcggtc atcttttact tttcggtttt ctcgttggcg ggtcagaggt agtcagatca 228900
tgagactgtc gtggtcgatg aaactgtgtc tgctcaagtg acgtccattt cttgtacgga 228960
gaaaaaagtc atcgggataa ataaggctat acaaggcgtt gtcaagcgtg cggctctaaa 229020
caaattaagc gatacaaaat tacagtaata cgaataataa attaccccc tccccctgtg 229080 gtcccccgag gcgagagcca cccatcgtgt actctcgcac cacccacgac cacagaggga 229140
gacgggacga agagacgacg cagagcgcca tctcctcctg gaggccggcg gcgttaactg 229200
ctacagctgc ggcggcgacg acagctgcga tttgtcggcc gacatgccga tggtatgggc 229260
ggcggcggca gtggccgcgg cagcggggag gagaggagag agaagaggag cggggcgtcc 229320
gaaggcgagg atggcatgat ctcgccggag cgccggcttt ttatgggata ctcgcgtccg 229380
gtcgggcagc gcccacagga agatgagtca aaacttttaa accatcctga acccgagta 229440 gcggtttaca ggccgcacgc cagtcttagc taaaaacagc ggacagtccc acgctgtttc 229500
tgttgtggct ctctccagtt tcctcatcgc cgtcccgatc tccgtcgtca tcggaagaat 229560
accatccgct ctcatgcggc agtcgatcga cctcgacgaa cgagacgcgg cgacgcctct 229620
ctacggccga ctggttgtgg tggtgaaaga agagcaccag caatcccagg aggagcaaca 229680
agccctcaca tgtccaggag gtcggggaga gggcctgtcg gagatggccg tgaggcatca 229740
cgtacggcag ctgaggagaa acggagaata aaggaaaatt accgtcaggg gccgggttc 229800 ttattagaga aacagcacgt aggtcaggat ccagatacta atggcgatca tgatgacgat 229860
gatcatgcag gccaagacgc ggcgcaccaa tgccgaatcc aagagccgcc gtgccgccgg 229920
ttggtggctg gcggcatcta gagacatggt ttgggggac cggcggcgcg aaaagacagg 229980
gagatggaca gtgtcacggt gttttgttat gattaggaca tggggaccgg aagccgagac 230040
agagtactac agagtgttga agggtaacgt gagggagatc atgtcatggg cgggctgaag 230100
accgtgcggg gaggatcgac gtgtgcggtg cttgtggaac acggtgtttt aatatgtatc 230160
cgcgtgtaat gcacgcggtg tgctttttag cattcggctt ggtaagctac gtggccttct 230220
```

```
gcgccgaaac cacggtcgcc accaactgtc ttgtgaaaac agaaaatacc cacctgacat   230280
gtaagtgcag tccgaataac acatctaata ccggcaatgg cagcaagtgc cacgcggtgt   230340
gcaaatgccg ggtcacagaa cccattacca tgctaggcgc atactcggcc tggggcgcgg   230400
gctcgttcgt ggccacgctg atagtcctgc tggtggtctt cttcgtaatt tacgcgcgcg   230460
aggaggagaa aaacaacacg ggcaccgagg tagatcaatg tctggcctat cggagcctga   230520
cacgcaaaaa gttggaacaa cacgcggcta aaaagcagaa catctacgaa cggattccat   230580
accgaccctc cagacagaaa gataactccc cgttgatcga accgacgggc acagacgacg   230640
aagaggacga ggacgacgac gtctgacaaa gaaggcgaga acgtgttttg caccatgcag   230700
acctacagca ccccctcac gcttgccata gtcacgtcgc tgtttttgtt cacaactcaa    230760
ggaggttcat cgaacgccgt cgaaccaacc aaaaaacccc taaagctcgc caactaccgc   230820
gccacctgcg aggaccgtac acgtactctg gttaccaggc ttaacactag ccatcacagc   230880
gtagtctggc aacgttatga tatctacagc agatacatgc gtcgtatgcc gccactttgc   230940
atcattacag acgcctataa agaaaccacg catcagggtg gcgcaacttt cacgtgcacg   231000
cgccaaaatc tcacgctgta caatcttacg gttaaagata cgggagtcta cctcctgcag   231060
gatcagtata ccggcgatgt cgaggctttc tacctcatca tccacccacg cagcttctgc   231120
cgagctttgg aaacgcgtcg atgcttttat ccgggaccag ggagagttgt ggttacggat   231180
tcccaagagg cagaccgagc aattatctcg gatttaaaac gccagtggtc cggcctctca   231240
cttcattgcg cctgggtttc gggactgatg atctttgttg gcgcactggt catctgcttt   231300
ctgcggtcgc aacgaatcgg ggaacaggac gctgaacagc tgcggacgga cctggatacg   231360
gaacctctat tgttgacggt ggacggggat ttggagtaaa agatgcgtac acaacatcga   231420
cggcgaaaca agtcatcgta cacgcaaata acatgcatgt ttatcatttt ttggattctg   231480
cagaaaagca agtgtaacaa caccactatc gctaatactt ccacgtcaat tacactcaca   231540
agcttgatat ctactgcaca actaacatct actttacaaa ccaccggaat gtctaccact   231600
acattcacat cctccgatgt caacgccaac acatccacag gattcactgc aagctctgca   231660
aaaagcacag acgtgatctc aactatttcc accataccca ctcaaacatc tacaattaac   231720
gcgactgtaa tgacaacctc accaaacgga ggcatgaatt tatcgacaca acatataatc   231780
agcagtaccg cgacttcgca agcaactaca tcattaccaa tcaatactag tacaatggta   231840
acaaatacaa ctcaaaacat cagtacacca ctcccaactt gctcatcatc taatagcaca   231900
ttcaatgata catcaaacaa ccgtacttgt catgaaaaca gtacaatatc acaagaatct   231960
gaaacattgt tgaaggcaat acaaggagac aatatcacta taatacacaa cctaaccacc   232020
acatcgtgct acaagacagc ttggcttaga catttttaata tatccacaca cagaaaatac  232080
acccatccca acataaagag tggaaaattt agtaaccatt cattaaagat cctccattcg   232140
cgtgtactgt gtgagtggca gacacattac ctaaaacatc actacgattt atgttttaca   232200
tgcgatcaga atttatcttt gtctctgtac ggtcttaatt ttactcactc tggtaaatat   232260
agctttcgat gttacaaaag tggccatccc tctgaacaaa atcaaaattt taatctacaa   232320
gtacatccta gaaacaacac gaacgagaca catgtgaacc cctggatatg cgaagaacca   232380
aagcacgaat gggatacttt ggctgctaca tctgataaac cgaccagtca taaagacgat   232440
acaaccacat catctacaga tcatctatac cgctataata atcattccaa cacatcacac   232500
ggcagacaca ctacgtggac tttagtgtta atttgtatag cctgcattct cctattttc    232560
```

```
gtccgacgag ctctaaacaa aaataccat  ccattaaggg acgatatcag tgaatcagaa    232620
ttcatagttc gatacaatcc tgagcatgag gattaagcaa cgtttccgga taaacatctt    232680
atgagaccac accacaaagt aaatgactat gaaagatcaa caacatccga agaaacatca    232740
atgcccatta accgaaatcc aacaacgtta tggactggca gtttacggtt aagtggaggt    232800
tactgatcat cacgttatct gaaggttgta atgatacatg cccttgttcg tgcaactgcc    232860
tcacctccac cgcctcaacc atcaaaaatt cgtctgattt tgtcactaac gctaccaaca    232920
tttcaactac tgcaaataaa accacgcaca aaccctctac cgcctcgtca gatacatcaa    232980
caattactcc aacgctgttg gaatcaccgt caagcgttac gcgaatatta acaacgttct    233040
ctaccgttca tagtaccatt ccctggttga ataccagcaa cgtaacttgc aacggtagtt    233100
tgtacaccat ctataaacaa tctaatttaa attacgaggt aattaacgta acagcgtatg    233160
tcggtggata cgtcactctg caaaattgca ctagaacgga tacatggtat gatgtagaat    233220
ggataaaata tggaactcgt acacaccaac tgtgcagaat tggaagttat cattcaacgt    233280
ctccactaaa cggcatgtgt ctagactgta acagaacctc tctcaccatc tacaacgtaa    233340
ccgtcgaaca cgctggaaaa tacgttttac atcgctacat tgacggtaaa aaggaaaact    233400
actatctaac tgtattatgg ggaaccacaa catcgtctcc tatacctgac aaatgcaaaa    233460
caaaagagga gtcagatcag cacaggcgcg gagcgtggga cgacgtaata acaactgtaa    233520
aaaacactaa cattcccctg ggaattcatg ctgtatgggc gggtgtagtc gtatctgtgg    233580
cacttgtagc cttatacatg ggtagccgtc gcgcttccag gaaaccgcgt tataaaaaac    233640
ttcccaaata tgatccagat gagttttgga ctaaaacctg a                        233681
```

<210> SEQ ID NO 21
<211> LENGTH: 4159
<212> TYPE: DNA
<213> ORGANISM: artificial
<220> FEATURE:
<223> OTHER INFORMATION: synthetic

<400> SEQUENCE: 21

```
ctaaattgta agcgttaata ttttgttaaa attcgcgtta aattttttgtt aaatcagctc      60 atttttaac caataggccg aaatcggcaa atcccttat aaatcaaaag aatagaccga        120
gatagggttg agtgttgttc cagttttgaa caagagtcca ctattaaaga acgtggactc       180
caacgtcaaa gggcgaaaaa ccgtctatca gggcgatggc ccactacgtg aaccatcacc       240
ctaatcaagt tttttggggt cgaggtgccg taaagcacta aatcggaacc ctaaagggag       300 ccccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac       420
cacacccgcc gcgcttaatg cgccgctaca gggcgcgtcc cattcgccat tcaggctgcg       480
caactgttgg gaagggcgat cggtgcgggc ctcttcgcta ttacgccagc tggcgaaagg       540
gggatgtgct gcaaggcgat taagttgggt aacgccaggg ttttcccagt cacgacgttg       600
taaaacgacg gccagtgagc gcgcgtaata cgactcacta gggcgaat tgggtaccgg         660 gccccccctc gaggtcgacg gtatcgataa gcttgatccc aagcttgata tcgaattcgg       720
atgggctccg gaatcggcgc agcaagcatg gaattttgtt ttgatgtatt caaggagctc       780
aaagtccacc atgccaatga gaacatcttc tactgcccca ttgccatcat gtcagctcta       840
gccatggtat acctgggtgc aaaagacagc accaggacag agataaataa ggttgttcgc       900
tttgataaac ttccaggatt cggagacagt attgaagctc agtgtggcac atctgtaaac      960
```

```
gttcactctt cacttagaga catcctcaac caaatcacca aaccaaatga tgtttattcg    1020
ttcagccttg ccagtagact ttatgctgaa gagagatacc caatcctgcc agaatacttg    1080
cagtgtgtga aggaactgta tagaggaggc ttggaaccta tcaactttca aacagctgca    1140
gatcaagcca gagagctcat caattcctgg gtagaaagtc agacaaatgg aattatcaga    1200
aatgtccttc agccaagctc cgtggattct caaactgcaa tggttctggt taatgccatt    1260
gtcttcaaag gactgtggga gaaaacattt aaggatgaag acacacaagc aatgcctttc    1320
agagtgactg agcaagaaag caaacctgtg cagatgatgt accagattgg tttatttaga    1380
gtggcatcaa tggcttctga gaaaatgaag atcctggagc ttccatttgc cagtgggaca    1440
atgagcatgt tggtgctgtt gcctgatgaa gtctcaggcc ttgagcagct tgagagtata    1500
atcaactttg aaaaactgac tgaatggacc agttctaatg ttatggaaga gaggaagatc    1560
aaagtgtact tacctcgcat gaagatggag gaaaaataca acctcacatc tgtcttaatg    1620
gctatgggca ttactgacgt gtttagctct tcagccaatc tgtctggcat ctcctcagca    1680
gagagcctga agatatctca agctgtccat gcagcacatg cagaaatcaa tgaagcaggc    1740
agagaggtgg tagggtcagc agaggctgga gtggatgctg caagcgtctc tgaagaattt    1800
agggctgacc atccattcct cttctgtatc aagcacatcg caaccaacgc cgttctcttc    1860
tttggcagat gtgtttcccc ttaagcggcc gccgcatcga attcctgcag cccgggggat    1920
ccactagttc tagagcggcc gccaccgcgg tggagctcca gcttttgttc cctttagtga    1980
gggttaattg cgcgcttggc gtaatcatgg tcatagctgt ttcctgtgtg aaattgttat    2040
ccgctcacaa ttccacacaa catacgagcc ggaagcataa agtgtaaagc ctggggtgcc    2100
taatgagtga gctaactcac attaattgcg ttgcgctcac tgcccgcttt ccagtcggga    2160
aacctgtcgt gccagctgca ttaatgaatc ggccaacgcg cggggagagg cggtttgcgt    2220
attgggcgct cttccgcttc ctcgctcact gactcgctgc gctcggtcgt tcggctgcgg    2280
cgagcggtat cagctcactc aaaggcggta atacggttat ccacagaatc aggggataac    2340
gcaggaaaga acatgtgagc aaaaggccag caaaaggcca ggaaccgtaa aaaggccgcg    2400
ttgctggcgt ttttccatag gctccgcccc cctgacgagc atcacaaaaa tcgacgctca    2460
agtcagaggt ggcgaaaccc gacaggacta taaagatacc aggcgtttcc ccctggaagc    2520
tccctcgtgc gctctcctgt tccgaccctg ccgcttaccg gatacctgtc cgcctttctc    2580
ccttcgggaa gcgtggcgct ttctcatagc tcacgctgta ggtatctcag ttcggtgtag    2640
gtcgttcgct ccaagctggg ctgtgtgcac gaaccccccg ttcagcccga ccgctgcgcc    2700
ttatccggta actatcgtct tgagtccaac ccggtaagac acgacttatc gccactggca    2760
gcagccactg gtaacaggat tagcagagcg aggtatgtag gcggtgctac agagttcttg    2820
aagtggtggc ctaactacgg ctacactaga aggacagtat ttggtatctg cgctctgctg    2880
aagccagtta ccttcggaaa aagagttggt agctcttgat ccggcaaaca aaccaccgct    2940
ggtagcggtg gtttttttgt ttgcaagcag cagattacgc gcagaaaaaa aggatctcaa    3000
gaagatcctt tgatctttc tacgggtct gacgctcagt ggaacgaaaa ctcacgttaa    3060
gggattttgg tcatgagatt atcaaaaagg atcttcacct agatcctttt aaattaaaaa    3120
tgaagtttta aatcaatcta agtatatat gagtaaactt ggtctgacag ttaccaatgc    3180
ttaatcagtg aggcacctat ctcagcgatc tgtctatttc gttcatccat agttgcctga    3240
ctccccgtcg tgtagataac tacgatacgg gagggcttac catctggccc cagtgctgca    3300
```

| | |
|---|---|
| atgataccgc gagacccacg ctcaccggct ccagatttat cagcaataaa ccagccagcc | 3360 |
| ggaagggccg agcgcagaag tggtcctgca actttatccg cctccatcca gtctattaat | 3420 |
| tgttgccggg aagctagagt aagtagttcg ccagttaata gtttgcgcaa cgttgttgcc | 3480 |
| attgctacag gcatcgtggt gtcacgctcg tcgtttggta tggcttcatt cagctccggt | 3540 |
| tcccaacgat caaggcgagt tacatgatcc cccatgttgt gcaaaaaagc ggttagctcc | 3600 |
| ttcggtcctc cgatcgttgt cagaagtaag ttggccgcag tgttatcact catggttatg | 3660 |
| gcagcactgc ataattctct tactgtcatg ccatccgtaa gatgcttttc tgtgactggt | 3720 |
| gagtactcaa ccaagtcatt ctgagaatag tgtatgcggc gaccgagttg ctcttgcccg | 3780 |
| gcgtcaatac gggataatac cgcgccacat agcagaactt taaaagtgct catcattgga | 3840 |
| aaacgttctt cggggcgaaa actctcaagg atcttaccgc tgttgagatc cagttcgatg | 3900 |
| taacccactc gtgcacccaa ctgatcttca gcatctttta ctttcaccag cgtttctggg | 3960 |
| tgagcaaaaa caggaaggca aaatgccgca aaaaagggaa taaggcgac acggaaatgt | 4020 |
| tgaatactca tactcttcct ttttcaatat tattgaagca tttatcaggg ttattgtctc | 4080 |
| atgagcggat acatatttga atgtatttag aaaaataaac aaatagggt tccgcgcaca | 4140 |
| tttccccgaa aagtgccac | 4159 |

<210> SEQ ID NO 22
<211> LENGTH: 6379
<212> TYPE: DNA
<213> ORGANISM: artificial
<220> FEATURE:
<223> OTHER INFORMATION: synthetic

<400> SEQUENCE: 22

| | |
|---|---|
| ctcgagttta ccactcccta tcagtgatag agaaaagtga agtcgagtt taccactccc | 60 |
| tatcagtgat agagaaaagt gaaagtcgag tttaccactc cctatcagtg atagagaaaa | 120 |
| gtgaaagtcg agtttaccac tcccatcag tgatagagaa aagtgaaagt cgagtttacc | 180 |
| actccctatc agtgatagag aaaagtgaaa gtcgagttta ccactcccta tcagtgatag | 240 |
| agaaaagtga agtcgagtt taccactccc tatcagtgat agagaaaagt gaaagtcgag | 300 |
| ctcggtaccc gggtcgaggt aggcgtgtac ggtgggaggc ctatataagc agagctcgtt | 360 |
| tagtgaaccg tcagatcgcc tggagacgcc atccacgctg ttttgacctc catagaagac | 420 |
| accgggaccg atccagcctc cgcggccccg aattcgagct cggtacccgg ggatccacca | 480 |
| tgtaccccta cgacgtgccc gactacgcca cgtccagact atccgtgaaa gtttgagaa | 540 |
| gcatcagtag gttcgtccag tgggagtgtt gttggatgct cgtcaacaag agcgcgcgct | 600 |
| accgagagtt ccgcgccgtc accagccagt cgccggggct ggggaaggtc tcctccaccg | 660 |
| acgacgggag atgtctcgcc gcctccatga tgcttttcag acgtgacggt aattttgtcc | 720 |
| tctgtctggt cgtcaataag gagccggtgg gtcagttcgg ctgcagtggc atgcggcgcg | 780 |
| agaagatggt catcgatgga ctccaggagc ccgtctacgt gatgcgtctc ctggcccccc | 840 |
| tcatccccgt caagctagga ttctcgcccct acatgttgcc gcctaagagc atcggcggct | 900 |
| ccggcggtct ggaccccagc gtcatctacc agaacgcgag tgtggtcacg cccgaagagg | 960 |
| ccgccaccgt cactatgcag ggttccggca tcgtgaccgt ggggctcagt ggcgttggct | 1020 |
| cctgggtgca gatcaaggat ggtgggaaca tgaagctctt cgtcttcgcc ctctgcttcg | 1080 |
| acgtcttta cgcctgctgc gatcggctcg ccttcccgtc cctggccaag atctacagcg | 1140 |
| aaactgtgtc ctgcgaggcc gacaagtgcg gattctgtcg agattccggt cggcacgtcg | 1200 |

```
atcccaccgg ccgcttcgtc ggctgcgtcc ccgacagtgg cgtgtgtctc tgttactcgc    1260
cgtgtcgcgg gacggatgcc gcggtcagcg tcagaagctg gttaccttac ctggaactgg    1320
aagacggtgc gaacacgcac agcctcttcg tgcggcgcta cgacggcagg aaaggactgc    1380
cggccacgat atctgactac ctcggcgcca ggaacagcga gggcgacgag atcccgctga    1440
ggaccgagcc ctggcagctc ttgaagatag aaccgacgct gtccgccatg atcatcatgg    1500
cctgtccctt actcaaaaag atcgttctcg agcacatgtg aagtcgactc tagcgcggcc    1560
gcatcgataa gcttgtcgac gatatctcta gagctgagaa cttcagggtg agtttgggga    1620
cccttgattg ttcttttcttt ttcgctattg taaaattcat gttatatgga gggggcaaag    1680
ttttcagggt gttgtttaga atgggaagat gtcccttgta tcaccatgga ccctcatgat    1740
aattttgttt ctttcacttt ctactctgtt gacaaccatt gtctcctctt attttctttt    1800
cattttctgt aactttttttc gttaaacttt agcttgcatt tgtaacgaat ttttaaattc    1860
actttcgttt atttgtcaga ttgtaagtac tttctctaat cacttttttt tcaaggcaat    1920
cagggtaatt atattgtact tcagcacagt tttagagaac aattgttata attaaatgat    1980
aaggtagaat atttctgcat ataaattctg gctggcgtgg aaatattctt attggtagaa    2040
acaactacat cctggtaatc atcctgcctt tctctttatg gttacaatga tatacactgt    2100
ttgagatgag gataaaatac tctgagtcca aaccgggccc ctctgctaac catgttcatg    2160
ccttcttctt tttcctacag ctcctgggca acgtgctggt tgttgtgctg tctcatcatt    2220
ttggcaaaga attcactcct caggtgcagg ctgcctatca gaaggtggtg gctggtgtgg    2280
ccaatgccct ggctcacaaa taccactgag atctttttcc ctctgccaaa aattatgggg    2340
acatcatgaa gccccttgag catctgactt ctgggtaata aggaaattt atttttcattg    2400 caatagtgtg tgggaatttttt tgtgtctct cactcggaag gacatatggg agggcaaatc    2460
atttaaaaca tcagaatgag tatttggttt agagtttggc aacatatgcc atatgctggc    2520
tgccatgaac aaaggtggct ataaagaggt catcagtata tgaaacagcc ccctgctgtc    2580
cattccttat tccatagaaa agccttgact tgaggttaga tttttttttat attttgtttt    2640 gtgttatttt tttctttaac atccctaaaa ttttccttac atgttttact agccagattt    2700
ttcctcctct cctgactact cccagtcata gctgtccctc ttctcttatg aactcgactg    2760
cattaatgaa tcggccaacg cgcggggaga ggcggtttgc gtattgggcg ctcttccgct    2820
tcctcgctca ctgactcgct gcgctcggtc gttcggctgc ggcgagcggt atcagctcac    2880
tcaaaggcgg taatacggtt atccacagaa tcaggggata acgcaggaaa gaacatgtga    2940
gcaaaaggcc agcaaaggcc aggaaccgt aaaaaggccg cgttgctggc gtttttccat    3000
aggctccgcc cccctgacga gcatcacaaa atcgacgct caagtcagag gtggcgaaac    3060
ccgacaggac tataaagata ccaggcgttt ccccctggaa gctccctcgt gcgctctcct    3120
gttccgaccc tgccgcttac cggatacctg tccgcctttc tcccttcggg aagcgtggcg    3180
ctttctcaat gctcacgctg taggtatctc agttcggtgt aggtcgttcg ctccaagctg    3240
ggctgtgtgc acgaacccc cgttcagccc gaccgctgcg ccttatccgg taactatcgt    3300
cttgagtcca acccggtaag acacgactta tcgccactgg cagcagccac tggtaacagg    3360
attagcagag cgaggtatgt aggcggtgct acagagttct tgaagtggtg gcctaactac    3420
ggctacacta gaaggacagt atttggtatc tgcgctctgc tgaagccagt taccttcgga    3480
aaaagagttg gtagctcttg atccggcaaa caaaccaccg ctggtagcgg tggttttttt    3540
```

```
gtttgcaagc agcagattac gcgcagaaaa aaaggatctc aagaagatcc tttgatcttt    3600
tctacggggt ctgacgctca gtggaacgaa aactcacgtt aagggatttt ggtcatgaga    3660
ttatcaaaaa ggatcttcac ctagatcctt ttaaattaaa aatgaagttt taaatcaatc    3720
taaagtatat atgagtaaac ttggtctgac agttaccaat gcttaatcag tgaggcacct    3780
atctcagcga tctgtctatt tcgttcatcc atagttgcct gactcccgt cgtgtagata     3840
actacgatac gggagggctt accatctggc cccagtgctg caatgatacc gcgagaccca    3900
cgctcaccgg ctccagattt atcagcaata aaccagccag ccggaagggc cgagcgcaga    3960
agtggtcctg caactttatc cgcctccatc cagtctatta attgttgccg ggaagctaga    4020
gtaagtagtt cgccagttaa tagtttgcgc aacgttgttg ccattgctac aggcatcgtg    4080
gtgtcacgct cgtcgtttgg tatggcttca ttcagctccg gttcccaacg atcaaggcga    4140
gttacatgat cccccatgtt gtgcaaaaaa gcggttagct ccttcggtcc tccgatcgtt    4200
gtcagaagta agttggccgc agtgttatca ctcatggtta tggcagcact gcataattct    4260
cttactgtca tgccatccgt aagatgcttt tctgtgactg gtgagtactc aaccaagtca    4320
ttctgagaat agtgtatgcg gcgaccgagt tgctcttgcc cggcgtcaat acgggataat    4380
accgcgccac atagcagaac tttaaaagtg ctcatcattg gaaaacgttc ttcggggcga    4440
aaactctcaa ggatcttacc gctgttgaga tccagttcga tgtaacccac tcgtgcaccc    4500
aactgatctt cagcatcttt tactttcacc agcgtttctg ggtgagcaaa aacaggaagg    4560
caaaatgccg caaaaaaggg aataagggcg acacggaaat gttgaatact catactcttc    4620
cttttcaat attattgaag catttatcag ggttattgtc tcatgagcgg atacatattt     4680
gaatgtattt agaaaaataa acaaataggg gttccgcgca catttccccg aaaagtgcca    4740
cctgacgtct aagaaaccat tattatcatg acattaacct ataaaaatag gcgtatcacg    4800
aggccctttc gtctcgaggc agtgaaaaaa atgctttatt tgtgaaattt gtgatgctat    4860
tgctttattt gtaaccatta taagctgcaa taaacaagtt aacaacaaca attgcattca    4920
ttttatgttt caggttcagg gggaggtgtg ggaggttttt taaagcaagt aaaacctcta    4980
caaatgtggt atggctgatt atgatcctct agaactctat tcctttgccc tcggacgagt    5040
gctggggcgt cggtttccac tatcggcgag tacttctaca cagccatcgg tccagacggc    5100
cgcgcttctg cgggcgattt gtgtacgccc gacagtcccg gctccggatc ggacgattgc    5160
gtcgcatcga ccctgcgccc aagctgcatc atcgaaattg ccgtcaacca agctctgata    5220
gagttggtca agaccaatgc ggagcatata cgcccggagc gcggcgatc ctgcaagctc     5280
cggatgcctc cgctcgaagt agcgcgtctg ctgctccata caagccaacc acggcctcca    5340
gaagaagatg ttggcgacct cgtattggga atccccgaac atcgcctcgc tccagtcaat    5400
gaccgctgtt atgcggccat tgtccgtcag gacattgttg gagccgaaat ccgcgtgcac    5460
gaggtgccgg acttcgggc agtcctcggc ccaaagcatc agctcatcga gagcctgcgc     5520
gacggacgca ctgacggtgt cgtccatcac agtttgccag tgatacacat ggggatcagc    5580
aatcgcgcat atgaaatcac gccatgtagt gtattgaccg attccttgcg gtccgaatgg    5640
gccgaacccg ctcgtctggc taagatcggc cgcagcgatc gcatccatgg cctccgcgac    5700
cggctgcaga acagcgggca gttcggtttc aggcaggtct gcaacgtgac accctgtgc    5760
acggcgggag atgcaatagg tcaggctctc gctgaattcc ccaatgtcaa gcacttccgg    5820
aatcgggagc gcggccgatg caaagtgccg ataaacataa cgatctttgt agaaaccatc    5880
ggcgcagcta tttacccgca ggacatatcc acgccctcct acatcgaagc tgaaagcacg    5940
```

```
agattcttcg ccctccgaga gctgcatcag gtcggagacg ctgtcgaact tttcgatcag    6000
aaacttctcg acagacgtcg cggtgagttc aggcttttc atggaagctt tttgcaaaag     6060
cctaggcctc caaaaaagcc tcctcactac ttctggaata gctcagaggc cgaggcggcc    6120
tcggcctctg cataaataaa aaaaattagt cagccatggg gcgagaatg ggcggaactg     6180 ggcggagtta ggggcgggat gggcggagtt aggggcggga ctatggttgc tgactaattg    6240
agatgcatgc tttgcatact tctgcctgct ggggagcctg ggacttcc acacctggtt      6300 gctgactaat tgagatgcat gctttgcata cttctgcctg ctggggagcc tggggactt     6360 ccacacccta actgacaca                                                 6379

<210> SEQ ID NO 23
<211> LENGTH: 9400
<212> TYPE: DNA
<213> ORGANISM: artificial
<220> FEATURE:
<223> OTHER INFORMATION: synthetic

<400> SEQUENCE: 23
ttcccggaaa atcactcaaa actacgtcca tgacacatca actcccgata actacctccc      60
tttgaaatcg gatccccca cgtaccaatc aatcacacaa cacacaggtt taaaaatcga     120
tcactcgtca attaggtttc aaaatcgata ccgtttatta tcaggaatct agactaattc    180
tacaatgaca gctctgaatt tctctctcgt cttccttgtc aggttctcat catcagttat    240
cacttccacc catcgaggag tcatcgtcgc tccaaaatcc tttggggtcg ctagttggaa    300
aagtctctga cacgatccag gcaccccgca cccagtccga ctgatctagc ttgcggagca    360
tctcaacagg catgagctgc agggccatgg ctgtcacggc actgtatcga tgtaacacta    420
gggactttct ttgcgatgta gccatcaaca cggcgtatgc cccatagttc gcgtgatacg    480
acgcatgatg ggttaaacgt tcccatccgg cagtgccgtc tcgggtccgt gcacacaaca    540
gctgcacggc attatgatgc ttaaaattaa ccataacgct ggggctactg atgaaggagt    600
agtaatgagc caggacgccg tacatcgaag gcagcaagaa agagtgacag cacaatagca    660
ccgggctctt atgtaggcga cagcttattt ttcctgacgt cggcaaaaag tacctaaatt    720
ccccacagat attcagacac ggttccgcaa agtgcttctt ttttttagtgc aggaattgga    780 aaaaataata aaaatatga acagctcatc tgtaattatc tgtgtgactt catcgtaccg     840
tgatgtaaaa acaacaacag gaagcttaca gggtgcggta gaaattttg ccgattgagc     900 aacactgttg gcatctctca ctccgatagg cggctataag atagaaaatt aaaagtatga    960
tacccacgag aaagatgaag agggacaacc aggctagagt atgacgacca ctttccctt     1020 gtttgacggt tacatgtgcg gtatgatttt gtcgttgctt gtgatgttgg acgcctggaa    1080
cggacaacga cgtataattc ttagatgcgc atacggtgtt attagtggaa gtgcagttac    1140
gaattgtaac ctcagtgtca ctacactcag tgcaattggt acaattgtaa agccctgata    1200
catacgtacc gttagggcaa agtgtacatg ttgtactcgt atattgcgta cattgtcctg    1260
taacacgata tccttgttta catgggggac aacactgact tcctaattgc acttcttcgg    1320
gtttgcatat ttcagttttc cctatgcatg ccaatagcat actcagcaaa ataagcatca    1380
ccagaggctt catgcctcct accggaagaa taaaaataac tcatggggcc gaacggtatc    1440
atcctctccg cggtttgtaa tacgagatcg taaacgtaaa taatgacat aacttcacta    1500 acccgcatac tgcaaagtcc acctacgacg ctgaaagctt ttccaggaca caacaggata   1560
```

```
gtcagccatc ttcacaggta accagtttct agtcacagta tagcgagcct aagagaccgc    1620
acacggtccc tgctggaaac acataccact acatcgattt gtcgtgtcgt acaaccgtca    1680
agttttccga acttttatac acgccaatgg cgttaggact atgtgtgctg ctgtgattgg    1740
aggcttcgag agttatgtga cagctgtgat tacacctgtc gccaaggctg acagcgatta    1800
cccaggtaga gcacaatcac atagctgatg gacgttggtt gatccgttga ttcccatgga    1860
cattttaacg gcgacagtac agctcccgtt aaacattaga ttaatagacg ctagtggatg    1920
acagcatgtt attcgcccaa ttgtgatggt ggttatactt tcttgttttt tgctcatatg    1980
ctgtaaggtg ttcgaggatc gtggggagta tatgtgttaa atcggaatca tatttactga    2040
ccgcgccata cttcgtatac gaacctaacc ggcgtaaagt gttttccgat atataaactg    2100
gcgcctattg tggctgtagc gcccataggt atggcatata cccacggtga tgttgtgtta    2160
ttcgtttttt gtgataaaac gtagtttatg tttaacgtgt gttccgtcac gttatgtgtg    2220
tcgttaaaag acggcgtctg tacagtatgg ctttgagttg tatcttgaat tgttattgca    2280
tttggaggtg tgtacagagt ggttgttgtg tgctgaggtt ttgttacgtt ttgaggcaca    2340
gttgtggtgt atacggactt caaggtgtag ttacggagtc tttctatgca ggtagtgttg    2400
agatatttgt gaatgctggt tatgttcgat tctgtgaggt taaagtgtgt actatttatg    2460
gcggtataat ttagacggtc ttgccatccc gaggatgtta gtgttaggta attcgtgttg    2520
tttacgtttg cttgatatgt ataggtaggt gtactgtttg tgaggtcgca agtgtgattt    2580
tcttgcagag attttatcca tcttgtgtga aaatattgag atacgcgatg aatgttttcg    2640
ctatctatat tgtaaagcgt ttcggtggta cttaggggtt gtttgctgta actcttattt    2700
tggacccagg atgtgaacca tgactccaat gtttgtatag taaggtgtcc tattaataaa    2760
gacgaactga ttcctaccgt aatgttatat cgcacaccta gggtgccgtt tacaaacacg    2820
gaaatgtttc cgttacaaac cacgttggca gatgaattag attccaggtg gtaacgatag    2880
gataatgacc gttcgctccc aacggatgac acaaagtatc cgaataacca acacgcccat    2940
tcaatccgca tattttaatc acactattca catttcacac actgcatttt ttaacatgtt    3000
atttttttat tttatgcgtg ttctcacctc ttcatctttt taacaccggg gtaactatcg    3060
taagtcggta ggcgtcgata gccctcacca cctcgtcgtc cccttcccgg cgtggggcac    3120
cagcgtccac agcactgcag gtaacacagg tagcatagga aacatacggt gaaaatactc    3180
caaaatccca aaaatgccgc gattccccga gtggcccagg gagacatccc ggtgtctatg    3240
tcggccggcg gtgctggcgt caccggtaaa aatttcggcg ggtgtggctg cgaacggtag    3300
cagtcgccgg ggagccggta acgctgtatc actgtccaac agcggtcggg ttcctcgtcc    3360
ggacatgcgg gtttccagca atcctcggcg tcggcgcggc cgatatagaa gtagttgcgt    3420
tgaaaaccgc ggtacatccc gcagtcgtga ttccgtagac gccagggcgt cggcgaccag    3480
atctggtctc ccagcgagta acgacctaac gccggcgtgc agcaaggttc gtcgggccgg    3540
ctgagcgtct ccagttgcgt gagaattacg aagcgttgca tgatgaggcc gtggctgtag    3600
ttgcgcagca cgcattcgta catgccggcc gtgtccgtcg atacgttgaa agtcagcgag    3660
aatatttggc cgagatgcaa ttgcgagaaa ttccaagtgg cgtacggcag gcggtactgg    3720
agtccgttca tcagccgatg gcctttgacg gcgtccagga tgagctcgtc gctgccgtcg    3780
tgggaacgac agaaacgtgc gcgaatggag accatgggcc aggagtgtgt catgaccgtg    3840
caggggatgg tataacttgc tctccctcgg cgaccaacac cggcgccggc gacgtggtct    3900
cataattctc ggcccacatc ttttcggcaa tgtcagcggt ggcgaagggg aacgaagagg    3960
```

```
aagaatattc gaggagtcgc gggcagctca acagcaccca gaacagccac ggcagagttc    4020
ggagcgactc tcggcggcac atgatgattc tttctttccc tttttcgcag agacgctgcg    4080
cgcctgctcc tgctccgtgt gtcggccgct caaacgtcgg gccggcgtgg tggtgaccac    4140
cgtgcgacgc agcttctcgc ccgggatgcc cgcgactgag cgtccggttt ttttgcaggt    4200
cttttttgct gcctcctcct cgccgtcgcc gtcgcggccg acgtggtgga ccagcaccgc    4260
gcaggaactc tcgcgtcgcc ggcggtacgc gacctgtctc attgctacct cggatgttta    4320
agaaggaacg ttcatctgcg tcacagggtc tgatgaagct gccaagagtc gtggctgtgg    4380
cgcagcgcgt tctgtacggc gcgtttcacc gctttctgca tggccgctac cacgtcgggt    4440
gggagcggct ccggcggaag ctcgatgagc agttgctgcg agtctcggcg ctcggtgtcc    4500
gccgtttcgt cggacgtggc gtaaaaaacc gaggtggttg cccagtcgtc cacgctgtcg    4560
acggcctctg tcagtgccgg gttgtcaaaa ccgccatcgg acgcgggtga taaagaacg    4620
tacgatgaca cgctgttagt acgactctcg tcgtcgctct gggaacgacg tgatggacga    4680
cggtagatga cctcgtcttg ccacgcgtcg aagcggtcgc agcagcgctg gatccaagcg    4740
cagcgaagca gcttacggaa cacgtcgttg ttccaaaagt agagcataaa gagaaagaaa    4800
agtagcgtaa taatgaagcc gaaaacgacg agggtcggca gggcactacc gccgctgccg    4860
ttttttgtgt cgtgcgggtg cacggtggta gtggcgttag tctgagctgg ggtcatgaca    4920
agtctgaaga gatgagagcg tgggtgctca tcaggaacag ttgaggtctc tccctaccga    4980
agccttagcc tccacggtgt tttatgatca acgtgtctac gaacgtcatt gtgaaagtga    5040
cgtctcaggc tttccgaaac cgcgtcagat tcaacgtggg tttcggttta gcctgcgtca    5100
ccgaggcgga ggtggaaatg agccgtcctg tggggagtg tacgaccctg tagtgcccat    5160
gggtaacgtc gcgtcggaag aagtgaatgc ggcattggtg tacgcgtggg ttgttttgct    5220
ctctgactcg gaggaattgc cgcagcagct gcagatttta cgtactaacc aaaagcagca    5280
aaagcagcag gtaaataaga gaaggagtcc agataatgtc cagccgctag cggcaagcag    5340
cgcgagctgt ggtactgtcc agctactgcc gttagaggca ttaatacatg tcgatacggt    5400
cgtgttggcg gtagcactag tagattgact ggaattagag ctggtacctg tagtggtttc    5460
actcgccgat gcggcgagtg caaataaaat taatatccac agcatgttta ttactatata    5520
attgatatac gaacccgtct gtcgtaacaa tcagcgttat acacgctgta tcggcatcgt    5580
tttaccggaa agtttatcgt aatgtaaccc gcgttgtgta cattcgtact gacagggaac    5640
ccccggtgat gtgcacatta tactctttca ttctggggtt tcccaatgac gtaaaaattt    5700
ccactacaca ataaaattac tgactcatgt gaaaagtgtg cttttattta acagagcaga    5760
gggtttacag tagatatatg tttgccaggg ccaccgtttt ctaacaccga tcaccgccac    5820
cattaccacc cgttgaactc cacacccggg agccgcctga tcgccaggga ctcctcaccg    5880
tccatcgtcc gaacaagctc ccgccaccga tgctgccacc atcaccgaga gaaagaaccg    5940
cttgctgcag atacgcttgg gctcgcctcc gtgcggacgc cgtttcgtgc agacgctgag    6000
tagatcgagc agagaatgtc aaaacgacat taccgcgatc cgctcccctc tttttttctt    6060
ttctcattca cgtgtattct tgatgataat gtaccatggc tacggtggtg aactgcgtcg    6120
cggatcccgt cacgggtttc aacagatcga cgtcggtcag cggcgccgtc accgccatgt    6180
ccggcggagg cacgctgttt ctctggttag cgacgtggac cgacgacgaa gacgatgaac    6240
ccgcgcggcg gtctgttatc cgcgacgacg cgtagctgca ctgggaagac acttcctccc    6300
```

```
aacggaccaa gatctcatcg ggccgttcgg agaaacggta tcgtctgtcc gactcccgcc    6360
gtacggcgcc gaggcccagc gacgacaggt ccgcgaaccg gcgctcgtat tccccgtaca    6420
gctcgcaaca gcggatcagc cagcggtagc tcaaaaacat gcgcaccagt ttgaaggtgt    6480
cgtgccaatg gtaagctaga tagcagagaa tggccacgat cagcacgagc atcacgccga    6540
tgatgggtaa cccgacgttc agcggcagat cgtccatggt gaccgtcctc tgtccggatc    6600
tacgtcccag tctctctctt ttgtacagca ctcgcgcggg aacggccccc tcaaccctct    6660
tacgtagcgg gagatacggc gttctcccgc gggccactta cttgcacggt cgcttgaacg    6720
gcggcttgga ccgccacatg taccgcatcc atccattctg gcagcagcgc gttcgacgac    6780
gtcgtacgag tcgcggatga tgttaccccg ccagcacctc cgccggcaac cgcgtcgtcg    6840
ttgctatcgt cgccggtttc gggcgatgac agccgccggc gcgcgggtct cgtctcgtcc    6900
accatttcca ccgtgtcgaa gcgacagccg ctgccgtagt acatggcccc gttcaacggc    6960
cggcgggccg ggtcgccgag ttccgggtcg ggcacatcca tggctcgccg tctgcttctc    7020
tgccgctcgt ggtgccgacg gcacttctca ggataatgac agccgcaaaa tagatcgtgg    7080
agcatgtctc gccaactgtc ctggtggtaa tatcttaagt acgcgatgag cgcgccgatg    7140
gccataatca taagcgtaag caaaacggca cagataacgc gaaacaccgc ggtcatccaa    7200
gtcgggcggc gtcggggacg cggtgggtcg gtttctctta cgccggcgtc actcagccac    7260
cacacccgta gtcgacattc ccagaaccgg tgaatgcgac tcaggccctt tcgacgccgc    7320
catttatttc caacgtccaa gtcccacgtc atttctggca tctccacgcc cttgactgac    7380
atactctctt tctctctctt agctgcggtg aaaaagaggg aaggcgtgtg ctgctataca    7440
actgtacaac ggacgcgctc gctgtttcgg tctcaggtca tctgcattga ctcggcgtcc    7500
ttcatgacgc tctgcaccgc cttttccaag agttcctcga tgtccgacca tcgaggaggc    7560
ggggctaact cggaaaccga cacgataggc agcgtggtcg gctccgtcgg cgtgcgggt    7620
cggggacagg gacacgagag tcccaccttc gagagattct ccagcccgac ggtgcgcggc    7680
agtctcggat tccgcggtgg cttttgtggc gtcggcgttt cgggaaggg cctgggcgtc    7740
accgccggtg tccagccgac cggcttgggt ttcgtgggcg gcggtgtttt cttggtgggc    7800
ggcgtgctca ggttcttacg cggcgcgggt atcggcgtcg ggggcctgtg cgacgacagc    7860
cgcgtggtgg gggcccggac cggcggcgta ggcggccgct tcttgcgccc gggcggcgga    7920
ggtggcttcc aggatggcgg cggctgatgc agtaccgtgt cgacgctggc cgaggacgac    7980
aaagagctcg acgaggagca atgcgacgga gatcggccga tgctggtcgg cgttcccggc    8040
gtggatacgt cggggatctc gaatcgcgcc ggaggaaact cgggtttatc tatcggcaga    8100
ccatcctctc ctatgtagag cgacgtacac cgcggcacct gcggcgtcgg cgggtgggtg    8160
gccacccgca tgagccccag ttccagatcc agcggctcga cgacgtcttc tttcggaatt    8220
cgatagcagc acgcgcaggc accacgctta tcagaagcag cacccgggag ccggcctcgc    8280
gacgaagtct cgtcggatcg cttgcggcct cggcgctggg taaataagga aatgccagg    8340
accagggaag ccagtccggt accgccgagg agcccgacgc cgagccacag ccacaccatg    8400
atcttctctc ctgcttggaa tctcaaactc cgtgtcggga agggccggtg tacgacatt    8460
tatgccttgg atttctggaa acgtcatttt ttggcaagga atgtgtttat tgtccaaaca    8520
ctgaggaagg agatgtgagc caagtcggaa aattccttat cacaccgggg gcgggttacg    8580
ttccggtctg atgctgctgc tgttgttgta gagccgcggc catggccgcc tgcacggcag    8640
cttgtaccgc ctcggccacg ccgggtggca tctgcggcat ggcgggggga gacgcgtcgg    8700
```

```
gcggaccgcc gggcatcgcc gtcggctgcg acggtggttg tgaactcacc gtcggctcgc    8760
acggagggtt gtccttcggt ttgctcttcg gtttatcttt cgccctacct ttcttcggtt    8820
tgggttccga tgtcggtgtt ggcggctgcg gtgggatgac gggctggtgg gactcctccg    8880
acggcggggg gacgaatact gtcggcgccg aaaccggggg actctcgact atctcgcaga    8940
tcaccctgtc gggatcgtcg ccgtgtccgg gacgccgtcg atgaccatat tgaaccatgt    9000
cgtaaatcat cgtctccttg taacacgctg aacagcagcg gctacaagga cccgaaatgc    9060
atttgcagct gcacttacag ctgcagctgc agtagcgcac ccatcggcag gtgaagacgt    9120
cgattacgga gtccttgaag aattcccggt aacggatgag atacgcgcag aggaaaatca    9180
tgaaaacaga acagccgact acggctgcga tgccgggtcc cgaaaacgta ttcggtgatc    9240
ctaccaaaca ccaaattccc agggccgcgc atgttatcca ggccacaata atcgtgggaa    9300
cgccccattg gcattgccac gaaggatcgt gcacgtcgca acccatcgct actgcgttct    9360
cccacaaacg ccatcgcact atttatccct acagcggctg                         9400

<210> SEQ ID NO 24
<211> LENGTH: 387
<212> TYPE: PRT
<213> ORGANISM: artificial
<220> FEATURE:
<223> OTHER INFORMATION: synthetic

<400> SEQUENCE: 24

Met Gly Ser Gly Ile Gly Ala Ala Ser Met Glu Phe Cys Phe Asp Val
1               5                   10                  15

Phe Lys Glu Leu Lys Val His His Ala Asn Glu Asn Ile Phe Tyr Cys
            20                  25                  30

Pro Ile Ala Ile Met Ser Ala Leu Ala Met Val Tyr Leu Gly Ala Lys
        35                  40                  45

Asp Ser Thr Arg Thr Gln Ile Asn Lys Val Val Arg Phe Asp Lys Leu
    50                  55                  60

Pro Gly Phe Gly Asp Ser Ile Glu Ala Gln Cys Gly Thr Ser Val Asn
65                  70                  75                  80

Val His Ser Ser Leu Arg Asp Ile Leu Asn Gln Ile Thr Lys Pro Asn
                85                  90                  95

Asp Val Tyr Ser Phe Ser Leu Ala Ser Arg Leu Tyr Ala Glu Glu Arg
            100                 105                 110

Tyr Pro Ile Leu Pro Glu Tyr Leu Gln Cys Val Lys Glu Leu Tyr Arg
        115                 120                 125

Gly Gly Leu Glu Pro Ile Asn Phe Gln Thr Ala Ala Asp Gln Ala Arg
    130                 135                 140

Glu Leu Ile Asn Ser Trp Val Glu Ser Gln Thr Asn Gly Ile Ile Arg
145                 150                 155                 160

Asn Val Leu Gln Pro Ser Ser Val Asp Ser Gln Thr Ala Met Val Leu
                165                 170                 175

Val Asn Ala Ile Val Phe Lys Gly Leu Trp Glu Lys Thr Phe Lys Asp
            180                 185                 190

Glu Asp Thr Gln Ala Met Pro Phe Arg Val Thr Glu Gln Glu Ser Lys
        195                 200                 205

Pro Val Gln Met Met Tyr Gln Ile Gly Leu Phe Arg Val Ala Ser Met
    210                 215                 220

Ala Ser Glu Lys Met Lys Ile Leu Glu Leu Pro Phe Ala Ser Gly Thr
225                 230                 235                 240
```

```
Met Ser Met Leu Val Leu Leu Pro Asp Glu Val Ser Gly Leu Glu Gln
            245                 250                 255

Leu Glu Ser Ile Ile Asn Phe Glu Lys Leu Thr Glu Trp Thr Ser Ser
            260                 265                 270

Asn Val Met Glu Glu Arg Lys Ile Lys Val Tyr Leu Pro Arg Met Lys
            275                 280                 285

Met Glu Glu Lys Tyr Asn Leu Thr Ser Val Leu Met Ala Met Gly Ile
            290                 295                 300

Thr Asp Val Phe Ser Ser Ala Asn Leu Ser Gly Ile Ser Ser Ala
305                 310                 315                 320

Glu Ser Leu Lys Ile Ser Gln Ala Val His Ala His Ala Glu Ile
                    325                 330                 335

Asn Glu Ala Gly Arg Glu Val Val Gly Ser Ala Glu Ala Gly Val Asp
            340                 345                 350

Ala Ala Ser Val Ser Glu Glu Phe Arg Ala Asp His Pro Phe Leu Phe
            355                 360                 365

Cys Ile Lys His Ile Ala Thr Asn Ala Val Leu Phe Phe Gly Arg Cys
370                 375                 380

Val Ser Pro
385

<210> SEQ ID NO 25
<211> LENGTH: 498
<212> TYPE: PRT
<213> ORGANISM: artificial
<220> FEATURE:
<223> OTHER INFORMATION: synthetic

<400> SEQUENCE: 25

Met Ser Gly Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Thr Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205
```

```
Gly Glu Asn Gly Arg Lys Thr Arg Ile Ala Tyr Glu Arg Met Cys Asn
            210                 215                 220
Ile Leu Lys Gly Lys Phe Gln Thr Ala Ala Gln Lys Ala Met Met Asp
225                 230                 235                 240
Gln Val Arg Glu Ser Arg Asn Pro Gly Asn Ala Glu Phe Glu Asp Leu
                245                 250                 255
Thr Phe Leu Ala Arg Ser Ala Leu Ile Leu Arg Gly Ser Val Ala His
            260                 265                 270
Lys Ser Cys Leu Pro Ala Cys Val Tyr Gly Pro Ala Val Ala Ser Gly
        275                 280                 285
Tyr Asp Phe Glu Arg Glu Gly Tyr Ser Leu Val Gly Ile Asp Pro Phe
    290                 295                 300
Arg Leu Leu Gln Asn Ser Gln Val Tyr Ser Leu Ile Arg Pro Asn Glu
305                 310                 315                 320
Asn Pro Ala His Lys Ser Gln Leu Val Trp Met Ala Cys His Ser Ala
                325                 330                 335
Ala Phe Glu Asp Leu Arg Val Leu Ser Phe Ile Lys Gly Thr Lys Val
            340                 345                 350
Leu Pro Arg Gly Lys Leu Ser Thr Arg Gly Val Gln Ile Ala Ser Asn
        355                 360                 365
Glu Asn Met Asp Ala Met Glu Ser Ser Thr Leu Glu Leu Arg Ser Arg
370                 375                 380
Tyr Trp Ala Ile Arg Thr Arg Ser Gly Gly Asn Thr Asn Gln Gln Arg
385                 390                 395                 400
Ala Ser Ala Gly Gln Ile Ser Ile Gln Pro Thr Phe Ser Val Gln Arg
                405                 410                 415
Asn Leu Pro Phe Asp Arg Thr Thr Ile Met Ala Ala Phe Asn Gly Asn
            420                 425                 430
Thr Glu Gly Arg Thr Ser Asp Met Arg Thr Glu Ile Ile Arg Met Met
            435                 440                 445
Glu Ser Ala Arg Pro Glu Asp Val Ser Phe Gln Gly Arg Gly Val Phe
450                 455                 460
Glu Leu Ser Asp Glu Lys Ala Ala Ser Pro Ile Val Pro Ser Phe Asp
465                 470                 475                 480
Met Ser Asn Glu Gly Ser Tyr Phe Phe Gly Asp Asn Ala Glu Glu Tyr
                485                 490                 495
Asp Asn
```

<210> SEQ ID NO 26
<211> LENGTH: 99
<212> TYPE: PRT
<213> ORGANISM: artificial
<220> FEATURE:
<223> OTHER INFORMATION: synthetic

<400> SEQUENCE: 26

```
Met Arg Ala Thr Val Gly Leu Val Glu Ala Ile Gly Ile Arg Glu Leu
1               5                   10                  15
Arg Gln His Ala Ser Arg Tyr Leu Ala Arg Val Glu Ala Gly Glu Glu
            20                  25                  30
Leu Gly Val Thr Asn Lys Gly Arg Leu Val Ala Arg Leu Ile Pro Val
        35                  40                  45
Gln Ala Ala Glu Arg Ser Arg Glu Ala Leu Ile Glu Ser Gly Val Leu
    50                  55                  60
```

Ile Pro Ala Arg Arg Pro Gln Asn Leu Leu Asp Val Thr Ala Glu Pro
65                  70                  75                  80

Ala Arg Gly Arg Lys Arg Thr Leu Ser Asp Val Leu Asn Glu Met Arg
            85                  90                  95

Asp Glu Gln

<210> SEQ ID NO 27
<211> LENGTH: 345
<212> TYPE: PRT
<213> ORGANISM: artificial
<220> FEATURE:
<223> OTHER INFORMATION: synthetic

<400> SEQUENCE: 27

Met Ala Trp Arg Ser Gly Leu Cys Glu Thr Asp Ser Arg Thr Leu Lys
1               5                   10                  15

Gln Phe Leu Gln Glu Glu Cys Met Trp Lys Leu Val Gly Lys Ser Arg
            20                  25                  30

Lys His Arg Glu Tyr Arg Ala Val Ala Cys Arg Ser Thr Ile Phe Ser
        35                  40                  45

Pro Glu Asp Asp Gly Ser Cys Ile Leu Cys Gln Leu Leu Leu Leu Tyr
    50                  55                  60

Arg Asp Gly Glu Trp Ile Leu Cys Leu Cys Cys Asn Gly Arg Tyr Gln
65                  70                  75                  80

Gly His Tyr Gly Val Gly His Val His Arg Arg Arg Arg Ile Cys
                85                  90                  95

His Leu Pro Thr Leu Tyr Gln Leu Ser Phe Gly Gly Pro Leu Gly Pro
            100                 105                 110

Ala Ser Ile Asp Phe Leu Pro Ser Phe Ser Gln Val Thr Ser Ser Met
        115                 120                 125

Thr Cys Asp Gly Ile Thr Pro Asp Val Ile Tyr Glu Val Cys Met Leu
    130                 135                 140

Val Pro Gln Asp Glu Ala Lys Arg Ile Leu Val Lys Gly His Gly Ala
145                 150                 155                 160

Met Asp Leu Thr Cys Gln Lys Ala Val Thr Leu Gly Gly Ala Gly Ala
                165                 170                 175

Trp Leu Leu Pro Arg Pro Glu Gly Tyr Thr Leu Phe Phe Tyr Ile Leu
            180                 185                 190

Cys Tyr Asp Leu Phe Thr Ser Cys Gly Asn Arg Cys Asp Ile Pro Ser
        195                 200                 205

Met Thr Arg Leu Met Ala Ala Ala Thr Ala Cys Gly Gln Ala Gly Cys
    210                 215                 220

Ser Phe Cys Thr Asp His Glu Gly His Val Asp Pro Thr Gly Asn Tyr
225                 230                 235                 240

Val Gly Cys Thr Pro Asp Met Gly Arg Cys Leu Cys Tyr Val Pro Cys
                245                 250                 255

Gly Pro Met Thr Gln Ser Leu Ile His Asn Asp Glu Pro Ala Thr Phe
            260                 265                 270

Phe Cys Glu Ser Asp Asp Ala Lys Tyr Leu Cys Ala Val Gly Ser Lys
        275                 280                 285

Thr Ala Ala Gln Val Thr Leu Gly Asp Gly Leu Asp Tyr His Ile Gly
    290                 295                 300

Val Lys Asp Ser Glu Gly Arg Trp Leu Pro Val Lys Thr Asp Val Trp
305                 310                 315                 320

Asp Leu Val Lys Val Glu Glu Pro Val Ser Arg Met Ile Val Cys Ser

```
                    325                 330                 335
Cys Pro Val Leu Lys Asn Leu Val His
            340                 345

<210> SEQ ID NO 28
<211> LENGTH: 12
<212> TYPE: PRT
<213> ORGANISM: artificial
<220> FEATURE:
<223> OTHER INFORMATION: synthetic

<400> SEQUENCE: 28

Val Thr Leu Gly Gly Ala Gly Ala Trp Leu Leu Pro
1               5                   10

<210> SEQ ID NO 29
<211> LENGTH: 190
<212> TYPE: PRT
<213> ORGANISM: artificial
<220> FEATURE:
<223> OTHER INFORMATION: synthetic

<400> SEQUENCE: 29

Met Gly Gly Glu Leu Cys Lys Arg Ile Cys Cys Glu Phe Gly Thr Thr
1               5                   10                  15

Ser Gly Glu Pro Leu Lys Asp Ala Leu Gly Arg Gln Val Ser Leu Arg
            20                  25                  30

Ser Tyr Asp Asn Ile Pro Pro Thr Ser Ser Asp Glu Gly Glu Asp
        35                  40                  45

Asp Asp Asp Gly Glu Asp Asp Asn Glu Glu Arg Gln Gln Lys Leu
    50                  55                  60

Arg Leu Cys Gly Ser Gly Cys Gly Gly Asn Asp Ser Ser Ser Gly Ser
65                  70                  75                  80

His Arg Glu Ala Thr His Asp Gly Pro Lys Lys Asn Ala Val Arg Ser
                85                  90                  95

Thr Phe Arg Glu Asp Lys Ala Pro Lys Pro Ser Lys Gln Ser Lys Lys
            100                 105                 110

Lys Lys Lys Pro Ser Lys His His His His Gln Gln Ser Ser Ile Met
        115                 120                 125

Gln Glu Thr Asp Asp Leu Asp Glu Glu Asp Thr Ser Ile Tyr Leu Ser
    130                 135                 140

Pro Pro Pro Val Pro Pro Val Gln Val Val Ala Lys Arg Leu Pro Arg
145                 150                 155                 160

Pro Asp Thr Pro Arg Thr Pro Arg Gln Lys Lys Ile Ser Gln Arg Pro
                165                 170                 175

Pro Thr Pro Gly Thr Lys Lys Pro Ala Ala Pro Leu Ser Phe
            180                 185                 190

<210> SEQ ID NO 30
<211> LENGTH: 345
<212> TYPE: PRT
<213> ORGANISM: artificial
<220> FEATURE:
<223> OTHER INFORMATION: syntehtic

<400> SEQUENCE: 30

Met Ala Thr Ser Arg Leu Ser Val Lys Ser Leu Arg Ser Ile Ser Arg
1               5                   10                  15

Phe Val Gln Trp Glu Cys Cys Trp Met Leu Val Asn Lys Ser Ala Arg
            20                  25                  30
```

Tyr Arg Glu Phe Arg Ala Val Thr Ser Gln Ser Pro Gly Leu Gly Lys
                35                  40                  45

Val Ser Ser Thr Asp Asp Gly Arg Cys Leu Ala Ala Ser Met Met Leu
 50                  55                  60

Phe Arg Arg Asp Gly Asn Phe Val Leu Cys Leu Val Val Asn Lys Glu
 65                  70                  75                  80

Pro Val Gly Gln Phe Gly Cys Ser Gly Met Arg Arg Glu Lys Met Val
                 85                  90                  95

Ile Asp Gly Leu Gln Glu Pro Val Tyr Val Met Arg Leu Leu Ala Pro
                100                 105                 110

Leu Ile Pro Val Lys Leu Gly Phe Ser Pro Tyr Met Leu Pro Pro Lys
            115                 120                 125

Ser Ile Gly Gly Ser Gly Gly Leu Asp Pro Ser Val Ile Tyr Gln Asn
            130                 135                 140

Ala Ser Val Val Thr Pro Glu Glu Ala Ala Thr Val Thr Met Gln Gly
145                 150                 155                 160

Ser Gly Ile Val Thr Val Gly Leu Ser Gly Val Gly Ser Trp Val Gln
                165                 170                 175

Ile Lys Asp Gly Gly Asn Met Lys Leu Phe Val Phe Ala Leu Cys Phe
            180                 185                 190

Asp Val Phe Thr Ala Cys Cys Asp Arg Leu Ala Phe Pro Ser Leu Ala
            195                 200                 205

Lys Ile Tyr Ser Glu Thr Val Ser Cys Glu Ala Asp Lys Cys Gly Phe
            210                 215                 220

Cys Arg Asp Ser Gly Arg His Val Asp Pro Thr Gly Arg Phe Val Gly
225                 230                 235                 240

Cys Val Pro Asp Ser Gly Val Cys Leu Cys Tyr Ser Pro Cys Arg Gly
                245                 250                 255

Thr Asp Ala Ala Val Ser Val Arg Ser Trp Leu Pro Tyr Leu Glu Leu
            260                 265                 270

Glu Asp Gly Ala Asn Thr His Ser Leu Phe Val Arg Arg Tyr Asp Gly
            275                 280                 285

Arg Lys Gly Leu Pro Ala Thr Ile Ser Asp Tyr Leu Gly Ala Arg Asn
            290                 295                 300

Ser Glu Gly Asp Glu Ile Pro Leu Arg Thr Glu Pro Trp Gln Leu Leu
305                 310                 315                 320

Lys Ile Glu Pro Thr Leu Ser Ala Met Ile Met Ala Cys Pro Leu
            325                 330                 335

Leu Lys Lys Ile Val Leu Glu His Met
            340                 345

<210> SEQ ID NO 31
<211> LENGTH: 353
<212> TYPE: PRT
<213> ORGANISM: artificial
<220> FEATURE:
<223> OTHER INFORMATION: synthetic

<400> SEQUENCE: 31

Met Tyr Pro Tyr Asp Val Pro Asp Tyr Ala Thr Ser Arg Leu Ser Val
 1               5                  10                  15

Lys Ser Leu Arg Ser Ile Ser Arg Phe Val Gln Trp Glu Cys Cys Trp
                20                  25                  30

Met Leu Val Asn Lys Ser Ala Arg Tyr Arg Glu Phe Arg Ala Val Thr
                35                  40                  45

-continued

```
Ser Gln Ser Pro Gly Leu Gly Lys Val Ser Ser Thr Asp Asp Gly Arg
 50                  55                  60

Cys Leu Ala Ala Ser Met Met Leu Phe Arg Arg Asp Gly Asn Phe Val
 65                  70                  75                  80

Leu Cys Leu Val Val Asn Lys Glu Pro Val Gly Gln Phe Gly Cys Ser
                 85                  90                  95

Gly Met Arg Arg Glu Lys Met Val Ile Asp Gly Leu Gln Glu Pro Val
                100                 105                 110

Tyr Val Met Arg Leu Leu Ala Pro Leu Ile Pro Val Lys Leu Gly Phe
            115                 120                 125

Ser Pro Tyr Met Leu Pro Pro Lys Ser Ile Gly Gly Ser Gly Gly Leu
        130                 135                 140

Asp Pro Ser Val Ile Tyr Gln Asn Ala Ser Val Val Thr Pro Glu Glu
145                 150                 155                 160

Ala Ala Thr Val Thr Met Gln Gly Ser Gly Ile Val Thr Val Gly Leu
                165                 170                 175

Ser Gly Val Gly Ser Trp Val Gln Ile Lys Asp Gly Gly Asn Met Lys
            180                 185                 190

Leu Phe Val Phe Ala Leu Cys Phe Asp Val Thr Ala Cys Cys Asp
        195                 200                 205

Arg Leu Ala Phe Pro Ser Leu Ala Lys Ile Tyr Ser Glu Thr Val Ser
210                 215                 220

Cys Glu Ala Asp Lys Cys Gly Phe Cys Arg Asp Ser Gly Arg His Val
225                 230                 235                 240

Asp Pro Thr Gly Arg Phe Val Gly Cys Val Pro Asp Ser Gly Val Cys
                245                 250                 255

Leu Cys Tyr Ser Pro Cys Arg Gly Thr Asp Ala Ala Val Ser Val Arg
            260                 265                 270

Ser Trp Leu Pro Tyr Leu Glu Leu Glu Asp Gly Ala Asn Thr His Ser
        275                 280                 285

Leu Phe Val Arg Arg Tyr Asp Gly Arg Lys Gly Leu Pro Ala Thr Ile
    290                 295                 300

Ser Asp Tyr Leu Gly Ala Arg Asn Ser Glu Gly Asp Glu Ile Pro Leu
305                 310                 315                 320

Arg Thr Glu Pro Trp Gln Leu Leu Lys Ile Glu Pro Thr Leu Ser Ala
                325                 330                 335

Met Ile Ile Met Ala Cys Pro Leu Leu Lys Lys Ile Val Leu Glu His
            340                 345                 350

Met
```

<210> SEQ ID NO 32
<211> LENGTH: 179
<212> TYPE: DNA
<213> ORGANISM: artificial
<220> FEATURE:
<223> OTHER INFORMATION: synthetic

<400> SEQUENCE: 32
gaccgcgcca cagcagagcc agcaccagca gaagagccag caccagcggg cccagagtcg    60
caaagcgcgc gggcagccac ggcccagact gcggtcgcga tggcccggag cgcgctcgcc   120
accacgatga cggtgcccaa cgataaccag tccgctcccg caccgacgcc accgccgat    179

<210> SEQ ID NO 33
<211> LENGTH: 38

-continued

```
<212> TYPE: DNA
<213> ORGANISM: artificial
<220> FEATURE:
<223> OTHER INFORMATION: synthetic

<400> SEQUENCE: 33
atgtctagcg ttttctcaac agcattcgtg cgccttga                            38

<210> SEQ ID NO 34
<211> LENGTH: 252
<212> TYPE: DNA
<213> ORGANISM: artificial
<220> FEATURE:
<223> OTHER INFORMATION: synthetic

<400> SEQUENCE: 34
cacggcctgg cccagcgagc cctgcgggac cggttccaaa acttcgaggc cgtgctggcc     60
cggggcatgc acgtggaggc cggccggcag gagcccgaga ccccccgggt gagcggccgg    120
cggctgccct tcgacgacct gtgatccgga ggacgacggc tcgtgtatct tgtgccaatt    180
gctgttgctc taccgcgacg gcgaatggat cctctgtctt tgctgcaacg gccgttatca    240
aggccactat gg                                                        252

<210> SEQ ID NO 35
<211> LENGTH: 67
<212> TYPE: DNA
<213> ORGANISM: artificial
<220> FEATURE:
<223> OTHER INFORMATION: synthetic

<400> SEQUENCE: 35
ctgggtcgcc aacagcgcca acgagtacgt cgtcagctcc gtgccccgcc ccgtcagtcc     60
gtagaag                                                               67
```